(12) United States Patent
Schentag et al.

(10) Patent No.: US 10,624,913 B2
(45) Date of Patent: *Apr. 21, 2020

(54) DIAGNOSTICS AND METHODS FOR TREATMENT OF NON-ALCOHOLIC HEPATIC STEATOSIS AND HEPATIC STEATOHEPATITIS, AND PREVENTION OF COMPLICATIONS THEREOF

(71) Applicant: VOLANT HOLDINGS GMBH, Feusisberg (CH)

(72) Inventors: Jerome Schentag, Amherst, NY (US); Joseph M. Fayad, Las Vegas, NV (US)

(73) Assignee: VOLANT HOLDINGS GMBH, Feusisberg (CH)

(*) Notice: Subject to any disclaimer, the term of this patent is extended or adjusted under 35 U.S.C. 154(b) by 0 days.

This patent is subject to a terminal disclaimer.

(21) Appl. No.: 16/133,322

(22) Filed: Sep. 17, 2018

(65) Prior Publication Data

US 2019/0255084 A1 Aug. 22, 2019

Related U.S. Application Data

(63) Continuation of application No. 15/601,497, filed on May 22, 2017, now abandoned, which is a (Continued)

(51) Int. Cl.
*A61K 38/00* (2006.01)
*A61K 31/7004* (2006.01)
*A61K 31/70* (2006.01)
*A61K 31/715* (2006.01)
*A61K 31/195* (2006.01)
*A61K 9/28* (2006.01)
*A61K 9/20* (2006.01)
*A61K 36/05* (2006.01)
*A61K 31/555* (2006.01)
*A61K 36/48* (2006.01)
*A61K 35/741* (2015.01)
*A61K 36/8998* (2006.01)
(Continued)

(52) U.S. Cl.
CPC ........ *A61K 31/7004* (2013.01); *A61K 9/2009* (2013.01); *A61K 9/2013* (2013.01); *A61K 9/2054* (2013.01); *A61K 9/2059* (2013.01); *A61K 9/282* (2013.01); *A61K 9/2846* (2013.01); *A61K 31/00* (2013.01); *A61K 31/155* (2013.01); *A61K 31/40* (2013.01); *A61K 31/4985* (2013.01); *A61K 31/555* (2013.01); *A61K 31/70* (2013.01); *A61K 31/7056* (2013.01); *A61K 31/7072* (2013.01); *A61K 35/741* (2013.01); *A61K 36/05* (2013.01); *A61K 36/48* (2013.01); *A61K 36/8998* (2013.01); *A61K 38/21* (2013.01); *A61K 38/212* (2013.01); *A61K 45/06* (2013.01); *A61P 1/16* (2018.01); *A61P 31/14* (2018.01); *G01N 33/6893* (2013.01); *A61K 2300/00* (2013.01); *G01N 2800/085* (2013.01)

(58) Field of Classification Search
CPC .... A61K 38/00; A61K 31/7004; A61K 31/70; A61K 31/715; A61K 31/195
USPC .................. 514/1.1, 7.1, 23, 53, 54, 60, 561
See application file for complete search history.

(56) References Cited

U.S. PATENT DOCUMENTS

| | | | |
|---|---|---|---|
| 5,769,793 A | 6/1998 | Pincus et al. | |
| 9,370,528 B2 * | 6/2016 | Schentag | A61K 45/06 |
| 9,730,951 B2 * | 8/2017 | Fayad | A61K 45/06 |
| 9,757,346 B2 | 9/2017 | Fayad | |
| 2013/0273154 A1 | 10/2013 | Fayad et al. | |
| 2013/0337055 A1 | 12/2013 | Schentag et al. | |
| 2014/0037739 A1 | 2/2014 | Schentag et al. | |
| 2014/0294951 A1 | 10/2014 | Fayad et al. | |
| 2016/0030361 A1 | 2/2016 | Schentag et al. | |
| 2017/0173060 A1 | 6/2017 | Schentag et al. | |

FOREIGN PATENT DOCUMENTS

| | | |
|---|---|---|
| WO | 2010/027498 A2 | 3/2010 |
| WO | 2012/118712 A2 | 9/2012 |
| WO | 2016/011335 A1 | 1/2016 |

OTHER PUBLICATIONS

International Search Report and Written Opinion in corresponding International Application No. PCT/IB2017/000780, dated Jan. 18, 2018.

(Continued)

*Primary Examiner* — Raymond J Henley, III
(74) *Attorney, Agent, or Firm* — J.A. Lindeman & Co., PLLC

(57) ABSTRACT

The present invention is directed to a System characterization of NASH that combines Modeling and Biomarkers, enabling pharmaceutical compositions and methods of treatment that relate to the inhibition, resolution and/or prevention of Non Alcoholic Fatty Liver Disease (NAFLD) and Non Alcoholic Steatohepatitis (NASH). Said conditions are Liver related complications among the array of manifestations of metabolic syndromes, including Type 2 diabetes, hyperlipidemia, weight gain, abdominal obesity, insulin resistance, hypertension, atherosclerosis, fatty liver diseases and certain chronic inflammatory states that lead to these manifestations, among others. In additional aspects, the present invention relates to compositions and methods which may be used to treat, inhibit or reduce the likelihood of NASH and NAFLD complications in patients with hepatitis viral infections, including Hepatitis B and Hepatitis C viral infections, as well as the secondary disease states and/or conditions which are often associated with such viral infections, including hepatic steatosis (steatohepatitis), cirrhosis, fatty liver and hepatocellular cancer, metabolic syndrome complications including cardiovascular diseases, neurodegenerative diseases and premature ageing, among other disease states or conditions.

20 Claims, 38 Drawing Sheets

Related U.S. Application Data continuation-in-part of application No. 15/162,941, filed on May 24, 2016, now Pat. No. 9,730,951, which is a continuation of application No. 14/002,642, filed as application No. PCT/US2012/026561 on Feb. 24, 2012, now Pat. No. 9,370,528.

(60) Provisional application No. 61/480,788, filed on Apr. 29, 2011, provisional application No. 61/514,174, filed on Aug. 2, 2011, provisional application No. 61/551,638, filed on Oct. 26, 2011, provisional application No. 62/339,904, filed on May 22, 2016.

(51) Int. Cl.

| | | |
|---|---|---|
| *A61K 45/06* | (2006.01) | |
| *A61K 31/7056* | (2006.01) | |
| *A61K 31/7072* | (2006.01) | |
| *A61K 38/21* | (2006.01) | |
| *A61K 31/00* | (2006.01) | |
| *A61P 1/16* | (2006.01) | |
| *A61P 31/14* | (2006.01) | |
| *G01N 33/68* | (2006.01) | |
| *A61K 31/40* | (2006.01) | |
| *A61K 31/155* | (2006.01) | |
| *A61K 31/4985* | (2006.01) | |

(56) References Cited

OTHER PUBLICATIONS

Kneeman et al., "Secondary causes of nonalcoholic fatty liver disease", Ther. Adv. Gastroenterol., 2012, 5(3), pp. 199-207.
Maljaars et al., "An ileal brake-through?" Am. J. Clin. Nutr., 2010, 92, pp. 467-468.

\* cited by examiner

Mechanism of Action of Brake™
- RYGB (ROUX-EN-Y Bariatric Surgery), increases secretion of body's own gut-derived hormones (GLP-1, PYY, GLP-2 etc...) secreted from L-cells
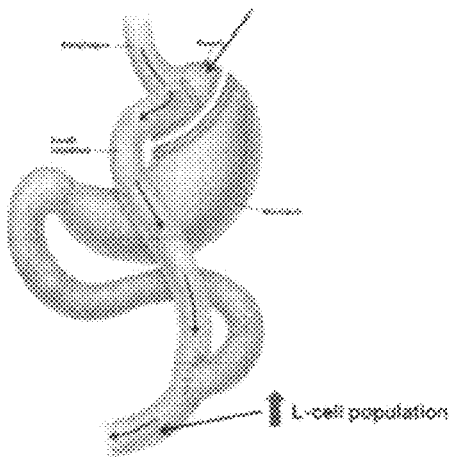
- Brake™ contains a GRAS carbohydrate substance (not absorbed!) released at the ileum to trigger the L-cells
BRAKE™ mimics RYGB Gastric Bypass Surgery effect with a pill
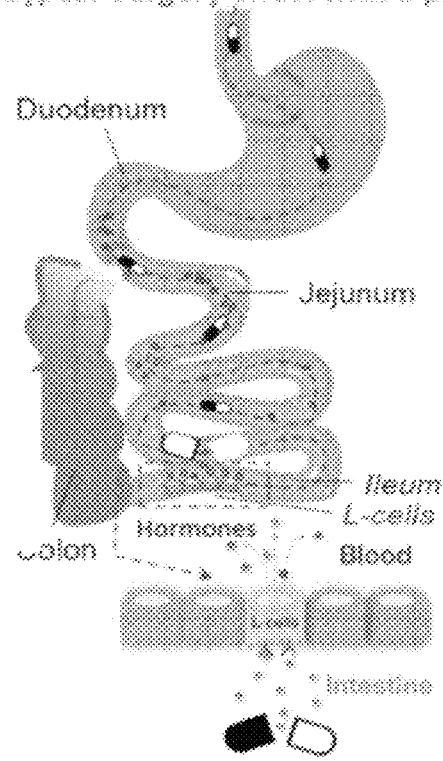
*Fig. 1*

| Input parameters predicting Outputs to Include Biopsy Score (total), and wComb Liver Signal | | | |
|---|---|---|---|
| Output: Biopsy Score (total) | | Output: WinCombLiver Signal | |
| Parameter | MMSE | Parameter | MMSE |
| All Included | 0 | WinCombLiver Signal | 0 |
| WinCombBiopsy Signal | 0 | All Included | 0 |
| Steatosis Score on biopsy | 325 | Bilirubin Direct | 383 |
| Fibrosis Score on biopsy | 409 | WinCombBiopsy Signal | 817 |
| Bilirubin Direct | 554 | Steatosis Score on biopsy | 876 |
| WinCombLiver Signal | 631 | Fibrosis Score on biopsy | 881 |
| Lymphocytes (%) | 864 | Bilirubin Total | 979 |
| Total Protein | 890 | Total Protein | 1190 |
| Waist Circumference | 935 | Lymphocytes (%) | 1216 |
| Albumin | 965 | Albumin | 1277 |
| Bilirubin Total | 972 | Mean Arterial Pressure | 1305 |
| Mean Arterial Pressure | 984 | Waist Circumference | 1332 |
| Neutrophils (%) | 1043 | Neutrophils Pct | 1376 |
| Weight | 1055 | hsCRP | 1410 |
| CV Index | 1060 | Total WBC count | 1415 |
| Total WBC count | 1070 | CV Index | 1417 |

*Fig. 2*

Input parameters and MMSE of Output of wComb Biopsy prediction over time wComb Biopsy Prediction Signal over time

| Input Parameter | MMSE | Input Parameter (con't) | MMSE |
|---|---|---|---|
| all Kept | 0 | | |
| Fibrosis score | 711.4 | Blood glucose | 1310 |
| wComb Steatosis score | 731.4 | HOMA-IR | 1330 |
| wAvg Inflammation | 792.2 | BMI | 1345 |
| wComb Liver Signal | 826.5 | HbA1c | 1377 |
| ALT to AST ratio | 856.5 | wComb Hepatitis C signal | 1398 |
| wCombFibrosis score | 1011.9 | Total Cholesterol | 1403 |
| FS index | 1034 | LDL Cholesterol | 1423 |
| CV index | 1092 | Fib4 calculated | 1432 |
| wComb Biopsy Signal | 1132 | Smoking | 1437.2 |
| Lymphocytes | 1197 | Triglycerides | 1437.6 |
| Insulin concentration | 1254 | | |

*Fig. 3*

BMI measured post intervention compared with BMI measured pre-intervention

ALT/AST ratio measured post intervention compared with ALT/AST ratio measured pre-intervention

TGs measured post intervention compared with TGs measured pre-intervention

FS index measured post intervention compared with FS index measured pre-intervention wComb Liver signal measured post intervention compared with wComb Liver signal measured pre-intervention

Steatosis Score measured post intervention compared with Steatosis Score measured pre-intervention

Fibrosis Score measured post intervention compared with Fibrosis Score measured pre-intervention

Biopsy Score measured post intervention compared with Biopsy Score measured pre-intervention

| Characteristic | Brake™ + SOC | RYGB + SOC | Lipitor + SOC |
|---|---|---|---|
| No. of subjects | 34 | 17 | 29 |
| Male Gender, No. (%) | 11 (32) | 5 (29) | 14 (48) |
| Age (years) | 50±11 | 43±11 | 58±11 |
| Body Mass Index (kg/m²) | 34±5.8 | 54±12 | 35±6.7 |
| Glycated hemoglobin ≥ 6.5% | 4 (12) | 10 (58) | 14 (48) |
| AST ≥ 25 U/L | 22 (65) | 9 (53) | 8 (28) |
| Total Cholesterol ≥ 200 mg/dl | 6 (18) | 9 (53) | 19 (65) |
| Triglycerides ≥ 150 mg/dl | 14 (41) | 8 (47) | 17 (59) |
| Low-density Lipoprotein ≥ 100 mg/dl | 5 (15) | 3 (18) | 10 (34) |
| High-density Lipoprotein ≤ 50 mg/dl | 22 (65) | 15 (88) | 24 (83) |
| FS Index >60 at baseline (%) | 17 (50) | 15 (88) | 24 (83) |
| Diabetes Medications, No. (%) | | | |
| Metformin | 4 (12) | 12 (71) | 7 (24) |
| Secretagogues | 0 | 6 (35) | 9 (31) |
| Insulin | 1 (3) | 5 (29) | 6 (21) |
| Thiazolidinediones | 0 | 4 (24) | 4 (14) |
| Incretin Mimetic | 2 (6) | 5 (29) | 0 |
| Statin Therapy | 8 (24) | 6 (35) | 29 (100) |
| Additional lipid lowering agent | 9 (25) | 3 (18) | 1 (3.4) |

*Fig. 15*

3D plot of FS index, CV index and Output of wComb Biopsy signal

| Para-meter | RYGB + SOC (N = 17) | | | | | Brake™ + SOC (N = 34) | | | | | Lipitor + SOC (N=29) | | | | |
|---|---|---|---|---|---|---|---|---|---|---|---|---|---|---|---|
| | No. at BL | BL | No. at 6 mos | Mean post-BL | % Ch | No. at BL | BL | No. at 6 mos | Mean post-BL | % Ch | No. at BL | BL | No. at 6 mos | Mean post-BL | % Ch |
| HBA1c [%] | 17 | 7.5±1.2 | 16 | 6.5±1.2 | -13 | 34 | 5.9±0.8 | 20 | 5.8±0.5 | -1.6 | 29 | 7.3±1.3 | 25 | 7.1±1.1 | -2.7 |
| AST [IU/L] | 17 | 25±12 | 16 | 25±12 | 0 | 34 | 42±34 | 21 | 31±15 | -26 | 29 | 22±5 | 25 | 21±4.5 | -4.5 |
| Weight [lb] | 17 | 346±70 | 16 | 273±67 | -21 | 34 | 211±43 | 21 | 201±40 | -4.7 | 29 | 220±56 | 25 | 212±48 | -3.6 |
| FS Index | 16 | 163±93 | 15 | 31±13 | -81 | 34 | 94±81 | 20 | 24±11 | -74 | 29 | 103±46 | 25 | 95±39 | -7.8 |
| CV Index | 16 | 211±92 | 15 | 81±14 | -62 | 34 | 145±66 | 20 | 77±13 | -47 | 29 | 154±53 | 25 | 139±48 | -9.7 |

Table XX. Changes from baseline to 6 months in metabolic parameters – all patients
Abbreviations: BL = baseline, Ch = change, LD = low dose, PS = paired samples, AST = aspartate aminotransferase, ALT = alanine aminotransferase, HBA1c = glycated hemoglobin

*Fig. 20*

Relative comparison of Brake and RYGB Surgery
Relative Potency: Brake vs. RYGB

| Parameter | Brake | | | RYGB | | | p value | Brake as % of RYGB Change |
|---|---|---|---|---|---|---|---|---|
| | N | Mean | SD | N | Mean | SD | | |
| % Weight loss, total in 6 mo | 18 | 5.33 | 4.01 | 15 | 25.33 | 3.88 | 0.203 | 20.97 |
| % Weight loss as excess kg in 6mo | 18 | 5.4 | 4.8 | 15 | 44.9 | 14.4 | 0.006 | 12.03 |
| % chg HOMA – IR: pre to post change in 6 mo | 18 | 36.3 | 17.8 | 15 | 66.8 | 18.6 | 0.002 | 62.99 |
| % change HBA1c: pre to post change in 6 mo | 6 | 11.2 | 4.35 | 15 | 20.5 | 12.2 | 0.019 | 54.63 |
| % change AST: pre to post change in 6 mo | 15 | 41.3 | 31.7 | 15 | 26 | 23.9 | 0.071 | 158.0 |
| %change ALT: pre to post change in 6 mo | 16 | 50.5 | 20.5 | 13 | 26.9 | 31.0 | 0.028 | 187.0 |
| % change Triglycerides: pre to post change in 6 mo | 11 | 32.5 | 15.2 | 6 | 40.3 | 24 | 0.498 | 81.0 |

Only the patients who start out with abnormal baseline values are included in some calculations.

*Fig. 22*

| Formulation | N | Age | BMI | GLP-1 (pM) AUC$_{0-10k}$ | PYY (pg/ml) AUC$_{0-10k}$ |
|---|---|---|---|---|---|
| 1 | 7 | 39 ± 11 | 30.8 ± 6.2 | 348 ± 45 | 213 ± 24 |
| 2 | 7 | 46 ± 18 | 29.4 ± 4.9 | 389 ± 121 | 241 ± 25 |
| 3 | 7 | 44 ± 13 | 31 ± 9.1 | 321 ± 62 | 215 ± 20 |
| 4 | 7 | 45 ± 6 | 27.5 ± 3.0 | 127 ± 60 | 292 ± 60 |
| 5 | 7 | 41 ± 17 | 27.7 ± 4.5 | 107 ± 48 | 263 ± 42 |
| 6 | 5 | 40 ± 8 | 27.6 ± 2.3 | 70 ± 34 | 258 ± 113 |
| 7 | 5 | 40 ± 11 | 29 ± 5.9 | 120 ± 44 | 398 ± 151 |
| RYGB | 5 | 45 ± 7.7 | 46 ± 5.4 | 306 ± 107 | 597 ± 136 |

(Formulation 2 was Chosen for Clinical Studies)

(Source of RYGB pts: Monte 2014)

Fig. 23

| hsCRP Level | Stroke (n=42) | Bleed (n=38) | MI (n=9) |
|---|---|---|---|
| <1.0 mg/L | 5 (12) | 8 (21) | 1 (11) |
| 1-3 mg/L | 14 (33) | 13 (34) | 1 (11) |
| 3-10 mg/L | 13 (32) | 14 (37) | 4 (44) |
| >10 mg/L | 9 (22) | 3 (8) | 3 (33) |

*Fig. 25*

| Pharmaceutical product contents | 1 Tablet (mg) | 7 Tablets (mg) | % |
|---|---|---|---|
| CanTab® (91% Dextrose) | 1429 | 10003 | 85.93% |
| Corn starch | 80 | 560 | 4.81% |
| Stearic acid | 19.5 | 136.5 | 1.17% |
| Magnesium Stearate | 7 | 49 | 0.42% |
| Silicon dioxide | 2.5 | 17.5 | 0.15% |
| Core Total: | 1538 | 10766 | 92.48% |
| Coat / Overcoat: | 125 | 875 | 7.52%* |
| Total Brake™: | 1663 | 11641 | 100.00% |

*7, 7.5, 8% w/w (coat / core) variations will be potentially produced during formulation

*Fig. 35*

| Coat* | mg | % |
|---|---|---|
| Marcoat 125 (Aqueous Shellac) | 38.84 | 79.09 |
| Hypromellose (Pharmacoat 606) | 3.24 | 6.60 |
| Triacetin, USP | 1.93 | 3.93 |
| Overcoat\*\* | mg | % |
| Opadry (Colorcon) | 4.8 | 9.77 |
| Chlorophyllin | 0.3 | 0.61 |

*Purified Water 176.1 mg (to disperse Coat) / **Purified Water 60.1 mg (to disperse Overcoat)
The coat solutions will be applied to the formulated pellet and coating thickness will be determined by weight increase. The shellac solution contains 25% solids and will be factored in when determining the amount of shellac needed.

Fig. 36

| dose/day | | |
|---|---|---|
| Brake™ 8.0% w/w coated | 1663 mg | 11641 mg |
| Atorvastatin Coating | | |
| Atorvastatin calcium (crystalline form) | 1.43 mg | 10 mg |
| Tween 80 | 0.5 mg | |
| Povidone (PVP) polyvinylpyrolidone | 10 mg | |
| Hydroxypropyl methylcellulose | 30 mg | |
| Opadry Clear (YS-1-7006) | 8.5 mg | |
| Opadry White Polishing Coat | 25 mg | |
| Candelilla Wax Powder | 15 mg | |
| Total Tablet weight | 1753 mg | 12271 mg |

*Fig. 37*

| Spray Rate | 15-27 | mL/min |
| Exhaust Temperature | 42-47° | C. |
| Atomization Air Pressure | 25 | psi |
| Pan Speed | 5-9 | rpm |
| Inlet Air Flow | 300-400 | CFM |

Fig. 38

DIAGNOSTICS AND METHODS FOR TREATMENT OF NON-ALCOHOLIC HEPATIC STEATOSIS AND HEPATIC STEATOHEPATITIS, AND PREVENTION OF COMPLICATIONS THEREOF

RELATED APPLICATIONS

This application is a continuation application of U.S. patent application Ser. No. 15/601,497, which is a continuation-in-part application of application Ser. No. 15/162,941, filed May 24, 2016, which is a continuation of application Ser. No. 14/002,642, filed Aug. 30, 2013, now U.S. Pat. No. 9,370,528, issued Jun. 21, 2016, which claims the benefit of priority of and is a United States national phase application of International Patent Application Number PCT/US2012/026561 filed in the United States Receiving Office on Feb. 24, 2012, which claims the benefit of priority from provisional application Ser. No. U.S. 61/480,788, filed Apr. 29, 2011 entitled, "Long Term Stimulation of Ileal hormones by an Orally Delivered, Ileal Released Natural Product Aphoeline", Ser. No. U.S. 61/514,174, filed Aug. 2, 2011, entitled, "Gut CFO: the ileal hormones. Decreasing insulin resistance, triglycerides, liver enzymes, signaling caloric intake, using caloric reserve, and turning body to health with every meal", and Ser. No. U.S. 61/551,638, filed Oct. 26, 2011, entitled "Oral Formulations Mimetic of Roux-en-Y Gastric Bypass Actions on the Ileal Brake; Compositions, Methods of Treatment, Diagnostics and Systems for Treatment of Metabolic Syndrome Manifestations, Including Insulin Resistance, Fatty Liver Disease, Hyperlipidemia and Type 2 Diabetes. This application also claims priority from provisional application Ser. No. 62/339,904, filed 22 May 2016 entitled "Compositions, Methods of Treatment and Diagnostics for Treatment of Non-Alcoholic Hepatic Steatosis and Hepatic Steatohepatitis, alone or in combination with a Hepatitis C Virus Infection", each of said aforementioned applications being incorporated by reference in their entirety herein.

FIELD OF THE INVENTION

The present invention is directed to diagnostics and model based methods of treatment, and computer-implementable systems that relate to the treatment of an array of the manifestations of Metabolic Syndromes (MetS), including Non Alcoholic Fatty Liver Disease (NAFLD), Type 2 diabetes, hyperlipidemia, weight gain, obesity, insulin resistance, hypertension, atherosclerosis, and certain chronic inflammatory states that lead to Non Alcoholic Steatohepatitis (NASH), among other inflammatory mediated manifestations of MetS. In additional aspects, the present invention relates to compositions and methods which may be used to diagnose, treat, inhibit or reduce the likelihood of NASH when the patient has a concomitant infection with hepatitis viral infections, including Hepatitis B and Hepatitis C, as well as the secondary disease states and/or conditions which are often associated with such viral infections, including NAFLD and NASH, and their closely associated complications including hepatic fibrosis, hepatic cirrhosis, and hepatocellular cancer, among other disease states or conditions.

BACKGROUND OF THE INVENTION

Non Alcoholic Steatohepatitis (NASH) is generally recognized as a serious progression of the more common Non-alcoholic fatty liver disease (NAFLD). NAFLD is a precursor state to NASH, because only with NASH is there a pattern of inflammation that leads to fibrosis and eventually cirrhosis. Ordinarily, fewer than 20% of patients with NAFLD progress to NASH, although those who progress account for the majority of the severe complications discussed in this application (1). NASH has become the third-leading cause of liver transplants in the U.S., with anywhere between 2% and 5% of the general population currently affected. Since 2001, liver transplants attributed to NASH have increased by an alarming 1,000%. By 2025, it's estimated that more than 25 million Americans will have hepatic steatosis with at least detectable fibrosis. For perspective, Hepatitis C affects just 3.2 million.

The main culprit for this rapid increase in NASH is none other than the rising incidence of Metabolic Syndrome (MetS) diseases, which are all linked to progression of underlying insulin resistance.

Type 2 diabetes mellitus (T2D), obesity and dyslipidemia are the principal MetS component factors associated with NAFLD, which is now considered the hepatic expression of MetS. Several studies have dealt with the relationship of NAFLD and MetS, the risk of liver disease associated with the classical features of MetS, and the importance of insulin resistance as the precursor condition of different MetS constituent diseases. In the past 10 years alone, the rate of obesity has doubled in adults and tripled in children. Not only does obesity contribute to the inherent cause of NASH, but it also increases the risk of T2D and high blood cholesterol, which can further complicate the health of a patient with NASH. Resolution of insulin resistance will resolve NAFLD, because triglycerides are lowered and the fatty deposits are primarily comprised of these lipids.

Both NAFLD and NASH are closely associated with insulin resistance, and insulin resistance is thereby linked to progression to hepatocellular carcinoma (2, 3).

The epidemics of obesity and diabetes of Western countries is expected to produce a significant increase of MetS associated liver disease in the next years. We still need to clarify the mechanism(s) responsible for liver disease progression from pure fatty liver, to steatohepatitis and to cirrhosis, and the reason(s) why only a few NAFLD cases actually progress to terminal liver failure while others (the majority) will have a cardiovascular outcome before the liver is end-stage. Prevention and intervention programs based on lifestyle are therefore mandatory to reduce the burden of metabolic liver disease.(4)

Nonalcoholic fatty liver disease is now recognized as the most common liver disease in the United States, with a prevalence of approximately 5% in the general population and up to 25% to 75% in patients with obesity and T2D. Nonalcoholic fatty liver disease is a clinicopathologic syndrome with a wide spectrum of histologic abnormalities and clinical outcomes. Hepatic steatosis has a benign clinical course, and it appears almost completely reversible if there is weight loss and a reduction in insulin resistance. In contrast, nonalcoholic steatohepatitis (NASH) may progress to cirrhosis and liver-related death in 25% and 10% of patients, respectively. Cases occur most commonly in obese, middle-aged women with diabetes. However, NASH may also occur in children and normal-weight men with normal glucose and lipid metabolism. The pathophysiology involves two steps. The first is insulin resistance caused by dietary excess and hepatic overload, recognized as steatosis. The second is oxidative stress, which produces lipid peroxidation and activates inflammatory cytokines resulting in NASH. Liver biopsy provides prognostic information and identifies NASH patients who may benefit from therapy.(5)

RYGB surgery definitively resolves insulin resistance, normalizes triglycerides, and thus completely resolves NAFLD. RYGB surgery also lowers inflammation and mitigates hepatocellular damage from inflammation, leading to resolution of elevated liver enzymes (ALT, AST). Studies in our laboratories have shown a resolution of systemic inflammation with RYGB(6), and studies by others have shown that RYGB not only prevents progression of fibrosis, but reverses at least some of the biopsy proven fibrosis in patients with NASH (7-12). In these RYGB patients, the first biopsy was at the time of surgery, when there was elevated ALT and AST as well as demonstrable hepatic fibrosis. When these patients had normalization of their elevated liver enzymes, in most cases they were considered to have resolved hepatic inflammation, and repeating the biopsy was not considered medically necessary. Thus while essentially all RYGB cases have normalization of insulin resistance, ALT, AST and Triglycerides, there are relatively small numbers of RYGB cases in the literature with biopsy proven resolution of fibrosis.

Imaging studies also show resolution of both hepatic steatosis (NAFLD) and fibrosis (NASH) after RYGB (13-15). These non-invasive methods are recognized as supporting evidence for approval in NASH, and it is possible that in the future, regulatory agencies may consider these methods as equivalent to biopsy.

Mathematical Models of NASH and NAFLD have not been developed, although there is the potential for such models to assist with diagnosis, risk stratification, and defining the effects of the various treatments. It would be a major advance in this field to have an integrated model of the disease based on biomarkers and non-invasive tests. Such a model must be predictive of the biopsy results however, in order for it to be considered useful for diagnosis, patient stratification and for monitoring treatment response.

On the basis of the laboratory biomarkers and the RYGB results of others to date, Brake™ is a promising approach to both NAFLD and NASH. As the first oral mimetic of RYGB surgery, Brake™ has thus far normalized insulin resistance, triglycerides, ALT, AST, and hyperglycemia. Except for RYGB surgery, no therapy has yet resolved either of these conditions, and RYGB itself is not indicated as a treatment for NASH, although patients with NASH conditions do have RYGB surgery if they qualify for the surgery overall.

The current standard for definitive diagnosis of NAFLD or NASH is a biopsy of the liver, which is an expensive and invasive procedure. Because this procedure is done very infrequently, and at great cost to the patients and their caregivers, we lack a readily available method to assess the effects of drug treatments for NAFLD or NASH. Single laboratory tests such a measurements of liver enzymes ALT or AST do not predict the total response of the liver, so the idea of non-invasively defining drug response and other useful effects has not advanced in medical practice nor in clinical research. It is a novel idea of the present invention to present a means of predicting changes in liver biopsy using simultaneous modeling of groups of biomarkers and laboratory tests. Efforts to date in this regard focus primarily on single parameter predictions, and have yielded some success, but overall the applicability of single parameters to predict biopsy endpoints in new patients has met with only marginal success.

Both NAFLD and NASH are Associated with Death from CV Causes

A complex interaction among metabolic factors, adipose tissue lipolysis, oxidative stress, and insulin resistance results in a deleterious process that may link nonalcoholic fatty liver disease (NAFLD) with severe cardiovascular (CV) outcomes such as myocardial infarction and stroke. Patients with NAFLD are at higher risk of atherosclerosis, new onset of CV events, and overall mortality. The strong association between NAFLD and CV disease should affect clinical practice, with screening and surveillance of patients with NAFLD(16)

Bril and colleagues studied patients with NAFLD in order to determine the contribution of the severity of steatohepatitis to atherogenic dyslipidemia. The study was conducted at a university hospital. Patients were recruited from outpatient clinics or from the general population (n=188). Patients had measurement of hepatic triglyceride content by magnetic resonance spectroscopy, histology (liver biopsy), metabolic profile by means of an oral glucose tolerance test, and lipoprotein analyses were performed. Outcomes measured included standard lipids, lipoprotein sub-fraction analysis (apolipoprotein B/A1 levels, low-density lipoprotein (LDL) particle size/phenotype, and LDL/high-density lipoprotein sub-fractions), and insulin resistance. Patients with NAFLD had severe insulin resistance, especially at the level of the adipose tissue, when compared with patients without NAFLD. Despite small differences in triglycerides and high-density lipoprotein-cholesterol, patients with NAFLD had a significantly higher plasma apolipoprotein B to apolipoprotein A1 ratio (0.66+/−0.02 vs 0.58+/−0.02, P=0.01) and smaller LDL particle size (216.2+/−0.7 vs 219.4+/−1.1 A, P=0.01). Of note, these differences between patients with/without NAFLD were independent of the presence of obesity. Severity of steatohepatitis did not significantly influence the lipoprotein profile. Worse atherogenic dyslipidemia was best predicted by the degree of liver fat accumulation and adipose tissue and systemic insulin resistance. Bril concluded that NAFLD was associated with a worse atherogenic lipoprotein profile, regardless of similar body mass index and other clinical parameters. They speculate that this lipoprotein profile is driven mostly by liver fat content and insulin resistance and appears not to be worsened by obesity or the severity of liver disease (17)

Non-alcoholic fatty liver disease (NAFLD) is associated with an increased risk of cardiovascular related death, particularly in those with hepatic fibrosis. Long and colleagues determined the prevalence of predicted fibrosis based on non-invasive fibrosis markers and the association of hepatic fibrosis with cardiovascular risk factors in a Cross-sectional study of 575 Framingham Heart Study participants with NAFLD based on computed tomography. They determined the prevalence of predicted fibrosis based on the aspartate aminotransferase (AST)/alanine aminotransferase (ALT) ratio, AST to platelet ratio index (APRI), the Fibrosis-4 score (FIB4), and the NAFLD Fibrosis Score (NFS). Using multivariable logistic regression models, they examined the association between low, indeterminate, or high risk for fibrosis according to the NFS and various cardiometabolic risk factors. The predicted risk of fibrosis was 12%, 4%, 5%, and 32% for the NFS, FIB4, APRI, and AST/ALT ratio, respectively. In multivariable models, participants with a high risk for advanced fibrosis by the NFS had a wider pulse pressure (adjusted mean difference=6.87 mm Hg; p=0.0002) and increased odds of hypertension (OR 2.92; p=0.007) compared to those with low risk of fibrosis. There were no statistically significant differences between other cardiovascular risk factors for those with a high versus low risk of fibrosis. The AST/ALT ratio, APRI, and NFS give widely disparate predictions of liver fibrosis. Participants with a high risk for fibrosis based on NFS had wider pulse pressure and increased odds of hypertension. Whether modifying these risk factors impacts cardiovascular endpoints in NAFLD patients remains unknown.(18).

While epidemiological studies have attempted to measure age acceleration and increased mortality rates in those with concurrent metabolic syndrome and chronic viral infections such as HCV and HIV, such measurements are made difficult by the myriad co-factors. For instance, metabolic syndrome associated disorders such as diabetes, HCV infection, and medication adherence are important factors of HIV infection that are also suspected to significantly affect mortality rates. While most previous studies have not attempted to control for these factors, the study by Gross and colleagues has focused specifically on well-characterized subjects. Their estimate of HIV age advancement was 4.9 years, calculated from a quantitative analysis of the methylome.(19). They state that further work will be needed to understand if the observed epigenetic age advancement is generalizable to broader slices of the HIV+ population (i.e., patients with complex co-morbidities such as drug use or additional viral infections). This study is based on the same metabolic syndrome mediated epigenetic model of biological aging as many others, including recent reports associating epigenetic aging increases of 6.6 years with Down's Syndrome(20), traumatic stress (21), and even all-cause mortality (22). Recent studies have identified biomarkers of chronological age based on DNA methylation levels. It is not yet known whether DNA methylation age captures aspects of biological age. Marioni and colleagues tested whether differences between people's chronological ages and estimated ages, DNA methylation age, predict all-cause mortality in later life. The difference between DNA methylation age and chronological age was calculated in four longitudinal cohorts of older people. Meta-analysis of proportional hazards models from the four cohorts was used to determine the association between chronological age and mortality. A 5-year higher chronological age is associated with a 21% higher mortality risk, adjusting for age and sex. After further adjustments for childhood IQ, education, social class, hypertension, diabetes, cardiovascular disease, and APOE e4 status, there is a 16% increased mortality risk for those with a 5-year higher Chronological age. Metabolic syndrome progression is intrinsic to the aging process because it pre-stages the onset of diseases which shorten lifespan, such as diabetes, NASH, Alzheimer's, Hypertension, Myocardial infarction, renal failure and CHF. Accordingly, it may be predicted that a roll back in the rate of progression of MetS, such as can be shown by RYGB or treatment with an ileal brake hormone releasing composition, could lengthen life expectancy by many years. As MetS can now be staged with risks in mind using calculated FS index and CV index, it follows that use of ileal brake hormone releasing substances in patients with MetS may extend the time before they develop these life-shortening conditions.

Inflammation measured as high sensitivity C-reactive protein (hsCRP) also manifests as a complication of MetS, and in a landmark study, weight loss (−11.23 kg; 95% confidence interval, −11.54 to −10.92; P<0.001) reduced not only hsCRP, but also low- and high-density lipoprotein cholesterol, triglycerides, and blood pressure. During the 26-week weight maintenance period in the intention-to-treat analysis, the further decrease of hsCRP blood levels was −0.46 mg/L greater (95% confidence interval, −0.79 to −0.13) in the groups assigned to low-glycemic-index diets than in those on high-glycemic-index diets (P<0.001). Groups on low-protein diets achieved a −0.25 mg/L greater reduction in hsCRP (95% confidence interval, −0.59 to −0.17) than those on high-protein diets (P<0.001), whereas lipid profiles and blood pressure were not differently affected(23). RYGB also lowers many biomarkers of inflammation(6), and it would be expected that the preferred embodiments of an ileal brake hormone releasing composition would also lower inflammation and thus lower the risks of complications of inflammation such as NASH in the liver.

The inflammation that converts NAFLD to NASH can arise from insulin resistance, abdominal obesity, or these chronic viral infections. Among the infectious causes of NASH, one must consider the rising incidence of Hepatitis C, which is also rapidly increasing worldwide. Hepatitis C infects 2-3% of the world's population, over 180 million persons, and is a cause of chronic hepatitis, liver cirrhosis, and hepatocellular carcinoma(24). The standard of care in the recent past was pegylated interferon plus ribavirin (pegIFN/Riba) combination therapy, although this therapy is both expensive and poorly tolerated. Treatment efficacy is approximately 50%. Telaprevir and boceprevir, two direct acting antiviral (DAA) protease inhibitors, have recently been approved for clinical use in the US(25). Addition of either of these new agents has the potential to improve sustained virological response in hepatitis C to 65-75%. However, the addition of a DAA to the current standard of care introduces the risk of side effects, including anemia and rash, and failure to achieve Sustained Viral Response (SVR) may pose an increased risk of accumulation protease inhibitor-resistant viral strains that may carry over resistance problems to future treatments. None the less, newer agents such as sofosbuvir (Sovaldi) and these in combination treatments have steadily increased the percentage of patients who achieve SVR in Hepatitis C treatments. Shorter courses of treatment to achieve SVR, as well as fewer side effects have both been advantages of these newer DAA antivirals None of these current or future treatments appear to provide any benefit to the patient beyond suppression of the virus. Specifically, the liver is typically not healed even when viral counts are very low. The hepatic damage may cease when there is SVR, or inflammation and associated fibrosis may even progress slowly in the presence of a small number of residual viral particles which presumably persist inside hepatocytes. Hepatic steatohepatitis, the primary accompanying condition of most patients with hepatitis C, continues and may progress even with complete viral suppression, and it is now time to propose the controversial position that NAFLD and NASH must be managed in lock step with Hepatitis C, even with the newest DAA antivirals and associated treatments. Likewise, it is possible that interferons were prematurely abandoned as combinations with DAAs, as there are recent papers that propose that Hepatocellular carcinoma incidence remains high even after SVR(26-28). On this basis, it is the goal of the present invention to lower the risk of Hepatocellular carcinoma, given that one beneficial aspect of the ileal brake hormone releasing substance treatment has been to lower Alpha Fetoprotein concentration.

Regardless of cause, NAFLD is a common diagnosis in populations as a whole, often as frequent as 25%(29). There is no FDA approved drug therapy for either NAFLD or NASH as of this writing in early 2017 (30), and most experts rely on lifestyle counseling alone. Of great concern, NASH is a histologic feature in approximately two thirds of liver biopsies of patients with chronic hepatitis C. Until recently, this common finding was not carefully documented, and there were no large longitudinal studies describing the progression of steatosis in chronic hepatitis C or even hepatitis B. In 2009, Lok and colleagues examined changes in steatosis on serial biopsies among chronic hepatitis C patients participating in the Hepatitis C Antiviral Long-term Treatment against Cirrhosis (HALT-C) trial(31). All 1050 patients in this trial had advanced fibrosis at baseline biopsy (NASH criteria) and were documented not to have had a sustained virological response to pegIFN/Riba. Most (94%) of these patients had genotype 1 infection. At least one protocol follow-up biopsy was read on 892 patients, and 699 had the last biopsy performed 3.5 years after randomization. Hepatic damage was well advanced at enrollment, as 39% had cirrhosis and 61% had bridging fibrosis; 18%, 41%, 31%, and 10% had steatosis scores of 0, 1, 2, and 3 or 4, respectively. The mean steatosis score decreased in the follow-up biopsies in both the pegIFN/Riba-treated patients and controls with no effect of treatment assignment (P=0.66). A decrease in steatosis score by > or =1 point was observed in 30% of patients and was associated with both progression to cirrhosis and continued presence of cirrhosis (P=0.02). Compared to patients without a decrease in steatosis, those with a decrease in steatosis had worse metabolic parameters at enrollment, and were more likely to have a decrease in alcohol intake, improvement in metabolic parameters, and worsening liver disease (cirrhosis, esophageal varices, and deterioration in liver function). Lok and colleagues(31) concluded that hepatic steatosis recedes during progression from advanced fibrosis to cirrhosis. However, there was no available means to produce a decline in either NAFLD or NASH in most patients with Hepatitis C, which then became the primary motivation to discover a means of treating hepatic steatosis as an integral part of treatment of hepatitis C patients.

In a further definitive examination of the role of hepatic steatosis on the course of hepatitis C therapy, Briceno and colleagues (2009) examined livers that were to be transplanted into patients with hepatitis C that had already destroyed the original liver (32). The aim of this study was to determine the influence of donor graft steatosis on overall outcome, viral recurrence, and fibrosis progression in orthotopic liver transplantation for hepatitis C virus cirrhosis. One hundred twenty patients who underwent OLT for HCV cirrhosis between 1995 and 2005 were included in the study. Donor steatosis was categorized as absent (0%-10%; n=40), mild (10%-30%; n=32), moderate (30%-60%; n=29), or severe (>60%; n=19). A Cox multivariate analysis for marginal donor variables and a Model for End-Stage Liver Disease index were performed. Fibrosis evolution was analyzed in liver biopsies (fibrosis <2 or > or =2) 3, 6, and 12 months post-OLT and in the late post-OLT period. Fifty-six grafts were lost (46%). The survival of the grafts was inversely proportional to donor liver steatosis: 82%, 72%, and 72% at 1, 2, and 3 years post-OLT in the absence of steatosis; 73%, 63%, and 58% with mild steatosis; 74%, 62%, and 43% with moderate steatosis; and 62%, 49%, and 42% with severe steatosis (P=0.012). HCV recurrence was earlier and more frequent in recipients with steatosis >30% (46% versus 32% at 3 months, P=0.017; 58% versus 43% at 6 months, P=0.020; 70% versus 56% at 12 months, P=0.058; and 95% versus 69% at 3 years post-OLT, P=0.0001).(32). Graft survival was lower in alcoholic liver disease recipients versus HCV recipients when steatosis was >30% at 3, 6, and 12 months post-OLT (P=0.042) but not when steatosis was <30% (P=0.53). A higher fibrosis score was obtained 3 months post-OLT (P=0.033), 6 months post-OLT (P=0.306), 12 months post-OLT (P=0.035), and in the late post-OLT period (P=0.009). The authors concluded that the degree of hepatic steatosis in the new liver greatly influences the recurrence of hepatitis C and its progression in the new liver. In fact, Steatosis affects the success of treatment the second time. Hepatitis C recurrence was more frequent and earlier in recipients of moderately and severely steatotic livers. Fibrosis evolution is more rapid and severe when graft steatosis is >30% (32). As pointed out by Lok as well, there is a need to manage the hepatic steatosis in order to optimize the outcome of antiviral therapy for hepatitis C.

Testino and colleagues (2009) examined the influence of improvement in MetS (typically associated with hepatic steatosis) biomarkers on the response of patients with hepatitis C to pegIFN/Riba(33). They examined baseline biomarkers such as Body Mass Index (BMI), cholesterol, triglycerides (TGs) and hepatic percentage of steatosis in the response to therapy with pegIFN/Riba in patients with recurrent hepatitis C (genotype 1). In this study, 30 consecutive prospectively followed patients diagnosed with recurrent hepatitis C were considered candidates for antiviral therapy. The observed distribution of BMI, cholesterol, TGs and steatosis were confirmed to be normally distributed by the one-sample Kolmogorov-Smirnov Goodness of fit test procedure. Comparison of BMI, cholesterol, TGs and steatosis between non responders (NR), sustained virological responders (SVR) and sustained biochemical responders (SBR) groups were analyzed by ANOVA with a post hoc Bonferroni test and correlation between variables was tested by Pearson test. The multivariate analysis was performed to estimate the chance of response on basis of the above-mentioned variables. In patients with abnormal results in at least two out of four steatosis-associated variables, the chance of no-response was 40 times higher than that of SBR and 96 times than that of SVR(33). On the basis of these epidemiological studies, they argued that diet and exercise therapy should improve BMI, liver histology and, therefore, the response to pegIFN/Riba(33). Indeed this study provides further justification for concomitant use of a treatment for hepatic steatosis in conjunction with a treatment for the hepatitis C virus itself. This unmet need is addressed by the present invention, an ileal brake hormone releasing composition that acts in a similar manner to RYGB surgery on MetS components in human patients.

There is also evidence that management of hepatic steatosis in patients with hepatitis C would be of value in the prevention of hepatocellular carcinoma (HCC). For example, Pekow and colleagues (2007) (34) retrospectively identified 94 consecutive patients with hepatitis C cirrhosis who underwent liver transplantation from 1992 to 2005 and had pathology available for review. Of these, 32 had evidence of HCC, and 62 had no HCC on explant histology. All explant specimens were then graded for steatosis by a single, blinded pathologist. Next, hepatic steatosis, age, sex, BMI, HCV RNA, HCV genotype, Model for End-Stage Liver Disease (MELD) score, chronic alcohol use, and diabetes were examined in univariate and multivariate analyses for association with HCC. In total, 69% of patients in the HCC group and 50% of patients in the control group had evidence of hepatic steatosis (1+) on histology. Odds ratios for the development of HCC for each grade of steatosis compared with grade 0 were as follows: grade 1 (1.61 [0.6-4.3]), grade 2 (3.68 [1.1-12.8]), and grade 3 or 4 (8.02 [0.6-108.3]) (P=0.03 for the trend). In univariate analyses, there was a significant association between increasing steatosis grade (P=0.03), older age (56 years versus 49 years; P<0.02), higher ALT aspartate aminotransferase (122.5 U/L vs. 91.5

U/L; P=0.005), higher AST alanine aminotransferase (95.8 U/L vs. 57.2 U/L; P=0.002), higher alpha-fetoprotein (113.5 ng/mL vs. 17.8 ng/mL; P<0.001), lower median HCV RNA (239,000 IU/mL vs. 496,500 IU/mL; P=0.02), higher biologic MELD score (21.8 vs. 20.3; P=0.03), and risk of HCC. In multivariate analysis, age (P=0.02), alpha-fetoprotein (P=0.007), and hepatic steatosis (P=0.045) were significantly associated with HCC(34). These authors concluded that in patients with Hepatitis C-related cirrhosis, the presence of hepatic steatosis is independently associated with the development of hepatocellular carcinoma(34). Clearly if the NAFLD and NASH could be reversed by a companion treatment to the anti-viral agent, there is plausible evidence that HCC might be prevented or at least there would be fewer cases that progress to this deadly complication of the combined problem of hepatitis C and NASH. The surprising finding of recent studies, is that the DAAs do not lower the risk of HCC and in fact may even increase it in settings where the HCC process has already started on a sub-clinical basis.(26-28)

BRIEF DESCRIPTION OF THE INVENTION

The invention is an interactive system comprised of diagnostic means, a mathematical model of disease progression and an integrated method of treatment for NASH and NAFLD. The mathematical model which informs decisions along the entire continuum of procedures from early diagnosis thru treatment responsiveness. The model based system consists of a NASH disease progression Model that definitively describes the novel aspects of the interaction between MetS and NASH to project the biopsy score, then incorporates the interactions between NASH and the underlying MetS factors which drive the progression of NAFLD and NASH along the axis of the biopsy score toward the severe complications experienced by afflicted patients at the end of their lives, including both hepatic complications and the overall rise in mortality from CV causes. In one aspect, the present invention is directed to a less invasive means of defining the NAFLD and NASH associated injury to the liver and other closely associated organs of the body. Said means is the development of a Neural Net Progression Model that for the first time predicts the results of a liver biopsy, should one be taken or needed. The underlying premise of the Neural Net Model is that progression of MetS and inflammation caused by dietary factors and imbalances drive the stages of Liver injury between NAFLD, then on to NASH, then to hepatic fibrosis and finally Cirrhosis or hepatocellular carcinoma. An appreciable number of NASH cases are further complicated by concomitant infection with Hepatitis C or Hepatitis B, and these patients are at elevated risk of hepatocellular carcinoma. All of these aspects are considered as inputs in the disclosed Neural Net Model of NASH, and the outputs of this model are the events along the continuum of progression of the liver disease toward eventual liver failure. The purpose of the model is to define risk factors for progression and to precisely define milestones where specific treatments may be of benefit without causing further harm. Throughout the model development, the goal of the inventors has been to use the model and the biomarkers to predict the histological condition of the liver, and specifically to predict the findings on liver biopsy. Accordingly, this model informs the diagnosis and monitoring of NAFLD and NASH in a novel and potentially useful way.

In another embodiment, the present invention is directed to the use of the model as a companion diagnostic and theranostic to select patients for responsiveness to the disclosed pharmaceutical compositions which stimulate the release of ileal brake hormones, along with methods for the treatment, and diagnostics and computer-implementable systems that relate to the treatment of an array of the manifestations of MetS and their resolution. While the primary goal of the present invention is healing the Liver and resolving NASH, it should be noted that throughout the model and in parallel we consider the other interacting components of the MetS that include but are not limited to insulin resistance, T2D, hyperlipidemia, weight gain, abdominal obesity, hypertension, atherosclerosis, NAFLD and certain chronic inflammatory states that lead to these manifestations as well as other outcomes such as cardiovascular events. The model includes a CV index which informs on the risk of cardiovascular complications in patients with insulin resistance and inflammation. The model considers a novel mathematical approach to MetS, and discloses the FS index as a means of defining progression of NAFLD and NASH as well as the aforementioned other components of MetS.

In the present invention, the primary target organ for improvement, reconstitution, or rehabilitation is the liver. The preferred embodiments of the invention provide compositions, methods of treatment, diagnostics, and related systems useful in stabilizing blood glucose and insulin levels, control of hyperlipidemia, control of inflammation in organs tissues and blood vessel walls. These compositions act by a heretofore unknown mechanism of action in NASH, which is activation of the ileal brake hormones to damp down injurious inflammation and to regenerate and remodel the hepatocytes of the liver.

In yet another aspect of the Invention, the Neural Net Model considers the effects of MetS and NASH on the cardiovascular system, chiefly in its predictions of severe complications such as Myocardial Infarction (MI), Stroke or Congestive Heart Failure. In the Neural Net Model disclosed herein, these severe cardiac complications are stages of progressive injury to the cardiovascular system. The model discloses a novel index of Cardiovascular risk, the CV index, and uses the CV index to monitor Cardiovascular health of the NASH and MetS patients disclosed herein. In an additional aspect of the invention, compositions and methods of treatment to prevent or ameliorate CV manifestations of MetS are disclosed.

These methods of treatment entail concomitant pharmacological and/or surgical intervention e.g. RYGB, both or all of which activate the ileal brake, which acts in the gastrointestinal tract and the liver of a mammal to control MetS manifestations and thereby reverse or ameliorate the cardiovascular damage (Myocardial infarction (MI), atherosclerosis, hypertension, lipid accumulation, and the like) resulting from progression of MetS.

In a preferred embodiment of the invention, the neural net model of MetS and the health of the liver is applied to each patient, and thereby calculates each output for each individual within a patient population, in a preferred example, "the biopsy score of the patient". Calculated biopsy scores are aligned to the well-known NAS categories for fibrosis, steatosis, inflammation and ballooning, which are based on actual biopsy data collected over many years by NIH. When conducting such modeling, there is advantage to the inclusion of a spectrum of patients that range from healthy without disease, to mild abnormalities in some laboratory biomarkers such as would be observed in pre-diabetes or healthy obese patients, to more severe disease cases such as those with cardiovascular events like myocardial infarction. In the operation of the model on such a mixture of patients, the task is to discover Inputs that strongly influence outputs, and then quantify the importance of each input on each output. An illustrative example might be the examination of 50-100 inputs for their ability to predict "a biopsy score of the patient", for illustrative example a predicted biopsy score of 8 in FIG. 14, which is a score consisting of very severe liver disease in said particular patient. FIG. 3 shows "wComb Biopsy Predict" as that specific output, and quantifies the predictive strength from the inputs as MMSE values. Said use of wComb Biopsy Predict might be when a physician wishes to learn whether there is a high probability that a biopsy would prove the extensive steatosis, ballooning and fibrosis and establish "the risk of progressive changes in the biopsy score" that is predicted by the model inputs of biomarkers, laboratory test results and physical measurements, and thereby avoiding the invasive procedure in a patient who is likely not to have an abnormal biopsy. Another example might be to use the model inputs that define "the degree of metabolic syndrome associated disease components" for example the FS index and the biomarkers and laboratory tests of hyperglycemia, insulin resistance, hyperlipidemia, hypertension and abdominal obesity to predict an impending myocardial infarction in a patient with advanced T2D, fibrosis of the liver, and hyperlipidemia, a situation where both CV index and FS index might be used in conjunction with wComb Liver signal (see FIG. 2) to predict both the risk of myocardial infarction and serious liver disease such as fibrosis score and steatosis score. The preferred inputs of the model are "the indices of cardiovascular and metabolic risk" consisting of biomarkers, physical measurements and laboratory tests that comprise FS index and CV index. Other preferred inputs are the determinants of the wComb Liver signal such as fibrosis signal and the time related "risk of progression of fibrosis" over time which is "wComb Fibrosis score" as quantified in FIG. 3, and as we have used it to show post to pre therapy changes in FIG. 13. Closely related but with different determinants is the "wComb Steatosis score", which informs on the degree and "risk of the progression of steatosis" when modeled alone such as in FIG. 12 and together in said composites such as wComb Liver signal. An additional preferred embodiment would be the demonstration that an intervention such as RYGB surgery lowers the risk of this myocardial infarction by improving said patients T2D, reversing said fibrosis of the liver and improving said patient's lipid profile. In these patients, the model also discloses the output of "wComb-HCC signal", the cumulative age and time related "risk of developing hepatocellular carcinoma". The model informs on the ongoing risk of developing hepatocellular carcinoma when inputs such as fibrosis and alpha fetoprotein and selected genomic and epigenetic biomarkers show increasing risk scores in wCombHCC signal. In this embodiment of the model, treatment of a high risk patient with an ileal brake hormone releasing composition in combination with drugs that lower the viral load of hepatitis C (see FIG. 30) does show model apparent lowering of inflammation as liver enzymes (see FIGS. 29 and 34) and a lowering of alpha fetoprotein (see FIGS. 31 and 33). Thus the present inventive model and any ongoing improvements from incorporation of new biomarkers all support the use of ileal brake hormone releasing compositions and anti-viral drugs as "synergistic" in the reduction of the "risk of developing hepatocellular carcinoma", and as defined on the model output of wCombHCC signal.

Thus the inventors are now disclosing a novel and very precise means of defining ongoing disease in specific patients, a treatment to modify the course of said disease in specific patients, and a means of quantifying the response of said patients to said treatment over time. As current statistical approaches do not provide reliable risk assessments for individual patients except as part of group averages, the disclosed disease modeling offers a unique means of informing personalized medicine for individuals. The best advantage of this approach is that more data and more input biomarkers and variables generally add to the predictive accuracy of the model outputs in individual patients, rather than confuse the statistical analysis with more subsets. From the inventor's perspective, this model is most useful in detecting the profound effects of RYGB surgery on MetS and the health of the liver, as well as the apparent CV protective effects in the patients who are usually also with T2D and at high risk for said CV events. In a preferred application of the model to a patient with both MetS and liver abnormalities, the goal for this patient would be treatment with RYGB surgery or with an ileal brake hormone releasing composition, and the prediction of "the responsiveness of said patient to said therapy".

The present invention is also directed to combination (co-administration) treatment between the RYGB surgery mimetic pathway and the more traditional antiviral agents, which together create a surprising synergy in the treatment of hepatic viral infections that cause inflammation in the liver and well as numerous secondary disease states and/or conditions of the liver, including but not limited to Hepatitis C, Hepatitis B, Herpes Simplex virus, as well as any virus that causes injury to the mammal by causing inflammation and fibrotic changes in the liver, a typical manifestation of NASH. As disclosed herein, the effect of the present invention is unexpectedly synergistic, acting even against the virus itself. Therefore, for the first time, a vital aspect of this combination treatment consists of providing ileal brake hormone releasing therapy in combination with an antiviral drug active against the virus itself, in a highly synergistic combination to alleviate both the viral infection and repair the damage the virus causes in the liver, which is diagnosed as NASH or hepatocellular carcinoma.

The method of treatment disclosed herein is shown in FIG. 1 as a composition that acts as a mimetic of RYGB surgery. It has the same mechanism of action, in that like RYGB surgery, it serves to stimulate the L-cells of the distal intestine, causing release of an array of ileal brake hormones. This is a novel mechanism of action and is disclosed as a means of controlling all the major manifestations of MetS. The novel composition disclosed herein also acts in concert with other pathway specific bioactive agents, such as an antiviral and/or anticancer agent, or alternatively, providing a method which activates the ileal brake such as RYGB in combination with the bioactive anti-viral agent. The combination treatment of the present invention resolves the hepatic steatohepatitis as well as the hepatic steatosis and thereby inhibits or otherwise reduces the likelihood of progressive injury to the liver that results from the fibrosis and cirrhosis, preferably in a synergistic manner. In a surprising additional aspect of the invention, the Neural Net Model predicts a degree of reversal of fibrosis, and a lowering of the risk of Hepatocellular carcinoma. Said reversal was demonstrated herein by lowering of Alpha Fetoprotein in the treated patients.

In yet another aspect of the present invention, these compositions and/or methods of treatment of NASH may be used alone or in combination with additional bioactive agents, especially including anti-viral agents such as anti-hepatitis viral agents, especially anti-HCV agents and/or anti-HBV agents to treat the virus which is causing hepatitis as well as any secondary disease states and/or conditions which are caused by the viral infection. The effect of the present invention is synergistic in the patient or subject treated.

The present invention surprisingly argues that effective anti-viral treatment, including a cure of the viral infection, requires a composition which inhibits or otherwise treats the hepatic steatohepatitis that is present in nearly all of these patients. This anti hepatic steatohepatitis treatment must be effectively combined with a treatment active against the virus to increase the chances of both eradicating the virus and then healing the injured liver. Thus, the invention provides methods of treatment and pharmaceutical compositions that can be used to prevent, reduce the likelihood of, or delay the onset of, a progressive damage to the liver which leads to cirrhosis, including fibrosis and related disease states and conditions of the condition, including hepatic steatosis and cirrhosis. It is noted that hepatic steatosis may also progress to hepatocellular carcinoma in patients with concomitant hepatitis viral infection, including hepatitis B and C virus infection. The combination of the present pharmaceutical composition with the anti-viral medication can be used to prevent, reduce the likelihood of, or delay the onset of, hepatocellular carcinoma in patients with hepatitis B and hepatitis C.

In one particular embodiment of the invention a novel formulation of glucose in dosages of approximately 10 grams per day (in general, from about 7.5 to about 12.5 grams per day), has both short and long term beneficial effects on patients with elevated triglycerides, insulin resistance and elevated liver enzymes indicative of hepatic steatosis. This is unexpected as dietary glucose and other sugars increase the manufacture of triglycerides which are prominent among the causes of fatty liver, and hepatic steatosis is an accessory pathway for viral replication. Dietary lipids accumulate in the liver as well. It is a recent discovery that releasing these dietary substances such as glucose at a distal location in the intestine by the unique intestinal site targeted-release properties of the present formulations, can ameliorate not only the hyperglycemic manifestations of T2D, but also to control the accumulation of fat in the liver.

These ileal brake compositions according to the present invention, when administered to a patient in need thereof, are useful to lower the patient's insulin resistance, lower triglycerides, reduce body weight, reduce HbA1c, and lower chronic liver inflammation (reduce ALT and AST), all in the manner similar to effect of RYGB surgery.

By means of careful study of enabling biomarkers, it becomes clear the ileal brake composition provides physiological and pharmacological actions on the same anatomical location of the patient and affects the same biochemical pathways as RYGB surgery, the biological target of both being the L-cells of the ileum and distal intestine.

In closely related embodiments, the present invention relates to compositions and methods useful for selective modulation of appetite in a manner similar to that of RYGB surgery. For example, the present invention also relates to ileal brake compositions (i.e., ileal brake hormone releasing substances), more particularly, a preferred oral formulation of ileal brake hormone releasing substances which contain a combination of carbohydrates and lipids, which are particularly adapted to treating insulin resistance and fatty liver, and are synergistic with specific anti-viral medicaments active against hepatitis viruses, including Hepatitis B and Hepatitis C viruses, among others.

In further embodiments, potential new treatments for NASH that have been disclosed by others act by different mechanisms of action than the ileal brake hormone releasing composition of the present invention. Therefore the addition of any of or combinations of treatments for NASH such as obeticholic acid, elafibranor, aramchol, simtuzumab, cenicriviroc, emricasan, IMM124E, BMS-986036, NGM282, GS9674, MSDC-0602, VK2809, MN-001, GS4998, GR-MD-02, NDI-010976, RG-125, DUR-928, CER-209, Solithromycin, PXS-4728A to the ileal brake hormone releasing agent disclosed herein are all within the scope of the present invention, provided that the Neural Net Model demonstrates beneficial and potentially synergistic actions of the combination on the liver and other afflicted organs. It should be noted that most of the effect of these combinations on NASH and NAFLD will be derived from the ileal brake hormone releasing compound, with the remaining effect computed from the change in biomarkers over that change produced by the ileal brake hormone releasing substance itself. In some cases the effect of combination will be synergy between the components.

Accordingly, the present invention discloses a System, Methods for diagnosis and risk identification, compositions and methods of treatment, a novel treatment means, methods of treatment of closely associated disease states, disorders and/or conditions, all of which are directed to the resolution of NASH in patients afflicted thereby. It should be added that there is no currently accepted pharmaceutical treatment for these conditions, and therefore the data in this application present the argument that RYGB and the oral mimetic formulation Brake encompass the widest array of beneficial treatments for NASH and NAFLD thus far discovered.

Pursuant to the present invention, embodiments or aspects of the present invention are directed to one or more of the following:

A method for the diagnosis and treatment of non-alcohol fatty liver disease (NAFLD) and/or non-alcoholic steatohepatitis (NASH) in a patient suspected of or having NAFLD and/or NASH, the method comprising obtaining a biological sample from the patient, measuring biomarkers in the biological sample which are indicative of inflammation, steatosis and/or fibrosis of the liver and other potentially affected organs of the patient and incorporating measurements of the biomarkers into a mathematical model, wherein the mathematical model computes the health of the liver and other affected organs to determine whether or not the patient requires therapy for NAFLD and/or NASH; and the patient undergoes therapy for the treatment of NAFLD and/or NASH based upon the results of the mathematical model, wherein the treatment comprises administering an effective amount of a traditional pharmacologically active agent, a composition comprising an ileal brake hormone releasing substance effective to increase the release of ileal brake hormones in the patient or a composition comprising an ileal brake hormone releasing substance effective to increase the release of ileal brake hormones in combination with a pharmacologically active agent.

A method wherein the measurements obtained from the biological sample of the patient indicate insulin resistance in the patient, the current biopsy score of the patient, the risk of progressive changes in the biopsy score, the risk of the progression of steatosis, the risk of progression of fibrosis, the risk of developing hepatocellular carcinoma, the degree of metabolic syndrome associated disease components, the indices of cardiovascular and metabolic risk and wherein the method is used to predict the responsiveness of the patient to the therapy.

A method as set forth above which comprises:
A. determining a calculated biopsy score as wCombBiopsy Predict;
B. determining a wCombLiver signal;
C. determining an FS index; and
D. determining a Cardiovascular risk index.

A method as set forth above, wherein the wCombLiver Signal is calculated using a weighted function comprised of biomarkers from the patient or subject which includes Alkaline Phosphatase, ALT, AST, Total Bilirubin, Insulin Concentration, hsCRP, platelet count, Total Protein, Prothrombin time, INR, Lymphocyte count, Waist circumference, Direct Bilirubin, lymphocytes, GGT, Weight, BMI, LDH, HbA1c, Statin dose, Use of Pioglitazone, Use of Fibric acid drugs and Use of Statins.

A method as set forth above, wherein the patient is found to have a wCombLiver signal greater than two standard deviations above normal which indicates that the patient is in need of the treatment to lower the risk of Progressive Liver Damage characterized by hepatic steatosis, fibrosis, cirrhosis, liver failure or combinations thereof, whether or not the complications are directly caused by Metabolic Syndrome in the patient or modified further by the additional risk factors placing the patient at risk for at least one Liver disease, Liver disease progression or complication, wherein the treatment comprises administering to the patient a composition comprising an ileal brake hormone releasing substance alone or in combination with a drug used to treat or resolve additional aspects of the Liver Damage condition or risk of disease progression to cirrhosis or hepatocellular carcinoma.

A method described above wherein the FS index is calculated as:

$$\frac{0.11\left((FBG+TG)+HBA1c\times\frac{HBA1c\times 20}{5}+BMI\times\frac{FBG+TG}{150}+AST\times\frac{TG\times 4}{100}+FB\text{ insulin}\times(BMI-22)\right)}{S/D\text{ ratio}}$$

FBG is Fasting Blood Glucose in mg/dl and normal value is 100 mg/dl
TG is Triglycerides in mg/dl normal value is <150
HBA1c is glycosylated hemoglobin calculated as a ratio to hemoglobin; normal value is <6%
BMI is body mass index as kg/m² where a normal value is 20 and obese begins above 25
AST is Aspartate Transferase (formerly SGOT) in IU/liter and a normal value is 5.50
FB insulin if fasting Blood insulin concentration in nmol/liter, a normal value is 4.0
Where S/D ratio is the $$\text{Glucose Supply }(S)/\text{Insulin Demand }(D) = \frac{1+((CE)+(HGU)+(GNG)+(IR))}{1+(PIE+PGU)}$$

Where S/D ratio (SD) is a ratio of Glucose Supply Index (S) to Insulin Demand Index (D); and wherein (S) is calculated as follows:

1+[aggregate of carbohydrate exposure (CE)+hepatic glucose uptake (HGU)+hepatic gluconeogenesis (GNG) and +insulin resistance (IR)], and (D) is calculated as follows:

1+[aggregate of peripheral glucose uptake (PGU)+ peripheral insulin exposure (PIE)].

A method as described above, wherein the patient with NAFLD or NASH is found to have an FS Index value above 60, which indicates that the patient is in need of the treatment to lower the risk of Metabolic Syndrome progression to include Insulin Resistance, Hyperglycemia, Type 2 Diabetes, Hyperlipidemia, Hypertension and/or Abdominal Obesity, whether or not the complications are directly caused by Metabolic Syndrome or modified by the NAFLD or NASH, placing the patient at risk for at least one FS index linked progression or complication, the method further comprising administering to the individual an ileal brake hormone releasing composition optionally in combination with a traditional pharmacologically active drug used to treat or resolve the metabolic syndrome complication or risk.

A method as described above, wherein the Cardiovascular risk index is calculated as:

$$CV\text{ Risk Index} = FS\text{ Index} + \frac{(LDL\text{ factor}+\text{age}/\text{sex}/\text{cigs factor}+hsCRP\text{ factor}+RP/200)}{(LL\text{ Drugs factor}+ASA\text{ factor})}$$

Where:
FS index is calculated as:

$$\frac{0.11*(FBG+TG+HBA1c\text{ factor}+(BMI\text{ factor})+(AST\text{ factor})+(FBInsulin\text{ factor})}{S/D\text{ ratio}}$$

Wherein said FS index, the FBG is Fasting Blood Glucose in mg/dl; the TG is Triglycerides in mg/dl; the HBA1c is hemoglobin A1c in %; the BMI is bodymass index in kg/m²; the AST is Aspartate Transferase in IU/liter; FB insulin is fasting Blood insulin concentration in nmol/liter; and the SD ratio (SD) is a ratio of Glucose Supply Index (S) to Insulin Demand Index (D); wherein (S) is calculated as follows:

1+[aggregate of carbohydrate exposure (CE)+hepatic glucose uptake (HGU)+hepatic gluconeogenesis (GNG) and+insulin resistance (IR)]

and (D) is calculated as follows:

1+[aggregate of peripheral glucose uptake (PGU)+ peripheral insulin exposure (PIE)];

Where:
HBA1c factor: HBA1c×((HBA1c/5)×20)
BMI factor: BMI×((FBG+TG)/(50×3))
AST factor: AST×((TG/100)×4)
FBInsulin factor (BMI−22)×FBInsulin
Low density Lipoprotein (LDL factor): 60+LDL/10
Age/gender/cigarettes factor:

(Packs/day×yrs/8)×age×gender, where gender is 1.0 for male, 0.6 for female

High sensitivity C-Reactive protein (hsCRP) factor: hsCRP×10
Rate Pressure (fac): (HR×SBP)/200 Where HR=Heart Rate and SBP=Systolic BP Lipid Lowering (LL) Drugs factor:

(0.9+Statin Dose, mg in Lipitor equivs/10)+(0.2+ other LL drugs factor/5)

ASA factor: 0.8+(ASA yrs/2) Where ASA is low dose Aspirin×years taken

A method as described above, wherein the patient is found to have a CV risk index value of greater than 100 which indicates that the individual is in need of treatment to lower the risk of Cardiovascular Events of Myocardial Infarction, Stroke, Hospitalization for unstable angina, congestive heart failure or combinations thereof, whether or not the complications are directly caused by Metabolic Syndrome or modified further by the additional risk factors of age, gender, cigarette smoking, high blood pressure, or inflammation as hsCRP, alone or in combination placing the patient at risk for at least one cardiovascular complication, the method further comprising administering to the individual a composition, wherein the composition comprises an ileal brake hormone releasing substance alone or in combination with a traditional pharmacologically active agent used to treat or resolve the risk of Cardiovascular events in the patient.

A method for treating NASH and/or NAFLD in a patient which includes biomarker testing, computation of the disease progression, diagnosis of extent and/or severity of disease, risk stratification, and personalized treatment, wherein beneficial outcome from treatment with an ileal brake hormone releasing substance improves the biopsy score thus indicating improvement in the severity of the disease and wherein the treatment lowers the risk for complications of the disease including fibrosis, cirrhosis, and hepatocellular carcinoma.

A method as described above, wherein the patient's risk of progression of NAFLD or NASH has been determined, and treatment of the patient with an effective amount of a traditional pharmacologically active agent results in a higher second wCombLiver signal, wCombBiopsy Predict signal, FS index and CV index value relative to a first value, indicates that the patient or subject is in need of a change in dosing of the first drug and/or the addition of an ileal brake hormone releasing substance and the patient is treated with a higher dose and/or the substance.

A method as described above comprising determining a higher second wCombLiver signal, wCombBiopsy Predict signal, FS index and CV index relative to the first wCombLiver signal, wCombBiopsy Predict signal, FS index and CV index value, wherein the higher second value in the patient justifies the addition of a composition comprising an ileal brake hormone releasing substance to the patient, the ileal brake hormone releasing substance being released in the ileum of the patient which stimulates the release of ileal brake hormones and produces a GLP-1 Area under the curve or AUC value of approximately or at least an AUC value of 250.

A method as described above, wherein the wCombLiver signal, FS index and CV index values are determined using a microprocessor and wherein risk in the patient is defined as a wCombLiver signal exceeding 2 standard deviations above normal, an FS index score above 60 and a CV index score above 100.

A method as described above, wherein the wCombLiver signal, wCombBiopsy Predict signal, FS index and/or CV index is calculated using a programmable spreadsheet or a website application.

A method as described above, wherein the patient is clinically diagnosed as being at risk for or having NASH and/or NAFLD and the patient is treated with the pharmacologically active agent and/or the composition comprising an ileal brake hormone releasing substance, wherein the patient responds to the treatment as evidenced by changes in wComb Biopsy Predict signal and calculated FS index or CV index after the patient undergoes treatment for at least six months, preferably at least 12 months.

A method as described above, wherein the method resolves NAFLD and hepatic steatosis.

A method as described above, wherein the method further inhibits or reduces the likelihood of the patient developing NASH, hepatic fibrosis and/or cirrhosis.

A method as described above, wherein the patient has a viral infection and is treated with an anti-viral agent in combination with the pharmacologically active agent and/or the composition comprising an ileal brake hormone releasing substance, the treatment resolving NASH and/or NAFLD, reducing the likelihood of fibrosis and/or cirrhosis and controlling the accelerated aging from chronic viral infection by controlling the onset and progression of aging associated MetS.

A method as described above, wherein the magnitude of measurement of one or more of wCombLiver Signal FS index and CV risk is reduced by at least 25% in response to the administration of the composition comprising the ileal brake hormone releasing substance to the patient.

A method as described above, wherein administering the composition comprising the ileal brake hormone releasing substance to the patient achieves an effective AUC of ileal brake hormone outputs of GLP-1 of approximately 245-255 and the threshold AUC of ileal brake hormone outputs of PYY of approximately 345-355.

A method as described above, wherein the traditional pharmaceutically active agent is selected from the group consisting of anti-diabetes drugs, SGLT-2 inhibitors, statin drugs, hormones, GLP-1 drugs, a biguanide (e.g. Metformin), a DPP-IV inhibitor (e.g. Sitagliptin), and mixtures thereof.

A method as described above, wherein the traditional pharmaceutically active agent is administered to the patient in combination with a composition comprising an ileal brake hormone releasing substance.

A method as described above, wherein the ileal brake hormone releasing substance is selected from the group consisting of starches, sugars, lipids, proteins, amino-acids and mixtures thereof.

A method as described above, wherein the ileal brake hormone releasing substance is at least one sugar or at least one sugar in combination with at least one lipid.

A method as described above, wherein the sugar is glucose and the lipid is an animal fat or oil or a vegetable oil.

A method as described above, wherein the ileal brake hormone releasing agent in the composition is overcoated with a low dose of statin wherein the composition lowers LDL to approximately the same level or lower than the levels obtained by administering a two-fold higher dose of the statin alone (in the absence of the ileal brake hormone releasing agent).

A method as described above, wherein the composition comprising the low dose of statin reduces statin side effects including myotoxicity and lowers risk in the patient of developing type 2 diabetes.

A method as described above, wherein the statin is at least one agent selected from the group consisting of atorvastatin, simvastatin, lovastatin, ceruvastatin, pravastatin and pitavastatin.

A method as described above, wherein the statin overcoating dissolves in the duodenum to release the statin in the patient's duodenum, and the majority of the ileal brake hormone releasing substance is released in the patients ileum.

A method as described above, wherein the composition comprises the ileal brake hormone releasing substance with a low dose of metformin and wherein the composition provides a magnitude of HBA1c lowering which is equivalent by comparison to a two-fold higher dose of metformin alone A method as described above, wherein the lower of metformin dose lowers the incidence of metformin side effects.

A method as described above, wherein the side effects include nausea and vomiting.

A method as described above, wherein the metformin is over-coated onto the surface of the ileal brake hormone releasing formulation or contained within the coating of the composition comprising the ileal brake hormone releasing substance.

A method as described above, wherein the composition comprises the ileal brake hormone release substance in combination with a low dose of a DPP-4 inhibitor which lowers HBA1c in the patient to a level which is equivalent to or lower than by comparison the results obtained from a four-fold higher dose of the low dose of DPP-4 inhibitor results in reduced DPP-4 inhibitor side effects.

A method as described above, wherein the ileal brake hormone releasing substance comprises glucose and one or more lipids in an amount of 5-20% of the total amount of ileal brake hormone releasing substance in the composition.

A method as described above, wherein the lipid in the ileal brake hormone releasing composition produces AUC of PYY up to 500 and AUC of GLP-1 up to 350 in the patient receiving the composition, wherein the lipid is a fish oil, a nut oil or a vegetable derived nutritional oil.

A method as described above, wherein the vegetable derived nutritional oil is olive oil, palm oil or a mixture thereof.

A method as described above, wherein the composition comprises an effective dose of an ileal brake hormone releasing substance, wherein the ileal brake hormone releasing substance on is administered in a dosage from 5 grams to 20 grams of dextrose combined with a dosage of from 0.25 grams to 4 grams of a lipid wherein at least 50% of the ileal brake hormone releasing composition is released in the ileum of the individual.

A method as described above, wherein the patient is infected with hepatitis B or C and the composition comprises at least one ileal brake hormone releasing substance which is co-administered with an at least one antiviral agent, and optionally an HMG-CoA reductase inhibitor.

A method as described above, wherein the patient has hepatitis C and interferon is used in combination with the ileal brake hormone releasing substance and optionally an HMG-CoA inhibitor in order to lower risk of the patient developing hepatocellular carcinoma, wherein the patient optionally is being treated with a direct acting antiviral agent (i.e., an agent that directly inhibits the virus).

A method as described above, wherein the patient is being treated for NAFLD or NASH with a combination of the ileal brake hormone releasing substance in combination with at least additional one agent selected from the group consisting of obeticholic acid, elafibranor, aramchol, simtuzumab, cenicriviroc, emricasan, IMM124E, BMS-986036, NGM282, GS9674, MSDC-0602, VK2809, MN-001, GS4998, GR-MD-02, NDI-010976, RG-125, DUR-928, CER-209, Solithromycin and PXS-4728A.

A method as described above, wherein over 60% of the beneficial effect on the predicted steatosis score, fibrosis score or wComb predicted biopsy score of the patient occurs from the action of the ileal brake hormone releasing compound, with the remaining effect on the patient occurring from the over-coated substance.

A method as described above, wherein beneficial outcome from treatment with the ileal brake hormone releasing substance is demonstrated by a comparison of calculated biopsy fibrosis and biopsy calculated steatosis prior to, at the start of or early in treatment (at a time very close to the start of treatment so as to enable a valid comparison) versus at a later time in treatment of the patient, wherein the comparison evidences an improvement in the liver and a lowering of biomarkers associated with fibrosis, cirrhosis, and hepatocellular carcinoma.

A method as described above, wherein the patient also has a chronic viral infection and the system for monitoring treatment comprises biomarker testing, computation of disease progression, diagnostic, risk stratification, and personalized treatment, wherein a beneficial change or outcome from treatment with the ileal brake hormone releasing substance is evidenced by a lowering of wComb biopsy score prediction, fibrosis score and steatosis score after treatment is commenced.

A method as described above, wherein the beneficial change or outcome is further evidenced by calculated scores of prevention or delay in development of hepatic complications of NASH and/or NAFLD including advanced fibrosis, cirrhosis and hepatocellular carcinoma.

A method as described above, wherein the treatment delays the onset of or reduces the likelihood of a worsening of metabolic syndrome, NASH and/or NAFLD in the patient, thereby prolonging the life of the patient.

A method as described above, wherein the beneficial change or outcome favorably impacts cardiovascular events, myocardial infarctions, angina, stroke, congestive heart failure and any of the complications of atherosclerotic heart disease.

A method as described above, wherein use of an effective dose of the composition comprising an ileal brake hormone releasing substance over a period of at least three months mimics the effects of Roux-en-Y gastric bypass surgery (RYGB) on NASH and/or NAFLD of the patient and wherein the composition synergistically lowers the post treatment biomarker amount or measured score of one or more of insulin resistance, liver enzymes including ALT and AST, ALT/AST ratio, Fib4, HDL, LDL, triglycerides, Alpha fetoprotein, lymphocytes, platelets, wComb liver signal, wComb predicted biopsy score and one or more of calculated or measured scores of steatosis or fibrosis, wherein the change in biomarker amount and the measured score(s) is defined by comparison of measurements taken before treatment commences and after treatment has occurred.

A method as described above, wherein the additional anti-viral agent co-administered in combination with the ileal brake hormone releasing substance produces a synergistic effect to decrease viral injury to steatotic hepatic cells, decrease the oversupply of glucose and triglycerides, lower the number of hepatic cells that are steatotic and/or become steatotic, inhibit and/or reduce viral infection, lower the risk of injury from inflammation associated with metabolic syndrome and improve steatosis and/or fibrosis.

A method as described above, wherein the outcome mimics the effects of Roux-en-Y gastric bypass surgery (RYGB).

A method as described above, wherein the patient is infected with hepatitis B or C and the composition comprising the ileal brake hormone releasing substance is coadministered with an antiviral agent.

A method as described above, wherein the ileal brake hormone releasing substance and the antiviral agent are combined in the same pharmaceutical formulation and administered simultaneously.

A method as described above, wherein the patient is infected with hepatitis C.

A method as described above, wherein viral counts in the patient are effectively lowered and health of steatotic cells in the liver of the patient is improved.

A method as described above, wherein the antiviral agent is an effective amount of sofosbuvir alone or optionally in combination with an effective amount of pegylated interferon and/or ribavirin.

A method as described above, comprising orally administering to the patient an effective amount of a composition comprising an ileal brake hormone releasing substance in oral dosage wherein at least 50% by weight of the ileal brake hormone releasing compound administered to the patient is released in the ileum of the patient, wherein the ileal brake hormone releasing composition is optionally coadministered with an HMG Co-A reductase inhibitor.

A method as described above, wherein the ileal brake composition activates or re-activates L-cells of the ileum, thereby producing the chemical and physiological characteristics of an activated ileal brake in a manner similar to RYGB surgery, whereby the use of the composition in an effective dosage in the patient with NASH or NAFLD, the composition synergistically lowers the post treatment biomarker amount or measured score of one or more of insulin resistance, liver enzymes including ALT and AST, ALT/AST ratio, Fib4, HDL, LDL, triglycerides, Alpha fetoprotein, lymphocytes, platelets, wComb liver signal, wComb predicted biopsy score and one or more of calculated or measured scores of steatosis or fibrosis, whereby the change in biomarker is further defined by comparison of measurements taken before versus after the treatment with the composition.

A method as described above, wherein the ileal brake hormone releasing substance comprises of one or more carbohydrates, starches or sugars to include monosaccharides, disaccharides, or polymeric sugars and optionally one or more lipids to comprise a core which is coated by a material wherein the thickness of the coated material controls the dissolution of the ileal brake composition, thereby delaying release of at least 50% of the composition until the composition reaches the patient's ileum, the release causing an increase in the PYY AUC in the patient to at least 350 and an increase in GLP-1 to at least 250 between 4 and 10 hours after administration of an effective dose of the composition to the patient.

A method as described above, wherein the coating is between 6% and 10% by weight of the composition.

A method as described above, wherein the coating is about 8% by weight of the composition.

A method as described above, wherein the ileal brake hormone releasing substance comprises an effective amount of glucose.

A method as described above, wherein the ileal brake hormone releasing substance is 10-90% by weight glucose in combination with 10-90% by weight of a lipid.

A method as described above, wherein the lipid is a fish oil, a nut oil or a vegetable derived nutritional oil.

A method as described above, wherein the lipid is olive oil or palm oil.

A method as described above, wherein the patient is infected with hepatitis C virus and wherein the oral dosage form comprising the ileal brake hormone releasing composition is administered once-daily or twice daily between meals, and the dosage enables an activation or re-activation of the ileal brake of the subject.

A method as described above, wherein the ileal brake hormone releasing substance compound is coated by a shellac, Eudragit® Eudragit L, Eudragit S, Eudragit L or S with Eudragit RL, Eudragit L or S with Eudragit RS polymer or mixtures thereof.

A method as described above, wherein the patient is found to have insulin resistance and a wCombLiver signal at least two standard deviations above normal which indicates that the patient is in need of treatment to lower risk of Progressive Liver Damage caused by a liver disease state or condition which is hepatic steatosis, hepatic steatohepatitis, hepatic fibrosis, Cirrhosis, Liver failure, hepatocellular carcinoma or a combination thereof.

A method as described above, whether the disease state or condition is directly caused by Metabolic Syndrome.

A method as described above, wherein the disease state or condition is modified further by additional risk factors placing the patient at risk for Liver disease, Liver disease progression and/or a complication thereof.

A method as described above, wherein the patient is treated with a composition comprising an ileal brake hormone releasing substance optionally in combination with a pharmacologically active drug effective to treat or resolve the Progressive Liver Damage condition or risk.

BRIEF DESCRIPTION OF THE FIGS.

FIG. 1. RYGB mimetic Mechanism of action of Brake, a stimulant of L-cells in the ileum, and the result is output of ileal brake hormones which modulate appetite, tissue and organ recovery after glucose supply side associated metabolic syndrome. Shown in the left frame is RYGB surgery, which diverts food down to the ileum and stimulates output of ileal brake hormones. Shown in the right frame is Brake, which is released at the ileum and offers the L-cells a stimulation approximately the same magnitude as RYGB, and thus produces about the same amount of ileal brake hormone release.

FIG. 2. Input-Output parameters for the Neural Net Model, showing lowest to highest Minimum Mean Squared Error (MMSE) rank order vs Biopsy score and wCombLiver Signal, each truncated to show the rank order pattern. In this embodiment of the modeling of wComb liver signal, there are more than 50 input parameters that are used to form a correlation matrix with each output.

FIG. 3. Input-Output parameters for the Neural Net Model, showing lowest to highest Minimum Mean Squared Error (MMSE) rank order vs wComb Biopsy Prediction signal. Rank order is shown as ascending MMSE values, with the lowest MMSE showing overall better prediction of the output values. In this embodiment of the modeling of wComb Biopsy prediction over time, there are more than 50 input parameters that are used herein to form a correlation matrix with each output FIG. 4. Plot of selected time related outputs derived from the Biopsy signal model for the Neural Net model of Adult NASH patients, with day zero being the day of NASH diagnosis FIG. 5. Plot of selected time related outputs derived from the Biopsy signal model for the Neural Net model of RYGB patients, with day zero being the day of RYGB surgery FIG. 6. Plot of selected time related outputs derived from the Biopsy signal model for the Neural Net model of Brake treated patients, with day zero being the day that Brake treatment began.

FIG. 7 shows the pre and post data plots for BMI for RYGB, Brake, NASH and HCC populations. Most of the data on RYGB and Brake treated patients are below the line of identity, indicating Post values lower than pre values. The weight change from RYGB surgery is very apparent on this graphic. Patients before and after NASH diagnosis or before and after HCC diagnosis are evenly distributed above and below the line of identity. For NASH and HCC pre was up to 90 days before time of diagnosis, and post was at least 90 days after diagnosis FIG. 8 shows the pre and post data plots for ALT/AST ratio for RYGB, Brake, NASH and HCC populations. Most of the data on RYGB and Brake treated patients are below the line of identity, indicating Post values lower than pre values, while patients before and after NASH diagnosis or before and after HCC diagnosis are evenly distributed above and below the line of identity. For NASH and HCC pre was up to 90 days before time of diagnosis, and post was at least 90 days after diagnosis FIG. 9 shows the pre and post data plots for Triglycerides for RYGB, Brake, NASH and HCC populations. Most of the data on RYGB and Brake treated patients are below the line of identity, indicating Post values lower than pre values, while patients before and after NASH diagnosis or before and after HCC diagnosis are evenly distributed above and below the line of identity. For NASH and HCC pre was up to 90 days before time of diagnosis, and post was at least 90 days after diagnosis FIG. 10 shows the pre and post data plots for FS index for RYGB, Brake, NASH and HCC populations. Most of the data on RYGB and Brake treated patients are below the line of identity, indicating Post values lower than pre values, while patients before and after NASH diagnosis or before and after HCC diagnosis are evenly distributed above and below the line of identity. For NASH and HCC pre was up to 90 days before time of diagnosis, and post was at least 90 days after diagnosis FIG. 11 shows the pre and post data plots for wComb Liver signal for RYGB, Brake, NASH and HCC populations. Most of the data on RYGB and Brake treated patients are below the line of identity, indicating Post values lower than pre values. The wComb Liver signal reduction caused by Brake and RYGB surgery is very apparent on this graphic. Patients before and after NASH diagnosis or before and after HCC diagnosis are evenly distributed above and below the line of identity. For NASH and HCC pre was up to 90 days before time of diagnosis, and post was at least 90 days after diagnosis FIG. 12. Pre and post data plots for Steatosis Score for RYGB, Brake, NASH and HCC populations. Most of the data on RYGB and Brake treated patients are below the line of identity, indicating Post values lower than pre values. The Steatosis Score reduction caused by Brake and RYGB surgery is very apparent on this graphic. Patients before and after NASH diagnosis or before and after HCC diagnosis are evenly distributed above and below the line of identity. For NASH and HCC pre was up to 90 days before time of diagnosis, and post was at least 90 days after diagnosis FIG. 13. Pre and post data plots for Fibrosis Score for RYGB, Brake, NASH and HCC populations. Most of the data on RYGB and Brake treated patients are below the line of identity, indicating Post values lower than pre values. The Fibrosis Score reduction caused by Brake and RYGB surgery is very apparent on this graphic. Patients before and after NASH diagnosis or before and after HCC diagnosis are evenly distributed above and below the line of identity. For NASH and HCC pre was up to 90 days before time of diagnosis, and post was at least 90 days after diagnosis FIG. 14. Pre and post data plots for Biopsy Score for RYGB, Brake, NASH and HCC populations. Most of the data on RYGB and Brake treated patients are below the line of identity, indicating Post values lower than pre values. The Biopsy Score reduction caused by Brake and RYGB surgery is very apparent on this graphic. Patients before and after NASH diagnosis or before and after HCC diagnosis are evenly distributed above and below the line of identity. For NASH and HCC pre was up to 90 days before time of diagnosis, and post was at least 90 days after diagnosis FIG. 15. Table of baseline demographic and treatment conditions across the three study groups: RYGB added to Standard of Care (SoC), Brake added to SoC, and Atorvastatin 10-40 mg added to SoC. The table includes concomitant medications and frequency of FS index values above 60 in the study populations.

FIG. 16. FS index before, at 6 months, and 12 months after the application of the three treatments: RYGB plus SoC (N=17), Brake plus SoC (N=34) and Atorvastatin plus SoC (N=29). Changes in FS index over pre treatment baseline are significant for RYGB and Brake, but not atorvastatin.

FIG. 17. CV index before, at 6 months, and 12 months after the application of the three treatments: RYGB plus SoC (N=17), Brake plus SoC (N=34) and Atorvastatin plus SoC (N=29). Changes in CV index over pre treatment baseline are significant for RYGB and Brake, but not atorvastatin.

FIG. 18. FS index regression relationship to CV index at baseline, including all patient groups RYGB plus SoC (N=17), Brake plus SoC (N=21) and Atorvastatin plus SoC (N=29) Patients with MIs (N=45) Matched controls for MI patients (N=41). Inset shows DF, Parameter estimate, standard error, t value and p<0.0001

FIG. 19. Three dimensional plot of the inputs FS index (x-axis) and the CV index (y-axis) in relationship to the wComb Biopsy signal output. Both inputs were strongly related to the wComb Biopsy signal.

FIG. 20. Table of baseline values and percent changes before, and after 6 months of treatment. Shown are changes in HBA1c, AST, and Body weight occurring with the treatments for the three study patient groups: RYGB added to SoC, Brake added to SoC, and Atorvastatin added to SoC.

FIG. 21. Composite illustration of percent changes before, and after 12 months of treatment in the three study cohorts: RYGB added to SoC, Brake added to SoC, and Atorvastatin added to SoC. Presented are percent changes in ALT, AST, HBA1c, Triglycerides, LDL, Weight, HDL and FS index.

FIG. 22. Relative comparison of Brake to RYGB surgery, expressed as a parameter by parameter percentage. The clinical data show Brake to be 62% as active as RYGB in Reducing HOMA-IR, a measure of insulin resistance. Brake is 54% as active as RYGB on HbA1c, and over 150% better at reduction of ALT and AST liver enzymes. Brake was 81% as active as RYGB on Triglycerides. Perhaps most surprisingly, Brake was only 20% as effective as RYGB at the task of weight loss.

FIG. 23. Development of the clinical test formulation #2 (shaded row) where the RYGB oral mimetic function was calibrated to the ileal brake hormone output of RYGB patients after a standard meal (last row). The oral vs RYGB calibration may be summarized as a volunteer study where 7 different coatings were applied to approximately 9.1 grams of dextrose and some minor ingredients. The inventors gave each to groups of 7 subjects and measured the output of ileal hormones as AUC and calibrated this output to that after a standard meal given to patients with RYGB surgery.

FIG. 24. The hsCRP (high sensitivity CRP) regression relationship to CV index at 12 months, including all patients treated with warfarin or controls and examined for bleeding side effects and strokes as CV endpoints FIG. 25. The hsCRP (high sensitivity CRP) group shows clustering of strokes and Myocardial infarctions (MIs) in the higher hsCRP values. In this analysis, most patients treated with warfarin or controls and examined for bleeding side effects did not have a hsCRP value measured, so the default value of 1.0 was entered into the calculation of CV risk index until a value was obtained FIG. 26 shows that the hepatitis C viral count in a patient administered a composition according to the present invention decreased rapidly to 100K.

FIG. 27 shows the effect on hepatic parameters after administration of an ileal brake composition (formulation 2) according to the present invention. Administration for six months shows a substantial impact on three of the four hepatic parameters followed FIG. 28 shows the effect of Aphoeline II (Formulation II) added to treat Hepatitis C, Genotype 1a TC, treated with Riba/PegIFN. The Fig. shows a substantial reducing in viral titer with a formulation according to the present invention in combination with a standard therapeutic regimen of pegylated interferon and ribavirin.

Figure 4:
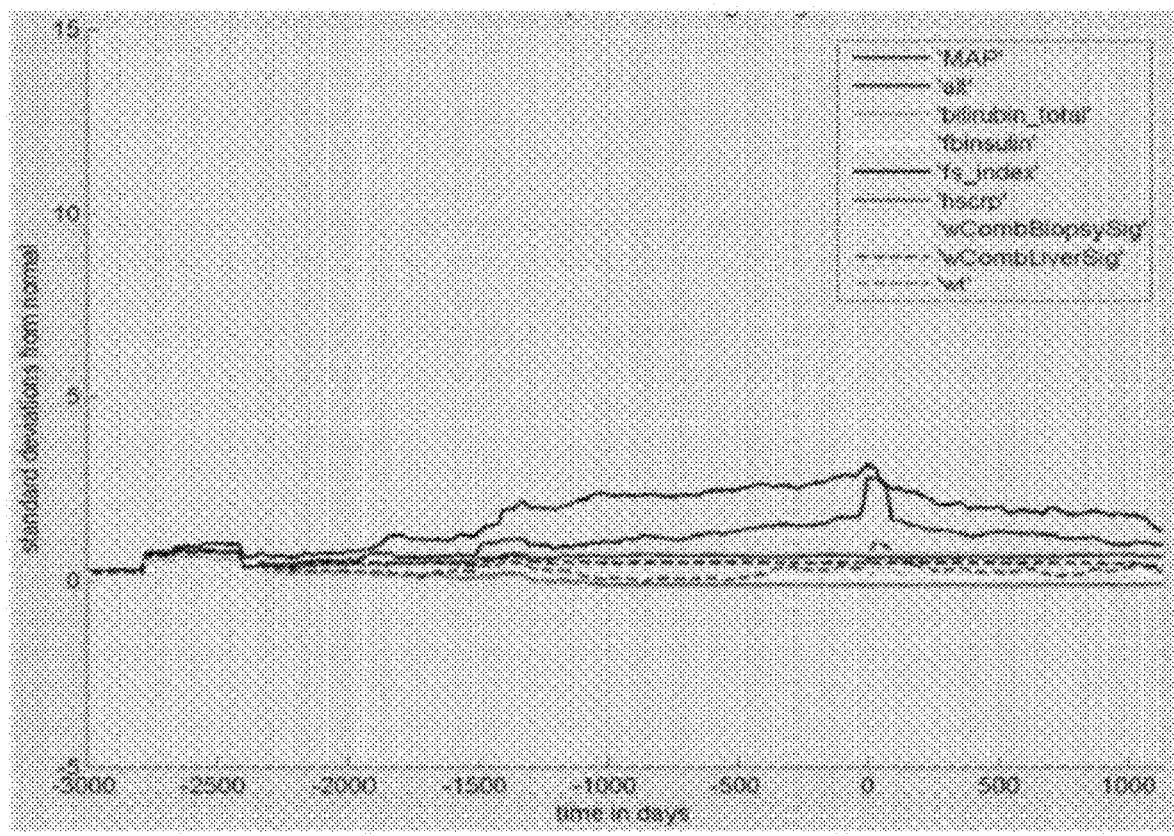

FIG. 35. Exact formulation composition of Brake Formulation #2 as tested in patients FIG. 36. Exact coating formulation composition of Brake Formulation #2 coating as tested in patients FIG. 37. Exact formulation composition of LipidoBrake 10 mg overcoated onto Brake formulation #2. There is 1.4 mg of atorvastatin overcoating each of the 7 Brake tablets that make up a 10 gm dose of Brake.

FIG. 38. Spray-coating conditions used for LipidoBrake overcoating of Brake Formulation #2 tablets.

DETAILED DESCRIPTION OF THE INVENTION

The following terms shall be used to describe the present invention. In instances where a term is not specifically defined herein, the term shall be accorded its meaning, within the context of its use, as understood by those of ordinary skill in the art.

Where a range of values is provided, it is understood that each intervening value, to the tenth of the unit of the lower limit unless the context clearly dictates otherwise (such as in the case of a group containing a number of carbon atoms in which case each carbon atom number falling within the range is provided), between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention. The use of the term "a" or "an" to describe an element or component may refer to more than one element or component within the context of the use of the term.

The term "patient" or "subject" or "individual" is used throughout the specification within context to describe an animal, generally a mammal, including a domesticated animal other than a laboratory animal (rat, mouse etc.) and preferably a human, to whom treatment, including prophylactic treatment (prophylaxis), with the compositions according to the present invention is provided. For treatment of those infections, conditions or disease states which are specific for a specific animal such as a human patient, the term patient refers to that specific animal.

The term "biological sample" is used throughout the specification within context to describe any sample taken from a subject or patient from which biomarkers and/or related elements may be obtained, used, measured, calculated and/or manipulated pursuant to the present invention to obtain an indication of the presence, absence, progression and/or regression of a disease state and/or condition in subject or patient. Biological samples include blood, serum, plasma, urine, feces, saliva, ocular discharge, sputum or samples obtained from tissue (e.g., by biopsy) from a patient or subject to be subjected to diagnosis and/or treatment pursuant to the present invention.

The term "compound" or "composition" shall mean any specific compound which is disclosed within this specification and typically means a single agent or a pharmaceutically acceptable salt thereof, or a bioactive agent or drug as otherwise described herein, including pharmaceutically acceptable salts thereof, generally a drug. Compounds are included in amounts effective to produce an intended physiological effect. Certain compounds or compositions according to the present invention may be used to treat secondary conditions such as type II diabetes, hepatic steatosis, hepatic steatohepatitis, hepatic fibrosis, cirrhosis, fatty liver and hepatocellular cancer or to suppress the immune system in liver transplant patients, or to treat viral infections directly (e.g., hepatitis B and/or C) in order to reduce the likelihood of a condition occurring or to advance therapies. Pharmaceutically acceptable salts are also compounds for use in the present invention.

The term "effective" when used in context, shall mean any amount of a compound or component which is used to produce an intended result within the context of its use. In the case of bioactive agents according to the present invention, the term effective generally refers to a therapeutically effective amount of compound which will produce an intended physiological effect associated with that agent, generally including antiviral activity. In the case of the treatment of hepatitis, hepatic steatosis and/or steatohepatitis (NASH), an effective amount of a compound or composition and/or bioactive agent is that amount which is effective to treat the condition which is being treated by administering the agent. The term "low dose" shall mean a dose of a pharmacologically active agent which is substantially lower than a dose typically used in the absence of coadministration with an ileal brake hormone releasing substance to provide an intended result. Often a low dose will be an amount of an agent which is 50% or less, 45% or less, 40% or less, 35% or less, 30% or less, 25% or less, 20% or less, 15% or less or 10% or less of the typical dose of an agent used to produce an intended effect, the low dose often resulting in substantially lower side effects than with the typical dose of an agent used.

The term "hepatitis" is used to describe a liver condition which implies injury to the liver characterized by the presence of inflammatory cells in the tissue of the organ. The condition can be self-limiting, healing on its own, or can progress to scarring of the liver, which is called fibrosis or cirrhosis. Hepatitis is acute when it lasts less than six months and chronic when it persists longer than six months. A group of viruses known as the hepatitis viruses is principally responsible for most cases of chronic liver damage worldwide. Hepatitis may run a subclinical course when the affected person may not feel ill. The patient becomes unwell and symptomatic when the disease impairs liver functions.

Hepatitis includes hepatitis from viral infections, including Hepatitis A through E (A, B, C, D and E—more than 95% of viral cause hepatitis, especially including hepatitis B and C), Herpes simplex, Cytomegalovirus, Epstein-Barr virus, yellow fever virus, adenoviruses; non-viral infections, including *toxoplasma*, Leptospira, Q fever and rocky mountain spotted fever, as well as alcohol, toxins, including *amanita* toxin in mushrooms, carbon tetrachloride, asafetida, among others, drugs, including paracetamol, amoxicillin, anti-tuberculosis medicines, minocycline and numerous others as described herein.

The term "Hepatitis C Virus" or "HCV" is used to describe the various strains of Hepatitis C virus. HCV is one of several viruses that can cause hepatitis. It is unrelated to the other common hepatitis viruses (for example, hepatitis A or hepatitis B, among others). HCV is a member of the Flaviviridae family of viruses. Other members of this family of viruses include those that cause yellow fever and dengue. Viruses belonging to this family all have ribonucleic acid (RNA) as their genetic material. All hepatitis C viruses are made up of an outer coat (envelope) and contain enzymes and proteins that allow the virus to reproduce within the cells of the body, in particular, the cells of the liver. Although this basic structure is common to all hepatitis C viruses, there are at least six distinctly different strains of the virus which have different genetic profiles (genotypes). Treatment of HCV according to the present invention is directed to all strains of HCV, including the six or more distinct strains described above, as well as related strains which are drug resistant and multiple drug resistant strains. In the U.S., genotype 1 is the most common form of HCV. Even within a single genotype there may be some variations (genotype 1a and 1b, for example). Genotyping is viewed as important to guide treatment because some viral genotypes respond better to therapy than others. HCV genetic diversity is one reason that it has been difficult to develop an effective vaccine since the vaccine must protect against all genotypes.

A "Hepatitis C virus infection" or "Hepatitis C infection" is an infection of the liver caused by the hepatitis C virus (HCV).

The term "synergy" or "synergistic" refers to an effect or result on viral inhibition and/or hepatic steatosis, cirrhosis and/or hepatocellular cancer as evidenced by hepatic function (e.g., viral load in monitoring viral infection or a hepatic marker in monitoring hepatic steatosis) which is greater than that which is or would expected from a simple combination of therapies, or providing a more rapid return to normalcy, cure or cure rate. Thus, if one were to combine the administration of an ileal brake composition with that of an antiviral compound or compounds pursuant to the present invention, a synergistic result is that result which is greater than the additive result one would expect from combining the two therapies.

A "synergistic result" for a particular compound or therapy is that result which occurs which is at a minimum two fold greater than the additive result, which may be defined as the effect one would expect from simply doubling the dose or amount of a compound or composition used. By way of example (and not by limitation), for viral load reduction, additive results will generally provide a 1 or 2 log reduction in viral titers, whereas a synergistic result provides a 3 or 4 log reduction in viral titers. In the case of hepatic enzymes, additive results generally provide about 25% reduction for at least one liver enzyme (alanine amino transferase or ALT, aspartate amino transferase or AST, gamma-glutamyl transpeptidase or GGTP and alpha fetoprotein or AFP) and preferably at least two, at least three and preferably all four liver enzymes and synergy provides at least about 75-100% reduction in at least one liver enzyme (at least two, at three, at least four of the liver enzymes).

The terms "hepatic steatosis" and "steatohepatitis" are used to describe conditions of the liver in which fat in the liver is closely associated with inflammation, and the inflammation, when present defines the stage where there is scarring which is called fibrosis or eventually cirrhosis. Hepatic steatosis is part of a group of liver diseases, among them the widely recognized variant known as nonalcoholic fatty liver disease ("fatty liver" or "fatty liver disease"), in which fat builds up in the liver and sometimes causes liver damage that gets worse over time (progressive liver damage). Non-alcoholic fatty liver disease (NAFLD) is fatty deposition, itself a normal process that becomes excessive. When there is an inflammation of the liver which is not due to excessive alcohol use, but is instead related to insulin resistance and metabolic syndrome, this condition responds to treatments according to the present invention which affects other insulin resistant states (e.g. T2D). Hepatic steatohepatitis, also called Non Alcoholic SteatoHepatitis or NASH is the most extreme progressive form of NAFLD, and is regarded as a major cause of cirrhosis of the liver as well as a precursor of hepatocellular carcinoma. The present invention may be used to treat all insulin resistance related forms of fatty liver disease with inflammation, especially including NAFLD and NASH.

Although a cause other than viral infection is not always known, hepatic steatohepatitis seems also to be related to certain other conditions, including obesity, high cholesterol and triglycerides, and T2D. Historically, treatment for hepatic steatohepatitis involved controlling those underlying diseases. Ileal brake (ileal brake hormone releasing) compositions according to the present invention, either alone or in combination with antiviral agents and/or anticancer agents as disclosed herein may be used to treat and/or reduce the likelihood of NASH, NAFLD and/or cirrhosis as well as liver cancer (hepatocellular carcinoma), especially when these disease states or conditions occur secondary to viral infection, especially a Hepatitis B or C viral infection.

Hepatic steatosis most commonly affects people who are middle-aged and are overweight or obese, have high cholesterol and triglycerides, or have diabetes. Despite these indications, hepatic steatosis can occur in people who have none of these risk factors. Excess body fat along with high cholesterol and high blood pressure are also signs of a condition called metabolic syndrome. This condition is closely linked to insulin resistance.

Hepatic steatosis usually gets worse over time (deemed "progressive"), especially where the patient is infected with a virus such as Hepatitis C or B. For this reason, a patient may have no symptoms until the disease progresses to the point that it begins to affect the way the liver works (liver function). As liver damage gets worse, symptoms such as tiredness, weight loss, and weakness may develop. It may take many years for hepatic steatosis to become severe enough to cause symptoms. In some limited cases, where viral infection is not implicated, the progress of the condition can stop and even reverse on its own without treatment. But in other cases, especially where viral infection is implicated, hepatic steatosis can slowly get worse and cause scarring (fibrosis) of the liver, which leads to cirrhosis and, in certain cases, hepatocellular carcinoma. In cirrhosis, the liver cells have been replaced by scar tissue. As more of the liver becomes scar tissue, the liver hardens and ceases to function normally.

The term "cirrhosis of the liver" or "cirrhosis" is used to describe a chronic liver disease characterized by replacement of liver tissue by fibrous scar tissue as well as regenerative nodules (lumps that occur as a result of a process in which damaged tissue is regenerated), leading to progressive loss of liver function. Cirrhosis is most commonly caused by fatty liver disease, especially including hepatic steatosis, as well as alcoholism and especially hepatitis B and C virus causing a low grade inflammation, which also causes hepatic steatosis, but has many other possible causes. Some cases are idiopathic, i.e., of unknown cause. Ascites (fluid retention in the abdominal cavity) is the most common complication of end stages of cirrhosis and is associated with a poor quality of life, increased risk of infection, and a poor long-term outcome. Other potentially life-threatening complications are hepatic encephalopathy (confusion and coma), bleeding from esophageal varices, and development of hepatocellular carcinoma. Prior to the present invention, hepatic steatosis and increasing hepatic cirrhosis was thought to be generally irreversible once it occurs, and historical treatment focused on preventing progression and complications. In advanced stages of cirrhosis, the only option is a liver transplant. The present invention may be used to limit, inhibit or reduce the likelihood or treat cirrhosis of the liver without regard to its etiology, although cirrhosis which is secondary to a viral hepatitis infection (especially including Hepatitis C and/or B) is a particular target of the present invention. In a preferred embodiment of the present invention, said composition is also useful to prevent hepatocellular carcinoma or decrease the risk thereof.

The term "treat", "treating", or "treatment", etc., as used herein, refer to any action providing a benefit to a patient for which the present compounds may be administered, including the treatment, inhibition or reduction in the likelihood (prevention) of metabolic syndromes, including T2D, hyperlipidemia, weight gain, obesity, insulin resistance, hypertension, atherosclerosis, fatty liver diseases and certain chronic inflammatory states that lead to these manifestations, among others. In additional aspects, the present invention relates to the treatment, inhibition or reduction in the likelihood (prevention) of hepatitis viral infections, including Hepatitis B and Hepatitis C viral infections, as well as the secondary disease states and/or conditions which are often associated with such viral infections, including hepatic steatosis (steatohepatitis), cirrhosis, fatty liver and hepatocellular cancer. Treatments with combination agents or combination therapy (e.g., ileal brake hormone releasing compositions and antiviral agent and/or anticancer agents or antiviral agents and/or anticancer agents combined with Roux-en-Y gastric bypass surgery (RYGB)) represent preferred embodiments of the present invention. These terms refer to treatment in any amount and for any duration effective to favorably impact the disease state and/or condition to be treated, in many instances for a period of at least 3-4 months up to several years. A treatment term of 3-4 months to 18 months or longer represents a preferred longer term treatment schedule which allows the assessment of the impact of a particular treatment on the disease state or condition to be treated. Traditional treatment refers to treatment which is provided through standard allopathic/pharmaceutical approaches to the resolution and/or management of symptoms of disease states and/or conditions.

The term "personal treatment" is used to describe a treatment which is used for disease states and/or conditions in patients or subjects based upon the diagnostic outcomes and/or risks which are determined to be present in a patient or subject for whom therapy is recommended as a consequence of utilizing the diagnostic and/or monitoring aspects of the present invention.

The term "FS index" also known as Fayad-Schentag Index is used throughout the present invention to define the degree and severity of MetS in patients who are considered candidates for treatment with the disclosed ileal brake hormone releasing composition. FS index calculations are used to define MetS and when repeated after a period of treatment, usually at least 3 months, the FS index is used to define response to said treatment. Throughout the present invention, FS index is calculated as:

$$\frac{0.11\left((FBG+TG)+HBA1c \times \frac{HBA1c \times 20}{5}+BMI \times \frac{FBG+TG}{150}+AST \times \frac{TG \times 4}{100}+FB \text{ insulin} \times (BMI-22)\right)}{S/D \text{ ratio}}$$

FBG is Fasting Blood Glucose in mg/dl and normal value is 100 mg/dl

TG is Triglycerides in mg/dl normal value is <150

HBA1c is glycosylated hemoglobin calculated as a ratio to hemoglobin; normal value is <6%

BMI is body mass index as kg/m$^2$ where a normal value is 20 and obese begins above 25

AST is Aspartate Transferase (formerly SGOT) in IU/liter and a normal value is 5.50

FB insulin if fasting Blood insulin concentration in nmol/liter, a normal value is 4.0

Where S/D ratio is the $$\text{Glucose Supply }(S)/\text{Insulin Demand }(D) = \frac{1+((CE)+(HGU)+(GNG)+(IR))}{1+(PIE+PGU)}$$

CE=Carbohydrate exposure mg/dl
HGU=Hepatic Glucose Uptake mg/dl

GNG=Hepatic Glucoeogenesis mg/dl
IR=Insulin Resistance mg/dl
PGU=Peripheral Glucose Uptake mg/dl
PIE=Peripheral Insulin Exposure mg/dl The term "CV index" or Cardiovascular Index, as used throughout the present invention, expands FS index with additional elements to include biomarkers of hyperlipidemia, inflammation, blood pressure and clinical modifiers of cardiovascular risk such as cigarette smoking, age, use of ASA for prophylaxis of myocardial infarction, and use of conventional lipid lowering drugs to lower risk of cardiovascular events. When forming the CV index, the inventors began with the glucose supply side FS index in its disclosed form, then incorporated the conventional viewpoint that additional cardiovascular risk also derives from the hyperlipidemia and hypertension these patients manifest. Essentially, the inventors have therefore advanced a means of considering both of the two parallel pathways that define cardiovascular events, specifically the glucose supply side and the lipid supply side. FS index describes the glucose supply side pathway, while the second function in the CV index equation incorporates the lipid supply side biomarkers and calculated functions, and uses lipid lowering drugs in the SD denominator of that section in the equation. There is no current CV risk scoring tool that considers both the glucose supply side pathways and the lipid supply side parallel pathways in the assessment of risk of cardiovascular events. As patients with NASH and NAFLD are likely to die of cardiovascular events with greater frequency than they die from liver events, it is necessary to model the outcomes of both liver and cardiovascular system. Because we have incorporated the other elements of glucose supply side diseases and all of MetS complications in the combined equation, it is anticipated that the CV index will serve all of the important outcomes and endpoints in these patient population.

Based upon the learning, knowledge and prior clinical use of the FS index to stratify cardiovascular risk, the revised equation, the CV risk index, is as follows:

$$CV \text{ Risk Index} = FS \text{ Index} + \frac{(LDL \text{ factor} + \text{age}/\text{sex}/\text{cigs factor} + hsCRP \text{ factor} + RP/200)}{(LL \text{ Drugs factor} + ASA \text{ factor})}$$

Where:
FS index is calculated as:

$$\frac{0.11 * (FBG + TG + HBA1c \text{ factor} + (BMI \text{ factor}) + (AST \text{ factor}) + (FBInsulin \text{ factor})}{S/D \text{ ratio}}$$

Wherein said FS index, the FBG is Fasting Blood Glucose in mg/dl; the TG is Triglycerides in mg/dl; the HBA1c is hemoglobin A1c in %; the BMI is body mass index in kg/m²; the AST is Aspartate Transferase in IU/liter; FB insulin is fasting Blood insulin concentration in mmol/liter; and the S/D ratio (SD) is a ratio of Glucose Supply Index (S) to Insulin Demand Index (D); wherein (S) is calculated as follows:

1+[aggregate of carbohydrate exposure (CE)+hepatic glucose uptake (HGU)+hepatic gluconeogenesis (GNG) and+insulin resistance (IR)]

and (D) is calculated as follows:

1+[aggregate of peripheral glucose uptake (PGU)+ peripheral insulin exposure (PIE)];

Where:
HBA1c factor: HBA1c×((HBA1c/5)×20)
BMI factor: BMI×((FBG+TG)/(50×3))
AST factor AST×((TG/100)×4)
FBInsulin factor: (BMI−22)×FBInsulin
Low density Lipoprotein (LDL factor): 60+LDL/10
Age/gender/cigarettes factor:

(Packs/day×yrs/8)×age×gender, where gender is 1.0 for male, 0.6 for female

High sensitivity: C-Reactive protein (hsCRP) factor: hsCRP×10
Rate Pressure (RP factor): (HR×SBP)/200 Where HR=Heart Rate and SBP=Systolic BP
Lipid Lowering (LL) Drugs factor:

(0.9+Statin Dose, mg in Lipitor equivs/10)+(02+ other LL drugs factor/5)

ASA factor: 0.8+(ASA yrs/2) Where ASA is low dose Aspirin×years taken

It should be noted that the presentation of FS index in the CV index equation above is somewhat different here (although all FX index equations as used in the present application are identical), because as presented, the FS index associated with the CV index equation above converts elements of the FS index to "factors" which are calculations performed in the normal operation of the equation on a spreadsheet. As disclosed in the CV index above, FS index presents these factors. The remainder of the equation presents factors designed to express the lipid supply elements added. Accordingly, both ways of presenting the FS index part of the equation are identical, correct and arrive at the same value. Presenting factors in the remainder of the equation is likewise correct and appropriate over the use of a longer version.

The term "cardiovascular event" in a patient or subject is used to describe an unfavorable cardiovascular event which occurs in a patient or subject and includes such events as myocardial infarction, stroke, hospitalization for unstable angina, congestive heart failure or combinations thereof, whether or not these events are directly caused by Metabolic Syndrome or occur as a consequence of additional risk factors of age, gender, cigarette smoking, high blood pressure, or inflammation (as hsCRP), alone or in combination which place the patient or subject at risk for at least one cardiovascular event.

It may be understood by those skilled in the art of developing predictive mathematical modeling equations, that the application of the equation to new patient populations and the collection of new data may lead the inventors to introduce modifications of the equation, and these modifications will be considered within the scope and intention of the model, provided that there remains a balance between the glucose supply side and the lipid supply side of the equations as modified, and provided that the principle intention remains the accurate description of patient outcomes when treated with ileal brake hormone releasing compositions alone or in combination with compounds which have effect on the biomarkers used in the CV index and FS index equations. Any modification of said equations that is within the art for the use of ileal brake hormone releasing compositions, monitoring their efficacy or defining the outcomes of said treated patients is within the scope of the invention.

With regard to the modeling of biomarkers of liver health and disease, terms used in modeling MetS and CV risk apply to terms used in modeling liver health and disease. All biomarkers, physical measurements, and laboratory test results used herein, relate to the use of a neural net mathematical model to describe "outputs" as related in degree and magnitude to "inputs". As used herein, inputs can be one or more biomarkers, laboratory test values, or physical parameters such as weight or blood pressure. Composite inputs can be assembled from weighted or unweighted groups of inputs, with the FS index composite being an illustrative but non limiting example. As used herein, outputs can be one or more biomarkers, laboratory tests or physical parameters such as weight, blood pressure, development of cancer, a cardiovascular event such as a myocardial infarction, or a final endpoint such as death of the patient or the onset of a terminal disease. The advantage of said input-output modeling is extreme flexibility and the avoidance of a fixed structural model which automatically constrains and limits the system to pre-specified conclusions. As used in the present invention, the additive modeling is directed to liver conditions and liver relevant endpoints, and this was necessary because MetS affects the liver, and patients with disease in their livers also have co-morbidities such as T2D, hyperlipidemia, hypertension, obesity and infecting viruses such as hepatitis C. The system and model for the liver must thereby incorporate a consideration of MetS and measures of all of these comorbid conditions associated with Insulin Resistance, and the outputs must consider linkages to endpoints of CV diseases, T2D, hyperlipidemia as related to MetS and also consider outputs linked to hepatitis infections and even linkage to cancers, given the strong associations with hepatocellular carcinoma in patients with hepatitis C and cirrhosis. All of the modeling is directed to defining the effectiveness of ileal brake hormone releasing compositions, or the effects of RYGB surgery, which is the only other means known to activate the ileal brake hormone releasing pathway. Thus, the present invention uses the effects that follow the activation of the ileal brake to define the important inputs and outputs of effects on MetS and most specifically in the present invention, on the liver.

Outputs of the liver health and disease model in the present invention, that are specific to the liver include "wComb Liver signal" which is calculated from the interaction of multiple biomarkers and physical findings, as shown in the table below: The means of calculation of the primary means of biomarker modeling of the liver status as wComb Liver signal over time is disclosed below.

The application of a mixture of biomarkers, physical parameters laboratory test results and drug therapy to predict the health of the liver illustrates the means of arriving at even weighting of input parameters used to predict outputs, and avoid the well-known tendency of larger numbers to overwhelm smaller numbers, a normalization method was developed in the construction of composite signals. The table below shows the normalization for wComb Liver Signal, and is meant to be illustrative of the process used to develop composite output signals for other parameters in this modeling process.

| Factor (F) | Normalization ($\eta$) |
|---|---|
| Alkaline Phosphatase | 1/82.7 |
| ALT | 2/21.4 |
| AST | 2/25.8 |

-continued

| Factor (F) | Normalization ($\eta$) |
|---|---|
| Bilirubin_total | 2/0.66 |
| Insulin Conc | 1/4.8 |
| hsCRP | 1/1.18 |
| platelet_count | 2/171.8 |
| Total Protein | 1/7.3 |
| PT | 2/4.0 |
| INR | 2/0.99 |
| Lymphocyte count | 2/2.38 |
| waist_circumference | 1/117.5 |
| waist_circumference | 1/117.5 |
| Bilirubin_direct | 2/0.23 |
| lymphocytes_% | 2/34.68 |
| GGT | 1/32.26 |
| Weight | 1/178.7 |
| BMI | 1/26.18 |
| LDH | 1/172 |
| HbA1c | 1/6.13 |
| drug_statin_dose_mg | 1 |
| drug_pioglitazone | 1 |
| drug_chol_fibric_acid_derivative | 1 |
| drug_chol_statin | 1 |

The windowed combined liver signal (wComb Liver signal) is generated by adding all normalized factors, F, given in the above table using the normalization quantity, $\eta$, based on the range of the factor.

It is given by the relationship:

$$wCombLiver = \Sigma \eta F$$

In a similar manner, the windowed combined biopsy signal "wComb Biopsy signal" is generated by adding all biopsy scores, including steatosis, fibrosis, ballooning and inflammation. Ballooning can have values of 0 (no ballooning) or 2 (ballooning present), while the remaining 3 biopsy factors have values between 0 and 3 based on the severity of the biopsy measurement. No further normalization was applied here because the numbers are all of similar magnitude. The wComb biopsy signal is thus determined by:

$$wCombBiopsy = Steatosis + Fibrosis + Inflammation + Ballooning$$

In the present embodiment, FIG. 2 shows the prediction matrix for the wComb Liver signal and the wComb biopsy signal outputs. In further embodiments of the present invention, the model was applied to the output of a predicted biopsy score, defined herein as "wComb Biopsy Predict". To arrive at this output, all available biomarkers and scores were used as inputs into the MatLab model, and the output of these biomarkers and scores was the wComb Biopsy Predict over time. This output was examined in a relative sense against each input using the calculation of MMSE, minimum mean squared error for each input-output pairing. The lower the MMSE, the better the predictive value when examining the output report in FIG. 3. As an illustrative but non limiting example, the wComb Biopsy predict was then graphically analyzed against outputs by calculating the wComb Biopsy predict value before an intervention and then after the intervention. The purpose of these illustrations was to define events that modify the model predicted biopsy score by comparing post event to pre event values. In these illustrative examples shown herein as FIGS. 7 to 12, it was clear that there was detectable change when NASH patients were treated with RYGB or Brake.

In certain embodiments, the following genomic and epigenetic biomarkers are useful in the modeling of Biopsy score: IRS-1, ENPP-1, GCKR, PPARG, TCF7L2, SLC2A1 for Insulin Resistance, SLC27A5, LIN1, MTTP, PEMT, ADIPOQ, ADIPOR2, ApoC3, TCF7L2, ApoE, NR1I2/PXR, PPARA, FADS1, PNPLA3, TM6SF2, MBOAT7 for Lipid and TC abnormalities; HFE, SOD2, GCLC, MRP2, ABCC2, MTHFR, for oxidative stress; TLR-4, CD14, TNF, STNFr-2, FDFT1, IL6 for inflammation linked to endotoxin; AGT, ATGR1, KLF6, TGFb1, COL13A1, CDKN1A, PNPLA3, TM6SF2, MBOAT7, miR-34a, SIRT1, pAMPK, miR122a, miR200a, YKL40, CHI3L1, HMGCR, LDLr, LXR, SREBP10, CPT1, IRS-2, IRS-3, SIRT6, CPT1, CRPT, HADH8, SRC1, SRC3, NFYC, Pro-C3, (PNPLA3 a big one like MBOAT7), LpPLA2, EIF2 and FXR/RXR, among others.

Thus, the present invention is comprised of a novel and comprehensive system mathematical model of liver health and disease within MetS, that defines and offers valuable prediction of the most difficult to obtain liver disease diagnosing constituent, A Liver Biopsy. The model has been tested in patient populations, and in the present embodiment, this model also defines the beneficial effects of ileal brake hormone releasing compositions such as Brake or the otherwise applicable RYGB surgery effect, which is currently the best agreed upon means of improving the biopsy score in patients with NASH. Thus the modeling means enables treatment of patients with ileal brake hormone releasing compositions also disclosed herein, and promises that these compositions will have beneficial effects on the liver biopsy after an effective dose for an effective duration of treatment.

It may be understood by those skilled in the art of developing predictive mathematical modeling equations, that the application of the disclosed equations to new or additional patient populations and the collection of new biomarkers to include but not limit to genomic or epigenetic markers or new physical or laboratory tests, may lead the inventors to introduce modifications to the equations. These modifications will be considered within the scope and intention of the model and the invention, provided that there remains a balance between the glucose supply side and the lipid supply side of the MetS equations as presented or as modified, and provided that the principle intention remains the accurate description of patient outcomes when treated with ileal brake hormone releasing compositions alone or in combination with compounds which have effect on the biomarkers used in the liver health and disease model to include but not limit to the CV index and FS index equations. Any modification of said equations that is within the art of use of ileal brake hormone releasing compositions in MetS associated diseases to include NASH, NAFLD and T2D, including use of equations to monitor the efficacy of ileal brake hormone releasing compositions, or defining the outcomes of said treated patients is within the scope of the invention.

The terms "ileal brake composition" and "ileal brake hormone releasing composition" are used in context to describe a compound or composition which comprises an "ileum hormone-stimulating amount of a nutritional substance" (also described as an "ileal brake hormone releasing substance" or "ileal brake compound" which includes any amount of a nutritional substance that is effective to induce measurable hormone release from the ileum into the blood, and induce feedback from the ileum or ileum-related stimulation of insulin secretion or inhibition of glucagon secretion, or other effect such as shutting down or decreasing insulin resistance and increasing glucose tolerance. The ileal brake composition used in the present invention may vary widely in dosage depending upon factors such as the specific nutrient at issue, the desired effect of administration, the desired goal of minimizing caloric intake, and the characteristics of the subject to whom the ileal brake hormone releasing substance is administered. Substances which can be used to release hormone in the ileum include one or more of proteins and associated amino acids, fats including saturated fats, monosaturated fats, polyunsaturated fats, essential fatty acids, Omega-3 and Omega-6 fatty acids, trans fatty acids, cholesterol, fat substitutes, carbohydrates such as dietary fiber (both soluble and insoluble fiber), starch, fibers (soluble and insoluble), sugars (including monosaccharides such as fructose, galactose, glucose, di-saccharides, (such as lactose, maltose, sucrose and alcohols), polymeric sugars including inulin and polydextrose, natural sugar substitutes (including brazzein, Curculin, erythritol, fructose, glycyrrhizin, glycyrrhizin, glycerol, hydrogenated starch hydrosylates, isomalt, lactitol, mabinlin, maltitol, mannitol, miraculin, monellin, pentadin, sorbitol, stevia, tagatose, thaumatin, and xylitol), sahlep, and halwa root extract. D-glucose (dextrose), alone or in combination with a lipid, is a preferred nutritional substance. Nutritional substances include all compositions that yield the aforementioned nutrients upon digestion or that contain such nutrients, including polymeric forms of these nutrients.

Preferred ileal brake compounds/ileal brake hormone releasing substances which are included in ileal brake compositions according to the present invention include carbohydrates such as starches, sugars, free fatty acids, lipids, polypeptides, amino acids, and compositions that yield sugars, free fatty acids, polypeptides, or amino acids upon digestion and numerous mixtures of these components.

In preferred aspects of the present invention the ileal brake composition/ileal brake hormone releasing substance is comprised of carbohydrates of the monosaccharide or disaccharide variety, including by not limited to glucose, fructose, galactose, sucrose, high fructose corn syrup and mixtures thereof and optionally, a GRAS lipid or triglyceride, preferably one or more selected from the group consisting of oil from nuts (various, such as peanut, cashew, walnut, pecan, brazil nuts, etc.), coconut, palm oil, corn oil, germ, olive oil, castor, sesame, fish oil (omega 3, oleic acid and derived liver oils) and mixtures thereof where the total amount of said ileal brake hormone releasing substance ranges from about 500 mg to about 20 grams, about 500 mg to about 12.5 grams, about 500 mg to about 7.5 grams, about 1 gram to about 5 grams about 500 mg to about 6 grams, 500 mg to about 3 grams, about 500 mg to about 2 grams, about 7.5 grams to about 12.5 grams. For example, in preferred aspects of the invention, at least about 500 mg of D-glucose is used, and a particularly preferred ileum hormonal-stimulating amount of D-glucose as the ileal brake compound includes between about 7.5-8 g to about 12-12.5 g (preferably around 10 g).

An ileal brake hormone releasing substance composition thus contains an effective amount of glucose or a related sugar (including but not limited to mono- or disaccharide sugars such as dextrose, galactose, sucrose, fructose) alone or in combination with lipids including oils (including but not limited to vegetable oils such as cottonseed, oils from most varieties of nuts, coconut, palm, corn, germ, olive, castor, sesame, fish oils including omega 3, oleic acid and derived liver oils). In the practice of the invention, oils, when included, are to be emulsified, allowed to become solids in emulsified form, and then coated for release in the ileum. When the ileal brake composition (Brake™) is produced to include both glucose and oil components as disclosed herein, the proportion of each of these components may vary from 10% by weight to 90% by weight. Indeed, it is envisioned by the inventors to produce a predominant glucose formulation, a predominant oil formulation and a 50:50 mixture of glucoses and oils and remain entirely within the spirit of the invention, since optimal formulations and combinations thereof can be defined by the direct impact on biomarkers of the ileal brake and biomarkers of hepatic steatosis.

In addition to the ileum hormone-stimulating amount of a nutritional substance (ileal brake compound) which is included in the ileal brake composition according to the present invention, the composition may also include "dietary components", which in addition to carbohydrates, sugars, especially glucose, lipids and other components which are included herein (e.g., such as glucose, other sugars, carbohydrates, lipids and other nutritional components as described above, which may be micro-encapsulated in certain embodiments) includes any natural substance which either itself evidences impact on the ileal brake, or alternatively, enhances the impact that glucose or other sugars and/or lipids have on the ileal brake, such components including other complex carbohydrates and nutritional components as otherwise described herein including, for example, alfalfa leaf, *chlorella* algae, chlorophyllin and barley juice concentrate, among a number of other agents, including probiotic bacteria, all of which are well known in the art.

The term "traditional pharmacologically active drug" or "traditional pharmacologically active agent" is used to describe a drug or agent which is typically or traditionally used to manage and/or assist in resolving the symptoms of the disease states and/or conditions which are described and treated herein. This term is used to describe all drugs or agents which exhibit biological activity and which are not used to upregulate or release hormones in the ileum of a patient or subject, which compositions or substances are referred to as an ileal brake hormone releasing substance as otherwise described herein.

Compositions for use in the present invention preferably comprise the micro-encapsulation of glucose, lipids and components of diet formulated to release these active compositions at pH values between about 6.8 and about 7.5, which allows substantial release and targets the action of said medicaments at the ileal brake in the distal intestine of the subject or patient. Conventional formulation strategies used for traditional pharmacologically active agents typically don't target release at pH values above 6.8, thereby releasing all of said pharmaceutical earlier in the intestine than the location of the L-cells and the ileal brake. The encapsulated compositions disclosed are a preferred medicament to reduce dietary glucose associated chronic inflammation, the primary driver of metabolic syndrome and eventual development of obesity and T2D. Use of the encapsulated compositions according to the present invention also preferably decreases appetite for glucose, which is beneficial to the patient with metabolic syndrome, and thereby lowers both insulin resistance and inflammation and is of benefit to the treatment of patients with metabolic syndrome and related disease states or conditions including T2D, hyperlipidemia, weight gain, obesity, insulin resistance, hypertension, atherosclerosis, fatty liver diseases and certain chronic inflammatory states that lead to these manifestations, among others. In additional aspects, the above compositions may be used alone or co-administered with anti-viral agents, including formulating with anti-viral agents to treat hepatitis viral infections, including Hepatitis B and Hepatitis C viral infections, as well as the secondary disease states and/or conditions which are often associated with such viral infections, including hepatic steatosis (steatohepatitis), cirrhosis, fatty liver and hepatocellular cancer, among other disease states or conditions.

Therapeutic methods according to the present invention may or may not include concomitant or even subsequent RYGB surgery, as control of MetS and related conditions and/or disease states, as well as treating Hepatitis B and Hepatitis C viral infections, and the secondary disease states and/or conditions which are often associated with such viral infections, including hepatic steatosis (steatohepatitis), cirrhosis, fatty liver and hepatocellular cancer, among other disease states or conditions. In preferred practice of the invention, most treatment modalities would be possible with oral use of the disclosed ileal brake compositions, alone or in combination with an anti-viral gents(s), with the use of RYGB surgery reserved for cases beyond the control of said encapsulated compositions alone.

In a preferred embodiment of the invention, oral dosing with about 1,000-2,000 to about 20,000 milligrams, about 2,500 to about 12,500 milligrams, preferably about 3,000 to about 10,000 milligrams, about 7,500 to about 10,000 milligrams depending on the components of a pharmaceutical formulation comprising microencapsulated glucose, lipids, and/or amino acids activates the ileal brake in a dose increasing magnitude and treats one or more of the following components of metabolic syndrome: insulin resistance, hyperlipidemia, weight gain, abdominal obesity, hypertension, atherosclerosis, fatty liver diseases and chronic inflammatory states. In alternative embodiments, the ileal brake compositions as otherwise described herein are used to treat hepatitis viral infections, including Hepatitis B and Hepatitis C viral infections, as well as the secondary disease states and/or conditions which are often associated with such viral infections, including hepatic steatosis and/or steatohepatitis (NASH), cirrhosis, fatty liver and hepatocellular cancer, among other disease states or conditions.

In various embodiments according to the present invention, the disclosed formulations and compositions have been described as Aphoeline which is trademarked. The other trademarked name for the ileal brake hormone releasing substances is Brake. Compositions of the invention may be used alone or in combination with medicaments ordinarily used to treat specific manifestations of metabolic syndromes such as diabetes, hyperlipidemia, atherosclerosis, hypertension, obesity, insulin resistance, or chronic inflammation and/or anti-viral compounds which are used for the treatment of hepatitis B and/or hepatitis C infections. The benefit of combination is a broader spectrum action for treatment of metabolic syndrome than the single agent, and additional potency of the combination over its components. For example, compositions and methods of treatment of the invention may employ co-administration of a drug such as a biguanide antihyperglycemic agent (e.g. metformin); DPP-IV inhibitors (e.g. Vildagliptin, Sitagliptin, Dutogliptin, Linagliptin and Saxagliptin); TZDs or Thiazolidinediones (which are also known to be active on PPAR), e.g. pioglitazone, rosiglitazone, rivoglitazone, aleglitazar and the PPAR-sparing agents MSDC-0160, MSDC-0602; alpha glucosidase inhibitor including but not limited to acarbose (including delayed release preparations of Acarbose, Miglitol, and Voglibose); Glucokinase Activators including but not limited to TTP399 and the like; HMG-CoA reductase inhibitors. (examples of similar agents, thought to act on the defined statin pathway or by HMG-CoA reductase inhibition, include atorvastatin, simvastatin, lovastatin, ceruvastatin, pravastatin pitavastatin); angiotensin II inhibitors (AII inhibitors) (e.g. Valsartan, Olmesartan, Candesartan, Irbesartan, Losartan, Telmisartan and the like); a phosphodiesterase type 5 inhibitor (PDE5 inhibitor) such as sildenafil (Viagra), vardenafil (Levitra) and Tadalafil (Cialis®); Antiobesity compositions that may benefit from combination with Brake™ include Lorcaserin and Topiramate; Anti-viral agents including anti-hepatitis B agents and anti-hepatitis C agents are as otherwise described herein and include, for example, Hepsera (adefovir dipivoxil), lanivudine, entecavir, telbivudine, tenofovir, emtricitabine, clevudine, val oricitabine, am doxovi r, pradefovir, racivir, BAM 205, nitazoxanide, UT 231-B Bay 41-4109, EHT899, zadaxin (thymosin alpha-1) and mixtures thereof for hepatitis B infections and ribavirin, interferon (such term including all forms of interferon, including pegylated interferon), boceprevir, daclatasvir, asunapavir, INX-189, FV-00, NM 283, VX-950 (telaprevir), SCH 50304, TMC435, VX-500, BX-813, SCH503034, R1626, ITMN-191 (R7227), R7128, PF-868554, TT033, CGH-759, GI 5005, MK-7009, SIRNA-034, MK-0608, A-837093, GS 9190, GS 9256, GS 9451, GS 5885, GS 6620, GS 9620, GS9669, ACH-1095, ACH-2928, GSK625433, TG4040 (MVA-HCV), A-831, F351, NS5A, NS4B, ANA598, A-689, GNI-104, IDX102, ADX184, ALS-2200, ALS-2158, BI 201335, BI 207127, BIT-225, BIT-8020, GL59728, GL60667, PSI-938, PSI-7977, PSI-7851, SCY-635, TLR9 Agonist, PHX1766, SP-30 and mixtures thereof for hepatitis C infections.

The term "anti-Hepatitis C agent" or "anti-HCV agent" is used throughout the specification to describe an agent which may be used alone or in combination in the treatment of HCV and/or secondary disease states and/or conditions of HCV infection and includes such agents as ribavirin, pegylated interferon, boceprevir, daclatasvir, asunapavir, INX-189, FV-100, NM 283, VX-950 (telaprevir), SCH 50304, TMC435, VX-500, BX-813, SCH503034, R1626, ITMN-191 (R7227), R7128, PF-868554, TT033, CGH-759, GI 5005, MK-7009, SIRNA-034, MK-0608, A-837093, GS 9190, GS 9256, GS 9451, GS 5885, GS 6620, GS 9620, GS9669, ACH-1095, ACH-2928, GSK625433, TG4040 (MVA-HCV), A-831, F351, NS5A, NS4B, ANA598, A-689, GNI-104, IDX102, ADX184, ALS-2200, ALS-2158, BI 201335, BI 207127, BIT-225, BIT-8020, GL59728, GL60667, PSI-938, PSI-7977(sofosbuvir), PSI-7851, SCY-635, TLR9 Agonist, PHX1766, SP-30, Grazoprevir, Uprifosbuvir, Velpatasvir, voxilaprevir, ombitasvir, Ruzasvir, Ledipasvir, Paritaprevir, simeprevir, daclatasvir, velpatasvir, elbasvir, Glecaprevir, Pibrantasvir, and mixtures thereof, especially including one or more of the above in combination with ribavirin. Anti-HCV agents which may be used in the present invention may be formulated in pharmaceutical compositions which include an effective amount of an ileal brake composition, which is formulated for release in the ileum pursuant to the present invention and may include immediate release and/or sustained release and/or controlled release compositions and/or components of anti-HCV agents as otherwise described herein.

The term "anti-Hepatitis B agent" or "anti-HBV agent" is used throughout the specification to describe an agent which may be used in the treatment of HBV and includes such agents as Hepsera (adetbvir dipivoxil), lamivudine, entecavir, telbivudine, tenofovir, entecavir, emtricitabine, clevudine, vaitoricitabine, amdoxovir, pradefovir, racivir. BAM 205, nitazoxanide, UT 231-B, Bay 41-4109, EHT899, zadaxin (thymosin alpha-1), alafenamide and mixtures thereof. Anti-HBV agents which may be used in the present invention may be formulated in pharmaceutical compositions which include an effective amount of an ileal brake composition, which is formulated for release in the ileum pursuant to the present invention and may include immediate release and/or sustained release and/or controlled release compositions and/or components of anti-HBV agents as otherwise described herein.

The term "anticancer agent" or "antihepatocellular cancer agent" is used throughout the specification to describe an anticancer agent which may be used to inhibit, treat or reduce the likelihood of hepatocellular cancer, of the metastasis of that cancer. Anticancer agents which may find use in the present invention in combination with an ileal brake hormone releasing compound and in certain instances, such compounds which are further combined with an anti-HCV or anti-HBV agent, include for example, nexavar (sorafenib), sunitinib, bevacizumab, tarceva (erlotinib), tykerb (lapatinib) and mixtures thereof. In addition, other anticancer agents may also be used in the present invention, where such agents are found to inhibit metastasis of cancer, in particular, hepatocellular cancer. In a preferred embodiment, the composition of the present invention may be used in combination with checkpoint inhibitors such as pembrolizumab, nivolumab and ipilumumab and the like, all of which have been shown to have some beneficial activity against solid tumors, to include hepatocellular carcinoma.

Other aspects of the invention relate to compositions which comprise an effective amount of an ileal brake hormone releasing substance as otherwise described herein, preferably glucose or dextrose which is formulated in delayed and/or controlled release dosage form in order to release an effective amount of ileal brake hormone releasing substance in the ileum of the patient or subject to whom compositions according to the present invention are administered, generally, at least about 50% of the total amount of the ileal brake hormone releasing substance present, and preferably at least about 70%, at least about 75%, at least about 80%, at least about 85%, at least about 90%, and at least about 95% or more of the ileal brake hormone releasing substance present in the composition. In the case of D-glucose or dextrose as the ileal brake hormone releasing substance, it is preferred that at least about 2.5 grams, at least about 3 grams, at least about 7.5 grams and more preferably about 10-12.5 grams or more of glucose be released in the patient's or subject's ileum in order to stimulate ileal hormone release.

Coatings for Ileal Brake Hormone Releasing Substances

Compositions according to the present invention comprise effective amounts of ileal brake hormone releasing substance, preferably D-glucose or dextrose, which may be combined with at least one delayed or controlled release component such as a delayed/controlled release polymer or compound such as a cellulosic material, including, for example, ethyl cellulose, methyl cellulose, hydroxymethylcellulose, hydroxypropylcellulose, polyvinylpyrrolidone, cellulose acetate trimellitate (CAT), hydroxypropylmethyl cellulose phthalate (HPMCP), polyvinyl acetate phthalate (PVAP), cellulose acetate phthalate (CAP), shellac, copolymers of methacrylic acid and ethyl acrylate, copolymers of methacrylic acid and ethyl acrylate to which a monomer of methyl acrylate has been added during polymerization, a mixture of amylose-butan-1-ol complex (glassy amylose) with Ethocel® aqueous dispersion, a coating formulation comprising an inner coating of glassy amylose and an outer coating of cellulose or acrylic polymer material, pectins (of various types), including calcium pectinate, carageenins, aligns, chondroitin sulfate, dextran hydrogels, guar gum, including modified guar gum such as borax modified guar gum, beta-cyclodextrin, saccharide containing polymers, e.g., a polymeric construct comprising a synthetic oligosaccharide-containing biopolymer including methacrylic polymers covalently coupled to oligosaccharides such as cellobiose, lactulose, raffinose and stachyose, or saccharide-containing, natural polymers including modified mucopolysaccharides such as cross-linked pectate; methacrylate-galactomannan, pH-sensitive hydrogels and resistant starches, e.g., glassy amylose. Other materials include methyl methacrylates or copolymers of methacrylic acid and methyl methacrylate having a pH dissolution profile that delays release in vivo of the majority of the ileal brake hormone releasing substance until the dosage form reaches the ileum may also be used. Such materials are available as Eudragit® polymers (Rohm Pharma, Darmstadt, Germany). For example, Eudragit® L100 and Eudragit® S100 can be used, either alone or in combination. Eudragit® L100 dissolves at pH 6 and upwards and comprises 48.3% methacrylic acid units per g dry substance; Eudragit® S100 dissolves at pH 7 and upwards and comprises 29.2% methacrylic acid units per g dry substance. Generally, the encapsulating polymer has a polymeric backbone and acid or other solubilizing functional groups. Polymers which have been found suitable for purposes of the present invention include polyacrylates, cyclic acrylate polymer, polyacrylic acids and polyacrylamides. A particularly preferred group of encapsulating polymers are the polyacrylic acids Eudragit® L and Eudragit® S which optionally may be combined with Eudragit® RL or RS. These modified acrylic acids are useful since they can be made soluble at a pH of 6 or 7.5, depending on the particular Eudragit chosen, and on the proportion of Eudragit® S to Eudragit® L, RS, and RL used in the formulation. By combining one or both of Eudragit® L and Eudragit® S with Eudragit® RL and RS (5-25%), it is possible to obtain a stronger capsule wall and still retain the capsule's pH-dependent solubility.

A delayed and/or controlled release oral dosage form used in the invention can comprise a core containing an ileum hormonal-stimulating amount of an ileal brake hormone releasing substance along with carriers, additives and excipients that is coated by an enteric coating. In some embodiments, the coating comprises Eudragit® L100 and shellac, or food glaze Eudragit® S100 in the range of 100 parts L100:0 parts S100 to 20 parts L100:80 parts S100, more preferably 70 parts L100:30 parts S100 to 80 parts L100:20 parts S100. In preferred alternatives, the preferred coating is a nutrateric coating which dissolves at the pH of the ileum (about 7-8, about 7.2-8.0, about 7.4-8.0, about 7.5-8.0) comprising a shellac, and emulsifiers such as triacetone and hypromellose, among others. Alternative nutrateric coatings include ethyl cellulose, ammonium hydroxide, medium chain triglycerides, oleic acid, and stearic acid. As the pH at which the coating begins to dissolve increases, the thickness necessary to achieve ileum-specific delivery decreases. For formulations where the ratio of Eudragit® L100:S100 is high, a coat thickness of the order 150-200 m can be used. For coatings where the ratio Eudragit® L100:S100 is low, a coat thickness of the order 80-120 m can be used in the present invention.

Compositions for use in the present invention preferably comprise the micro-encapsulation of the ileal hormone releasing compounds, e.g., glucose, lipids and dietary components as described hereinabove formulated to release these active compositions at pH values between about 6.8 and about 7.5 preferably about 7.0 to about 7.5, which allows substantial release and targets the action of said medicaments at the ileal brake in the distal intestine. Conventional formulation strategies used for pharmaceuticals never target release at pH values above 6.8. These compositions may be used alone or formulated in combination with an anti-viral agent (preferably an anti-HCV or anti-HBV agent) or other bioactive agent (an anticancer agent effective for example in the treatment of hepatocellular cancer) as otherwise described herein, where the antiviral and/or other bioactive agent is formulated as an immediate release composition and/or a sustained and/or controlled release composition in combination with the ileal hormone releasing compounds. Use of the encapsulated compositions according to the present invention decreases appetite for glucose, which is beneficial to the patient with metabolic syndrome, and thereby lowers both insulin resistance and inflammation and is of benefit to the treatment of patients with metabolic syndrome and related disease states or conditions including T2D, hyperlipidemia, weight gain, obesity, insulin resistance, hypertension, atherosclerosis, fatty liver diseases and certain chronic inflammatory states that lead to these manifestations, among others. In additional aspects, the above compositions may be used alone or co-administered with anti-viral agents, including formulating with anti-viral agents to treat hepatitis viral infections, including Hepatitis B and Hepatitis C viral infections, as well as the secondary disease states and/or conditions which are often associated with such viral infections, including hepatic steatosis (steatohepatitis), cirrhosis, fatty liver and hepatocellular cancer, among other disease states or conditions.

Compositions according to the present invention may be administered at various times during the day (e.g., once a day, twice a day, four times a day) in order to produce the intended effect, i.e., effective treatment of metabolic syndrome, including T2D, hyperlipidemia, weight gain, obesity, insulin resistance, hypertension, atherosclerosis, fatty liver diseases and certain chronic inflammatory states that lead to these manifestations, among others, as well as to treat, inhibit or reduce the likelihood of hepatitis viral infections, including Hepatitis B and Hepatitis C viral infections, as well as the secondary disease states and/or conditions which are often associated with such viral infections, including hepatic steatosis (steatohepatitis), cirrhosis, fatty liver and hepatocellular cancer, among other disease states or conditions related to same. Preferably, compositions according to the present invention are administered once daily, whereby all components, i.e., the ileal hormone release compound and any bioactive agent (including an antiviral agent and/or an anticancer agent as otherwise described herein), if included, are in sustained or controlled release form. In certain aspects, the ileal hormone release compound is in sustained or controlled release form and the bioactive agent is in both immediate and sustained or controlled release form.

In another embodiment, the invention provides a method of treatment comprising once-daily administration to the subject of a delayed and/or controlled release oral dosage form with the target site being the ileal brake. In this aspect of the invention, the dosage form is administered while the subject is in the fasted state and at a time of around six to around nine hours prior to the subject's next intended meal. The dosage form comprises an enterically-coated, ileum hormone-stimulating amount of ileal brake hormone releasing substance and releases the majority of the ileal brake hormone releasing substance in vivo upon reaching the subject's ileum. This formulation may be used alone or in combination with another bioactive agent, including an anti-viral agent such as an anti-HCV or anti-HBV agent or an anticancer agent. Additionally, this formulation may be further combined with immediate, sustained or controlled release bioactive agent, including an anti-viral agent such as an anti-HCV or anti-HBV agent or anticancer agent, or combined with both immediate and sustained or controlled release bioactive agent in order to influence the bioavailability of the bioactive agent combined with the ileal brake hormone releasing substance.

In still another embodiment, the invention provides a method of treatment by administering to the subject a delayed and/or controlled release oral dosage form comprising an enterically-coated, ileum hormone-stimulating amount of an ileal brake hormone releasing substance. The dosage form is administered while the subject is in the fasted state and at a time of around four and one-half to ten hours, more preferably around six to around nine hours prior to the subject's next intended meal. The dosage form comprises an enterically-coated, ileum hormone-stimulating amount of ileal brake hormone releasing substance and releases the majority of the ileal brake hormone releasing substance in vivo upon reaching the subject's ileum. This formulation may be used alone or in combination with another bioactive agent, including an anti-viral agent such as an anti-HCV or anti-HBV agent. Additionally, this formulation may be further combined with immediate, sustained or controlled release bioactive agent, including an anti-viral agent such as an anti-HCV or anti-HBV agent, or combined with both immediate and sustained or controlled release bioactive agent in order to influence the bioavailability of the bioactive agent combined with the ileal brake hormone releasing substance.

In still other preferred embodiments, the invention provides methods for control of MetS and its various detrimental actions, through specific biochemical pathways that stabilize blood glucose and insulin levels, and treating gastrointestinal and hepatic inflammatory disorders comprising once-daily administration to a subject in need thereof of a delayed and/or controlled release composition which may comprise an emulsion or a microemulsion containing an ileum hormone-stimulating amount of ileal brake hormone releasing substance. The composition is administered while the subject is in the fasted state and at a time of around four to ten, preferably around six to around nine hours prior to the subject's next intended meal. The composition releases the majority of the ileal brake hormone releasing substance in vivo upon reaching the subject's ileum, the site of its intended effect. Other bioactive agents are released pursuant to the formulation provided, whether immediate release, sustained or controlled release or immediate and sustained or controlled release.

In preferred embodiments of the aforementioned methods of treatment of the invention, the dosage form is administered once-daily at bedtime, or in AM.

By administering the dosage form to a subject in the fasted state at around four to ten, around six to around nine hours prior to the subject's next intended meal, and delivering substantially all of the ileal brake hormone releasing substance to the ileum, methods and compositions of the invention achieve improved levels of plasma gastrointestinal hormones and prove useful in the treatment or prevention of one or more of MetS and/or T2D, as well as hyperlipidemia, weight gain, obesity, insulin resistance, hypertension, atherosclerosis, fatty liver diseases and certain chronic inflammatory states that lead to these manifestations, among others, as well as hepatitis viral infections, including Hepatitis B and Hepatitis C viral infections, as well as the secondary disease states and/or conditions which are often associated with such viral infections, including hepatic steatosis (steatohepatitis), cirrhosis, fatty liver and hepatocellular cancer, among other disease states or conditions The benefit of obtaining at least twenty-four hour appetite suppression and improved blood glucose and insulin levels from a single oral dosage of an inexpensive ileal brake hormone releasing substance alone or in combination with a bioactive agent as otherwise described herein increases the likelihood that the subject will adhere to the methods of treatment for an extended time (improved patient compliance), thereby achieving a maximum health benefit. Further, compositions and methods of the invention utilize ileal brake hormone releasing substances that are free of the safety and cost concerns associated with pharmacological and surgical intervention, and can induce long-term control of appetite, inflammation, insulin resistance and hyperlipidemia.

In another embodiment, the invention provides a delayed and/or controlled release oral dosage form comprising an effective amount of an ileal brake hormone releasing substance, preferably D-glucose or dextrose in an amount effective when released in the ileum to stimulate or inhibit the release of hormones in that portion of the small intestine of a subject or patient. This dosage form is administered in accordance with, and achieves the advantages of, the aforementioned methods of treatment of the invention. In addition, the present invention provides a method for diagnosing MetS and/or T2D in a patient or subject.

Thus, the invention provides methods of stimulating or inhibiting the hormones (depending on the hormone) of the ileum in an easy and reproducible or standardized way (orally) which did not exist prior to the present method. Indeed, RYGB surgery is the only other way to release these ileal brake hormones and invoke mimicry of the effects of the present invention. Pursuant to the present application, the testing on a large scale of the ileal release to study and classify the variation or pathology of the hormone releases as such release relates to control of MetS or T2D and related pathological states and conditions, and the effect these hormones have on the rest of the metabolic and hormonal status of the body is another aspect of the invention. Thus, the present method allows the introduction of one or more dosages in oral dosage form to the ileum of the patient which can be standardized sufficiently to allow the creation of a normal reference range for the hormonal stimulation. It has been discovered that the present invention can be used to probe different diseases stemming from the relative or absolute increase or decrease of the ileal hormones, not only in treating the overweight/obesity metabolic syndrome axis but a number of other gastrointestinal diseases as otherwise described herein.

In particular aspects, the present invention is directed to treating, inhibiting or reducing the likelihood of hepatitis infections, especially including hepatitis C or B viral infections and secondary disease states and conditions which may occur as a consequence of such infection, which may include MetS, T2D, hyperlipidemia, weight gain, obesity, insulin resistance, hypertension, atherosclerosis, fatty liver diseases and certain chronic inflammatory states that lead to these manifestations, and especially such secondary disease states and conditions including hepatic steatosis (steatohepatitis), cirrhosis, fatty liver and hepatocellular cancer, among other disease states or conditions.

In a particular aspect, the present invention is directed to the collection of Biomarkers and measurements of physical parameters, and the use of these parameters in calculation of the state of health of the liver in patients who are considered for treatment where the intention is to predict the results of biopsy on the liver, or in patients already under treatment, where the intention is to monitor the effects of said treatment on the health of the liver and other organs or tissues. More than one biomarker can be collected from any number of sources and still remain within the scope of the invention. Collection of data and biomarkers can be from any media, to include blood, plasma, serum, urine, breath body fluids of any type or constituency or saliva among others.

Scope of Additional Brake Formulation Embodiments

The teachings of the present invention further accommodate the following understandings and provide the following embodiments.

An ileal brake hormone releasing substance composition containing an effective amount of a sugar such as glucose, (including but not limited to dextrose and further including sucrose, and fructose, among other sugars) alone or in combination with oils (including but not limited to vegetable oils such as cottonseed, oils from most varieties of nuts, palm, corn, germ, olive, castor, sesame, fish oils including omega 3, oleic acid and derived liver oils) may be provided as an ileal brake composition. In the practice of the invention, when oils are used, they must be emulsified and allowed to become solids in emulsified form, and then coated for release in the ileum. When the ileal brake compositions of the present invention are produced to include both glucose and oil components as disclosed herein, the proportion of each of these components may vary from 10% by weight to 90% by weight. Indeed, in various aspects of the invention an ileal brake composition comprises a predominant glucose formulation (from about 50% to 90% by weight glucose or other sugar and about 10% to 50% of an oil as otherwise described herein), a predominant oil formulation (from about 50% to 90% by weight glucose or other sugar and about 10% to 50% of an oil as otherwise described herein) and about a 50:50 mixture (preferably a 50:50 by weight mixture) of glucoses and oils and remain entirely within the spirit of the invention, since optimal formulations and combinations thereof can be defined by the direct impact on biomarkers of the ileal brake and biomarkers of hepatic steatosis.

Other included ileal brake compositions as defined herein, optionally and preferably may comprise effective amounts of one or more of alfalfa leaf, *chlorella* algae, chlorophyllin and barley grass juice concentrate or sodium alginate, alone or in combination with the other ingredients or components.

The final composition in the preferred embodiments should be tested in humans for release of ileal brake hormones, and after this testing, a comparison should be made with the PYY and GLP-1 values for AUC of RYGB patients. Target AUC values for an optimized composition include an AUC of GLP-1 at least 250 and an AUC of PYY at least 350. It will be apparent to one skilled in the art that these are minimum specifications, and values above these minimums may be entirely within the scope of the invention.

The ileal brake compositions according to the present invention may be formulated with a delayed release base adapted to release the composition in the lower gut (ileum), that is, in a delayed and/or controlled release oral dosage form. The coated ingredients of the ileal brake composition of the present invention comprises micro granules or tablets have a pH dissolution profile that delays the release in vivo of the majority of the ileal brake hormone releasing substance (ileal brake compound) until the dosage form reaches the subject's ileum. A delayed and/or controlled release oral dosage form used in the invention can comprise a core containing an ileum hormonal-stimulating amount of an ileal brake hormone releasing substance that is coated by an enteric coating. Coatings for ileal brake compositions according to the present invention are selected from the group consisting of cellulose acetate trimellitiate (CAT), hydroxypropylmethyl cellulose phthalate (HPMCP), hydroxypropylmethyl cellulose, ethyl cellulose and mixtures of hydroxypropylmethyl cellulose and ethyl cellulose each of which contains a subcoating, polyvinyl acetate phthalate (PVAP), cellulose acetate phthalate (CAP), shellac, copolymers of methacrylic acid and ethyl acrylate, and copolymers of methacrylic acid and ethyl acrylate to which a monomer of methyl acrylate has been added during polymerization. In some embodiments, the coating comprises Eudragit® L100 and shellac, or food glaze Eudragit® S100 in the range of 100 parts L100:0 parts S100 to 20 parts L100:80 parts S100, more preferably 70 parts L100:30 parts S100 to 80 parts L100:20 parts S100. As the pH at which the coating begins to dissolve increases, the thickness necessary to achieve ileum-specific delivery decreases. For formulations where the ratio of Eudragit® L100:S100 is high, a coat thickness of the order 150-200 m can be used. For coatings where the ratio Eudragit® L100:S100 is low, a coat thickness of the order 80-120 m can be used.

Oral dosage forms used in methods of preparation of ileal brake compositions according to the present invention can include one or more pharmaceutically acceptable carriers, additives, or excipients. The term "pharmaceutically acceptable" refers to a carrier, additive or excipient which is not unacceptably toxic to the subject to which it is administered. Pharmaceutically acceptable excipients are described at length by E. W. Martin, in "Remington's Pharmaceutical Sciences", among others well-known in the art. Pharmaceutically acceptable carriers, such as sodium citrate or di-calcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents.

In addition to the preferred formulations of micro granules or tablets, exemplary dosage forms that will release the majority of the ileal brake hormone releasing substance in vivo upon reaching the ileum include oral dosage forms such as coated tablets, troches, lozenges, dispersible powders or granules, suspensions, emulsions or hard or soft capsules, each of which are formed after coating the ileal brake hormone releasing substance with an enteric coating. In the case of capsules, tablets and pills, the pharmaceutical compositions may also comprise buffering agents to maintain local pH at values below those that would allow the coating to disintegrate or dissolve. Solid compositions of a similar type may also be employed as fillers in soft and hard-filled gelatin capsules using such excipients as lactose or milk glucoses, as well as high molecular weight polyethylene glycols and the like.

Particular and Preferred Methods of the Present Invention:

NAFLD and NASH, when defined by said mathematical model, may be effectively treated by an orally administered, ileal brake hormone releasing composition according to the present invention. The beneficial use of the ileal brake hormone releasing substance immediately lowers elevated insulin resistance, and lowers elevated liver enzymes such as ALT and AST, and lowers serum triglycerides. The ileal brake hormone releasing substances disclosed as components of a composition and described herein, act on the liver and other organs of nutrition and metabolism as a mimetic of the effect of RYGB surgery.

When said ileal brake hormone releasing treatment described herein is applied to treatment of a patient afflicted with Hepatitis C, the primary beneficial action of the ileal brake hormone releasing substance (ileal brake compound) is to decrease the supply of glucose to the liver and thereby engaged in triglyceride synthesis that the virus also uses as part of this pathway to reproduce, and thereby lower the degree of fatty accumulation in the liver, and limit viral reproduction and further injury to the liver.

Example 1. Predictive Mathematical Modeling for Outcomes in NASH and NAFLD Patients It remains difficult to predict the status of the liver using single biomarkers, and this often necessitates a biopsy or a scanning method for both diagnosis and monitoring of treatment response. We have been developing multi-parameter models of Metabolic Syndrome (MetS) driven diseases such as Insulin Resistance, T2D and obesity. The application to NASH and NAFLD was a logical extension of these methods, and the goal was to predict the biopsy results and also to define improvement and define optimal time for a repeat biopsy. To quantify these changes, we developed the FS (Fayad-Schentag) index to quantify the progression of MetS and to characterize its remission after RYGB surgery. RYGB surgery remediates insulin resistance and abdominal obesity, and what follows is a concomitant improvement in the lab biomarkers of T2D, NAFLD and NASH. Brake™ is an oral mimetic of the RYGB effect on the ileal brake, as it releases carbohydrates at the ileum and produces the same magnitude of ileal hormone release. The purpose of our work was to develop a Neural Net Model descriptive of the progression from MetS to NASH and its laboratory biomarker response to treatments including RYGB and potentially oral Brake™. However, just the modeling of FS index does not directly predict biopsy, so further work was undertaken by the inventors to arrive at this important means.

Neural Net Models have been developed in MatLab, in order to generate transfer functions of factor vs. output to generate predictive scores based on RMS error from the reference. The Neural Net Model considered a minimum of 50 input parameters for their relative strength of correlation with the output of a predicted biopsy score. Inputs of liver signal and biomarkers were combined to define predictive biopsy fibrosis and steatosis scores, and these values were compared with measured values in patients. The input correlation with these four outputs was expressed as rank ordered Minimum Mean Squared Error (MMSE) values. Composite outputs such as wCombLiver signal, and FS index were more predictive of biopsy findings than any single parameter. Among single biomarkers, Bilirubin, GGT, Insulin, MAP, hsCRP, BMI and Albumin displayed the lowest MMSE values. Treatment with RYGB or Brake resolved all of the output markers, offering the potential for improvement in both NAFLD and NASH.

This Neural Net Model illustrates NAFLD as a consequence of MetS, and when inflammation develops, there is progression to NASH. The Liver enzymes, Lipid ratios, T2D parameters, and other biomarkers of MetS are predictive of the development of NAFLD. The prospects for effective treatment of NAFLD with RYGB or Brake are validated by the Neural Net Model developed here, as similar improvements in predictive biomarkers were seen between Brake™ treated and RYGB treated patients. Finally, the results on biopsy were predicted by the biomarker patterns used to define the model and its outputs.

Calculation Parameters for Modeling Progression from Normal to NAFLD to NASH

Identifying Enriched Patients

Patients are identified as enriched using the combined and windowed MI output from the model for this particular case. Particularly the data are normalized and the standard deviation is computed. For each data entry point, the distance from norm is calculated based on the standard deviation multiples. Using these data patterns of enrichment are characterized by the triangular function defined as:

$$\Lambda(t) = \begin{cases} m\left(1 - \frac{|\alpha t|}{\tau}\right) & \text{when } |\alpha t| < \tau \\ \mu & \text{otherwise} \end{cases}$$

Where $\tau$ is the rise and fall time of the deviation from normal in days, t is the time displacement from max deviation, is the minimum standard deviation m is the maximum standard deviation and $\alpha$ is a scaling factor.

The simulation first identifies the maximum standard deviation from normal and the adjacent minimum standard deviations to compute the relation. Time values for each value are identified based on the available data and the $\Lambda(t)$ is populated. $\Lambda(t)$ is overlaid with the normalized standard deviation based windowed MI data for a qualitative review and the data are cross-correlated to identify the quantitative relationship. The correlation coefficient $C_P$ is used as the measurement of similarity between the two signals where $0 < |C_P| < 1$. Coefficient values above 0.7 are considered strong and are defined as enriched. Visual inspection of graphic output is always used to verify the population included.

Modeling the Systems

Modelling is completed in the following manner. First, data are loaded into the MatLab environment via data files which include all of the parametric patient data. The data are then organized such that for each patient all recorded factors (e.g., blood pressure, albumin levels, etc.) and their corresponding values are part of a structured time based array. Each patient's data array thus includes multiple factors, typically more than 25. Patients are assigned ID numbers so that duplicate entries are not possible. As the data are loaded, input data are verified using the unique IDs and stored in a sequential manner based on their time stamps. In addition to structuring the data, patients are also sorted in "control" and "load" groups. The populations are pre-sorted in the load data and no unique algorithm is used for sorting during the loading process.

After the data are loaded patient lists may be modified to include or remove patients with or without certain factors. For example, if blood pressure is an essential factor for analysis, we may remove patients without these data. This is accomplished by a simple looped investigation of all patients and their parameter lists. For this particular study, filtering was limited to patients who included at a minimum the following factors: TG, HDL, BMI, systolic blood pressure (bps), and diastolic blood pressure (bpd).

Following this preliminary filtering, patient data are analyzed to ascertain the first and last dates available for all factors listed. Each patient is loaded separately into a looping function which examines all factors in the structured array, and determines the minimum, $T_{Min}$, and largest, $T_{Max}$, time. The purpose is to determine time scales for events occurring, measurement data times, and time constants for the simulation as will be described later. For this analysis, discrete time intervals of $\delta_{Time}=30$ days are created between $T_{Min}$ and $T_{Max}$. The number of data points for all patients is therefore defined by eq. (X.1).

$$N_T = \frac{T_{Max} - T_{Min}}{\delta_{Time}} \quad (X.1)$$

$$F_i = F_1 + (F_2 - F_1)\frac{T_i - T_1}{T_2 - T_1} \quad (X.2)$$

$$D_{PFN} = \frac{D_{PFO} - \mu_{PF}}{\sigma_{PF}} \quad (X.3)$$

Note that this represents a much larger data set of possible values than are given in the loaded data. To deal with this, we populate arrays of time data for each patient's list of factors by filling it in initially with existing data that falls within the time limits, and then given intervals, and the populate the remaining cells in the array with zero values to create empty data cells. The simulation searches for all zero values, and interpolates using a linear interpolant to populate the remaining cells, as described by eq. (X.2). Where, $F_i$ is the value of the factor data in the $i^{th}$ cell of the time data, $T_i$, is the time which that factor data occurs in 30 day discrete intervals, $F_1$ and F2 are the most proximal real data before and after the empty time data cell, respectively, and $T_1$ and T2 are the times of the most proximal real data points before and after the empty time data cell.

These time data are then split into two groups, original data, $D_{PFO}$, as presented above, and normalized data, $D_{PFN}$, which is defined in eq. (X.3). Where P denotes the patient, and F is the factor. Each patient will have a different mean, $\mu$, and standard deviation, $\sigma$, of the time data array for each factor. These normalized data are used to define models which represent the input/output characteristics of each patient. Particularly, the loaded factor lists are patient inputs, while conditions such as MI, Stroke, and Bleeding are outputs we wish to identify.

$$H_x(\xi) = \frac{\hat{g}_o(\xi)}{\hat{f}_i(\xi)} \quad (X.4)$$

$$\hat{g}_o^*(\xi) = H_x(\xi) * \hat{f}_i(\xi) \quad (X.5)$$

$$W = G * G^P \quad (X.6)$$

$$H_{Opt} = W * \{H_x(\xi)\} \quad (X.7)$$

The model aims to identify the relationship between these inputs and pre-defined output. We accomplish this by determining transfer functions for all factors simultaneously, as well as all factors individually. The transfer functions are determined first by taking the fast Fourier transform (FFT) of each input, $\hat{f}_i$, (i.e., each factor) and output, $\hat{g}_o$, (i.e., MI, stroke, bleed) signal and rearranging them so that the zero-frequency is in the middle. All possible transfer functions are then determined for each patient by deconvolution of the output and inputs as per eq. (X.4); where x is a number in the set of all possible transfer functions which is defined by the number of factors for each patient, and $\xi$ is a real number. Before convolution it is required that any empty data sets (or zero signals) are removed to eliminate the possibility of dividing by zero. Then, we create output estimates, $\hat{g}_o^*$, using each input, $\hat{f}_i$, and each transfer function, $H_x(\xi)$ as per eq. (X.5). This creates a matrix of output estimates, $G_p$, for each patient, p. By combining all $G_p$'s into a single matrix, we can solve for the simple optimized transfer function. This is accomplished by first taking the Moore-Penrose pseudo-inverse of G, denoted as $G^P$ and convolving the two to find a matrix of weights, W, as per eq. (X.6). We then solve for the simple optimum transfer function for each patient by solving eq. (X.7).

When the simple optimized transfer function is determined, we rerun the simulations using a sequential optimization and a rank ordered optimization. The sequential optimization runs each input parameter individually, and the best model is selected as a residual based on the minimum calculated error (see subsequent section). Then the residual model is used to rerun all the inputs again, to find the next best model, and this continues, as the process is looped until all models are solved, and are rank ordered sequentially and are given minimum mean squared error scores based on the subsequent section.

This list provides a learned optimization ranking of the models and their efficacy to use the factors as a predictive marker for the output of interest. To complete the optimization however, the learned sequential optimization is rerun one more time through an ordered optimization to create the final rank ordered output of models. The ordered optimization takes the top 5 factor indicators and groups them into a single model, then each factor is rerun individually to identify the lowest error (as described in the next section), and are ranked in that order.

Model Error Calculations

For any step in the analysis which includes a selected model (i.e., transfer function), the following method is used for calculating the error. First, an estimated output is calculated as per eq. (X.5). Then, an RMS error is computed by eq. (X.8). The error is then normalized based on the RMS of the signal, eq. (X.9).

$$\varepsilon = \sqrt{\left(\frac{\Sigma \hat{g}_{o,n} - \hat{g}_{o,n}^*}{N}\right)^2} \quad (X.8)$$

$$\hat{\varepsilon} = \frac{\varepsilon}{\sqrt{\left(\frac{\Sigma \hat{g}_{o,n}}{N}\right)^2}} \quad (X.9)$$

When we use the same transfer function to determine errors for multiple factors, or patients, then we compute the cumulative sum of errors to define the overall error of the transfer function for all systems, as depicted in the results.

Additional Calculated Factors

There are some additional factors included in the simulations which are calculated as a combination of other factors which are part of the existing database. Those of interest include mymap, mygap, lipidrat, and tgRatH given by the following equations.

$$mymap = bpd + \frac{1}{3}(bps - bpd) \quad (X.10)$$

$$mygap = bps - bpd \quad (X.11)$$

$$lipidrat = \frac{ldl}{hdl} \qquad (X.12)$$

$$tgRatH = \frac{ldl + tg}{hdl} \qquad (X.13)$$

Where it is assumed that any factors combined have matching time data so that, for example in eq. (X.12), LDL and HDL have data taken at the same time, so that lipidrat becomes an array of data of the same size as LDL and HDL.

Biomarkers Used in NASH and NAFLD Modeling

A database was assembled to test the Model of Combined liver signal vs the Result of liver biopsy and other definitive diagnostic criteria of NASH. This database was assembled from direct review of de-identified Medical Records over years of follow-up. The Model development database contained 104 pediatric patients (ages 8-20 year old) and 96 adults with diagnosis of NASH, aged 45-68. Also included were RYGB patients (N=17) and Brake treated patients (N=18) described later in this disclosure. All patients had serial measurements of laboratory biomarkers, but only the 104 pediatric patients had a liver biopsy. All input calculations (wCombLiver Signal, wCombBiopsy, FS index, CV index and each individual laboratory biomarker) were made serially and related to outputs as described on each patient by the Model.

An example of the output of the Model, shown as MMSE rank ordered outputs, is provided as FIG. 2 for biopsy score and wCombLiver Signal and FIG. 3 for wComb Biopsy prediction over time.

Figure 5:
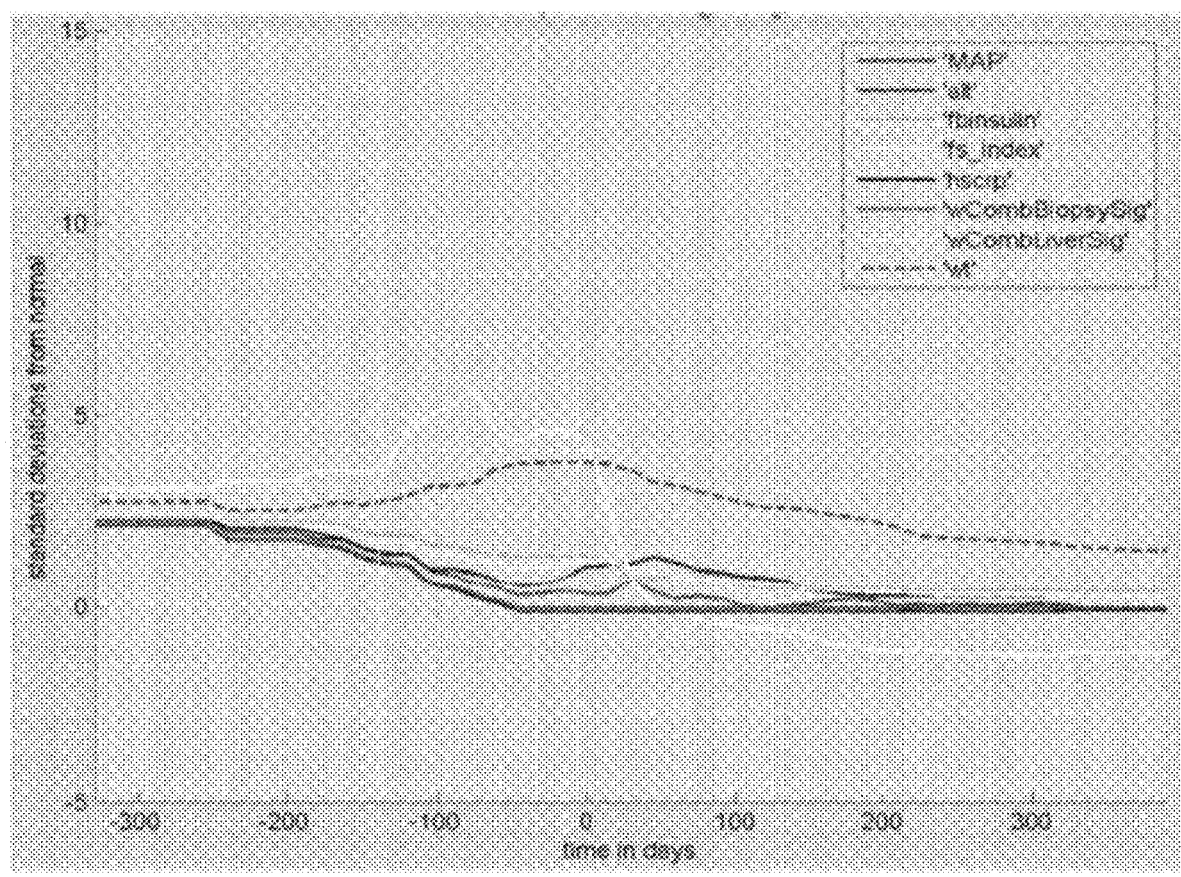
Figure 6:
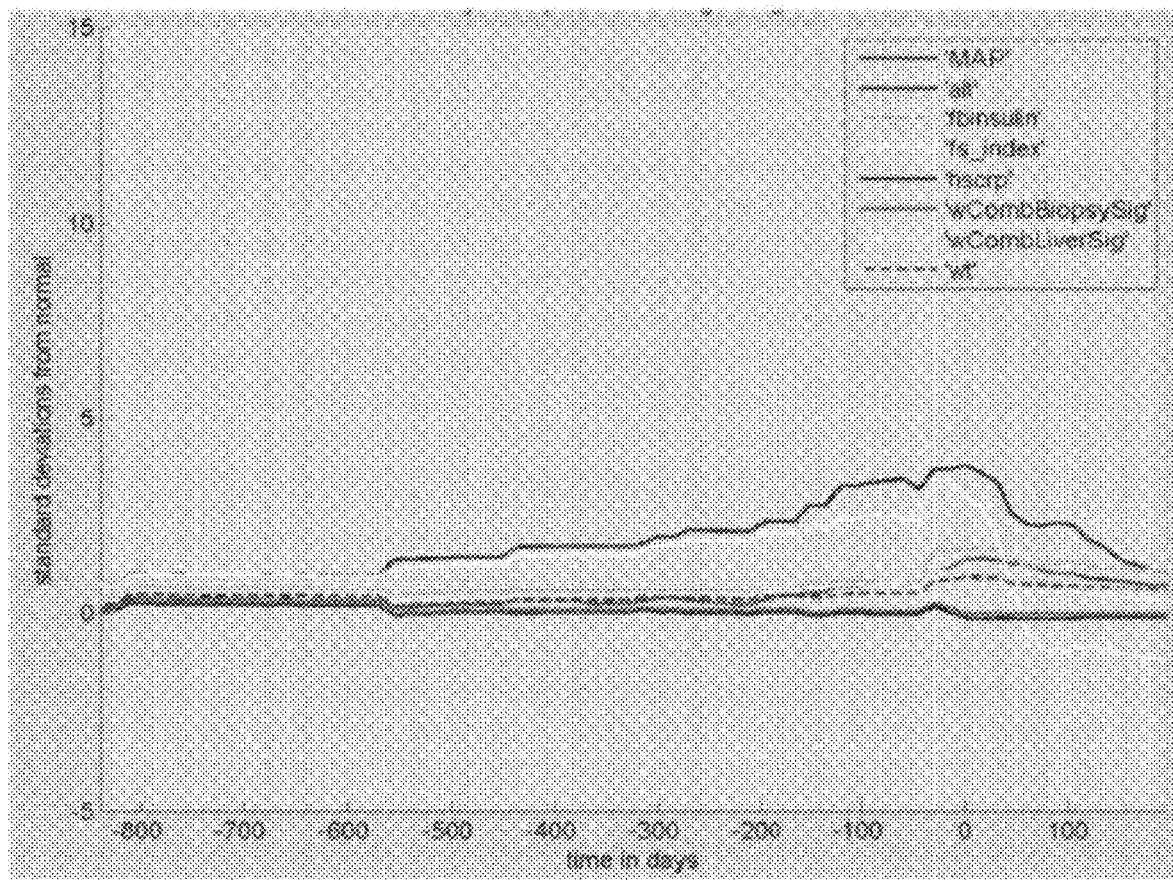

The next three Figs. show time related outputs of the model for the component populations, whereby FIG. 4 illustrates the NASH patients, FIG. 5 illustrates the RYGB patients, and FIG. 6 illustrates the Brake patients.

One additional aspect of Input-Output modeling of the predictive parameters is to develop a graphical output that shows change in a parameter between each patient's value pre versus that same patients value post treatment. Illustrative examples are provided for some of the biomarkers, in order to illustrate their behavior around an intervention, such as RYGB surgery or starting treatment with Brake. Or simply pre and post a diagnosis, such as NASH or HCC.

Figure 7:
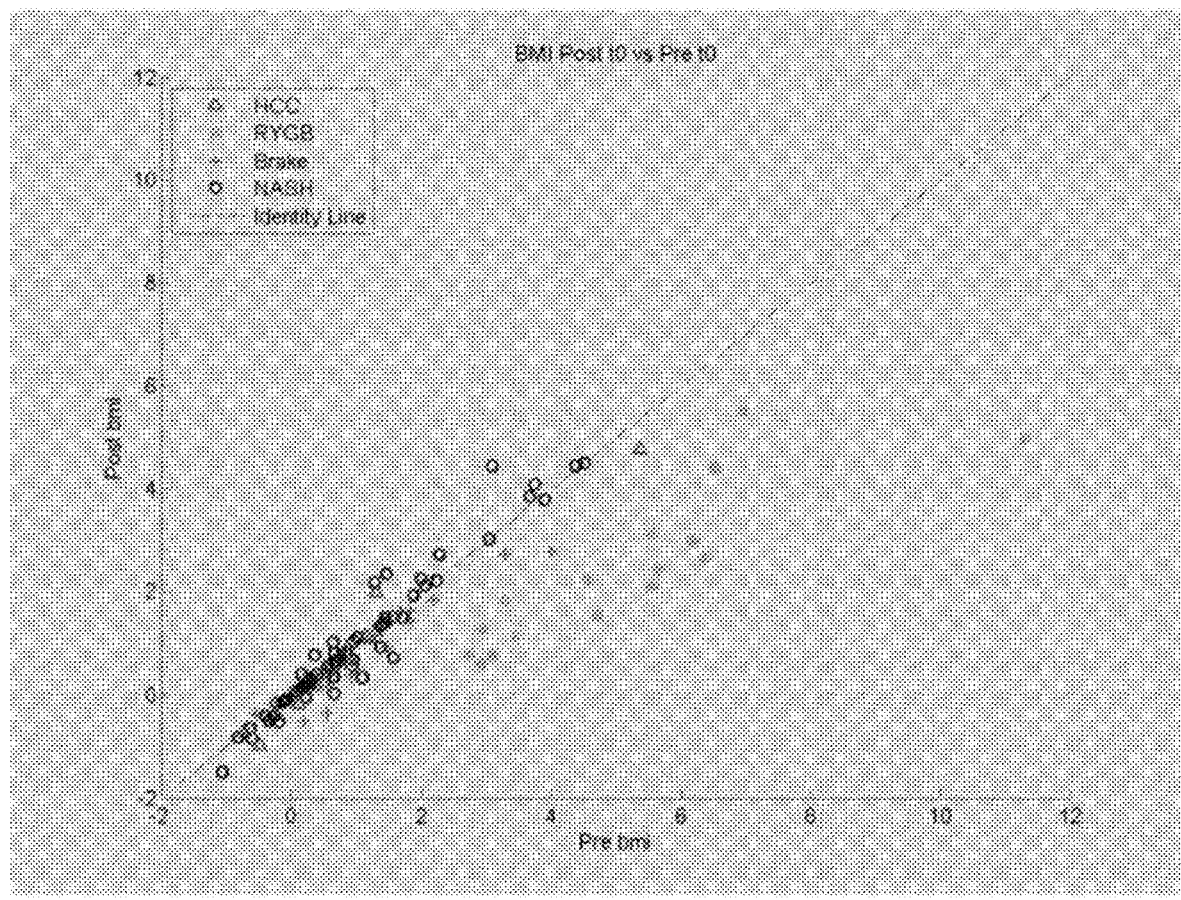

FIG. 7 shows BMI as an example and illustrative parameter, where the BMI measured post intervention was compared with the BMI measured pre-intervention. In FIG. 7, the numerical value of BMI post is the same as pre for the NASH and HCC patients, while BMI is affected by RYGB in a dramatic way so all the values are below the line of identity, as would be expected for dramatic weight loss. Brake also decreases BMI to some extent because there is weight loss in both situations, so most points post are below the line of identity as shown in FIG. 7. The line of identity is shown so that it may be appreciated that the post value is lower than the pre value for RYGB and Brake, while the NASH is somewhat worse in many patients because they are not treated and as a consequence they continue to gain weight.

Figure 8:
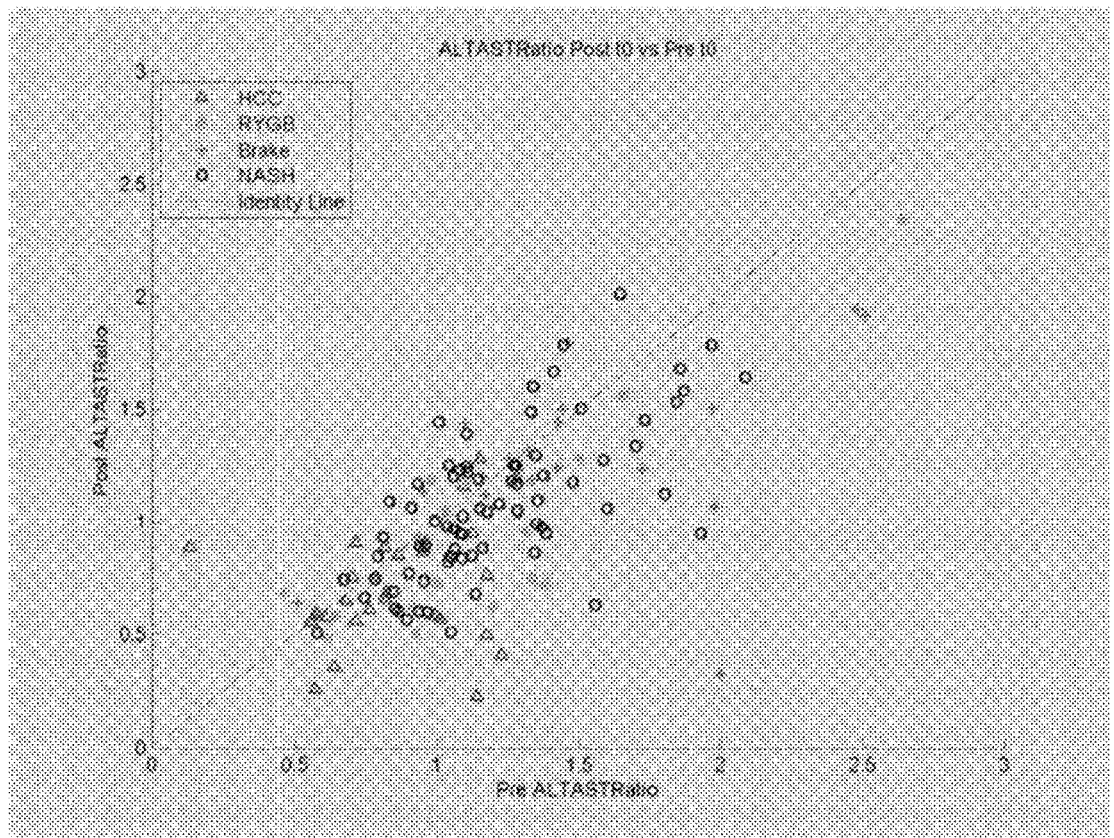

FIG. 8 shows ALT/AST ratio as an example and illustrative parameter, where the ratio measured post intervention was compared with the ratio measured pre-intervention. In FIG. 8, the numerical value of the ratio post is the same as pre, for the NASH and HCC patients, while the ratio is affected by RYGB in a dramatic way so nearly all those values are below the line of identity, as would be expected for dramatic lowering of inflammation and weight loss. Brake also decreases ALT/AST ratio to some extent because there is weight loss in both situations, so most points post are below the line of identity as shown in FIG. 8.

Figure 9:
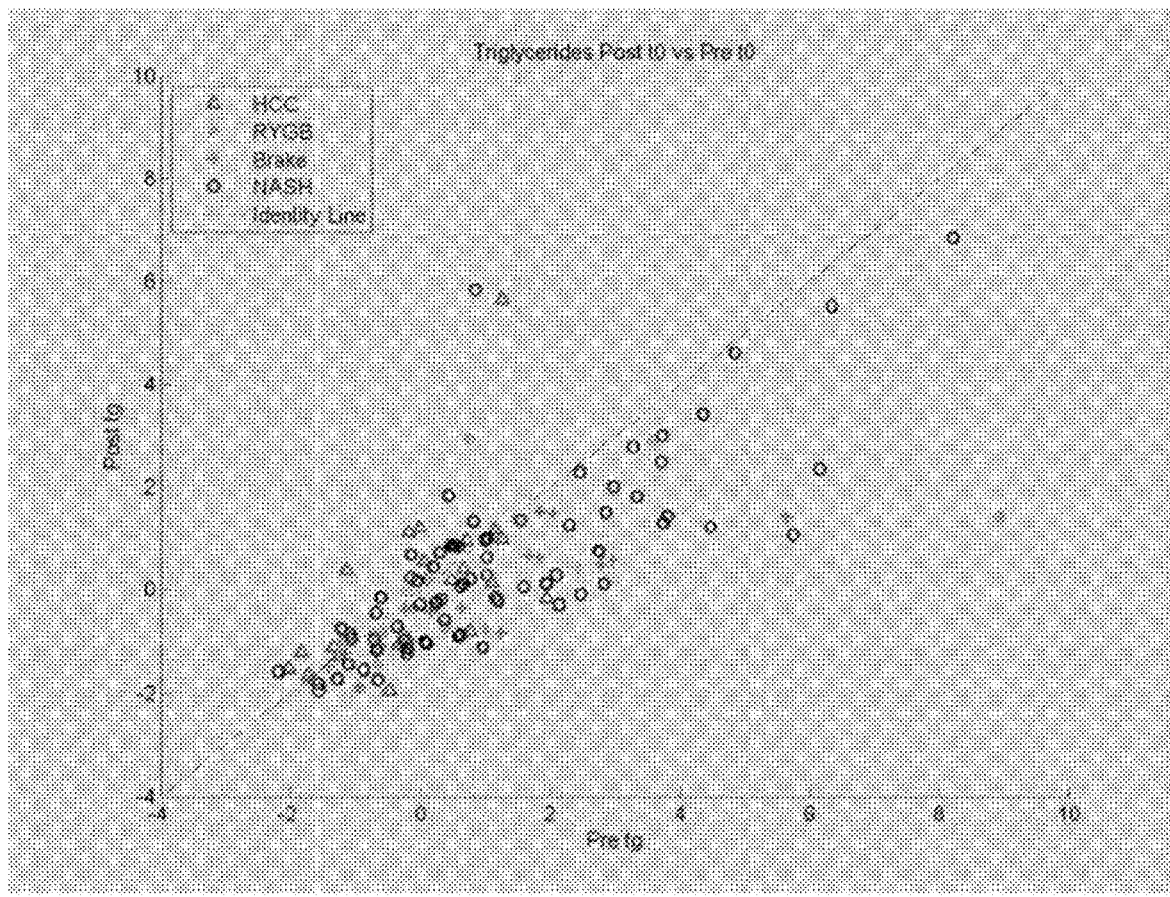

FIG. 9 shows Triglyceride (TG) concentration plotted as SD multiples over normal as an example and illustrative parameter, where the TG measured post intervention was compared with the TG measured pre-intervention. In FIG. 9, the numerical value of the TG post is the same as pre, for the NASH and HCC patients, while the TG is affected by RYGB in a dramatic way so $$\frac{0.11\left((FBG+TG)+HBA1c\times\dfrac{HBA1c\times 20}{5}+BMI\times\dfrac{FBG+TG}{150}+AST\times\dfrac{TG\times 4}{100}+FB\text{ insulin}\times(BMI-22)\right)}{S/D\text{ ratio}}$$

$$\text{Glucose Supply }(S)/\text{Insulin Demand }(D)=\frac{1+((CE)+(HGU)+(GNG)+(IR))}{1+(PIE+PGU)}$$

nearly all those values are below the line of identity, as would be expected for dramatic lowering of inflammation and weight loss. Brake also decreases Triglycerides to some extent because there is about the same decline in insulin resistance in both situations, so most points post are below the line of identity as shown in FIG. 9.

FS index and Biomarkers of Progression of the MetS Signal

Figure 10:
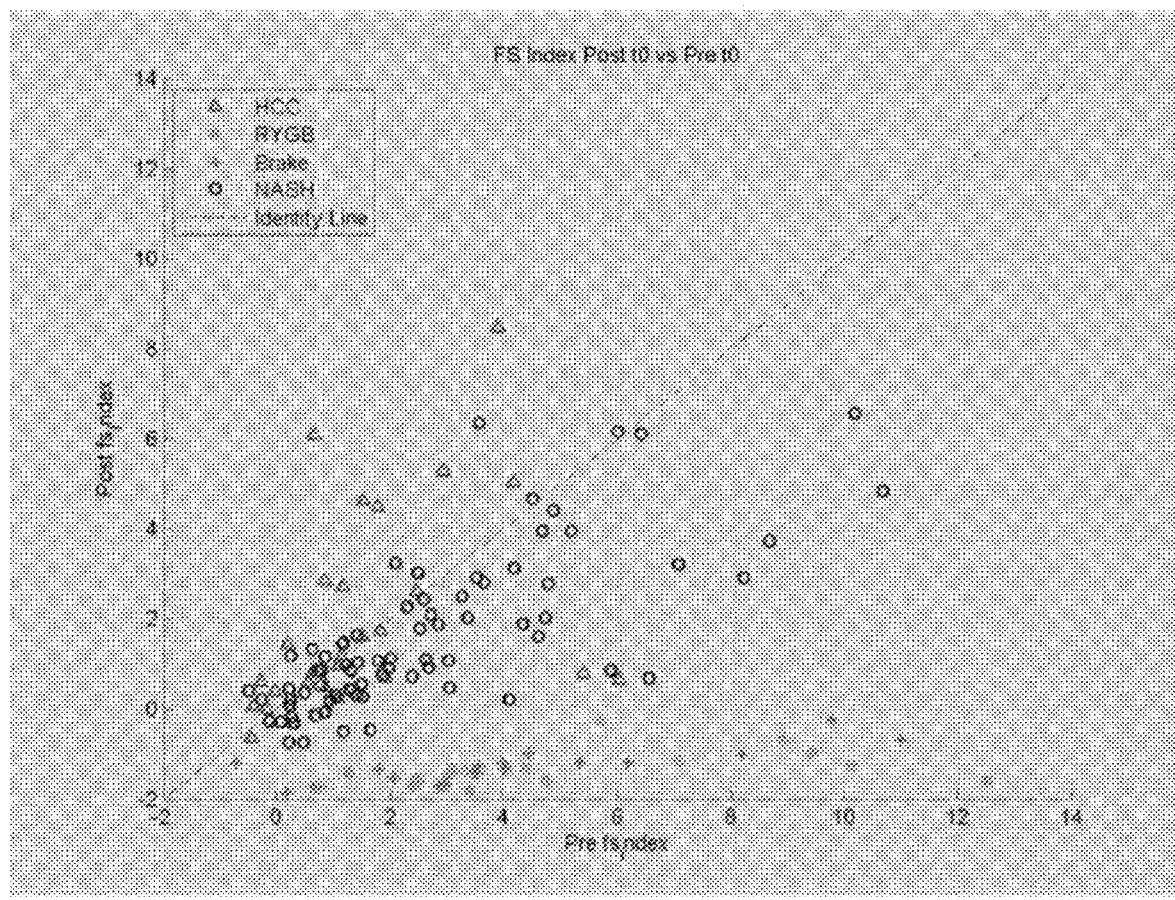

In the modeling, FS index is calculated as:

FIG. 10 shows FS index plotted as SD multiples over normal as an example and illustrative parameter, where the FS index measured post intervention was compared with the FS index measured pre-intervention. In FIG. 10, the numerical value of the FS index post is the same as pre, for the NASH and HCC patients, while the FS index is affected by RYGB in a dramatic way so nearly all those values are below the line of identity, as would be expected for dramatic lowering of inflammation and weight loss. As a mimetic of RYGB surgery, Brake also decreases FS index to about the same extent because there is about the same decline in insulin resistance in both situations, so most points post are below the line of identity as shown in FIG. 10.

Predictive Methods for Liver Biopsy Markers

Disease progression in non-alcoholic fatty liver disease (NAFLD) is not well understood and there is controversy about whether non-alcoholic fatty liver (NAFLD, i.e., steatosis alone or with mild inflammation not qualifying for steatohepatitis) can evolve towards steatohepatitis (NASH) with fibrosis. The authors reviewed 70 patients with untreated NAFLD and obtained two biopsies performed more than one year apart. Clinical and biological data were recorded at the time of both liver biopsies. Alcohol consumption did not change during follow-up. Initially 25 patients had NAFLD and 45 had NASH and/or advanced fibrosis. After a mean follow-up of 3.7 years (s.d. 2.1), 16 NAFLD patients developed NASH, eight with severe ballooning and six with bridging fibrosis on the follow-up biopsy. Patients with mild lobular inflammation or any degree of fibrosis were at higher risk of progression than those with steatosis alone. Those with unambiguous disease progression were older and had worsening of their metabolic risk factors (higher weight and more diabetes at baseline and during follow-up). In the whole cohort, ballooning progression and bridging fibrosis often occurred together and co-existed with a reduction in ALT, higher weight gain, and a higher incidence of diabetes during follow-up. The authors found that a substantial proportion of patients with NAFLD can progress towards well-defined NASH with bridging fibrosis, especially if metabolic risk factors deteriorate. Even mild inflammation or fibrosis could substantially increase the risk of progression when compared to steatosis alone(35)

Liver biopsy is considered as the gold standard for assessing non-alcoholic fatty liver disease (NAFLD) histologic lesions in patients with severe obesity. The aim of this study was to perform an overview of 3 studies which assessed the performance of non-invasive markers of fibrosis (FibroTest), steatosis (SteatoTest) and steato-hepatitis (NASH Test, ActiTest) in these patients. METHODS: 494 patients with interpretable biopsy and biomarkers using of three prospective cohorts of patients with severe obesity (BMI>35 kg/m2) were included. Histology (NAS score) and the biochemical measurements were blinded to any other characteristics. The area under the ROC curves (AUROC), sensitivity, specificity, positive and negative predictive values were assessed. Weighted AUROC (wAUROC Obuchowski method) was used to prevent multiple testing and spectrum effect. Two meta-analyses were performed; one used the individual patient, and the other a classical meta-analysis. RESULTS: Prevalence of advanced fibrosis (bridging) was 9.9%, advanced steatosis (>33%) 54.2%, and steato-hepatitis (NAS score >4) 17.2%. The mean wAUROCs were: FibroTest for advanced fibrosis (95% CI; significance)=0.85 (0.83-0.87; P<0.0001); SteatoTest for advanced steatosis=0.80 (0.79-0.83); and ActiTest for steato-hepatitis=0.84 (0.82-0.86; P<0.0001). Using the classical meta-analysis (random effect model) the mean AUROCs were: FibroTest=0.72 (0.63-0.79; P<0.0001); SteatoTest=0.71 (0.66-0.75; P<0.0001); and ActiTest=0.74 (0.68-0.79; P<0.0001). Despite more metabolic risk factors in one cohort, results were similar according to gender, presence of diabetes and between the 3 cohorts. Thus in patients with severe obesity, a significant diagnostic performance of FibroTest, SteatoTest and ActiTest was observed for liver lesions.(36)

wComb Liver Signal and wComb Biopsy Signal

The means of calculation of the primary means of biomarker modeling of the liver status over time is disclosed as a composite equation. In order to arrive at even weighting of input parameters used to predict outputs, and avoid the tendency of larger numbers to overwhelm smaller numbers, a normalization method was developed in the construction of composite signals. The table below shows the normalization for wComb Liver Signal, and is meant to be illustrative of the process used to develop composite signals for other parameters in this modeling process.

| Factor (F) | Normalization ($\eta$) |
| --- | --- |
| Alkaline Phosphatase | 1/82.7 |
| ALT | 2/21.4 |
| AST | 2/25.8 |
| Bilirubin_total | 2/0.66 |
| Insulin Conc | 1/4.8 |
| hsCRP | 1/1.18 |
| platelet_count | 2/171.8 |
| Total Protein | 1/7.3 |
| PT | 2/4.0 |
| INR | 2/0.99 |
| Lymphocyte count | 2/2.38 |
| waist_circumference | 1/117.5 |
| waist_circumference | 1/117.5 |

-continued

| Factor (F) | Normalization ($\eta$) |
| --- | --- |
| Bilirubin_direct | 2/0.23 |
| lymphocytes_% | 2/34.68 |
| GGT | 1/32.26 |
| Weight | 1/178.7 |
| BMI | 1/26.18 |
| LDH | 1/172 |
| HbA1c | 1/6.13 |
| drug_statin_dose_mg | 1 |
| drug_pioglitazone | 1 |
| drug_chol_fibric_acid_derivative | 1 |
| drug_chol_statin | 1 |

The windowed combined liver signal (wComb Liver signal) is generated by adding all normalized factors, F, given in the above table using the normalization quantity, r, based on the range of the factor.

It is given by the relationship:

$$wCombLiver = \Sigma \eta F$$

In a similar manner, the windowed combined biopsy signal (wComb Biopsy signal) is generated by adding all biopsy scores, including steatosis, fibrosis, ballooning and inflammation.

Ballooning can have values of 0 (no ballooning) or 2 (ballooning present), while the remaining 3 biopsy factors have values between 0 and 3 based on the severity of the biopsy measurement. No further normalization was applied here because the numbers are all of similar magnitude. The biopsy signal is thus determined by:

$$wCombBiopsy = Steatosis + Fibrosis + Inflammation + Ballooning$$

The windowed combined biopsy signal disclosed herein is also generated by adding all biopsy scores, including steatosis, fibrosis, ballooning and inflammation. Ballooning can have values of 0 (no ballooning) or 2 (ballooning present), while the remaining 3 biopsy factors have values between 0 and 3 based on the severity of the biopsy measurement. The biopsy signal is thus determined by:

$$wCombBiopsy = Steatosis + Fibrosis + Inflammation + Ballooning$$

Further discussion of these descriptive composite output parameters is provided below in the Figs.

Figure 11:
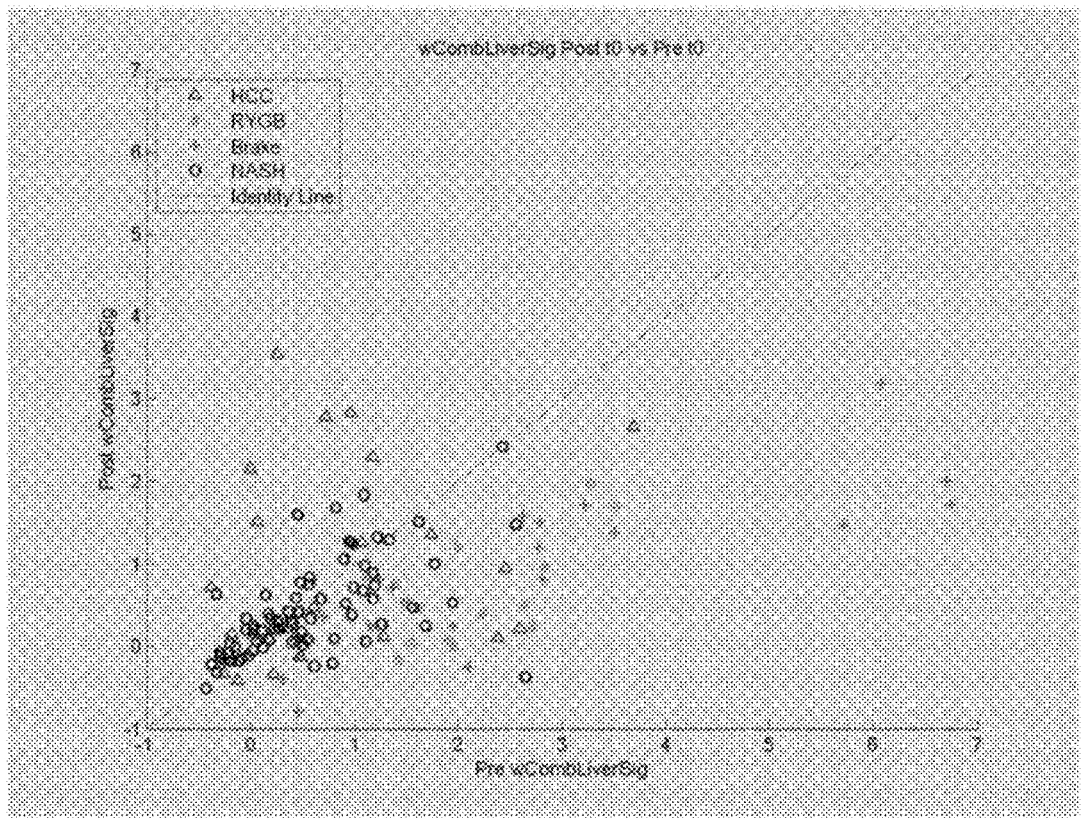

FIG. 11 shows wComb Liver signal plotted as SD multiples over normal as an example and illustrative parameter, where the wComb Liver signal calculated by the model post intervention was compared with the wComb Liver Signal calculated pre-intervention. In FIG. 11, the numerical value of the wComb Liver Signal post is the same as pre, for the NASH and HCC patients, while the wComb Liver Signal is affected by RYGB in a dramatic way so nearly all those values are below the line of identity, as would be expected for dramatic lowering of inflammation and weight loss. As a mimetic of RYGB surgery, Brake also decreases wComb Liver Signal to about the same extent because there is about the same decline in insulin resistance in both situations, so most points post are below the line of identity as shown in FIG. 11.

Figure 12:
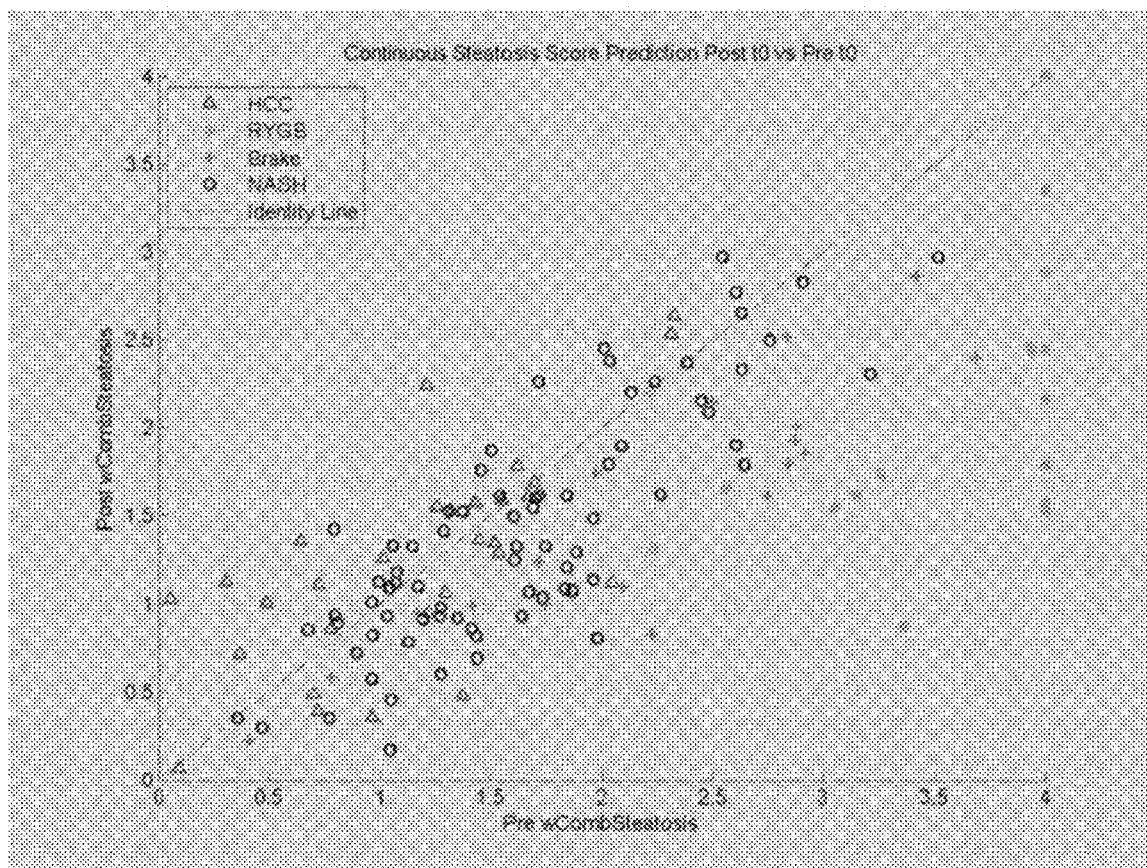

FIG. 12 shows the calculated steatosis score plotted as an example and illustrative parameter, where the steatosis score calculated by the model post intervention was compared with the Steatosis score calculated pre-intervention. In FIG. 12, the numerical value of the calculated steatosis score post is similar to the score pre, for the NASH and HCC patients. In contrast, the steatosis score is affected by RYGB in a dramatic way so nearly all those values are below the line of identity, as would be expected for dramatic lowering of inflammation and weight loss. As a mimetic of RYGB surgery, Brake also decreases steatosis score to about the same extent because there is about the same decline in insulin resistance in both situations, so most points post are below the line of identity as shown in FIG. 12

Figure 13:
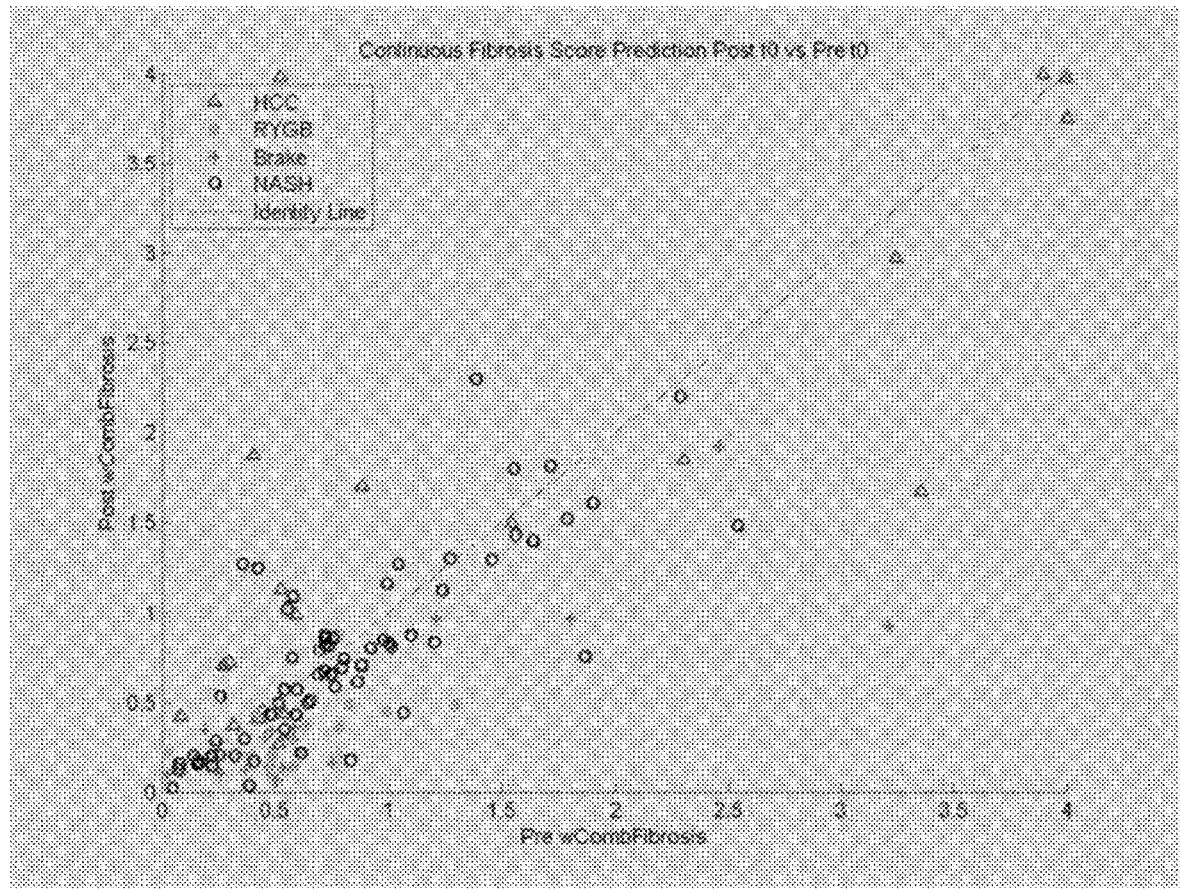

FIG. 13 shows the calculated fibrosis score plotted as an example and illustrative parameter, where the fibrosis score calculated by the model post intervention was compared with the fibrosis score calculated pre-intervention. In FIG. 13, the numerical value of the calculated fibrosis score post is similar to the score pre, for the NASH and HCC patients. In contrast, the fibrosis score is affected by RYGB in a dramatic way so nearly all those values are below the line of identity, as would be expected for dramatic lowering of inflammation and weight loss. As a mimetic of RYGB surgery, Brake also decreases fibrosis score to about the same extent because there is about the same decline in insulin resistance in both situations, so most points post are below the line of identity as shown in FIG. 13

Figure 14:
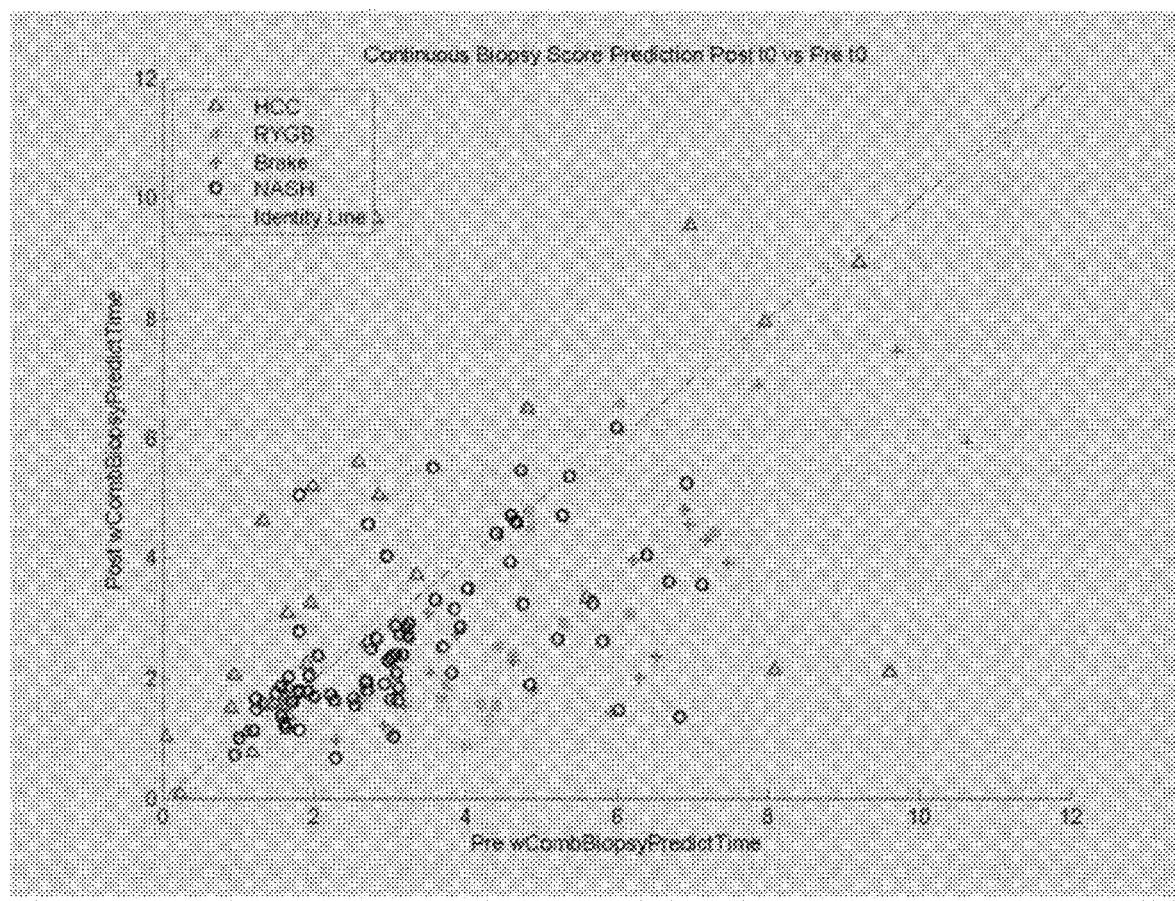

FIG. 14 shows the calculated biopsy score (wComb Biopsy Predict) plotted as an example and illustrative parameter, where the biopsy score calculated by the model post intervention was compared with the biopsy score calculated pre-intervention. In FIG. 14, the numerical value of the calculated biopsy score post is similar to the score pre, for the NASH and HCC patients. In contrast, the biopsy score is affected by RYGB in a dramatic way so nearly all those values are below the line of identity, as would be expected for dramatic lowering of inflammation and weight loss. As a mimetic of RYGB surgery, Brake also decreases biopsy score to about the same extent because there is about the same decline in insulin resistance in both situations, so most points post are below the line of identity as shown in FIG. 14.

Predictive Methods applied to Patients with NASH, HCC, RYGB and Brake
Summary of Findings and Conclusions:

Metabolic Syndrome underlies NAFLD and works together with inflammation to produce the NASH pattern of fibrosis and cirrhosis.

Biopsy results overall and individually for steatosis and fibrosis, were well predicted by the MatLab Neural Net modeling in these patients.

The Combination of Liver signal biomarkers and the FS index become a novel approach to evaluation of baseline risk in MetS and the associated risk of CV events; These indices are also a means of identifying the effects of treatment with novel therapy.

In the biopsy MatLab Model, RYGB resolves the NAFLD/NASH phenotype and should work for treatment across the range of age.

The ileal brake hormone releasing substance (Brake™) was similar to RYGB in control of all aspects of MetS, even though there was greater weight loss with RYGB Oral treatment of NAFLD and NASH with Brake™ appears feasible, with biomarkers relevant to change in biopsy results expected as early as 6 months into treatment
Progression of CV risk and Injury in NAFLD and NASH Patients with NAFLD and NASH are at high risk for Cardiovascular (CV) complications such as Myocardial infarction and eventually Congestive Heart Failure. In fact, it has been said that patients with NAFLD are far more likely to die of CV causes than of liver failure. Thus, the important components of MetS lead to CV complications in patients who also have NAFLD and NASH. This is a major component of the FS index as disclosed herein. It is also necessary to consider other CV risk components beyond the MetS components in FS index, which led us to develop the CV index as further disclosed herein. Essentially the Expanded CV risk Equation manages the two drivers of CV risk, the glucose supply side FS index component and the lipid supply side components which are added to form the CV index. The expand equation of the present invention represents a Dual glucose and Lipid supply side pathway for prediction of CV risk in patients with MetS.

In the present invention, we are including the discovery that cardiovascular risk also comes from the hyperlipidemia these patients manifest. Essentially, the inventors have therefore advanced a means of considering both of the two parallel pathways to cardiovascular events that are heretofore either selectively underemphasized or sometimes completely ignored. There is no current CV risk scoring tool that considers both parallel pathways.

Based upon the learning, knowledge and clinical use of the revised index to stratify cardiovascular risk, the revised equation, the CV risk index, is as follows:

$$CV \text{ Risk Index} = FS \text{ Index} + \frac{(LDL \text{ factor} + \text{age/sex/cigs factor} + hsCRP \text{ factor} + RP/200)}{(LL \text{ Drugs factor} + ASA \text{ factor})}$$

Where:
FS index is calculated as:

$$\frac{0.11 * (FBG + TG + HBA1c \text{ factor} + (BMI \text{ factor}) + (AST \text{ factor}) + (FBInsulin \text{ factor})}{S:D \text{ ratio}}$$

Wherein said FS index, the FBG is Fasting Blood Glucose in mg/dl; the TG is Triglycerides in mg/dl; the HBA1c is hemoglobin A1c in %; the BMI is body mass index in kg/m$^2$; the AST is Aspartate Transferase in IU/liter; FRB insulin is fasting Blood insulin concentration in nmol/liter; and the S/D ratio (SD) is a ratio of Glucose Supply Index (S) to Insulin Demand Index (D); wherein (S) is calculated as follows:

1+[aggregate of carbohydrate exposure (CE)+hepatic glucose uptake (HGU)+hepatic gluconeogenesis (GNG) and+insulin resistance (IR)]

and (D) is calculated as follows:

1+[aggregate of peripheral glucose uptake (PGU)+ peripheral insulin exposure (PIE)];

Where:
HBA1c factor: HBA1c×((HBA1c/5)×0.20)
BMI factor: BMI×((FBG+TG)/(50×3))
AST factor: AST×((TG100)×4)
FBInsulin factor: (BMI−22)×FBInsulin
Low density Lipoprotein (LDL factor): 60+LDL/10
Age/gender/cigarettes factor:

(Packs/day×yrs/8)×age×gender, where gender is 1.0 for male, 0.6 for female

High sensitivity C-Reactive protein (hsCRP) factor: hsCRP×10
Rate Pressure (RP factor): (HR×SBP) 0.200 Where HR=Heart Rate and SBP=Systolic BP Lipid Lowering (LL) Drugs factor:

(0.9+Statin Dose, mg in Lipitor equivs/10)+(0.2+ other LL drugs factor/5)

ASA factor: 0.8+(ASA yrs 2) here ASA is low, dose Aspirin×years taken

Modeling NASH and MetS Together Allows Combinations to Lower CV Risk in Populations The previously disclosed "glucose supply side" link to MetS (37, 38) apparently has also a "lipid supply side". Like the glucose supply side, the lipid supply side is also impacted by drug therapy, in this case the statins, which lower lipids because they interfere with synthesis. Together these two supply side aspects refine the relationships between nutrition, signaling in the ileum, and the resulting course of their metabolic syndrome. They also allow us to use the model to predict and inform dosages when there is a combination treatment envisioned or clearly required. We will show the biomarker analysis of the effects of both glucose supply side and lipid supply side treatment, bring these pathways together in both a combined index, then disclose how both pathways can be treated with a modified formulation of the ileal brake hormone releasing composition called Brake.

One novel aspect of the present invention is a denominator term which reflects the available supply of lipids (LDL and cholesterol). The lipid supply side is impacted by synthesis inhibitors like the statin drugs. Thus, the new equation deals with both supply side glucose and supply side lipids, each considering the respective drug therapy. It is notable that no index of cardiovascular risk explains the driver of cardiovascular events as a supply side equation, and here for the first time we consider both supply side glucose and supply side lipids, each modified by targeted drug therapy including Brake. For the first time, we are including a balanced representation of all of the risks of the disease components into one equation. Furthermore, the effects of treatments are considered, with the predominant treatment for all aspects of the metabolic syndrome being Brake, which modifies the ileal brake hormone response to diet, and thus acts on the supply side.

Some parameters foster a crossover between the risks of the glucose supply side and the lipid supply side, notably Triglycerides. Assay of Triglycerides thus reflects the combined supply of dietary glucose and lipids. It is noted that Triglycerides, in addition to dietary drive, also are modified by hepatic synthesis. This approach allows triglycerides to remain in a prominent position in the numerator of the CV risk equation. Hence Triglycerides reflect dietary ingestion and hepatic synthesis, as well as reflect back on both peripheral obesity and NAFLD, which is the effect of obesity drivers and suppliers on the liver itself.

Inflammation occupies a central role in the progression of cardiovascular risk and it also is an important measure in the transformation of NAFLD to NASH. Inflammation has long been considered a means of precipitating the CV event itself, but in the equation, it has been represented as a driver of coagulopathy (opposed by ASA) and a driver of both glucose and lipid supply side progression to atherosclerosis and the resulting cardiovascular events. Age and cigarette smoking, while not directly part of the metabolic syndrome, are significant modifiers incorporated into the progression model to influence the risk adjustments that follow an understanding of longer term consequences of metabolic syndrome.

The change in FS index noted amongst a cross-comparison of RYGB added to standard of care, Brake added to standard of care and atorvastatin added to standard of care. We see both RYGB and Brake have similar decreases in FS index with no significant differences. However, when either intervention is compared to atorvastatin we observe significant differences in FS index over the initial 6 months. Atorvastatin is first-line treatments for their respective disease states, but either intervention does not have a significant impact on metabolic syndrome as a whole.

These responses required the modification of the FS index to consider the statin effects which are known to be protective of cardiovascular injury. Clearly, the commonly used statins affect only the lipid supply side aspect of the metabolic syndrome, and it was clear that this was not addressed by the 5 parameters of the FS index. RYGB surgery on the other hand, resolves all aspects of metabolic syndrome in less than 6 months, in at least 85% of patients who undergo this procedure. Based on the FS index changes observed here, it is clear that Brake has a similar response profile as RYGB surgery with respect to metabolic syndrome, and thus qualifies as an oral mimetic of RYGB surgery.

Detailed in Example 2 are the comparisons between the currently offered FS index and the Newly expanded CV index including the data for all the graphs on the individual parameters, when the CV index is applied to the same patients for comparison with the FS index. From the foregoing, it will be appreciated that, although specific embodiments of the invention have been described herein for the purpose of illustration, various modifications may be made without deviating from the spirit and scope of the invention. Accordingly, the present invention is not limited except as by the appended claims.

Example 2—Cross Comparison Between FS Index and CV Index

Here we compare the same patients using FS index and CV index, in order to establish concordance in the risk scoring. We also include patients with MIs as examples of patients with CV events. For each of these patients, the FS index was calculated and the CV index was calculated, using an electronic spreadsheet designed for this purpose, and with the goal to evaluate concordance in the risk scoring. We also include patients with MIs as examples of patients with CV events.

Primary objectives of this analysis included the comparison of both indices of CV risk with each other in patients treated with RYGB, Brake or Atorvastatin, each added to SoC which had not changed the index prior to adding our treatment interventions. This analysis showed pronounced effects of RYGB and Brake, but not atorvastatin on FS index, verifying the impact of RYGB and Brake on all aspects of metabolic syndrome.

Patients used for this comparison are described therein, with the addition of 50 cases with MI and 50 controls without MI who have similar baseline data as long as five years before the onset of MI. We have previously studied these patients in this application, and details on these MI cases have been published (37, 38). In the initial publication, neither the FS index nor the CV index had been derived, so the application of the formula are novel to all patients, since additional data needed to be collected and analyzed in order to derive and apply the CV index to these patients.

Results of Cross Comparisons—FS Index and CV Index FIG. 14-18

At baseline, the patients comprising each of the study groups were similar, as might also be appreciated from their baseline parameters in FIG. 15. There was remarkable concordance between the FS index and the CV risk assigned at baseline in the patient populations.

Figure 16:
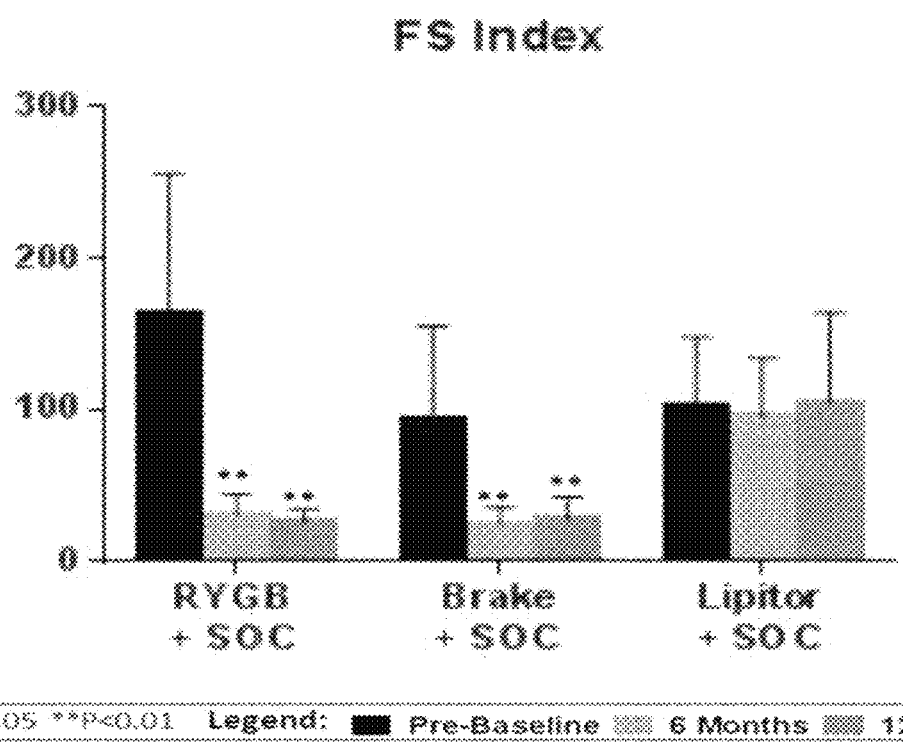

FIG. 16. FS index before, at 6 months, and 12 months after the application of the three treatments: RYGB plus SoC (N=17), Brake plus SoC (N=34) and Atorvastatin plus SoC (N=30). Changes in FS index over pre-treatment baseline are significant for RYGB and Brake, but not atorvastatin.

Figure 17:
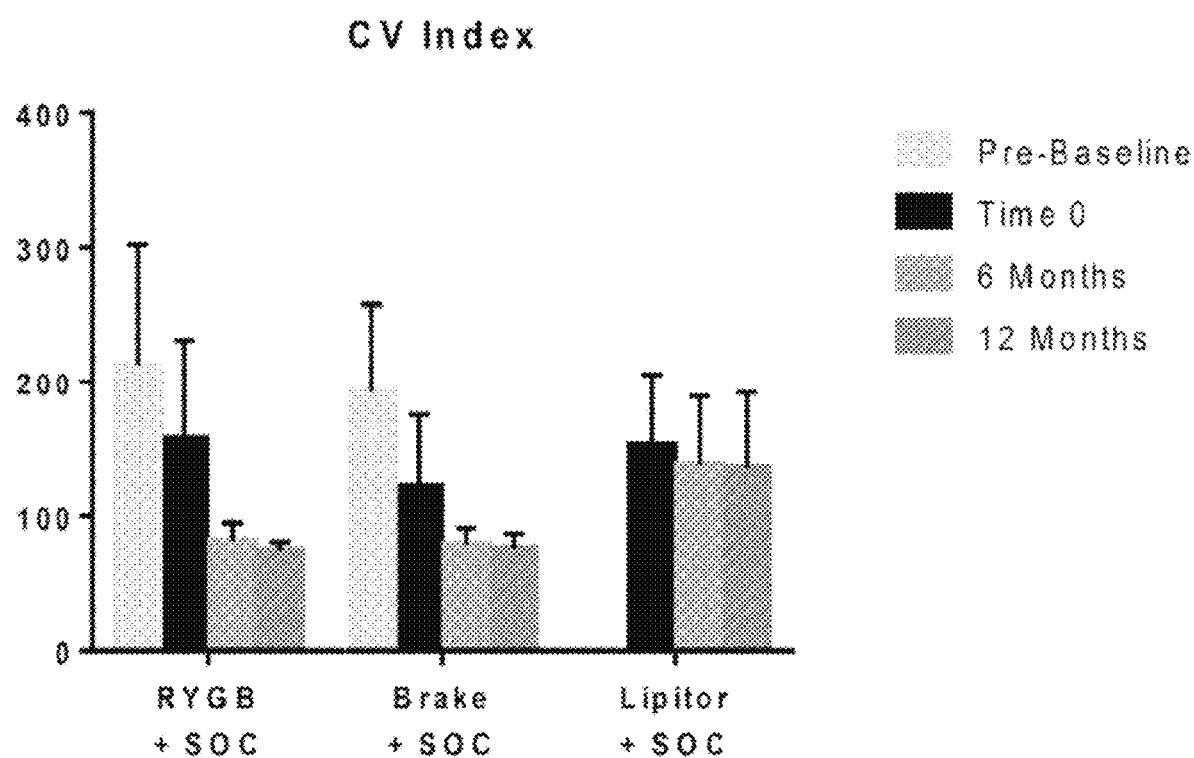

FIG. 17. CV index before, at 6 months, and 12 months after the application of the three treatments: RYGB plus SoC (N=17), Brake plus SoC (N=34) and Atorvastatin plus SoC (N=30). Changes in CV index over pre-treatment baseline are significant for RYGB and Brake, but not atorvastatin.

The following analysis includes patients with MI and their respective controls, presented earlier by Monte and Schentag (37, 38) and described in U.S. Pat. No. 8,367,418 (39). The additional analysis of these cases was used to define the CV index and the relationship between CV index and FS index in these patient groups. The analysis is conducted based on additional findings during the study of these patients, and compares the MI and MI controls with the patients we have treated with RYGB, Brake and Atorvastatin.

Figure 18:
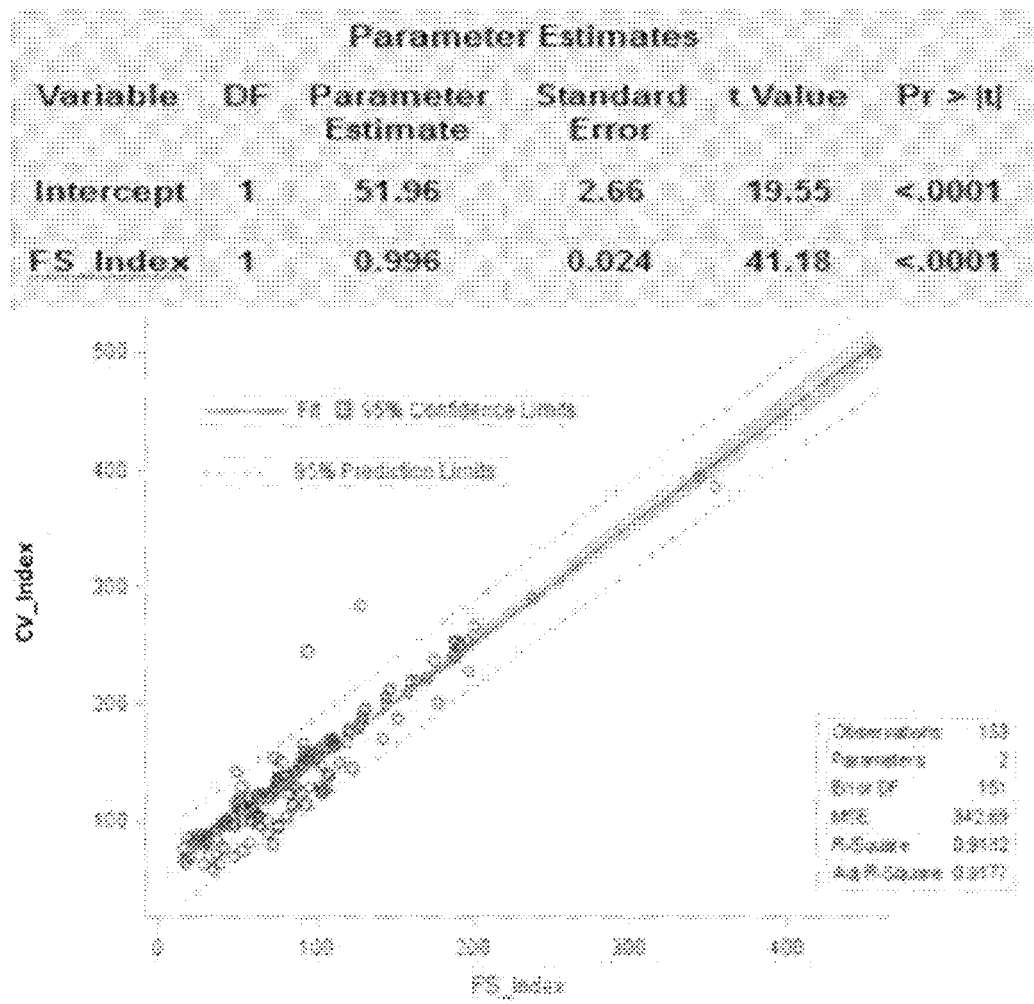

FIG. 18. FS index regression relationship to CV index at baseline, including all patient groups RYGB plus SoC (N=17), Brake plus SoC (N=34) and Atorvastatin plus SoC (N=29) Patients with MIs (N=45) Matched controls for MI patients (N=41). Inset shows DF, Parameter estimate, standard error, t value and p<0.0001.

NASH Patients and Comparing FS Index and CV Index

Primary objectives of this analysis included the comparison of both indices of CV risk with each other in patients treated with RYGB, Brake or Atorvastatin, each added to SoC which had not changed the index prior to adding our treatment interventions. This analysis showed pronounced effects of RYGB and Brake, but not atorvastatin on FS index, verifying the impact of RYGB and Brake on all aspects of metabolic syndrome.

Figure 19:
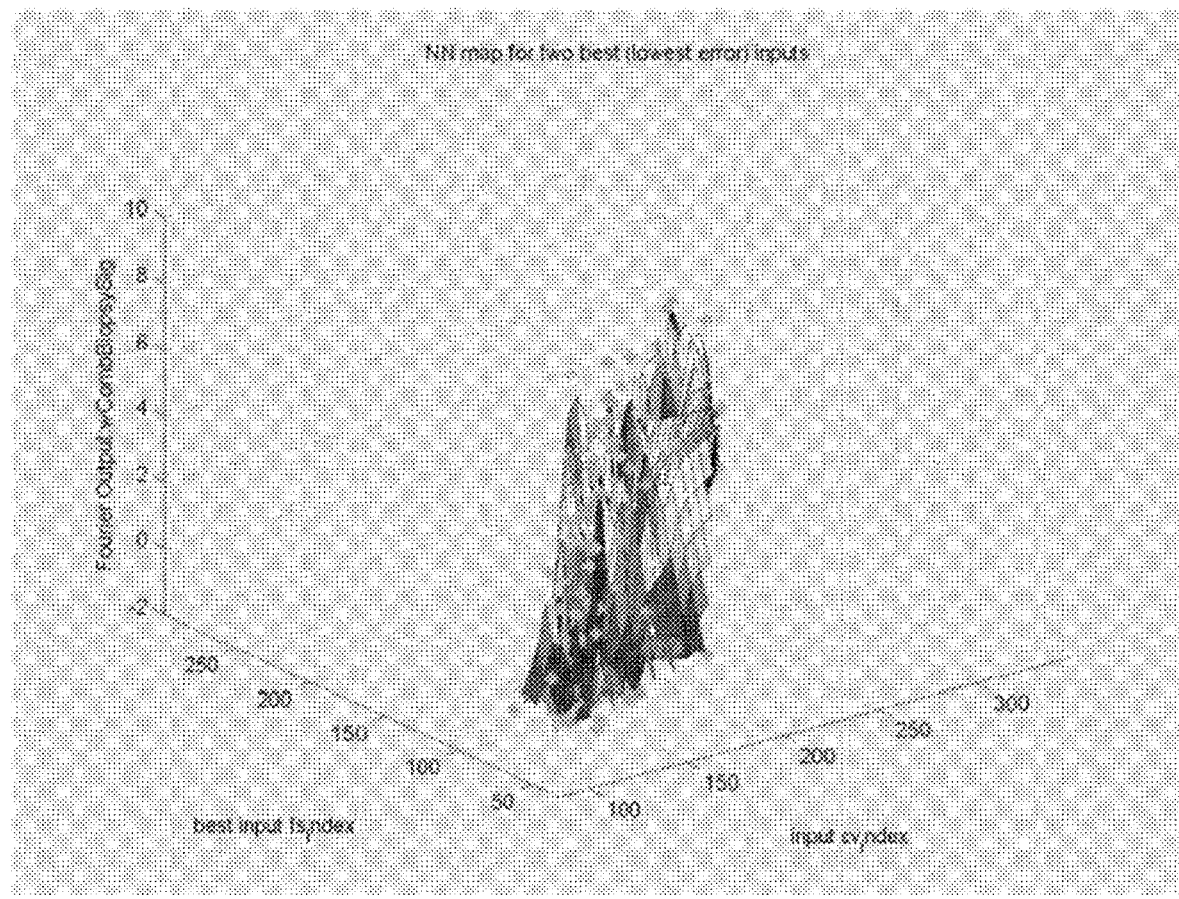

At baseline, the patients comprising each of the study groups were similar, as might also be appreciated from their similar baseline parameters. There was remarkable concordance between the FS index and the CV risk index at baseline in the patient populations, as shown in FIG. 19, whereby both FS index and CV index predict output such as wComb Biopsy signal. FIG. 19 shows the Neural Net Model 3D relationship between Biopsy score and Both FS index and CV index on the patients with NASH, HCC, RYGB and Brake. Both MetS indicies are strongly linked to the biopsy score and output.

Example 3—Treatment Comparison—RYGB-Brake-SOC Lipitor

Thirty-four patients received Brake™ plus SOC within the cohort, 17 patients had a RYGB procedure with SOC and 29 patients were taking Lipitor (atorvastatin) plus additional medications considered SOC for patients with multiple manifestations of MetS. FIG. 20. The mean age in the Brake™ plus SOC group was 50±11 years with a mean BMI of 34±5.8 and the majority of subjects were female (68%). No significant differences were noted in age or gender between groups, however the RYGB groups had a higher baseline BMI as compared to Brake™ and atorvastatin (P<0.0001). Except for this large difference in baseline weight in RYGB patients, baseline metabolic characteristics were similar between case cohorts. Subjects treated with atorvastatin plus SOC had a higher percentage of patients with a baseline total cholesterol above 200 mg/dL (P<0.0001). There were no other significant differences in baseline lipid indices. The RYGB plus SOC group had the highest percentage of patients on diabetic or cardiovascular medications. Brake™ plus SOC group had 8 (24%) patients on statin therapy, 9 (25%) on an additional lipid lowering agent and 4 (12%) on metformin.

Atorvastatin patients (N=29) were chosen from the electronic medical records of a group model health maintenance organization. This de-identified database has been previously described and approved for exempt status (37)

Brake™ Treatment Population

Briefly, Aphoeline Brake™ formulation 2 (disclosed previously) was given for a minimum of 6 months to a group of 18 patients. Demographics of the 18 patients were as follows.

9 males, 9 females, ages 26-71

1 African, 1 Asian, 3 Hispanics, 13 Caucasians 11 pre/early diabetic with insulin resistance and elevated insulin, pro-insulin or HBA1c 9 patients with NAFLD and probable NASH; 2 with liver biopsies, 7 of these were diabetic or pre-diabetic 3 patients with Hepatitis C not on any antiviral treatments. Two of these had biopsy proven cirrhosis All patients were given 10 gm Brake™ once Daily, orally, 4 hrs prior to their main meal Patients treated and followed for at least 6 months Serial laboratory and biomarkers including BMI, body weight, hepatic profiles, Triglycerides and lipid profiles, HBA1c measurements.

RYGB Reference Population

Reference population was 17 RYGB patients that the inventors followed after their surgery for outcomes. Aspects of these RYGB patients used as controls have been published(40) and the entire description of these cases is herein incorporated by reference. Briefly, 15 adults with morbid obesity and T2D undergoing RYGB were studied. After an overnight fast, a baseline blood sample was collected the morning of surgery and at 180 days to assess changes in glycemia, insulin resistance, LPS, mononuclear cell nuclear factor (NF)-kappaB (NFkB) binding and mRNA expression of CD14, TLR-2, TLR-4, and markers of inflammatory stress. At 6 mo after RYGB, subjects had a significant decrease in body mass index (52.1+/−13.0 to 40.4+/−11.1), plasma glucose (148+/−8 to 101+/−4 mg/dL), insulin (18.5+/−2.2 mmuU/mL to 8.6+/−1.0 mmuU/mL) and HOMA-IR (7.1+/−1.1 to 2.1+/−0.3). Plasma LPS significantly reduced by 20+/−5% (0.567+/−0.033 U/mL to 0.443+/−0.022E U/mL). NFkB DNA binding decreased significantly by 21+/−8%, whereas TLR-4, TLR-2, and CD-14 expression decreased significantly by 25+/−9%, 42+/−8%, and 27+/−10%, respectively. Inflammatory mediators CRP, MMP-9, and MCP-1 decreased significantly by 47+/−7% (10.7+/−1.6 mg/L to 5.8+/−1.0 mg/L), 15+/−6% (492+/−42 ng/mL to 356+/−26 ng/mL) and 11+/−4% (522+/−35 ng/mL to 466+/−35 ng/mL), respectively. We found that LPS, NFkB DNA binding, TLR-4, TLR-2, and CD14 expression, CRP, MMP-9, and MCP-1 all decreased significantly after RYGB. The mechanism underlying resolution of insulin resistance and T2DM after RYGB may be attributable, at least in part, to the reduction of endotoxemia and associated inflammation, as shown by declines in pro-inflammatory mediators following RYGB.(41)

Comparison of Biomarkers of Efficacy

Figure 21:
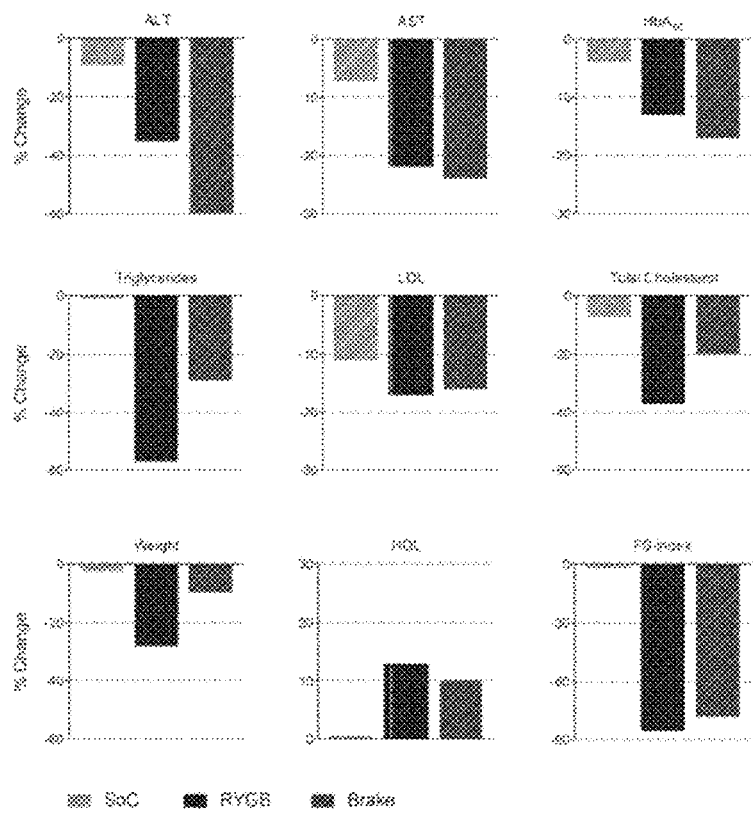

Pertinent demographic and clinical data were retrieved from medical records for all patients, and shown in FIG. 21. Variables included age, gender, body weight, lipid panel (low-density lipoprotein [LDL], high-density lipoprotein

[HDL], triglycerides [TG], and total cholesterol [TC]), HbA1c, and liver function tests (aspartate aminotransferase [AST] and alanine aminotransferase [ALT]). Patients were followed monthly for up to one year to assess changes in the above stated variables. Changes in the Brake population were analyzed versus patients treated with RYGB, and atorvastatin, each added to SoC. Patients were included in the metabolic analysis if their FS index variables were initially abnormal and had clinical data collected for at least up to 6 months, with most cases 12 months of data available at the time of analysis.

In common with other regulatory-mechanism compounds, Brake™ does not change laboratory biomarkers that are already within the normal range. Although this is good because it provides evidence of excellent safety, there clearly must be an abnormal biomarker in order to detect a clear efficacy signal with this compound. Thus, it becomes necessary to examine only the cases with abnormal baselines if one wishes to further understand the magnitude of the Brake™ effect on patients with typical metabolic syndrome conditions. Accordingly, these data were analyzed by biomarker, and subgroups were formed to compare the effects in those with initially abnormal baseline values and compare them with both the total population and the initially normal baseline patients. From the beginning, the patients who began the study with abnormal findings were separated from the patients with initially normal values and those with abnormal findings were further analyzed to define the magnitude of change as well as the percent change from baseline pre-therapy.

In all cases, the analysis perspective is the comparison of the pre therapy baseline with the 6 months and 12 months on-treatment values, and the cases are divided into those with initially abnormal baselines, initially normal baselines, and the third table is all patients included. The Figs. and tables therefore illustrate the changes in selected laboratory biomarkers from baseline to end of treatment in patients with abnormal initial values and in patients with normal initial values. Particularly large changes were noted in patients with initially abnormal values, and notably, many of these achieved normal or near normal values by the end of 6 or 12 month's treatment. Values in patients with initially normal biomarkers were further decreased in some cases, but remained within the normal range of the test in all cases. No patient experienced an unexpected rise in any biomarker value.

Statistical Analysis

Descriptive statistics were used in analyzing the baseline characteristics of each cohort. In addition to counts of how many patients had values above threshold, all descriptive characteristics are reported for each group as percentages and mean values, or where appropriate, the binary distribution percentages. The two-sample paired t-test was used to determine if there was a significant decrease in the mean biomarker profiles (lab tests, weight, FS index) from baseline pre-treatment to 6 months and 12 months post treatment values. This testing was applied to case and control cohorts: (a) using data for all treated patients, (b) using data for only those with abnormal range baselines (c) using cases where the initial value was within the normal range for the laboratory. Data were subsequently analyzed for percent change by biomarker from both of these two perspectives.

We also studied the subset of patients who had abnormal biomarker values prior to intervention. Subsequent comparisons were made between the abnormal baseline value subset and the entire population for each comparison biomarker, which recognizes that no patient had all baseline values abnormal, so the numbers in each comparison cell were likely to differ by biomarker. Some patients with abnormal liver enzymes would have normal HbA1c, for example. Within the comparison of abnormal baseline vs all patients, the analysis perspective was to define the percent change, the amount of absolute change and to quantify how many patients who presented with abnormal initial values that subsequently normalized those abnormal baseline values.

The primary aim of this study was to assess the long-term effects of Brake on glucose supply side associated T2D, using weight loss and other metabolic indices including lipid profile, glycated hemoglobin (HbA1c), and liver function tests, all in a group of patients characterized for CV risk with both the FS index and the newly disclosed CV index.

This example therefore assumes that SoC did not change the CV risk profile of the patients, and in fact that continued treatment with Atorvastatin did not change the CV risk of Atorvastatin added to SoC.

Comparisons between groups were performed by mixed analysis of variances with a post hoc correction for multiple comparisons to analyze differences between treatments. Data are presented as mean±standard deviation (unless otherwise specified). A $p<0.05$ was considered evidence of significant change. All statistical analyses were conducted using SAS version 9.4 (SAS institute, Cary, N.C.).

Results—RYGB—Brake—Atorvastatin Patients

On FIG. 21, each of the biomarkers from the analysis are provided for the RYGB patients, the Brake treated patients, and the Standard of Care patients given Lipitor.

What follows is a parameter by parameter discussion of the graphics in FIG. 21. Changes in HbA1c over pre-treatment baseline, are significant for RYGB and Brake, but not atorvastatin. HbA1c (in % glycated hemoglobin) before, at 6 months, and 12 months after the application of the three treatments: RYGB plus SoC (N=17), Brake plus SoC (N=34) and Atorvastatin plus SoC (N=29). Changes in HbA1c were rather low for all Brake and atorvastatin groups, ranging from −6.5% to 1.7%. Only RYGB subjects experienced a notable decrease in HbA1c values (−18.7%). If Brake was given simultaneously with low-dose atorvastatin the effect was increased notably.

RYGB and Brake treated patients had similar beneficial effects on the liver function tests. Only minor changes in AST and ALT were seen with 10 mg or 40 mg atorvastatin, however, the normal baseline values have to be considered, as these patients are not a risk. If Brake was added on to low-dose atorvastatin, the therapeutic effect was enhanced. For both ALT and AST (in activity units) before, at 6 months, and 12 months after the application of the three treatments: RYGB plus SoC (N=17), Brake plus SoC (N=34) and Atorvastatin plus SoC (N=29). Changes in ALT and AST over pre treatment baseline, are significant for RYGB and Brake, but not SoC. RYGB and Brake treated patients had similar beneficial effects on the liver function tests. Baseline Hepatic enzyme biomarkers of inflammation were higher in Brake™ cohorts, because 4 patients had concomitant Hepatitis C, many had NAFLD associated with obesity and Hepatitis C. In three cases, there was also biopsy proven NASH with both fibrosis and cirrhosis, and these patients all responded to either Brake alone or in combination with Hepatitis C therapy. As can be appreciated in FIG. 21 there was major AST declines of 16% in RYGB and 35% in Brake™ patients, compared with 3.5% decline in Lipitor® cases.

As shown in FIG. 21, The ALT declined 35% in RYGB and 39% in Brake™ treated cases, compared with essentially no decline in Lipitor® cases. All of these Figs.

demonstrate cohort differences in response for Brake™ Lipitor® and RYGB at 6 months, and these changes were sustained and even greater at 12 months. Changes in patients with normal baselines were negligible. Overall, there was no significant decline from baseline with Lipitor® with regard to these indices of hepatic inflammation, regardless of 6 or 12 month's perspective.

In these patients, use of Brake™ significantly reduced hepatic inflammation as measured by the biomarkers AST (SGOT) & ALT (SGPT). The effect of Brake™ was as great as produced by RYGB at 6 months of treatment, even though there were more cases with underlying hepatic disease in the Brake™ treated cohort. While the degree of hepatic inflammation was greater at baseline in the Brake™ groups, it would be expected that RYGB patients had greater degrees of baseline NAFLD.

Although none of the RYGB patients had liver biopsy, there were three cases of biopsy proven NASH in the Brake™ group. Three of the Brake™ treated patients in the abnormal cohort (one with Hepatitis B and two with Hepatitis C) had biopsy proven Cirrhosis & Fibrosis in addition to NAFLD, and these two cases experienced a similar normalization of Liver enzymes, lipids and Alpha Fetoprotein over 6-12 months. The notable effects of Brake™ in this case are the subject of our issued NASH patent(42, 43).

Further understanding of these changes is provided in FIG. 8, which shows the pre and post data plots for ALT/AST ratio for RYGB, Brake, and also illustrates the NASH and HCC populations. Most of the data on RYGB and Brake treated patients are below the line of identity, indicating Post values lower than pre values, while patients before and after NASH diagnosis or before and after HCC diagnosis are evenly distributed above and below the line of identity.

T2D, obesity and Triglycerides are closely associated with NAFLD. Baseline Triglyceride concentrations were highest in RYGB patients as might be expected in insulin resistant and massively obese subjects. As shown in FIG. 21, there was major decline in Triglyceride concentration of 50% in RYGB and a 30% decline in Brake™ treated cases, compared with an 18% decline in Lipitor® cases. All of these Figs. demonstrate cohort differences in response for Brake™ Lipitor® and RYGB at 6 months, and these changes were sustained and even greater at 12 months. Changes in patients with normal baselines were negligible. Overall, there was no significant decline from baseline with Lipitor® with regard to these indices of NAFLD, regardless of 6 or 12 month's perspective.

With regard to changes baseline to post treatment in triglycerides, the effect of Brake™ was similar to the effect of RYGB surgery, and in all cases the effect of Lipitor was negligible. Consistent with the known pharmacology of statins, there was little change in the triglyceride concentrations in patients taking statins alone. It should be noted that there was a triglyceride lowering in some of the statin treated patients. This was probably a data artifact, caused by the observation that there were some patients taking fish oils in the atorvastatin 10 mg group, and the effect on Triglycerides was from a combination of statin and fish oils.

Further understanding of these changes is provided in FIG. 9, which shows the pre and post data for RYGB, Brake, and also illustrates the NASH and HCC populations. Most of the data are below the line of identity, indicating Post values lower than pre values.

The statin effect is on cholesterol synthesis, and primarily impacts total cholesterol and LDL cholesterol. While T2D, obesity and Triglycerides are closely associated with NAFLD and NASH, there is only a marginal relationship between cholesterol and NASH itself.

The precise declines in LDL cholesterol are shown as percent changes in FIG. 21. Changes in patients with normal baselines were negligible. All of these Figs. demonstrate cohort differences in Brake™ Lipitor® and RYGB at 6 months, and these changes were sustained and even greater at 12 months. In general, RYGB, Brake and atorvastatin all affect LDL values, as shown in FIG. 21. Baseline LDL concentrations were highest in Lipitor patients. As seen before, higher dose statins lowered LDL more than lower dose statins, but Brake™ added on to the low dose statins achieved a similar lowering of LDL to high dose 40 mg atorvastatin. The lowering of LDL and total cholesterol on RYGB and Brake™ were similar to the lowering of these parameters achieved by the statins. LDL decreased to a similar degree in patients receiving Brake or low dose atorvastatin (−13.3% and −10.1%, respectively) and showed larger decreases with RYGB (−17.4%), Brake plus low dose atorvastatin (−31.5%) and high dose (40 mg) atorvastatin treatment (−22.7%). As seen before, higher dose statins lowered LDL more than lower dose statins, but Brake™ added on to the low dose statins achieved a similar lowering of LDL to high dose 40 mg atorvastatin.

Abnormal baseline cases were examined at 6 and 12 months of treatment, and at this time there was major Total cholesterol decline of 38% in RYGB and a 22% decline in Brake™ treated cases, compared with a 3.2% decline in Lipitor® cases. All of these Figs. demonstrate cohort differences in response for Brake™ Lipitor® and RYGB at 6 months, and these changes were sustained and even greater at 12 months, as shown in the same Figs.

The precise increases in HDL cholesterol are shown as percent changes in FIG. 21. All of the biomarkers in FIG. 21 demonstrate cohort differences in response for Brake™ Lipitor® and RYGB at 6 months, and these changes were sustained and even greater at 12 months. Changes in patients with normal baselines were negligible. HDL percent changes are shown in FIG. 21. HDL values increased with RYGB, Brake, Brake plus low dose atorvastatin, and low dose atorvastatin treatment, with the largest increase in RYGB and Brake plus atorvastatin treated patients, but decreased in patients who received high dose (40 mg) atorvastatin alone. This points us to the desirability of combining Brake and atorvastatin for treatment of metabolic syndrome patients with abnormal HDL values. Overall, there was a modest decline in TC and LDL, and a modest rise in HDL from baseline with Lipitor® regardless of 6 or 12 month's perspective.

It should be noted that only negligible changes occurred when patients started with normal baseline TC, LDL or HDL. Perhaps more important, the cohort of all patients obscured the important changes that were clearly visible in those with abnormal initial baseline, with the findings in the abnormal cases being clearly less distinct when cohort data is averaged between an appreciable number of abnormal cases and the remainder who do not have the elevated biomarker. As would be anticipated from the known pharmacology of statins, higher dose statins lowered LDL more than lower dose statins, although in this group of 29 patients the highest dose of atorvastatin was 40 mg.

Perhaps surprisingly, Brake™ added on to the low dose statins (7 of the Brake patients were taking statins as part of SOC) achieved a similar lowering of LDL to high dose 40 mg atorvastatin alone. This demonstrated synergy between the two pathway treatments, as the effect of Brake™ itself on LDL cholesterol was modest. Mechanistically, Brake affects dietary cholesterol supply, but there is no expected Brake™ effect on hepatic cholesterol synthesis, so this synergistic pathway reflects the dietary lowering of cholesterol load from Brake™ in combination with the inhibitory effects of synthesis by statins.

To assess changes in metabolic syndrome, patient characteristics were analyzed using the FS Index.(44) Briefly, the FS index is a method for assessing cardiovascular risk associated with the glucose supply side in metabolic syndrome and T2D patients. The FS index is obtained from the individual patient's biological parameters, wherein a FS index value of greater than 60 is indicative that the individual is in need of therapy for metabolic syndrome or at risk for at least one cardiovascular complication associated with metabolic syndrome.

Because FS index is a composite biomarker of insulin resistance, T2D, obesity, inflammation and Triglycerides, it would be expected to link to both NAFLD and NASH. Furthermore, any intervention which can normalize all of the components of NAFLD and NASH progression should normalize FS index. Normalizing the FS index would predict efficacy in NAFLD and NASH cases.

FIG. 21 shows the percent change in FS index values at 12 months after the application of the treatments: RYGB plus SoC, Brake plus SoC, and atorvastatin. In general, RYGB and Brake both lowered FS index, while atorvastatin and metformin did not change the FS index.

Changes in FS index over pre-treatment baseline, are significant for RYGB and Brake but not atorvastatin added to SoC.

Baseline FS index values were highest in RYGB patients. RYGB is both a stimulation of L-cell output and a restrictive process where patients have only a tiny residual stomach so they cannot easily overeat. Further understanding of these changes as relevant to NASH and NAFLD are provided in FIG. 10, which shows the pre and post data for RYGB, Brake, and also illustrates the NASH and HCC populations. Most of the data for RYGB and Brake post are far below the line of identity, indicating Post values that are nearly normal compared to the pre values and a large effect of these interventions on FS index compared to NASH and HCC which do not change FS index pre to post diagnosis.

As can be appreciated where the abnormal baseline cases were examined at 6 months of treatment, there was Major decline in body weight only in RYGB treated cases. Body Weight (in pounds) before, at 6 months, and 12 months after the application of the three treatments: RYGB plus SoC (N=17), Brake plus SoC (N=34) and Atorvastatin plus SoC (N=29) is shown in FIG. 21. Percent Changes in Body weight over pre-treatment baseline are significant for RYGB, but not atorvastatin.

The weight loss is near constant per week, and therefore these changes were sustained and even greater at 12 months. The decline at 12 months was 28% in RYGB and the decline was 9.7% in Brake™ treated cases, compared with a 2.6% decline in Lipitor® cases. Changes in patients with normal baselines were also measurable for 6 months and at 12 months. Further understanding of these changes as relevant to NASH and NAFLD is provided by examining the BMI data in FIG. 7, which shows the pre and post BMI data for RYGB, Brake, and also illustrates the NASH and HCC populations. Most of the data are below the line of identity, indicating Post values lower than pre values. Patients with NASH and HCC generally did not have changes in weight pre to post, but then again they were not treated with an effective composition.

Safety

The ingredients of Brake™ have been characterized as Generally Recognized As Safe (GRAS) by the FDA. Brake™ was well-tolerated within both studies with one patient dropping out due to a GI adverse effect related to the study drug, presumably resolved but this patient was lost to follow-up. There were no instances in any patients where a normal laboratory biomarker became abnormal, and there were no instances where an abnormal laboratory biomarker showed further elevation. Thus to date there have been no adverse event signals in the laboratory biomarkers monitored in our patients. At each visit, the patients were asked in a non-leading manner if they had any side effects and if they were satisfied with treatment. Every one of the patients felt better, in particular reporting "I have more energy". The only side effect reported was mild flatulence in a few patients, out of whom none reported to have it continually and none discontinued taking the medication reporting side effects. There were no reports of intestinal discomfort, diarrhea or other harbingers of the dumping syndrome. In general, patients did not complain about either the size or the number of pills taken per day. No patient discontinued therapy for this reason. Additional studies are necessary to quantify the apparent short and long term safety profile of Brake™.

Overview—RYGB—Brake—Atorvastatin in Patients

Overall, the results show a composite effect of Brake™ on the biomarkers of metabolic syndrome of these patients. As will be shown by case control group comparisons, the effect of daily Brake™ use on the laboratory profiles of these 34 patients is a true mimetic to the ileal brake hormone associated changes after RYGB. The net effect of the Brake™ treatment is a milder weight loss and otherwise very similar biomarker changes as RYGB surgery. Patients report less hunger for sugar and fat, and as a consequence can easily lower their intake of sugar and fat rich processed foods, which is very similar to the food choices made after RYGB surgery.

In FIG. 22, we show the direct potency comparison of Brake as a percentage of RYGB surgery. The clinical data show Brake to be 62% as active as RYGB in Reducing HOMA-IR, a measure of insulin resistance. Brake is 54% as active as RYGB on HbA1c, and over 150% better at reduction of ALT and AST liver enzymes. Brake was 81% as active as RYGB on Triglycerides. Perhaps most surprisingly, Brake was only 20% as effective as RYGB at the task of weight loss. The inventors interpret this finding as further evidence that weight loss is not the key to managing MetS. In fact, one must manage insulin resistance first, and once this is accomplished, the rest of the beneficial effects soon follow.

We see both RYGB and Brake have similar decreases in FS index and CV indices, and these changes are important for the identification and prognostication of NASH and NAFLD. However, when either intervention is compared to atorvastatin we observe significant differences in FS index over the following 6-12 months, with no significant change noted after atorvastatin. Atorvastatin is a first-line treatment for hyperlipidemia, but it is clear from the results herein, that this intervention does not have a significant impact on MetS as a whole. Rather, atorvastatin changes only cholesterol and LDL values, which are important in CV risk but not the entire story since all of the other metabolic syndrome parameters need to be considered.

The FS index alone is a good reflection of the dietary decrease in glucose and the effect of glucose supply side reduction on insulin resistance. However, there was evidence that Brake (and RYGB) were not greatly lowering cholesterol or LDL. In fact, as shown in FIG. 21, the atorvastatin effect from 40 mg dosing is greater than the atorvastatin 10 mg effect. Furthermore, it is also clear that 10 mg atorvastatin added to Brake is approximately the same effect on LDL as was seen with 40 mg of atorvastatin. So the statin sparing effect of Brake can be demonstrated when 10 mg of atorvastatin can be added to Brake, with the resulting lowering of LDL approximately equal to atorvastatin 40 mg. From these relationships, we would anticipate that 20 mg of atorvastatin added to Brake would equal 60-80 mg of atorvastatin alone on LDL. This statin sparing property of Brake is very important, and suggests that the CV index needs to consider both the glucose supply side and the hepatic cholesterol synthesis pathway together for optimal protection.

We were surprised at the modest effect of Brake and RYGB on the lipid supply side, because both RYGB and Brake alter cravings for dietary sugar and fats. The Lipid supply side is not the major action of the ileal brake stimulation. When given Brake, there was a modest effect on LDL, but the statin effect was also greater. In order to lower lipid related risk of Cardiovascular events, you must lower the impact of the Lipid Supply side, specifically, you must lower LDL, and this is further justification for combining Brake with a low dose of a statin, as is discussed in example 7. While this combination is important, one should note that there is ample evidence that you cannot only affect the Lipid supply side, thus a combination of Brake and a statin is synergistic almost by definition.

Glucose reduction does impact supply side glucose related CV risk, and weight reduction as well as decreased inflammation are important. Reduced hepatic synthesis of lipids appears necessary in addition to the important actions in the Brake mediated glucose supply side pathway, necessitating the use of a concomitant statin with Brake if patients have elevated LDL associated risk.

This work points strongly to the need to combine statins with Brake for full protection from CV injury. CV index is the best means so far developed to assess the entire risk profile.

The FS index was originally devised to mathematically quantify the link between diabetes, obesity and eventually the frequent occurrence of cardiovascular events. It was calculated from the weight and hyperglycemic changes of patients undergoing RYGB surgery. The early prototypes of the FS index lead to treatment strategies to modify cardiovascular risk for patients with diabetes and glucose driven metabolic syndrome. In spite of some success with treatments based on glucose based prediction of CV events, there were some patients identified that clearly had a different driver of their risk, and that discovery not only required a change in the equation, it also lead to a need for a modification of the pH encapsulated glucose formulation used to stimulate their ileal brake hormone release.

Specifically, the need to modify the FS index equation was clear from new discoveries in the use of pH encapsulated glucose to treat diabetes, the subsequent data analysis, and the need to reconcile the findings with the conventional recommendations of experts and thereby minimize discord. The need to expand the equation was not anticipated in advance but was clearly the next step after we viewed the data from our studies. The unexpected combination of effects of metabolic syndrome on both the lipid pathways and the diabetes pathways was documented, and did lead us to include a greater emphasis on lipid pathways and consideration of additional variables of age, cigarette smoking, gender and blood pressure. Prior use of these four factors was not considered related to diabetes CV risk or any other aspect of metabolic syndrome. The added importance of these added factors necessitated revision of CV risk prediction including lipids to lay the foundation of disease prevention using a combination of a statin drug with Brake for certain high risk patients, as well as to enable the monitoring of drug effects in lower risk patients treated similarly with pH encapsulated glucose.

Clinical testing focused on the relative changes in key metabolic parameters from RYGB when added to standard of care (SoC) therapy, compared with Brake treatment added to SoC, and compared with Lipitor (Atorvastatin) added to SoC as a control population. All three were compared in similar patients, and in all cases we calculated both the FS index and the CV index in each patient for assessment of CV risk and for assessment of relative improvement in the individual laboratory markers of the effect of RYGB, Brake and atorvastatin Brake is an oral mimetic of the RYGB effect composed of carbohydrates formulated for release in the distal small intestine, the location of the target sensor called the ileal brake. The development of the clinical test formulation was based on an oral mimetic of RYGB surgery, where the mimetic function was calibrated to the ileal brake hormone output of RYGB patients. This calibration may be summarized in FIG. 23, where 7 different coatings were applied to approximately 9.1 grams of dextrose and some minor ingredients. Formulation test cohorts comprised of 7 or 5 subjects each were given single doses of 7 tablets of Brake in the morning, and remained fasting for the next 10 hours. There were 19 males and 26 females. Mean age of the participants was 43.5+12.1 years. Mean weight was 191+41 lbs. Each formulation was given at 8 am. Blood samples were taken pre dose and hourly for 10 h post dose. Samples were treated with protease inhibitors to stabilize peptides and frozen until assay. Samples were assayed by a commercial reference laboratory for glucose, insulin, GLP-1, GLP-2, PYY, c-peptide, glucagon, and leptin. GLP-1 and PYY values were converted to 10 hr AUCs for purposes of comparing the release of these hormones after topical release of dextrose to those in RYGB subjects.

The results lead us to choose Formulation Coating #2 for a series of pilot study treatments in patients at risk of CV events.

Inspection of our own RYGB patients allowed us to calibrate GLP-1 hormone output of formulation #2 to the output of RYGB patients given a standard meal. There were 5 RYGB patients in the calibration dataset. Importantly, none of our formulations matched the PYY output of RYGB surgery, which is the lipid sensitive component. Nevertheless, Formulation #2 matched the glucose sensitive GLP-1 output between the study volunteers and the RYGB patients, so we began clinical studies to define the impact of long term use of Formulation #2 in relation to RYGB surgery and to atorvastatin, each added on to SoC.

Brake in MetS: Summary and Discussion

Brake displayed similar effects on metabolic syndrome markers as RYGB. Except for more weight loss with RYGB, we found no significant differences between Brake and RYGB with regard to HbA1c, TC, LDL, TG and HDL. In general, similar to the lipid parameters, RYGB and Brake™ treatment lowered HbA1c to normal values. We observed similar trends with Brake as compared to RYGB over 6-12 months of follow-up.

The largest reduction in liver enzyme values was shown with Brake over RYGB, but the baseline was more elevated in some of the Brake patients. As seen before, higher dose statins lowered LDL more than lower dose statins, but Brake™ added on to the low dose statins achieved a similar lowering of LDL to high dose 40 mg atorvastatin.

We have shown the impact that a small amount (in the range of 10 gm) of pH encapsulated glucose, when delivered to the ileum, can activate the ileal brake and result in hormone release. When this occurs from the oral use of Brake formulation, the result is a similar response in metabolic indices comparable to RYGB surgery. Studies on activation of the ileal brake by nutritional intake in humans are scarce. To our knowledge this is the first systematically gathered information to assess the long-term activation of the ileal brake process through oral stimulation with a carbohydrate formulation. We hypothesize that a sustained activation of the ileal brake will lead to an increase in satiety causing changes in weight and lipids as well as an increase in GLP-1 resulting in normalization of their glucose. We hypothesize that the increase in ileal brake hormones from ileal stimulation by Brake causes an overall improvement in cardiovascular markers by lowering insulin resistance, then it follows that there is a general improvement in organ function which starts in the liver and carries over to the heart, pancreas and even brain. In addition, the same mechanism may play a role in decreasing the HbA1c of patients on Brake. Only four patients on Brake were initially abnormal (HbA1c≥7%), however after 6 months the average decrease was almost 13%, which is greater than with most of the current treatments available for T2D.

An important response to RYGB surgery is a massive decrease in weight. RYGB has become an alternative to failed interventions on other diabetes treatment pathways, with positive results and acceptable morbidity and mortality associated with the surgery.(45, 46). RYGB creates a very small stomach, so there is no way to eat more than minimal amounts of food. However, because the resolution of metabolic syndrome was equally dramatic in Brake even though weight loss was modest, we hypothesize a different mechanism beyond just weight loss in our Brake patients. We believe Brake is activating the L-cells within the ileum eliciting an increase in GLP-1. The activation is the same in magnitude to RYGB because we calibrated the delivery and the dose of carbohydrates to achieve the same output of GLP-1. Previous data from healthy volunteers has shown a similar GLP-1 response from Brake as an individual would achieve post-RYGB surgery.(47) In summary, we found a similar trend in resolution of MetS with Brake, so it clearly is not weight loss per se that is important in resolving MetS.

A change in diet and affinity for certain foods has been associated with a post-RYGB effect, which we believe is also occurring within our Brake cohort. A combination of both may be the reason patients are showing similar responses as patients treated pharmacologically and surgically. A strength of this study is the long-term follow-up of Brake treated patients. There was substantial diversity among patient disease states and medications allowing for a real-world analysis of Brake.

Rather, each of the commonly used medications in SoC affect only one part of the metabolic syndrome. RYGB surgery on the other hand, resolves all aspects of metabolic syndrome in less than 6 months, in at least 85% of patients who undergo this procedure. Based on the FS index changes observed here, it is clear that Brake has a similar response profile as RYGB surgery with respect to metabolic syndrome, and thus qualifies as an oral mimetic of RYGB surgery.

The first line therapy for the treatment of hyperlipidemia has long been recognized as statins and in 2013 the guidelines on cardiovascular risk released from the American Heart Association expanded statin related treatment recommendations.(48, 49) Based on the new guidelines, the number of adults eligible for statin therapy would increase by 12.8 million.(50) Our preliminary evidence suggests short-term utilization of Brake has similar effects as low dose atorvastatin with an advantageous safety profile. Brake alone was not significantly different when compared to low and high dose atorvastatin regimens with regards to LDL, HDL and TC over the initial 6 months of therapy. Furthermore, Brake was shown to have a significant decrease in Triglycerides over the same time period as compared to high dose atorvastatin.

Additionally, the cross-comparison and randomization of RYGB and atorvastatin subjects provided an alternative perspective of treatment of a single disease state versus the overall disease. Across all parameters, patients who received atorvastatin in addition to Brake often presented with changes at least as high or even exceeding those observed for high dose (40 mg) atorvastatin treatment, indicating a beneficial and statin sparing effect of adding Brake to the atorvastatin formulation. Unexpectedly, the apparent synergy seen between low dose stains and Brake point to the use of Brake as a "Statin Sparing" therapeutic for patients with metabolic syndrome and at risk for developing statin associated T2D as well as CV events.

In a preferred embodiment of the present invention, the proof of principle study would be a randomized, double-blind, comparator-controlled multicenter study. It would compare the lipid parameter responses of LipidoBrake 10 mg atorvastatin with those of atorvastatin 40 mg. This study is designed to show non-inferiority with regard to LDL lowering as well as all the biomarker effects and on wComb biopsy score.

Disclosed Actions of RYGB and Brake™ on Insulin Resistance and Hepatic Steatosis The comparative potency of Brake™ vs. the RYGB procedure is shown in Table 1 below. Brake™ was nearly as efficient at lowering insulin resistance and triglycerides as RYGB, and produced a greater overall lowering of hepatic enzymes than seen in the RYGB patients. There were no significant side effects, all Brake™ treated patients had beneficial weight loss, and overall there was a similar improvement in the health of the liver in both patient groups.

Stimulation of ileal segment L cell hormone release is the primary mode of action of both RYGB and Brake™

Hepatic storage and release of triglycerides and lipids is controlled by the Gastrointestinal tract expression of L-cell hormones Excess Hepatic Lipid accumulation is secondary to altered or defective signaling resulting in an insult from a greater than needed supply of glucose and triglycerides, plus higher insulin exposure in an unbalanced response to the absorption of glucose.

Maintenance of Liver cells and control of insulin resistance is a primary benefit of controller L cells in the ileum. The action is that of the ileal brake for repair and regeneration.

When there is excessive intake of carbohydrates and lipids, the oversupply leads to insulin resistance in both liver and the rest of the body.

Dietary Overload of the intestinal L-cells such as in T2D with obesity down-regulates the release of ileal brake hormones, and the ileal brake response to dietary overload is diminished, leading to steatosis, T2D, hypertension and hyperlipidemia.

Liver inflammatory response to the combined insults of Hepatitis C virus and excess dietary carbohydrates and lipids is an end organ disorder of signaling maintenance and stimuli in the L cell pathways, and the inflammatory response to the virus.

Hepatitis C virus is easier controlled if the liver is optimally managed by L cell hormones and there is central control of the nutrients absorbed.

In a patient population treated with RYGB or Brake, similar effects are expected between these two therapies, so long as similar AUC of ileal brake hormones are observed in response to dosing.

Clinical manifestations of treatment with RYGB or Brake would lead to resolution of insulin resistance and any or all associated MetS diseases.

From the comparison study, it is postulated that RYGB and Brake™ might have a dual role in remediation of hepatic steatosis. Initially, the decline in insulin resistance, and lowered supply of triglycerides and glucose reduce fatty liver. Longer term, the decline in liver enzymes such as ALT, AST, GGTP and others as well as the decline in Alpha fetoprotein inform a Brake™ controlled anti-inflammatory pathway. In summary, the action of Brake™ on the liver in patients with NASH and NAFLD is to reduce steatosis and reduce inflammation. Both mechanisms are applicable to Brake™ in combination improving the outcome of Hepatitis C antiviral therapy with these synergistic added benefits over the actions of the antiviral alone. One additional reason that this is considered synergy by the inventors is that Alpha Fetoprotein decline is not associated with decline in the viral titers of HepC in early studies(51). Hence the decline in Alpha Fetoprotein experienced here is due to the ileal brake hormone releasing composition taken by these patients, and these effects are on the MetS, although the anti-viral effect was also notable.

Summary—Clinical Use of Brake as RYGB Mimetic in MetS

We see both RYGB and Brake have similar decreases in FS index and CV indices. However, when either intervention is compared to atorvastatin we observe significant differences in FS index over the following 6-12 months, with no significant change noted after atorvastatin. Atorvastatin is a first-line treatment for hyperlipidemia, but it is clear from the results in Example 3 that this intervention does not have a significant impact on MetS as a whole. Rather, atorvastatin changes only cholesterol and LDL values, which are important in CV risk but not the entire story since all of the other MetS parameters need to be considered.

The FS index alone is a good reflection of the dietary decrease in glucose and the effect of glucose supply side reduction on insulin resistance. However, there was evidence that Brake (and RYGB) were not greatly lowering cholesterol or LDL. In fact, as shown in FIG. 21, the atorvastatin effect from 40 mg dosing is greater than the atorvastatin 10 mg effect. Furthermore, it is also clear that 10 mg atorvastatin added to Brake is approximately the same effect on LDL as was seen with 40 mg of atorvastatin. So the statin sparing effect of Brake can be demonstrated when 10 mg of atorvastatin can be added to Brake, with the resulting lowering of LDL approximately equal to atorvastatin 40 mg. From these relationships, we would anticipate that 20 mg of atorvastatin added to Brake would equal 60-80 mg of atorvastatin alone on LDL. This statin sparing property of Brake is very important, and suggests that the CV index needs to consider both the glucose supply side and the hepatic cholesterol synthesis pathway together for optimal protection.

We were surprised at the modest effect of Brake and RYGB on the lipid supply side, because both RYGB and Brake alter cravings for dietary sugar and fats. The Lipid supply side is not the major action of the ileal brake stimulation. When given Brake, there was a modest effect on LDL, but the statin effect was also greater. In order to lower lipid related risk of Cardiovascular events, you must lower the impact of the Lipid Supply side, specifically, you must lower LDL. On the other hand, there is ample evidence that you cannot only affect the Lipid supply side.

Glucose reduction does impact supply side glucose related CV risk, and weight reduction as well as decreased inflammation are important. Reduced hepatic synthesis of lipids appears necessary in addition to the important actions in the Brake mediated glucose supply side pathway, necessitating the use of a concomitant statin with Brake if patients have elevated LDL associated risk.

This work points strongly to the need to combine statins with Brake for full protection from CV injury. CV index is the best means so far developed to assess the entire risk profile in NAFLD and NASH patients at risk for CV events.

Brake™ is a true mimetic of RYGB surgery. It works by stimulating the same amount of ileal brake hormones as RYGB, in the same order. This is why the effects are similar between Brake™ and RYGB in all respects. This is the first study to show the long term impact of oral activation of the ileal brake process in comparison to reference populations. Although it was not a randomized trial, the patient populations had similar degree of metabolic syndrome at the beginning. The effects of Brake™ were clearly demonstrated as affecting those with abnormal baseline biomarkers. Brake™ displayed similar trends as RYGB in regards to a variety of metabolic markers and in some instances significant differences in comparison to atorvastatin. Activation of the L-cells of the ileal brake by an oral mimetic is a novel approach in the treatment of metabolic syndrome, but it clearly works similarly to RYGB on every biochemical marker except weight. Less weight loss would be expected because Brake does not create a small stomach and it does not prevent the patient from eating what they wish. Detailed dietary studies in Brake™ treated cases will be the subject of subsequent reports. Further research is necessary to confirm our results and to test Brake™ vs Brake™ placebo in a targeted metabolic syndrome population manifesting either NASH or T2D.

Example 4. Inflammation Study—hsCRP—FS Index-CV Index

There has always been a seemingly random incidence of myocardial infarction in patients seemingly at low risk. Post mortem examinations invariably associate these cases with clot formation in damaged coronary vessels. The most common term in the literature for this phenomenon of unexpected sudden death from myocardial infarction is "coronary thrombosis". For unexplained reasons, coronary thrombosis occurs even in relatively young persons where there may be little evidence of underlying atherosclerosis. Myocardial infarction may occur in some patients who would not be predicted to have their heart attack because of some factors other than progressive atherosclerosis. These patients have sudden death but they may or may not have atherosclerosis when examined at autopsy. Invariably, there is a clot found in coronary arteries to explain the infarction.

Clearly, when there is significant atherosclerosis the FS index may account for this means of Myocardial infarction as associated with metabolic syndrome and abnormalities on the glucose supply side, and to some extent with lipid supply side. But in cases they do not have atherosclerosis, their CV events can only be linked to inflammation if inflammation increases the risk for coagulopathy. This is suspected as a means of explaining sudden coronary thrombosis, and thus an element of the CV risk equation we developed included hsCRP (high sensitivity CRP) as a measure of inflammation.

The hsCRP factor has been studied in patients who have experienced myocardial infarction (MI) and in association with pre or post MI interventional procedures such as PCI (percutaneous coronary intervention). This focus of work is important because patients after PCI have an increased incidence of second MI and they also have strokes and congestive heart failure (CHF). Standards of care in cardiovascular risk assessment do not consider the additional CV risks associated with inflammation. After interventions during or after MI, such as PCI, anti-platelet therapy is given, but patients are not given systemic anti-coagulation or anti-inflammatory therapy.(52). Thus current standard of care does not consider isolated inflammation, and as a consequence, hsCRP was not even measured in the largest recent study of complications post PCI(52).

Many of these second MI patients did not have MetS and it is also not clear whether any of them had elevated hsCRP since this was typically not measured. To make it even more complicated, generally there is little attention to MetS during the assessment of acute events, and paradoxically there is little attention to inflammation during management of chronic progressive components of MetS such as diabetes.

Typical MACE events include Myocardial Infarction, Angina Pectoris necessitation hospital care and vascular intervention, cardiovascular-related death, nonfatal heart attack, and nonfatal stroke, or Congestive Heart Failure (CHF). Elevated hsCRP and associated inflammation has a measurable effect on the CV risk lowering methods, when CV risk is defined as the risk of Major Adverse Cardiovascular Events (MACE):

Thus to cover both aspects of the assessment of risk for CV events, the FS index was augmented with a factor to account for the importance of inflammation in both acute and chronic prediction of risk.

Results—Inflammation Study

Records of patients with CV events are studied in an ongoing analysis to link CV events with predictive risk factors. Risk assessment tools are utilized to estimate the risk for stroke and need of anticoagulation therapy for patients with atrial fibrillation (AF). These risk stratification scores are limited by the information inputted into them and a reliance on time-dependent variables. Moreover, these scores only evaluate stroke risk but do not take into account possible bleeding risk or other cardiac events, such as myocardial infarction (MI). The objective of this study was to develop a time independent model to identify AF populations at higher risk of poor health outcomes.

Hypothesis:

We assessed the hypothesis that an enriched AF population was at higher risk of poor clinical outcomes Methods:

We performed a longitudinal, cohort study with pharmacy and medical claims from 1997 to 2008 from a local health maintenance organization. Participants were identified with incident AF irrespective of warfarin status and followed through their duration within the database. Three clinical outcome measures were assessed including stroke, myocardial infarction, and bleeding. A neural net model was developed to identify patients at high risk of clinical event and defined to be an 'enriched' patient. The model defines the enrichment based on the top 10 minimum mean square error (MMSE) output parameters that describe the three clinical outcomes. The MMSE ranks the parameters in order from best to worst predictability when modeling the outputs. Predictors and outcome measures were ascertained with cox proportional hazards models.

Results:

Among 285 patients with a mean age of 74±12 years, and mean follow-up of 4.3±2.6 years, 154 (54%) were treated with warfarin. Following adjustment for age and $CHADS_2$, warfarin use was associated with an increased risk of negative clinical outcomes (aHR=1.35, 95% CI 0.85, 2.13) though not statistically significant. Within the neural net model, patients at high risk of poor outcomes were identified and labeled as 'enriched.' The enriched population was associated with an increased risk of negative outcomes (aHR, 2.02, 95% CI 1.22, 3.36) with the top predictive marker being a low albumin level (53)

Examination of these cases found considerable numbers of patients with very high hsCRP values, and indeed these cases had more Strokes, CHF and Myocardial infarctions. Results of these studies have been combined with calculations of the FS index and CV index with and without hsCRP values, which are available in a proportion of our entire study sample.

Patients on anticoagulation with Warfarin (a surrogate for risk of stroke or MI in a patient with inflammation and/or atherosclerosis) had calculations of CV risk index, which included measured hsCRP where available and a default to a normal value of 1.0 if there was no measurement. These cases were then graphically analyzed and subjected to statistical testing. Results are presented as FIGS. 24 and 25.

Figure 24:
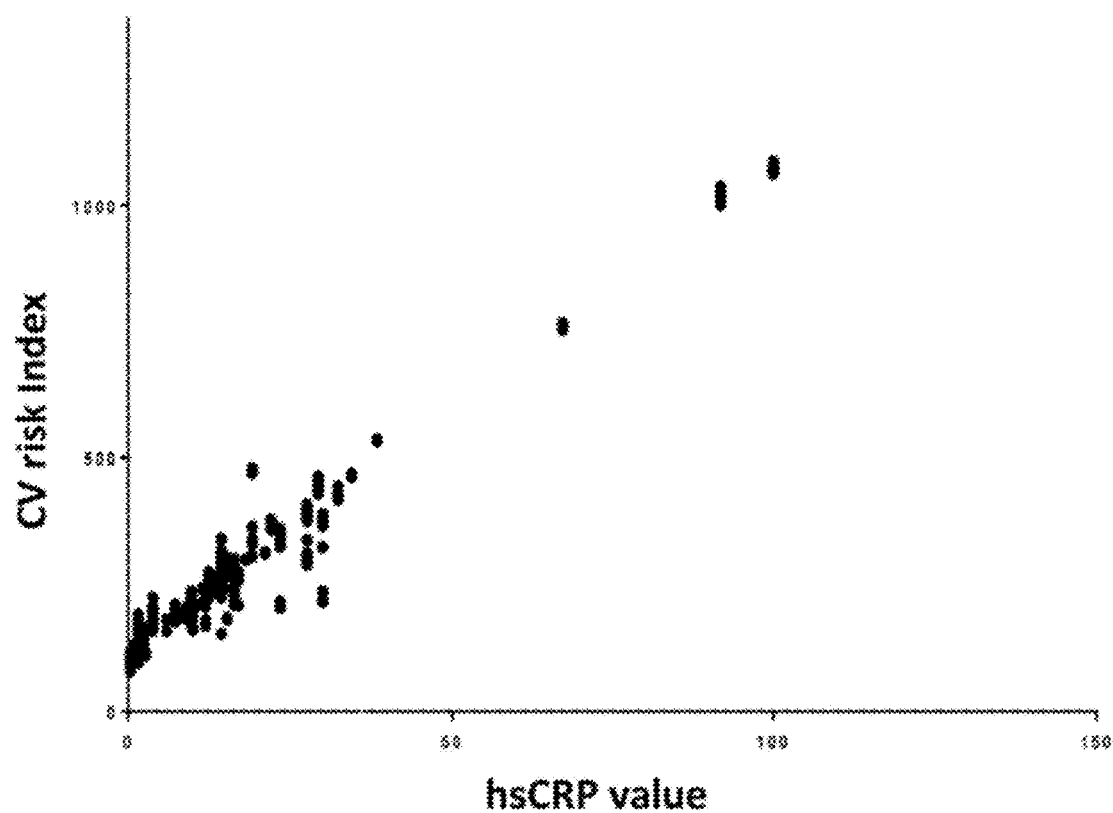

FIG. 24. The hsCRP (high sensitivity CRP) regression relationship to CV index at 12 months, including all patients treated with warfarin or controls and examined for bleeding side effects and strokes as CV endpoints. The data show a relationship between CV index elevations and CV events, which favors in general the idea that combined hsCRP and metabolic syndrome place patients at highest risk of acute events.

FIG. 25. The hsCRP group shows clustering of strokes in the higher values, where the value was measured. In this analysis, most patients treated with warfarin or controls and examined for bleeding side effects did not have a hsCRP value measured, so the default value of 1.0 was entered into the calculation of CV risk index.

It was not always the case that high hsCRP patients had worse metabolic syndrome, as also found by vanWijk (54). Thus to account for heretofore unrecognized inflammation associated Risk for sudden CV events in patients with and without metabolic syndrome, we incorporated hsCRP into the CV index equation. The previously unrecognized complex linkage between inflammation and metabolic syndrome can now be addressed within this expanded CV risk equation.

Summary MetS and Inflammation

Now for the first time, a patient with metabolic syndrome AND inflammation has a higher CV risk score than a patient with metabolic syndrome alone. The close correlation between CV index and hsCRP value in FIG. 25 demonstrates the importance of inflammation to CV risk stratification, and the use of the CV Index should be an advance in the practice of risk stratifying patients with metabolic syndrome and eventually giving them the best treatment to prevent further CV events.

Now with the addition of our new analysis, the CV index is predictive of stroke, which clusters with the newly included hsCRP value in the equation provided.

Treatments of patients with high CV risk scores and with combined Inflammation and Metabolic Syndrome One certain treatment for these patients is and remains the use of statins, which do preferentially lower hsCRP in patients who have received PCI (55). Thus in addition to better control of metabolic syndrome associated LDL and total cholesterol, we have a second strong reason to include statins along with Brake therapy. Even low doses of statins lower hsCRP when it is elevated. The combination of Brake with low (and very safe) doses of a statin is a preferred means of preventing inflammation associated CV events, and the FS index changes that occur after Brake therapy will indicate some additional measures of protection for the patient at risk because of a high CV index. The inflammation associated further elevation in CV risk in such a patient would not be detected from an elevated FS index, because the FS index did not include the patient's hsCRP value in the assessment tool.

Thus the inclusion of inflammation with Metabolic syndrome in a combined equation may now enable CV risk screening to deal with a vexing part of previous attempts to predict the Stroke component of accelerating CV risk, as previous risk stratification scores did not consider both metabolic syndrome severity and the added risk from this newly discovered link between inflammation and coagulopathy.

Example 5. Predictive Methods for Response in Hepatitis C Patients

The hepatic steatosis treatment as described above, may be preferably combined with an anti-viral drug active against Hepatitis C and/or Hepatitis B, to lower elevated virus counts and concomitantly improve the health of the inflamed and steatotic cells in liver of the patient with hepatitis C.

The synergistic combination of the specific antiviral treatment and ileal brake hormone releasing substance combination used for treatment of hepatitis C (and in certain instances, hepatitis B); where the primary beneficial action of the antiviral is to decrease the viral injury to steatotic hepatic cells and the primary beneficial action of the ileal brake hormone releasing substance (ileal brake compound) is to decrease the supply of glucose and triglycerides synthesis in the liver, and thereby lower the number of hepatic cells that become steatotic and at risk for extension of the viral infection and further hepatic injury. The favorable effect on other secondary conditions such as cirrhosis, fatty liver and hepatocellular cancer is also significant and in most instances, synergistic.

The present invention is also directed to the synergistic combination treatment for hepatitis C by administering an ileal brake compound as described above in combination with an anti-hepatitis C viral agent wherein the antiviral medicament is interferon, especially pegylated interferon and/or ribavirin in a therapeutically useful dosage and duration. This treatment can be used alone or combined with an effective amount of at least one additional anti-HCV agent as otherwise described herein. These agents include, for example, boceprevir, daclatasvir, asunapivr, INX-189, FV-100, NM 283, VX-950 (telaprevir), SCH 50304, TMC435, VX-500, BX-813, SCH503034, R1626, ITMN-191 (R7227), R7128, PF-868554, TT033, CGH-759, GI 5005, MK-7009, SIRNA-034, MK-0608, A-837093, GS 9190, GS 9256, GS 9451, GS 5885, GS 6620, GS 9620, GS9669, ACH-1095, ACH-2928, GSK625433, TG4040 (MVA-HCV), A-831, F351, NS5A, NS4B, ANA598, A-689, GNI-104, IDX102, ADX184, ALS-2200, ALS-2158, BI 201335, BI 207127, BIT-225, BIT-8020, GL59728, GL60667, PSI-938, PSI-7977, PSI-7851, SCY-635, TLR9 Agonist, PHX1766, SP-30 and mixtures thereof. These agents may be used alone, in combination, or further in combination with effective amounts of ribavirin, interferon, especially pegylated interferon or mixtures thereof.

For example, in a particular aspect, the present invention is directed to the synergistic co-administration of an ileal brake compound/composition with an effective antiviral combination of interferon, especially a pegylated interferon and/or ribavirin in a therapeutically useful dosage and duration, combined with boceprevir in a dosage of at least 800 mg three times daily.

In a further aspect, the present invention is directed to the synergistic co-administration of an ileal brake compound/composition with an effective antiviral combination of interferon, especially a pegylated interferon and/or ribavirin in a therapeutically useful dosage and duration, combined with telaprevir in a dosage of at least 750 mg three times daily.

In a further aspect, the present invention relates to a synergistic co-administration of an ileal brake compound/composition with an effective antiviral combination of the NS5A replication complex inhibitor daclatasvir in an effective dose combined with the NS3 protease inhibitor asunaprevir in an effective dose and either or both of these protease inhibitors can be used alone or in combination with interferon, especially a pegylated interferon and/or ribavirin in an effective amount.

In still an additional aspect, the present invention relates to a synergistic co-administration of an ileal brake compound/composition with an effective antiviral in combination wherein the antiviral medicament is daclatasvir, an NS5A replication complex inhibitor used in an effective amount alone or in combination with interferon, especially a pegylated interferon and/or ribavirin in an effective amount.

In still another aspect, the present invention relates to a synergistic co-administration of an ileal brake compound/composition with an effective antiviral in combination, wherein the antiviral medicament is asunaprevir a NS3 protease inhibitor used in an effective amount alone or in combination with interferon, especially pegylated interferon and/or ribavirin in an effective amount.

In yet an additional aspect, the present invention relates to a synergistic co-administration of an ileal brake compound/composition with an effective antiviral in combination, wherein the antiviral medicament is INX-189, a nucleotide polymerase inhibitor used in an effective amount, alone or in combination with interferon, especially pegylated interferon and/or ribavirin in an effective amount.

In still another aspect, the present invention relates to a synergistic co-administration of an ileal brake compound/composition with an effective antiviral in combination, wherein the antiviral medicament is FV-100, a bicyclic nucleoside analogue, used in an effective amount, alone or in combination with interferon, especially pegylated interferon and/or ribavirin in an effective amount.

In still another aspect, the present invention relates to a synergistic co-administration of an ileal brake compound/composition with an effective antiviral in combination, wherein the antiviral medicament is GS 9190, a non-nucleoside polymerase inhibitor, used in an effective amount, alone or in combination with interferon, especially pegylated interferon and/or ribavirin in an effective amount.

In still another aspect, the present invention relates to a synergistic co-administration of an ileal brake compound/composition with an effective antiviral in combination, wherein the antiviral medicament is GS 9256, a NS3 protease inhibitor, used in an effective amount, alone or in combination with interferon, especially pegylated interferon and/or ribavirin in an effective amount.

An additional aspect of the present invention relates to a synergistic co-administration of an ileal brake compound/composition with an effective antiviral in combination, wherein the antiviral medicament is GS 9451, a NS3 protease inhibitor, used in an effective amount, alone or in combination with interferon, especially pegylated interferon and/or ribavirin in an effective amount.

In still a further aspect, the present invention relates to a synergistic co-administration of an ileal brake compound/composition with an effective antiviral in combination, wherein the antiviral medicament is GS 5885, a NS5A inhibitor, used in an effective amount, alone or in combination with interferon, especially pegylated interferon and/or ribavirin in an effective amount.

In another aspect, the present invention relates to a synergistic co-administration of an ileal brake compound/composition with an effective antiviral in combination, wherein the antiviral medicament is GS 6620, a nucleotide polymerase inhibitor, used in an effective amount, alone or in combination with interferon, especially pegylated interferon and/or ribavirin in an effective amount.

Still another aspect or the present invention relates to a synergistic co-administration of an ileal brake compound/composition with an effective antiviral in combination, wherein the antiviral medicament is GS 9620, a TLR-7 agonist, used in an effective amount, alone or in combination with interferon, especially pegylated interferon and/or ribavirin in an effective amount.

In another aspect, the present invention relates to a synergistic co-administration of an ileal brake compound/composition with an effective antiviral in combination, wherein the antiviral medicament is GS 9669, a non-nucleoside polymerase inhibitor, used in an effective amount, alone or in combination with interferon, especially pegylated interferon and/or ribavirin in an effective amount.

In a further aspect, the present invention relates to a synergistic co-administration of an ileal brake compound/composition with an effective antiviral in combination, wherein the antiviral medicament is PSI-938, a guanine nucleotide analog polymerase inhibitor, used in an effective amount, alone or in combination with interferon, especially pegylated interferon and/or ribavirin in an effective amount.

In yet another aspect, the present invention relates to a synergistic co-administration of an ileal brake compound/composition with an effective antiviral in combination, wherein the antiviral medicament is Sofosbuvir (PSI-7977), a nucleotide analog, used in an effective amount, alone or in combination with interferon, especially pegylated interferon and/or ribavirin in an effective amount.

In yet a further aspect, the present invention relates to a synergistic co-administration of an ileal brake compound/composition with an effective antiviral in combination, wherein the antiviral medicament is SCY-635, a non-immunosuppressive cyclophilin inhibitor, used in an effective amount, alone or in combination with interferon, especially pegylated interferon and/or ribavirin in an effective amount.

In another aspect, the present invention relates to a synergistic co-administration of an ileal brake compound/composition with an effective antiviral in combination, wherein the antiviral medicament is BI 201335, an inhibitor of NS3/4A protease, used in an effective amount, alone or in combination with interferon, especially pegylated interferon and/or ribavirin in an effective amount.

In yet another additional aspect, the present invention relates to a synergistic co-administration of an ileal brake compound/composition with an effective antiviral in combination, wherein the antiviral medicament is BI 207127, an inhibitor of the NS5B non-nucleoside polymerase, used in an effective amount, alone or in combination with interferon, especially pegylated interferon and/or ribavirin in an effective amount.

In an additional aspect, the present invention relates to a synergistic co-administration of an ileal brake compound/composition with an effective antiviral in combination, wherein the antiviral medicament is ACH-2928, an inhibitor of the NS5A non-nucleoside polymerase, used in an effective amount, alone or in combination with interferon, especially pegylated interferon and/or ribavirin in an effective amount.

In another aspect, the present invention relates to a synergistic co-administration of an ileal brake compound/composition with an effective antiviral in combination, wherein the antiviral medicament is INX-189, a protide which is a phosporamidate nucleotide analog used in an effective amount, alone or in combination with interferon, especially pegylated interferon and/or ribavirin in an effective amount.

In another aspect, the present invention relates to a synergistic co-administration of an ileal brake compound/composition with an effective antiviral in combination, wherein the antiviral medicament is ALS-2200, an inhibitor of the NS5B non-nucleoside polymerase used in an effective amount alone or with interferon, especially pegylated interferon and/or ribavirin in an effective amount.

In an additional aspect, the present invention relates to a synergistic co-administration of an ileal brake compound/composition with an effective antiviral in combination, wherein the antiviral medicament is ALS-2158, an inhibitor of the NS5B non-nucleoside polymerase used in an effective amount alone or with interferon, especially pegylated interferon and/or ribavirin in an effective amount.

In yet a further aspect, the present invention relates to a synergistic co-administration of an ileal brake compound/composition with an effective antiviral in combination, wherein the antiviral medicament is BIT-225, an inhibitor of the targeted p& protein used in an effective amount, alone or with interferon, especially pegylated interferon and/or ribavirin in an effective amount.

In another further aspect, the present invention relates to a synergistic co-administration of an ileal brake compound/composition with an effective antiviral in combination, wherein the antiviral medicament is BL-8020, an inhibitor of Hepatitis C virus (HCV)-induced autophagy used in an effective amount alone or with interferon, especially pegylated interferon and/or ribavirin in an effective amount.

Biomarkers and Outcomes in Patients with Hepatitis C Infection

Predicting clinical outcomes in patients with chronic hepatitis C is considered challenging. Ghany and colleagues (56) used the Hepatitis C Long-Term treatment against Cirrhosis (HALT-C) trial database to develop two prediction models, using baseline values of routinely available laboratory tests together with changes in these values during follow-up to predict clinical decompensation and liver-related death/liver transplant in patients with advanced hepatitis C. Patients randomized to no treatment and who had >/=2-year follow-up without a clinical outcome were included in the analysis. Four variables (platelet count, aspartate aminotransferase [AST]/alanine aminotransferase [ALT] ratio, total bilirubin, and albumin) with three categories of change (stable, mild, or severe) over 2 years were analyzed. Cumulative incidence of clinical outcome was determined by Kaplan-Meier analysis and Cox regression was used to evaluate predictors of clinical outcome. In all, 470 patients with 60 events were used to develop models to predict clinical decompensation. Baseline values of all four variables were predictive of decompensation. There was a general trend of increasing outcomes with more marked worsening of laboratory values over 2 years, particularly for patients with abnormal baseline laboratory test values. A model that included baseline platelet count, AST/ALT ratio, bilirubin, and severe worsening of platelet count, bilirubin, and albumin was the best predictor of clinical decompensation. A total of 483 patients with 79 events were used to evaluate predictors of liver-related death or liver transplant. A model that included baseline platelet count and albumin as well as severe worsening of AST/ALT ratio and albumin was the best predictor of liver-related outcomes. These authors concluded that both the baseline value and the rapidity in change of the value of routine laboratory variables were shown to be important in predicting clinical outcomes in patients with advanced chronic hepatitis C(56).

Another means of predicting response of Hepatitis C to pegIFN/Riba is the viral response linked change in insulin resistance, a parameter of interest to us because it is one of the earliest effects of both RYGB and Brake™ In their study, Thompson and colleagues(57) examined genotype-specific associations between hepatitis C virus and insulin resistance. Specifically, this study investigated the association between a sustained virological response (SVR) and insulin resistance after chronic treatment with interferon/ribavirin therapy. They enrolled 2255 treatment-naive patients with chronic HCV genotype 1 or 2/3 from two phase 3 trials where patients were treated for either 24 or 48 weeks. Insulin resistance was measured before treatment and 12 weeks after treatment using homeostasis model assessment (HOMA)-IR. Paired HOMA-IR measurements were available in 1038 non-diabetic patients (497 with genotype 1; 541 with genotype 2/3). At baseline the prevalence of HOMA-IR>3 was greater in patients with genotype 1 than 2/3 (33% vs. 27%; p=0.048). There was a significant reduction in the prevalence of IR in patients with genotype 1 achieving SVR (delta 10%; p<0.001), but not in genotype 1 nonresponders or those with genotype 2/3. Multivariate analysis indicated that SVR was associated with a significant reduction in mean HOMA-IR in patients with genotype 1 (p=0.004), but not in those with genotype 2/3, which was independent of body mass index, ALT, GGTP and lipid level changes. It was thought that genotype 1 may have a direct effect on the development of insulin resistance, independent of host metabolic factors, and may be partially reversed by viral eradication(57). This study partially justifies the study of parameters linked to hepatic steatosis, but this variable was not directly measured in this trial.

Several studies of T2D and metabolic syndrome patients with and without Hepatitis C provide further support for Hepatic steatosis, common in diabetes, (58, 59) as the usual cause of elevated liver enzymes, and link the insulin resistance, glucose intolerance and elevated triglycerides to the development of hepatic steatosis. Stated simply, the steatosis is present because of the metabolic syndrome even without overt T2D. Once present, the hepatic steatosis interacts with the hepatitis C virus to make eradication more difficult. Finally, the liver enzymes only decline in hepatitis C treatments where the metabolic syndrome is also resolved, such as in the study of Thompson(57). Dixon and colleagues (60) directly studied the effect of gastric banding associated weight loss on nonalcoholic fatty liver disease in a case series of 36 selected obese patients. These 36 patients (11 males, 25 females) had paired liver biopsies, the first at the time of laparoscopic adjustable gastric band placement and the second after weight loss. Second biopsies were obtained from two groups: those requiring a subsequent laparoscopic procedure (n=19) and those with index biopsy score of 2 or greater for zone 3-centric hepatic fibrosis (n=17). All biopsies were scored, blinded to the patient's identity and clinical condition, for individual histological features and for NASH stage and grade. Initial biopsies demonstrated NASH in 23 patients and steatosis in 12 patients. Repeat biopsies were taken at 25.6+/−10 months (range, 9-51 months) after band placement. Mean weight loss was 34.0+/−17 kg, and percentage of excess weight loss was 52+/−17%. There were major improvements in lobular steatosis, nacre-inflammatory changes, and fibrosis at the second biopsy (P<0.001 for all). Portal abnormalities remained unchanged. Only four of the repeat biopsies fulfilled the criteria for NASH, implying that this procedure was essentially a cure. There were 18 patients with an initial fibrosis score of 2 or more compared with 3 patients at follow-up (P<0.001). The patients with the metabolic syndrome in this series (n=23) who had more extensive changes before surgery, had greater improvement with resulting weight loss. Dixon and colleagues concluded that weight loss after bariatric surgery provides major improvement or resolution of obesity and metabolic syndrome-associated abnormal liver histological features in severely obese subjects(60).

Hickman and colleagues noted that raised liver enzymes are common in T2D, but often considered benign. Non-alcoholic fatty liver, including hepatic steatosis was the cause in 65% of cases but other causes included alcoholic liver disease and viral hepatitis. Cirrhosis was identified in 11 patients. These investigators noted a significant burden of advanced liver diseases from a variety of etiologies in patients with T2DM. (61).

Forlani conducted an observational point prevalence study on hepatic disease and raised liver enzymes in T2D in eight hospital-based Italian diabetes units. Data of 9621 consecutive T2D patients (males, 52.4%; median age, 65 yr) were analyzed, and alanine and aspartate aminotransferase (ALT, AST) and gamma-glutamyl transferase (GGPT) levels were related to body mass index (BMI), metabolic control and the presence of the metabolic syndrome. They noted ALT, AST, and GGPT levels exceeding the upper limit of normal were present in 16.0%, 8.8%, and 23.1%, respectively, the prevalence being higher in males, increasing with obesity class and poor metabolic control, and decreasing with age. Elevated enzymes were systematically associated with most parameters of the metabolic syndrome. After correction for age, gender, BMI, and differences across centers, elevated triglyceride levels/fibrate treatment [odds ratio (OR), 1.57; 95% confidence interval (CI), 1.34-1.84] and an enlarged waist circumference (OR, 1.47; 95% CI, 1.17-1.85) were the only parameters independently associated with high ALT. In a separate analysis, the presence of metabolic syndrome (Adult Treatment Panel III criteria) was highly predictive of raised liver enzymes. After exclusion of hepatitis B and C positive cases, tested in 2 centers, the prevalence of raised enzymes decreased by approximately 4%, but the association with the metabolic syndrome did not change significantly. In conclusion, the high prevalence of elevated liver enzymes in T2D is in keeping with the well-demonstrated risk of progressive liver disease(62).

Probiotics are closely associated with metabolic syndrome and hepatic steatosis. A study by Kirpich and colleagues examined the potential therapeutic role of probiotics in alcohol-induced liver injury in 66 adult Russian males admitted to a psychiatric hospital with a diagnosis of alcoholic psychosis. Patients were randomized to receive 5 days of *Bifidobacterium bifidum* and *Lactobacillus plantarum* 8PA3 versus standard therapy alone (abstinence plus vitamins). Stool cultures and liver enzymes were performed at baseline and again after therapy. Results were compared between groups and with 24 healthy, matched controls who did not consume alcohol. Compared to healthy controls, alcoholic patients had significantly reduced numbers of bifidobacteria (6.3 vs. 7.5 log colony-forming unit [CFU]/g), lactobacilli (3.15 vs. 4.59 log CFU/g), and enterococci (4.43 vs. 5.5 log CFU/g). The mean baseline ALT, AST, and GGTP activities were significantly elevated in the alcoholic group compared to the healthy control group (AST: 104.1 vs. 29.15 U/L; ALT: 50.49 vs. 22.96 U/L; GGT 161.5 vs. 51.88 U/L), indicating that these patients did have mild alcohol-induced liver injury. After 5 days of probiotic therapy, alcoholic patients had significantly increased numbers of both bifidobacteria (7.9 vs. 6.81 log CFU/g) and lactobacilli (4.2 vs. 3.2 log CFU/g) compared to the standard therapy arm. Despite similar values at study initiation, patients treated with probiotics had significantly lower AST and ALT activity at the end of treatment than those treated with standard therapy alone (AST: 54.67 vs. 76.43 U/L; ALT 36.69 vs. 51.26 U/L). In a subgroup of 26 subjects with well-characterized mild alcoholic hepatitis (defined as AST and ALT greater than 30 U/L with AST-to-ALT ratio greater than one), probiotic therapy was associated with a significant end of treatment reduction in ALT, AST, GGT, lactate dehydrogenase, and total bilirubin. In this subgroup, there was a significant end of treatment mean ALT reduction in the probiotic arm versus the standard therapy arm. In conclusion, patients with alcohol-induced liver injury have altered bowel flora compared to healthy controls. Short-term oral supplementation with *B. bifidum* and *L. plantarum* 8PA3 was associated with restoration of the bowel flora and greater improvement in alcohol-induced liver injury than standard therapy alone(63). This study points to additional methods for control of hepatic inflammation and liver enzyme elevation.

Progressive liver disease in hepatitis C is also monitored with biomarkers of hepatic fibrosis. Fontana and colleagues examined serum fibrosis marker levels during the lead-in treatment phase of patients enrolled in the Hepatitis C Antiviral Long-term Treatment against Cirrhosis (HALT-C) trial. After the trial, the week 0, 24, 48, and 72 serum samples were analyzed for YKL-40, tissue inhibitor of matrix metalloproteinase-1, amino-terminal peptide of type III procollagen (PIIINP), and hyaluronic acid (HA) levels. All 456 chronic hepatitis C patients received pegIFN/Riba for 24 to 48 weeks. Mean age of the patients was 49.2 years, 71% were male, and 39% had cirrhosis at baseline. Lower pretreatment serum YKL-40, tissue inhibitor of matrix metalloproteinase-1, PIIINP, and HA levels were associated significantly with a week-20 early virologic response (P<0.0001). In multivariate analysis, non-1 genotype, non-black race, prior interferon monotherapy, and lower baseline serum ALT/AST levels and log (10)YKL-40 levels were associated independently with week-20 virological response. Statistically significant declines in all marker levels were observed at week 72 compared with baseline in the 81 patients with a sustained virologic response, but not in the 72 patients with breakthrough or relapse. At weeks 24 and 48, significant increases were observed in serum PIIINP and HA levels in nonresponders compared with virological responders (P<0.0001). Fontana and colleagues concluded that elevated pretreatment YKL-40 levels are an independent predictor of initial virological response to pegIFN/Riba treatment. Levels of all 4 serum fibrosis markers decreased significantly in the SVR patients, consistent with reduced hepatic fibrogenesis. Measuring serum fibrosis marker levels before and after antiviral therapy may provide important indicators of response in patients with hepatitis C(64).

New agents are here for treatment of hepatitis C, for example boceprevir, an NS3 protease inhibitor, which is approved for use in combination with pegIFN/Riba. PegIFN/Riba alone achieves sustained virological response (SVR) in fewer than half of patients with genotype 1 chronic hepatitis C virus infection treated for 48 weeks. Kwo and colleagues tested the efficacy of boceprevir, an NS3 hepatitis C virus oral protease inhibitor, when added to pegIFN/Riba for genotype 1 hepatitis C virus. The primary endpoint was SVR 24 weeks after treatment. In patients with untreated genotype 1 chronic hepatitis C infection, the addition of the direct-acting antiviral agent boceprevir to standard treatment with pegIFN/Riba doubles the sustained response rate compared with that recorded with standard treatment alone(65). There are similar studies with telaprevir. Although over 60% of the study patients have hepatic steatosis at baseline, data on any endpoint of response other than viral load is completely absent in these studies, and there are no biomarkers of metabolic syndrome measured or assessed.

Thus, it does not appear that the newer drugs such as boceprevir or telaprevir change liver enzymes or any marker of hepatic steatosis in patients, even though these two newer protease inhibitor drugs are used in combination with pegIFN/Riba (25, 66-71)

Regarding the role of antiviral agents in the control of hepatic steatosis, it would be unexpected to see change in liver enzymes or resolution of hepatic inflammation with the use of any of the antiviral drugs available, particularly if the regimen does not include pegIFN/Riba. Clearly, none of these drugs directly manages the hepatic steatosis, which is a highly significant predictor of treatment failure or relapse (72). Thus the discovery that management of hepatic steatosis with either RYGB or orally administered Brake™ offers promise of another major advance in the treatment of hepatitis C infection.

Case 1 Hepatitis C Treatment with Brake Alone

Case 1: A Hepatitis C Patient with Moderate Viral Load Treated with Brake™ Alone, with the Goal to Evaluate the Secondary Antiviral Impact of Improving the Hepatic Steatosis Patient M1 was a 55 yo female with a normal BMI. She had a renal transplant in 1998 and has been taking prednisone, Rapimmune, Synthroid, Nexium and Cozaar.

Figure 26:
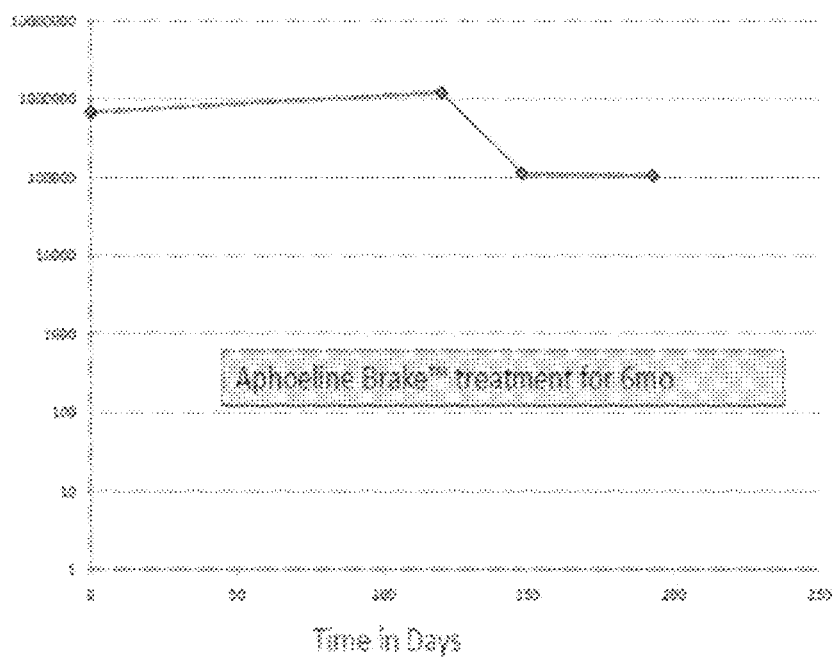

This patient had a test positive for Hepatitis C Genotype 3 in 1998, She failed to respond to treatment with IFN/Riba approximately 4 yr prior to this episode of care. A Liver Biopsy In 2004 revealed Cirrhosis w. bridging fibrosis, stage 3 out of 4. She was not on Hepatitis C treatment since 2007; no antiviral drugs in the 3 years prior to Brake™ therapy. Treatment Course: Aphoeline Brake™ (formulation II) was added to her treatment at her second visit. Subsequently, her Liver enzymes improved to normal over 3 mo; Serum Creatinine decreased to normal over 3 mo; Here, Alpha fetoprotein decreased rapidly; Her Hepatitis C Viral count decreased rapidly to 100K, also indicative of synergistic effects between the ileal brake hormone releasing substance, since this patient was not given anti-viral drugs (See FIG. 26)

Figure 27:
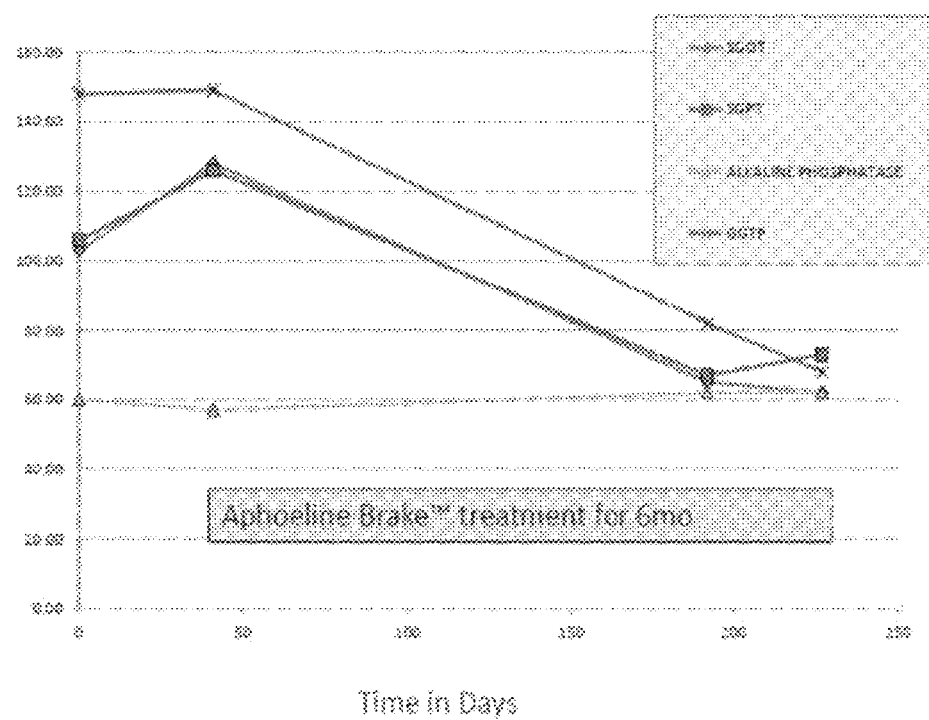

Summary and Comment: Patient M1 had one log reduction in viral titers without any anti-virals, which means that the use of Brake allowed her to clear some virus. As M1 had previously failed IFN/Riba in 2004, was immunosuppressed with prednisone and had established cirrhosis. It would have been a great surprise if this patient had viral eradication even for a short time. Her T2D parameters were unaffected, (patient did not have T2D); Her Alpha fetoprotein declined from 8.5 ng/ml pre-treatment to <4 ng/ml post. Her liver enzymes all declined to normal on Brake™ therapy, even though the hepatitis C virus was still present in lower numbers. Overall, there was an unexpected but interesting improvement in hepatic function, without major changes in the Hepatitis C viral load (See FIG. 27). Prior to these observations it was considered unlikely to improve hepatic steatosis unless the virus was eradicated. However, these results show that improving the hepatic steatosis actually improves the overall viral response, presumably by boosting the body's ability to respond to the viral effects with improved hepatic functioning.

Case 2 Hepatitis C Patient Treated with Brake in Combination

A Hepatitis C Patient with Combination Treatment of Brake™ and pegIFN/Riba, a Test of the Ability of Combinations to Reduce Viral Load Over that of pegIFN/Riba Alone Patient E1 was a 36 year old male who was 5'7" 185 lb and had a BMI of 29 upon presentation for treatment of his hepatitis C genotype 1a TC virus. His pre-treatment liver biopsy showed hepatic steatosis and fibrosis 1 of 4. He was started on pegIFN/Riba with initial one log decline in viral load, but after the first month his dose was increased because of a plateau in viral load response. There was only a one log further decline. After two months with only moderate viral load response to this increased dosage, the patient had the addition of 10 gm per day of Aphoeline Brake™ added to his maximal dose pegIFN/Riba regimen.

Figure 28:
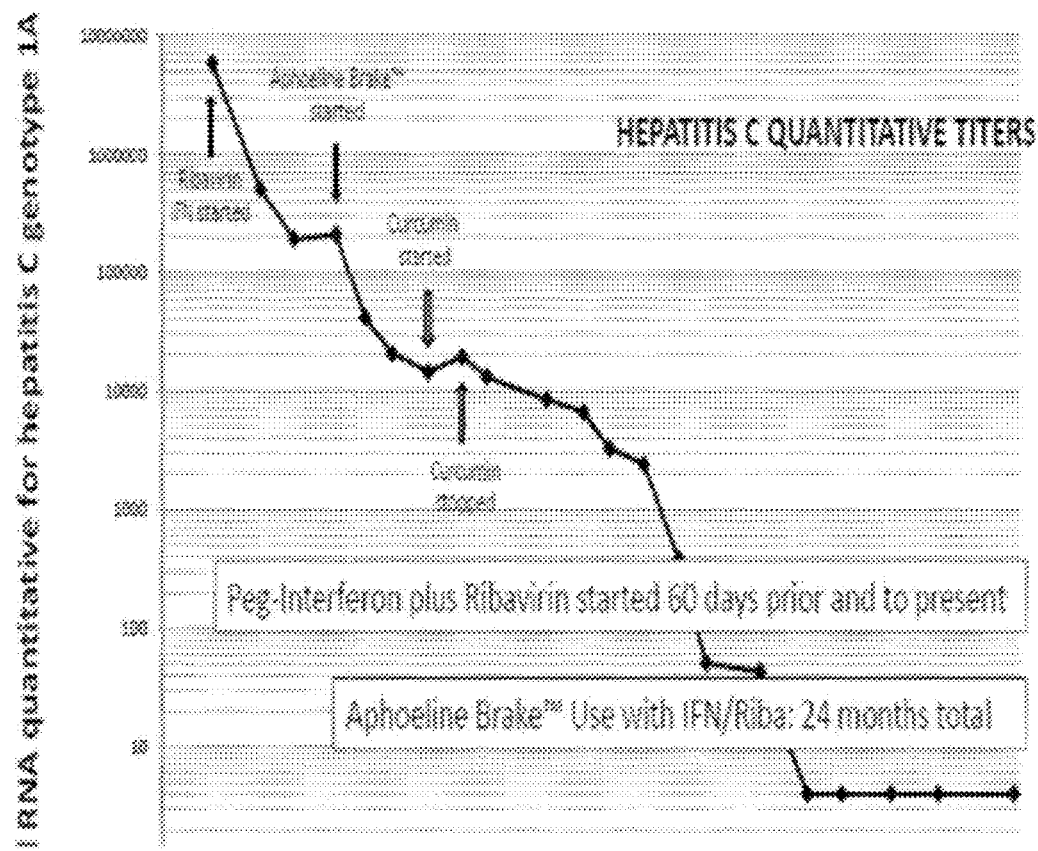

As shown in FIG. 28, which describes this patients Hepatitis C viral load over time, he received this combination for 24 months and became negative for Hepatitis C virus for the past 10 months, which in the case is a 7 log decline in viral load. Thus, the viral load response to the ileal brake compound of formulation II plus the pegylated interferon and ribavirin is a synergistic result, because it far exceeds the antiviral actions of either compound alone or their expected additive effects. In the middle of his course of treatment, he started taking curcumin, with loss of control for viral load. This was not surprising as the action of Brake™ is antagonized by curcumin. After stopping curcumin his viral load again began to drop.

Figure 29:
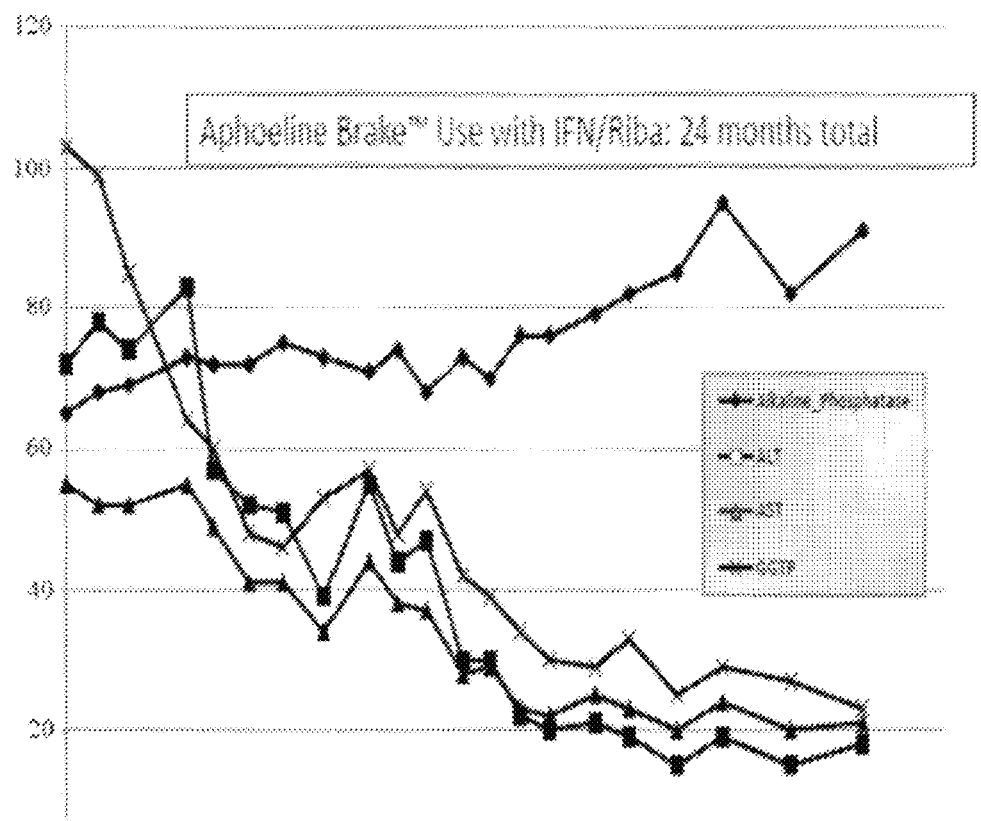
FIG. 29 shows the effect on hepatic parameters of a patient who was put on a combination of formulation II in combination with pegylated interferon and ribavirin for a period of 24 months.

On Formulation II, there has been major and unanticipated improvement of Liver health with regard to steatosis. The patient's initially elevated triglycerides and liver enzymes on pegylated interferon/ribavirin (see FIG. 29) which declined by less than 25% on the antiviral alone, are now normal, and there is no clinical evidence of steatosis at the present time. Thus, the 100% decline in hepatic inflammatory response to the combination of the brake compound (formulation II) and pegylated interferon/ribavirin was also synergistic in nature.

Figure 30:
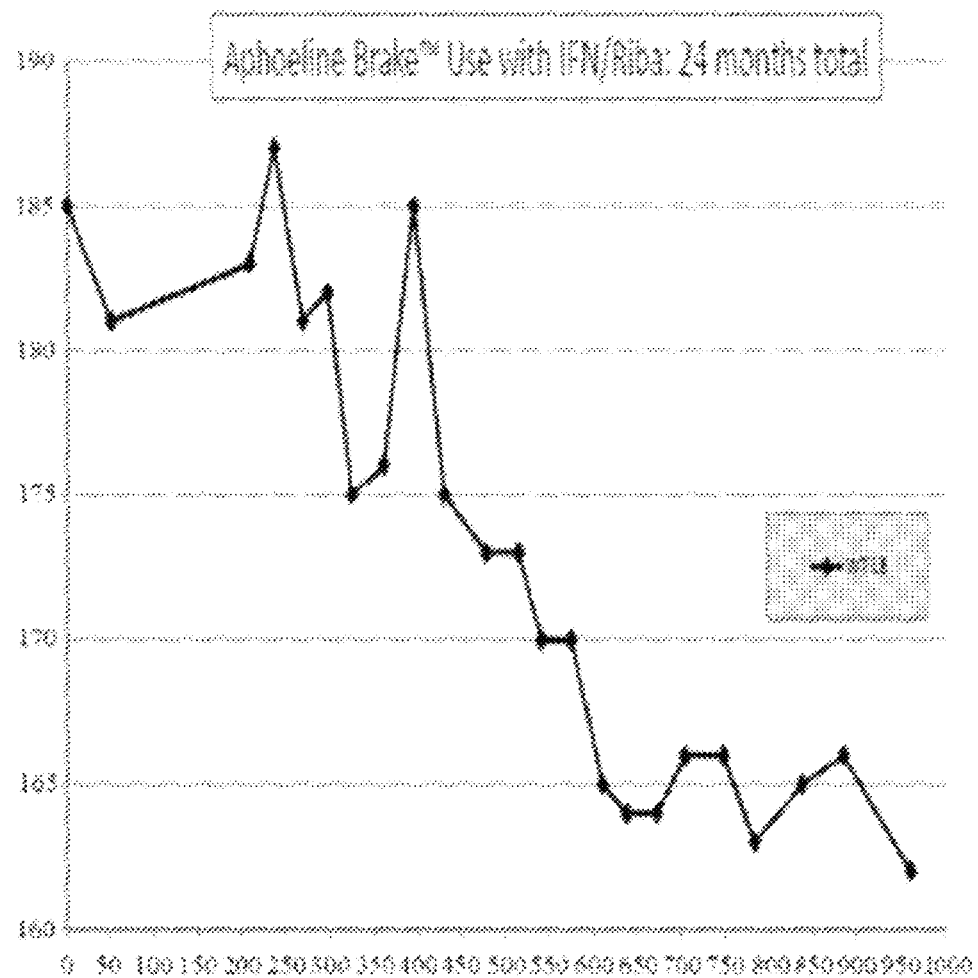
FIG. 30 shows effect on the weight of the patient in FIGS. 28 and 29, after a period of 24 months. Note that the patient lost more than 20 pounds during that period.

Follow-up. After 24 months of treatment, the patient has lost 23 lb (see FIG. 30), continues to do well and is working. After beneficial (synergistic) response to the combination therapy for 24 months, antivirals and Brake™ are now stopped and the patient is in the 6-12 month follow-up phase to determine if the virus will return.

Alpha Fetoprotein (AFP) is a glycoprotein of 591 amino acids and a carbohydrate moiety. Many functions have been proposed for AFP such as an anti-cancer active site peptide. Its function in adults is unknown, but a concentration above 500 ng/ml of AFP in adults can be indicative of hepatocellular carcinoma, germ cell tumors, and metastatic cancers of the liver. Alpha fetoprotein values above 10 ng/ml are considered a risk in hepatitis C patients, and the goal of therapy with pegIFN/Riba is to reduce the AFP below this value(73). Many patients with hepatitis C have elevated alpha fetoprotein concentrations. Alpha fetoprotein may be more closely linked to hepatic steatosis than to the hepatitis C viral load(51). Goldstein and colleagues (74) noted that patients with chronic viral hepatitis and cirrhosis often have elevated serum alpha-fetoprotein (AFP) values, and studied 81 patients with chronic hepatitis C. They examined the relationships of serum AFP and alanine aminotransferase (ALT) values, hepatic histologic features, and hepatocyte proliferation activity scores. Twenty-two of their patients had nil to mild fibrosis, 34 had moderate fibrosis, and 25 had marked fibrosis-cirrhosis. The mean serum AFP value was significantly greater in patients with more fibrosis. Serum ALT values were slightly greater in the marked fibrosis-cirrhosis patient group. Among all patients, increasing serum AFP values significantly correlated with increasing ALT values. There was no association between serum AFP values and immunohistochemical staining for AFP within hepatocytes. These results suggest that elevated serum AFP values are the result of altered hepatocyte-hepatocyte interaction and loss of normal architectural arrangements. The presence of marked fibrosis or cirrhosis, a state of significant altered hepatocyte architecture, may be the underlying cause of increased serum AFP, rather than necrosis or active regeneration. Others would agree with this view(73, 75-79), lending utility to use of declines in alpha-fetoprotein as a monitor of improving hepatic cellular architecture and decreasing risk for cirrhosis and possibly hepatocellular carcinoma.

Figure 31:
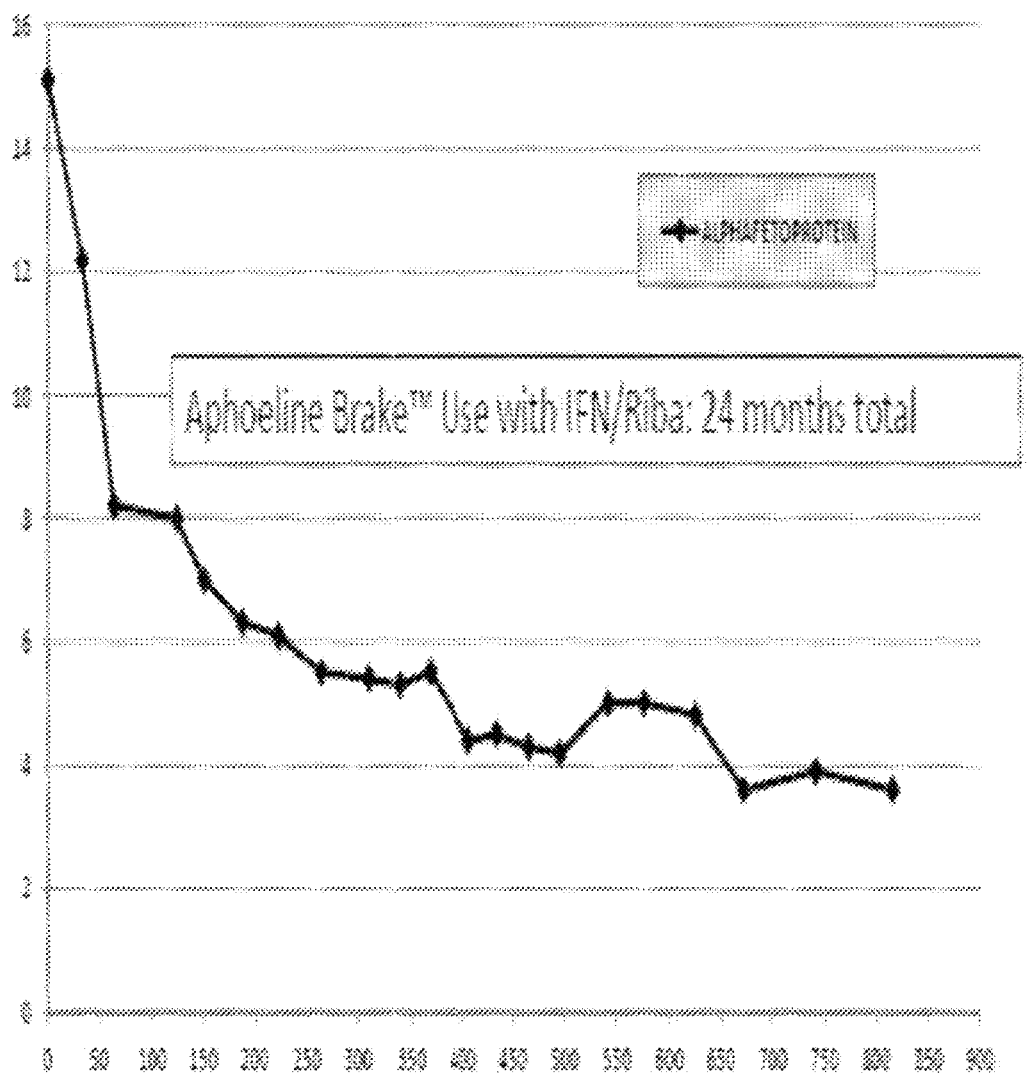
FIG. 31 shows effect of the ileal brake composition and viral combination therapy on alpha-fetoprotein after 24 months total therapy in the patient in FIGS. 28-30.

The graph of this biomarker for patient E1 over time is shown below as FIG. 31. From the pre-treatment AFP baseline of 15 ng/ml, there was an extensive decline in alpha fetoprotein in patient E1; this may indicate improvement in the health of the liver, a decline in steatosis, and a lower risk of cirrhosis under combined treatment with pegIFN/Riba and Brake™. Patient E1 had undetectable viral load in association with alpha fetoprotein values <4 ng/ml.

Case 3 Hepatitis C Patient with Cirrhosis Treated with Brake Alone

Figure 32:
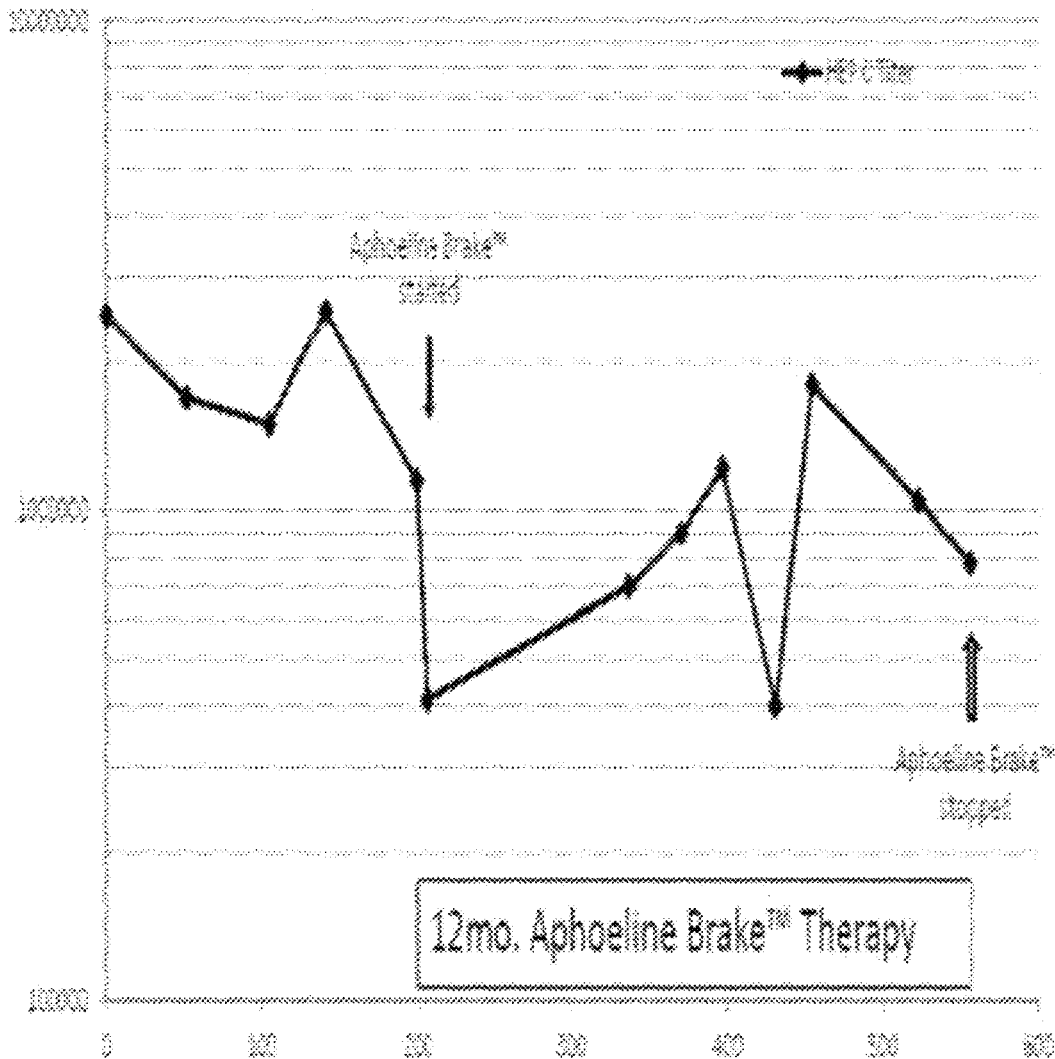
FIG. 32 shows the effect on Hepatitis C titers in a patient after 12 months of therapy on the ileal brake composition (formulation II).

Case 3: A Hepatitis C Patient with Advanced Cirrhosis, Treated with Brake™ Alone, a Test of the Ability to Control Hepatic Steatosis in the Face of Minimal Action on the Viral Load Patient L1 is a 66 yo Overweight (5'3" 202 lb) but not overtly T2D female with Hepatitis C genotype 1a since ~2002. She had previously been treated with pegIFN/Riba but had been considered a failure in 2005. She has been untreated for Hepatitis C since that time. Her liver biopsy in 2006 revealed cirrhosis with fibrosis 4/4. Her bilirubin was 1.5 when seen and she was on the liver transplant list. Her chronic medications included spironolactone, rifaximin, and nexium. In view of this history she was given a course of Aphoeline Brake™ in 2010-2011, with a promising decline in viral load (approximately 1 log). This is illustrated in FIG. 32.

Figure 33:
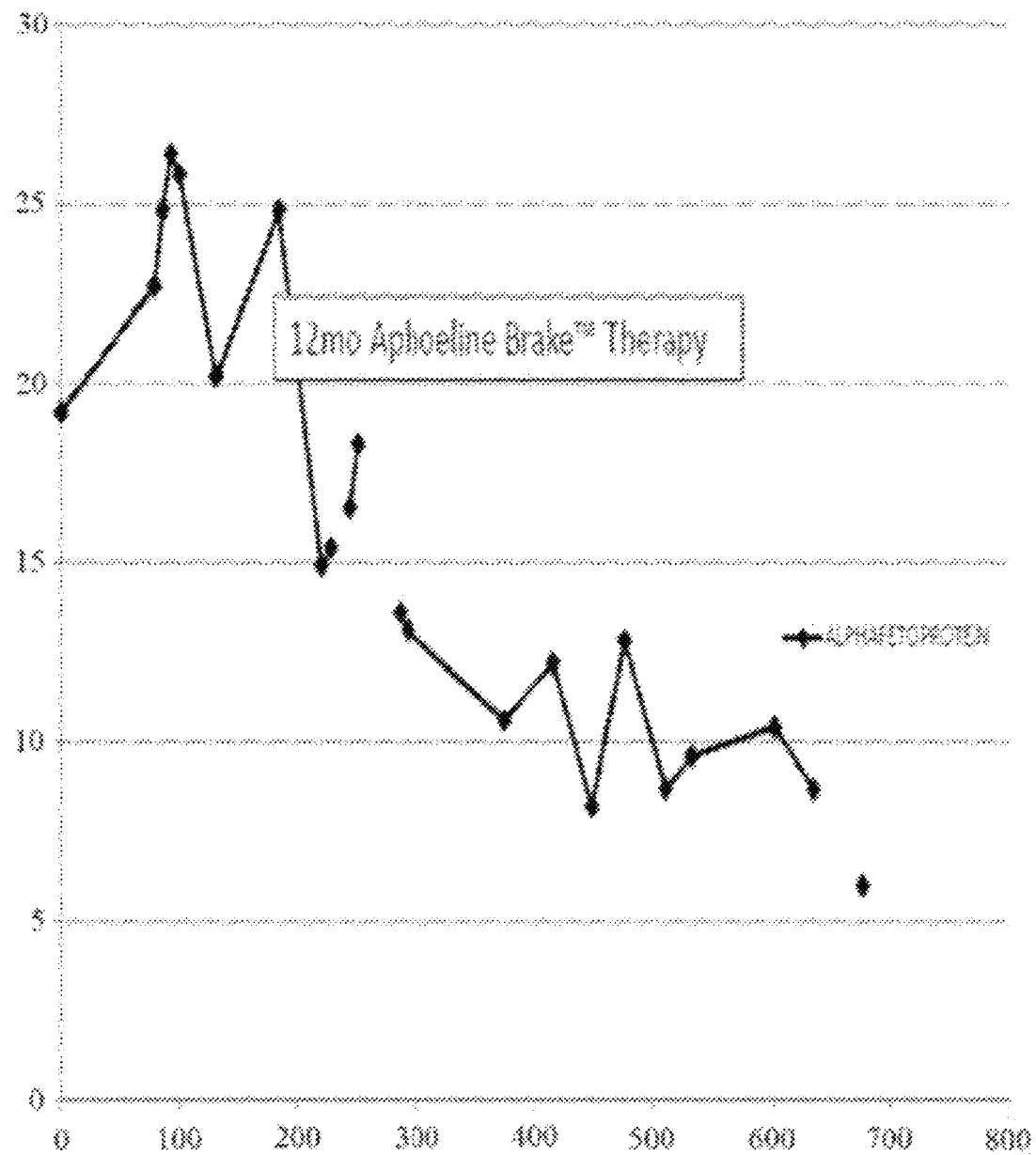
FIG. 33 shows the effect on alpha-fetoprotein on a patient after 12 months of therapy on the ileal brake hormone releasing composition (formulation 2).

The patient had markedly elevated alpha fetoprotein values, 25 ng/ml at baseline prior to treatment with Brake™. Values are illustrated in FIG. 33. During treatment over the next 12 months, these alpha fetoprotein values declined to 6 ng/ml, which is not normal but very good for a patient with 4/4 fibrosis and cirrhosis. This decline is related to the healing of the liver and the decline in steatosis, which may be entirely due to the administration of the ileal brake composition (Aphoeline formulation II).

Figure 34:
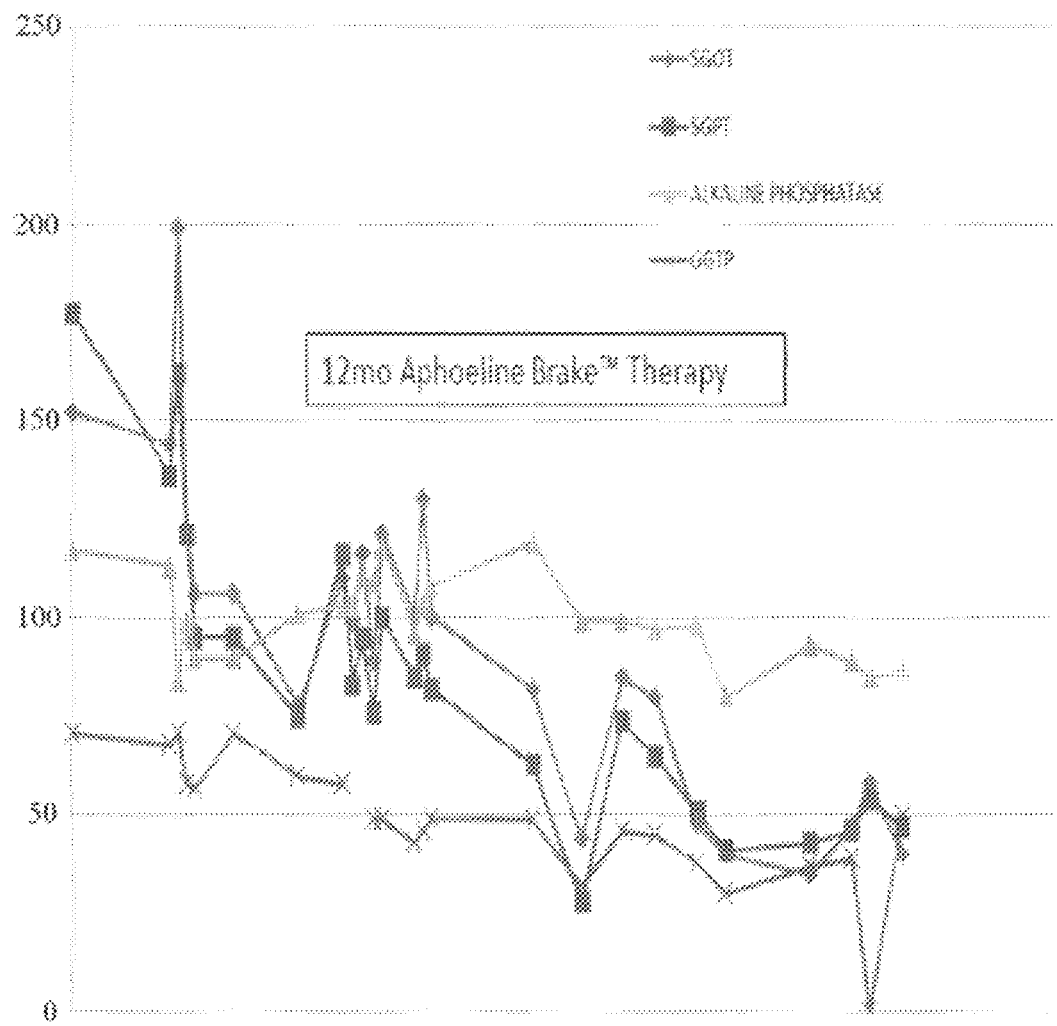
FIG. 34 shows that liver enzymes also decline, consistent with the healing, improvement in steatosis and the lowering of inflammation after 12 months of therapy on the ileal brake composition (formulation 2).

Liver enzymes also decline, consistent with the healing, improvement in steatosis and the lowering of inflammation, as shown in FIG. 34. It was notable that her viral load was not reduced to negative, and in fact with 4/4 fibrosis it would not have been expected to see a negative viral load. However, the impact of Brake on the liver was clearly distinguishable in this case where there was only modest anti-viral associated effect itself. It therefore seems plausible to treat the hepatic steatosis, realizing that this will be of major benefit to the patient even without concomitant antiviral medication. The overall impression is that Brake is acting synergistically with endogenous antiviral activity, because the improving hepatic function itself can control the hepatitis C virus to some degree.

Follow-up: Brake™ clearly improved her hepatic function and this treatment alone was associated with decline in viral load. It is not expected that this decline in viral load was an anti-viral effect of Brake™, but rather it followed a marked improvement in her hepatic steatosis. Indeed although she was not subjected to a repeat of her biopsy, she clearly improved hepatic function by all measures. Bilirubin declined to 0.9 which is normal, she had no further episodes of encephalopathy and she returned to work as Lawyer. Total weight loss was 35lb, and her weight stabilized at 170 lb. She was taken off the transplant list and was lost to FU in 2012

Hepatic Steatosis and Steatohepatitis Formulation of Brake. Disclosure of a Formulation of Brake™ that would be Effective in the Treatment of Hepatic Steatohepatitis, for Use in Patients with Hepatitis C that are Treated with Antiviral Agents The significant difference between normal and overweight or obese patients, is the response of the ileal brake to the intake of the mixed meal (80, 81), and more specifically to sugars. Therefore, it seems the natural appetite suppressive pathways become tolerant to the intake of sugars. This partially explains the success of no carbohydrate programs such as the Adkins diet, even though in this case there are no demonstrable differences in the anatomy or histology of those two groups, except in rare cases of severe morbid long term obesity associated with atrophy of the ileum. Given the fact that food delivered to the distal intestine via RYGB is capable of stimulating those hormones independently of oral intake and the fact that the ileal stimulation during a mixed meal can be inhibited by suppressing the neurotransmission, it may be about the transmission of the signal from gut to brain. Ileal infusions of oleic acid in different amounts induced a dose-dependent increase of PYY (P<0.01) and a borderline decrease of motilin (P=0.05) levels (82), and these have central actions in appetite suppression. This study showed among its findings that the ileal brake effect on gastric emptying can be evoked by low doses of lipids in the distal ileum and that the delay of gastric emptying is related to the release of PYY. Both phenomena are dose dependent with regard to infused oleic acid. Thus the ileal brake is activated by lipids and sugars, and the optimal mixture can regulate a variety of the hormonal and immune-modulatory effects collectively considered that of the ileal brake itself.

It is probable from the oral Brake™ formulation work described herein, and that of the RYGB and supply side modeling of diabetes(37, 38, 40), that a reset of a carbohydrate-tolerant ileal brake pathway will re-set the control of the appetite center and down-regulate the feedback loop that interrupts eating(83), and the consequences of this down regulation of the ileal brake is acceleration of the dietary supply driven progression to a metabolic syndrome. Brake acts directly to restore this down-regulated appetite controller in those with obesity and T2D, the action is termed "wake up the Brake™".

With the promise of a beneficial interruption of hyperglycemia and hyper-triglyceridemia from decreased sugar and lipid intake (84, 85) indeed it appears that the glucose supply side acting Brake™ (37, 38) is a primary means of controlling metabolic syndrome and the hepatic manifestation thereof, which is steatosis. Therefore, if we are able to directly stimulate the ileum in the manner of RYGB with an orally administered formulation of Brake™, we should be able to restore the ileal brake signal and at least partially restore the visceral signals that control the intake of selected foods such as sugars and lipids. These control pathways also benefit hepatic steatosis treatment, since lipids accumulate in the liver itself.

These visceral signals are not only important to control of metabolic syndrome abnormalities but as reported in review articles (86-91) these hormones are extremely beneficial to the patient. They control the most fundamental of processes, which may be called eating behavior, and they do not extinguish or even reset with food deprivation diets (92). Their persistence during starvation diets could be what the patients are seeking unconsciously when they overeat in times of food in plenty.

The surprise of these hormonal ileal brake pathways is that they are down-regulated as patients overeat, allowing a new set point at a higher body weight and eventually leading to obesity and diabetes (93). Since these hormones are also very important in the homeostasis of the insulin and glucose levels they will help tremendously in the use of the reserves that are already present. Finally there is new evidence that gut derived inflammation of the liver and pancreas, itself an effect of food and intestinal bacteria, is regulated by the hormones released by the ileal brake pathway, and that for the first time RYGB surgery and oral administration of Brake™ control these long term inflammation pathways (40).

A conceptual analysis of these pathways clearly places the portal system and the liver at the center of the regulatory organs in the diet and obesity axis. When the ileal brake pathway is out of control and over-eating accelerates, these controlling hormonal pathways lead to metabolic syndrome manifestations such as obesity, fatty liver disease, and atherosclerosis. Fatty liver disease is a precursor of hepatic fibrosis, cirrhosis and even hepatocellular carcinoma(94). Thus the use of Brake™ in patients with hepatic steatosis and hepatitis C is a novel means of controlling the underlying system that leads to progression of hepatocellular diseases in the presence of the hepatitis C virus, and the response of hepatic steatosis to RYGB surgery(95) predicts that oral use of Brake formulations would accomplish the same neuro-hormonal effects currently attributed to RYGB surgery.

By stimulating the endogenous and established hormones with Aphoeline Brake™ the present inventors are delivering the majority of the elucidated GI hormones where they belong (in the portal system), where they have the most powerful impact on the pancreas and the liver(96). We were also encouraged by the fact that RYGB surgery for obesity is capable of stimulating those hormones in essentially all patients, and the effects are apparent well before any weight loss occurs (95, 97-102), indicating that the patients with obesity, diabetes, and hepatic steatosis retain their innate ability to respond at the level of the ileal brake when normal hormonal levels are restored. Acting via these hormonal and neuro-hormonal pathways, RYGB changes the diets of patients, to lower their intake of refined sugars and fats, while shifting dietary preferences to intake of fruits and vegetables(103). Meat intake goes down and is more in moderation along with less fat, plant proteins and complex carbohydrates (103-111). Thomas and Marcus(112) further studied the issue of preference for fats by making a comparison of both food selection and food intolerance frequency of High-fat grouped foods versus Low-fat grouped foods in Roux-en-Y bariatric clients during their dietary adaptation phase (DAP). Thirty-eight bariatric surgery patients in their dietary transition phase (3 months-2.5 years) filled out a 236-food item questionnaire. From the larger set of primary data, 24 high-fat (30% or greater fat) and 22 low/lower-fat food items were itemized by selection frequency and food intolerance frequency for comparison. Briefly, high-fat food selection was 38.3% against low fat at 50.4% (p=0.0002). For comparison, the complete questionnaire's 236-item food selection percentage was 41%. Frequency of "Never" experiencing food intolerance was similar between both groups with a combined mean of 1.92%. "Seldom to Sometimes" intolerance in low-fat foods was 13.3%, and 24.9% in high fat (p=0.002). Finally, "Often to Always" experiencing food intolerance in the Low-fat food group was 85.5% versus 72.2% for the High-fat group (p=0.002). Overall, RYGB patients in the DAP demonstrated typical "dieting behavior" by selecting low-fat foods at a greater frequency than high-fat foods. Future bariatric studies are needed to further explore this and other commonly practiced "dieting behaviors" in bariatric patients. Leahey and colleagues (107) examined the effects of bariatric surgery on food cravings and especially sweet cravings, and also determined whether surgery patients' cravings differ from those of normal weight (NW) controls. Their objective was to examine changes in bariatric surgery patients' frequency of food cravings and consumption of craved foods from before to 3 and 6 months after surgery and to compare surgery patients' frequency of food cravings to those of NW controls. Bariatric surgery patients (n=32) and NW controls (n=20) completed the Food Cravings Inventory and had their height and weight measured. Before surgery, the patients reported more overall cravings and cravings for high fat and fast foods and a greater consumption of craved high-fat foods than the NW controls. Comparing overall findings from before to 3 and 6 months after surgery, the patients had significant reductions in overall cravings for, and consumption of, craved foods, with specific effects for sweets and fast food. Of interest, surgery had virtually no effect on the cravings for high-fat foods. Moreover, high-fat and fast food cravings did not reduce to normative levels. The postoperative patients were less likely to consume craved sweets than NW controls, and the patients' postoperative weight loss was largely unrelated to food cravings. Thus, Leahey found that bariatric surgery is associated with significant reductions in food cravings and consumption of craved foods, with the exception of high-fat foods. For these reasons the mixture of Brake™ invented for the improved management of hepatic steatosis and the dosages to be used are disclosed herein. Miras and colleagues (113) studied the pre and postoperative dietary habits and food preferences of patients who had bariatric surgery, and overall concluded that a fundamental aspect of the change caused by RYGB was in the taste for sweets and fats, and in most cases, taste favoring vegetables.

The inventors set a goal to stimulate the ileal hormones with an oral formulation of food component and generally recognized as safe (GRAS) ingredients, created to become an ileal brake hormone releasing substance that mimics the action of RYGB surgery. The data provided herein, derived from a comparison of Aphoeline Brake™ treated patients with RYGB are compelling and the stimulation of the ileal brake pathway seems independent of age or weight or diabetes. This establishes that the intestine still functions in obesity, albeit with less hormonal oversight and control. Thus, the fundamental problem in both obesity and hepatic steatosis (fatty liver) seems to be in the down-regulation of the signaling from the ileum.

What we discovered from oral formulations targeted to the precise site which controls ileal brake hormone release, is that local stimulation of the ileum in this manner has a very powerful effect on the glucose and insulin homeostasis, leading to a rapid decline in of insulin resistance. Insulin resistance is the first major biomarker to change in response to either the oral use of Brake or to RYGB surgery. The inventors discovered that physiologically, the ileal brake pathway is not a means of further stimulating insulin, but in contrast to a prevailing viewpoint, a reduction of glucose supply-side delivery leads to a reduction of insulin resistance that occurs well before the patient begins to lose weight. This novel viewpoint is also consistent with the data from RYGB surgery, where the reduction in insulin resistance occurs within a few hours of surgical anastomosis, again much earlier than any weight loss.

The more powerful effect on steatohepatitis, observed in our patients by marked decline of the ALT, AST and GGTP to normal within 3-4 weeks of treatment with Aphoeline Brake™ need to be studied with before and after liver biopsy over a much longer duration of years, to confirm that the trend and the gains reported herein from laboratory data also apply to liver histology. However, it appears from the patient data and the RYGB data that the reduction in endotoxin, inflammation, insulin resistance and the trend to normalize triglyceride and cholesterol are all involved in rapid reduction of hepatic steatosis, just as occurs with bariatric surgery (95). The optimal formulation of Brake™ should consider the impact on hepatic lipid accumulation, itself under control of the mixture of signaling and mimetic substances reaching the ileal brake in RYGB. Various foods and components are beneficial beyond the glucose component and the lipid component, and some of these are incorporated by reference to the studies linking them to metabolic syndromes in model systems or epidemiological studies. For example, (114) Tulipani and colleagues examined changes in the urinary metabolome of subjects with metabolic syndrome, following 12 weeks of mixed nuts consumption (30 g/day), compared to sex- and age-matched individuals given a control diet. The urinary metabolome corresponding to the nut-enriched diet clearly clustered in a distinct group, and the multivariate data analysis discriminated relevant mass features in this separation. The metabolomics approach revealed 20 potential markers of nut intake, including fatty acid conjugated metabolites, phase II and microbial-derived phenolic metabolites, and serotonin metabolites. An increased excretion of serotonin metabolites was associated for the first time with nut consumption. Additionally, the detection of urinary markers of gut microbial and phase II metabolism of nut polyphenols confirmed the understanding of their bioavailability and bioactivity in the determination of the health effects derived from nut consumption. The results confirmed how a non-targeted metabolomics strategy may help to access unexplored metabolic pathways impacted by diet, thereby raising prospects for new intervention targets.

An ileal brake composition of micro-granules to control hepatic steatosis is informed by the research presented above and the results obtained from testing Aphoeline Brake™ in patients with hepatic steatosis, relies on the following analysis and information:

1. Hepatitis C is a chronic viral infection of 2% of the world's population that, if untreated, leads to progressive hepatic fibrosis and then cirrhosis.
2. A significant fraction of HCV infected patients develop hepatocellular carcinoma, but the usual cause of death is cirrhosis and its complications.
3. Hepatitis C is presently treated with the combination of pegylated interferon and ribavirin (pegIFN/Riba), but numerous agents have been synthesized and a number show promise as anti-HCV agents.
4. Two new antiviral agents have been introduced, these are telaprevir and boceprevir. Each of these two agents may be given alone or in combination with pegIFN/Riba in further combination with an ileal brake composition according to the present invention.
5. Changes in viral load result from these antiviral treatments alone, and if a patient can be converted to undetectable numbers of virus particles by such treatment, that is considered a favorable response to antiviral treatment.
6. If the patient with undetectable virus at the end of treatment does not relapse within 6-12 months, that patient might be considered cured of Hepatitis C by that treatment.
7. However, it is quite difficult to predict the course of Hepatitis C treatment from clinical parameters. However, when liver enzymes are elevated at the beginning of Hepatitis C therapy, and they rise further during treatment, that event usually defines increasing liver inflammation, treatment failure and would be expected to lead to progressive injury to the liver, thus exacerbating the disease state.
8. pegIFN/Riba responses are observed in slightly more than 50% of patients, and the response is correlated with a decline in numbers of viral particles, although not necessarily a cure. In treated patients with a decline in virus particles, liver enzymes such as ALT and AST may remain elevated but do not increase further, except on rare occasion as in the case of the advanced fibrosis and early on in the treatment, while in patients with no change in virus particles there is usually no associated decline in liver enzymes such as ALT and AST. It might be said that the decrease in the number of virus particles permits a decrease in hepatic inflammation, which then explains the decline in ALT and AST.
9. When the Hepatitis C virus particle count remains high and the liver enzymes are high or rising showing continued inflammation, then the unchecked Hepatitis C leads to cellular changes occurring in the liver which manifest as increasing fibrosis and eventually cirrhosis (a severe and irreversible form of hepatic fibrosis).
10. Hepatic Steatosis, or fatty liver disease, is commonly seen (25% of all adults over age 30). It is estimated that there are over 1.0 billion persons in the world with hepatic steatosis.
11. Hepatic Steatosis is associated with obesity, elevated serum triglycerides, T2D, MetS and diet high in fats or refined sugar.
12. Patients with hepatic steatosis usually have elevated liver enzymes.
13. There is no known effective treatment for hepatic steatosis except dietary decrease in sugars or fats and increased exercise/improved lifestyle/weight loss.
14. Depending on the study, the incidence of infection with hepatitis C in patients with Hepatic Steatosis is 3-6%, and more than 50% in association with genotype 3.
15. Patients with Hepatic steatosis who have infection with hepatitis C, are more difficult to treat with antivirals including pegIFN/Riba and resolution of the disease state is difficult.
16. When hepatic steatosis is present and hepatitis C is present in the same patient, treatment with antivirals alone often may not be associated with decline in the liver enzymes, because even elimination of the virus particles does not change the hepatic steatosis as the cause of elevation in the liver enzymes.
17. Thus the return of elevated liver enzymes to normal requires BOTH treatments to eradicate the hepatitis C virus AND treatment to resolve the hepatic steatosis. The surprising result is essentially a cure for hepatitis viral infections, something which can be obtained in only limited or rare instances using present protocol.
18. Treatments according to the present invention that work together to improve the disease and to eradicate an infection are synergistic in nature, because the combination is more effective than both components when provided alone, given an expectation for the additive benefits of combination therapy.
19. The presently claimed compounds, in particular, the ileal brake compounds and compositions according to the present invention are active against hepatic steatosis. These compounds alone may bring liver enzymes to normal in a patient with hepatic steatosis, including instances where the patient has a hepatitis viral infection (C or B, but most often C).
20. Of the hepatitis C drugs available, interferons may have the most capability for decreasing liver enzymes, more than the newer protease inhibitors at the same level of viral load decline. This may be explained by a general anti-inflammatory effect on the liver from interferons, and if this is true it justifies the use of other general liver treatments that are supportive of the liver in conjunction with antivirals. However, toxicity of the interferons, including liver toxicity, remains a potential problem.
21. The effect of the ileal brake compound/compositions alone on liver enzymes is greater than the effect of antiviral drugs for hepatitis C on liver enzymes.
22. The ileal brake compound/composition of the present invention alone is associated with only modest decline in the number of virus particles in a patient with hepatitis C. Usually, viral counts do not rise using an ileal brake compound alone and viral titers will fall, although they do not decline to low detection limits.
23. The experiments conducted and presented in the present application evidence that the ileal brake compound/composition according to the invention provides synergistic therapy in combination with antivirals for Hepatitis C, when the two are used in combination in patients who have hepatic steatosis secondary to viral infection.
24. Most patients (66+%) exhibit hepatic steatosis concomitant with hepatitis C infection.
25. When combined with any antiviral treatment for hepatitis C as described herein, the use of an ileal brake compound/composition will lower liver enzymes, resolve hepatic steatosis, reduce the likelihood and in certain instances, reverse cirrhosis of the liver and further help to lower virus particle counts in a patient with hepatitis C and hepatic steatosis as a secondary disease state and/or condition.

Beneficial Regenerative Aspects of the Invention in Patients with Hepatitis C and HIV Patients with HCV and HIV are surviving longer than in the era before there were effective antivirals to prevent the acute mortality. Now however, almost 30 years after antivirals became available, patients are typically in their 60s and are accumulating the metabolic diseases typically seen as causes of death in their 70s. It has been recently estimated that 50% of patients with HIV infection die of non-HIV causes: 16.6% from CV disease, 23.5% from non-HIV malignancy, and 14.4% from Liver associated complications (NATAP ref 12). In a study conducted in treated patients with viral load suppression, 50% of cases over 60 years of age had 2 or more co-morbidities, and as patients aged, they increased to three co-morbidities. Among the more important co-morbidities, patients manifest Hypertension (43%), COPD (20%), Fractures/osteoporosis (20%), Cancers (12%) chronic liver diseases (9%) and CV diseases/T2D (7%). As these cases are already taking 7-12 chronic medications, it will be expected that they have a life shortening of 10-15 years if this pattern goes unchecked. In several studies, mortality risk was linearly associated with the number of medications beyond five, and those on 5 or more medications had a 30% higher risk of mortality. Increasingly many more older patients in their mid-60s are unable to perform ordinary daily activities and functions. These patients are already disabled and the problem is rapidly worsening. It appears that MetS diseases are appearing much earlier in patients living with anti-viral therapy compared to those uninfected. In fact, early onset of MetS leads to direct shortening of life expectancy and now we are seeing an example of accelerated early mortality and intense co-morbidity as we develop antiviral drugs. The drugs are controlling the virus, but apparently not the underlying progressive development of inflammatory and metabolic abnormalities that lead to MetS and life shortening by 10-15 years.

The experiments conducted and presented in the present application evidence that the ileal brake compound/composition according to the invention provides synergistic therapy in combination with antivirals for Hepatitis C, when the two are used in combination in patients who have hepatic steatosis secondary to viral infection. And is now well known that patients who survive the acute infection with HIV or HCV because of anti-virals develop a MetS condition which is more rapidly progressive than seen in patients without chronic viral infection. For example, most patients (66+ %) exhibit hepatic steatosis concomitant with hepatitis C infection, most have CV diseases or diabetes, and many are obese and have the full spectrum of MeS syndrome complications on top of their chronic antivirals.

It is vitally important to delay the onset of MetS in patients with chronic viral infections, and it is abundantly clear that the anti-virals themselves do not accomplish this objective. According to the present invention, treating patients with anti-virals and an ileal brake hormone releasing substance will lower liver enzymes, resolve hepatic steatosis, lower Alpha Fetoprotein and clearly lowers the inflammation and cancer associated biomarkers that are present in these cases, whether or not the viral load is increased or suppressed almost to baseline. There is an element of regenerative synergy associated with combined anti-virals and the disclosed ileal brake hormone releasing substance, and the combination both reduces the likelihood and in certain instances, reverses established fibrosis of the liver. The combination of the antiviral and the ileal brake hormone releasing substance synergistically lowers risk by reversing hepatic steatosis and synergistically lowers virus particle counts in a patient with hepatitis C and hepatic steatosis as a secondary disease state and/or condition. The associated reduction of inflammation further lowers the fibrosis score of the patient and apparently reverses broad markers of MetS such as the FS index and the CV index. This may be considered a means of controlling the accelerated ageing of chronic viral infections by controlling the onset and progressing of the ageing associated MetS.

The improvement shown in patients taking the ileal brake hormone releasing substance is associated with avoiding morbidity and mortality. Prior to the present studies, there has been no means of lowering MetS in patients with chronic viral infections, and now it would appear that the present invention has said beneficial properties. The significance of these beneficial properties for those living with HIV and HCV cannot be overstated, as it would appear that delay in the onset of chronic viral infection linked MetS would lengthen life span by 5-10 years.

Composition: Ileal Brake Hormone Releasing Substance

By way of example and illustration of the role of an ileal brake compound or composition (Brake™) in hepatitis C treatment, the inventors describe here some patient cases to demonstrate unexpected favorable outcomes in difficult treatment cases with hepatitis C where the response was better than expected when the patient was given Brake™

Aphoeline Formulation 1
600 mg/capsule glucose
1000 mg capsule
10% Eudragit coating
Plasticizer (propylene glycol, triethyl acetate and water)
Magnesium stearate
Silicon Dioxide
Formulation II

|  | Amount | Range |
|---|---|---|
| Blend: | | |
| Alfalfa Leaf | 3.00 | 1-10+ |
| Chlorella Algae | 3.00 | 1-10+ |
| Chlorophyllin | 3.00 | 1-10+ |
| Barley Grass Juice Concentrate | 3.00 | 1-10+ |
| Dextrose | 1429.00 | 500-3000+ |
| Other Tablet Ingredients: | | |
| Coating * | 388.40 | 125-750+ |
| Corn Starch NF | 80.00 | 25-160+ |
| Hypromellose USP | 32.40 | 10-65+ |
| Stearic Acid NF (Vegetable Grade) | 19.50 | 6.5-35+ |
| Triacetin FCC/USP | 19.30 | 6.5-40+ |
| Magnesium Stearate NF/FCC | 7.00 | 2.5-15+ |
| Silicon Dioxide FCC | 2.50 | 0.75-5.0+ |

* Depending upon the composition used, 10% by weight Aqueous Shellac (Mantrose Haeuser, Inc. Aphoeline-1), 8% by weight Aqueous Indian Shellac (Aphoeline-2) was used to coat the formulations.

Formulation II was provided by mixing the actives with corn starch, stearic acid, magnesium stearate and silicon dioxide and pressing into a tablet, and coating the tablet with shellac (either 10% or 8% shellac), triacetin and the hypromellose. A Eudragit coating could alternatively be used, similar to that which coats formulation I, as described above.

Example 6. Manufacturing of Brake Preferred Embodiments for NASH

Manufacturing of Brake tablets will consist of the formulation/process development of the tablet composition in FIG. 35 and of the coating of the tablet with shellac in FIG. 38. The compositions, procedures and processes are not meant to be limiting, as it is recognized that departure from the exact formulation is within the scope of the invention, provided that ileal brake hormone release matches the output of RYGB surgery patients as in FIG. 23. Granulated dextrose USP will be used for the Brake formulated product. The starting characteristics and amounts will be appropriate to achieve a final tablet of about 1660-1690 mg in weight. Conditions for GMP pharmaceutical Brake tablet formation will be developed. Additional ingredients may be required to facilitate the tablet making process. This process will be scaled up to yield approximately 200,000 tablets in a batch.

After drying, sample tablets of this material will be removed as a dissolution testing sample. Dissolution testing procedures for Brake tablets should mimic GI physiological conditions, where the disclosed dissolution procedure is to subject the tablets to 2 hrs of acidic pH and then place them at pH 7.4. The 8% coating has performed better in this testing than either 6% or 10% (6% was releasing too early and 10% was releasing too late). Dissolution testing results from these experiments led to the selection of the clinical formulation at 8% shellac coating. Final dissolution testing standards for Brake tablets have not been established, and a variety of dissolution testing means do not correlate with the release of ileal brake hormones in vivo.

Brake Tablet Coating

The tablets of the formulation will be coated with shellac (Marcoat 125N) to various levels of weight gain, ranging 6-10%, with the preferred embodiment about 8%. The composition used to collect the pilot patient data had 8% coating by weight. As far as reasonable departures from the art, the inventors believe that there may be some improvements in ileal brake hormone release performance from the manufacture and use of 7% to 7.5% coatings. Accordingly, these coating formulations are included in the present preferred embodiments of the invention, as they will be manufactured and subjected to dissolution testing, followed by some use in humans to evaluate ileal brake hormone release to develop a means of predicting ileal brake hormone profiles as in FIG. 23.

The Quantity of shellac coating for FIG. 36 is calculated based on a solution with 25% solids and may need to be altered if additional ingredients are added to the shellac. For example, for 2% weight gain, 3.2 kg of shellac solution will be added to the base formula.

It will be recognized by one skilled in the art of formulation that reasonable variations on these conditions that result from minimal experimentation with materials and manufacturing methods are within the scope of the invention. It is stated by the inventors that the final determination whether a modification is within the scope of the invention is defined by testing of ileal brake hormone release in humans and the achievement of the GLP-1 and PYY values of RYGB patients as shown in FIG. 23. Stated explicitly, any formulation that produces within +/−50% variation on the ileal brake hormones in FIG. 23 is still within the scope of the disclosed invention. From the foregoing, it will be appreciated that, although specific embodiments of the invention have been described herein for the purpose of illustration, various modifications may be made without deviating from the spirit and scope of the invention. Accordingly, the present invention is not limited except as by the appended claims.

For the avoidance of doubt, profiles of ileal brake hormone release that are like formulation 1 and 3 in FIG. 23 remain within the scope of the invention. The GLP-1 values from Formulations 4-7 are too low to be considered effective, and the PYY AUC values from 4, 5 and 6 are considered too low to offset the low GLP-1 AUC of these formulations. These three are beyond the scope of acceptable formulations on the basis of their ileal brake hormone release.

Results on Clinical Use of the Composition

The patient data collected with Brake Formulation #2 and disclosed herein (see Example 3) exposed three fundamental and unexpected synergistic properties of Brake used in combination with a low dose statin, each reflected in the CV index as lowering CV risk. The first was the lowering of dietary fat via the central effects of GLP-1 and PYY, which augments the supply side lipid pathway, and works synergistically with statins. Statins have their primary effect on cholesterol synthesis, which is synergistic with the Brake effect, which is on the Dietary Lipid Supply side pathway. The second beneficial property of the combination of low dose statin and Brake was reduction in hsCRP, which in turn lowers inflammation and reduces cardiovascular risk markedly. The third surprising beneficial effect of the combination was to raise HDL cholesterol, an extremely beneficial contribution from the Brake effect that is not often seen at any statin dose, much less a low dose. HDL is considered "Good Cholesterol" and is a long sought target of the Pharmaceutical industry. The effect on HDL is shown in FIG. 21.

One surprising aspect of the combination of the two pathways was apparent synergy between low doses of statin and Brake, which fostered an increased safety margin yet no loss of efficacy. Since up to 15% of all statin treated patients are intolerant of these drugs at full doses, this novel aspect of combination is not only reflected in decreased CV risk, it also adds a large number of patients to the group who can be given statin drugs safely.

Many of these additional patients are not diabetic so the net result was a need to cover the risk of the hepatic synthesis in a manner beyond the current Brake tablets, and the CV index needed to incorporate LDL and statins to reflect these deficiencies of the current index. However, statin treated patients are at increased risk of developing diabetes(115). Now with the combination of Brake and lower doses of atorvastatin, this risk of diabetes is essentially lowered to zero by treatment of the combined glucose supply side and lipid supply side. Such benefit has never been achieved within either statins alone or in combination with any other drug substance.

Low dose statin and Brake is a new therapeutic platform combining a statin in a statin sparing dose with an ileal brake hormone releasing substance and offering the promise of dramatically lowering CV risk in human therapeutics. This new combination is called LipidoBrake.

Example 7. Combination of Statins and Brake—LipidoBrake for NASH

There is a need for a Brake combination product in the treatment of NAFLD and NASH, and a preferred embodiment is the combination of Brake with a statin. The primary problems with the use of statin drugs alone is their dose limiting side effects, chiefly muscle weakness and the onset of T2D. Statin doses could be raised above minimum to further lower LDL. However, the severity of the resulting side effects may become dose limiting. Hence one approach is to exploit the natural synergy between Brake and low doses of statins in order to comprehensively manage NASH and NAFLD. One of the most important synergies is the known property of statins as protective against the development of hepatocellular carcinoma.(116). This property is expected to be an additional synergy between the ileal brake hormone releasing composition and atorvastatin. The statin effect would be expected with other statin compounds as well.

Brake did not lower LDL or Total cholesterol sufficiently on its own, but in the course of patient studies it was discovered that small doses of statins could work synergistically with Brake to provide the same amount of LDL lowering as with higher doses of statins. There were novel and surprising aspects found when combining Brake with Statins, as we will discuss in this example as well as disclose a means of formulating statins with Brake to achieve a statin sparing effect with regards to avoiding the two primary side effects of statins, namely muscle weakness and development of T2D.

Our work with Formulation #2 of the ileal brake hormone releasing composition confirms that low dose statin can be given concomitantly with Brake, and the result is equivalent lowering of LDL to higher dose of statins. Thus 10 mg of atorvastatin added to Brake creates a similar lowering of LDL cholesterol as noted with 40 mg or more of atorvastatin. This is demonstrated in the body of our data, where the LDL lowering ability of Brake adds considerably to low dose statin to arrive at a "statin sparing" property.

LipidoBrake is the disclosed composition of Low dose statin overcoating the tablets of Brake. The specific disclosure of LipidoBrake is a combination of atorvastatin in a low dose of 10 mg overcoating an ileal brake hormone releasing substance.

One skilled in the art will appreciate that any statin drug could be used in any dose in place of atorvastatin as used in the present disclosure, with only the anticipated experimentation to achieve a successful overcoating of the statin component. Examples of similar agents, thought to act on the defined statin pathway or by HMG-CoA reductase inhibition, include atorvastatin, simvastatin, lovastatin, ceruvastatin, pravastatin, pitavastatin, and rosuvastatin. One skilled in the art will also appreciate that any chosen statin, in dose defined by the invention of synergy with Brake in LDL lowering, must be overcoated onto the Brake tablet, since immediate release of the statin is required for success of the statin component of the formulation, and the statin overcoating must not interfere in any way with the action of the Brake tablet on the L-cells of the ileal brake.

FIG. 37 and FIG. 38, when combined, disclose the formula for Brake that is associated with the novel aspect called "Statin Sparing". Brake is the combination of the base formula and the shellac coating. Different formulations are separated due to the variable amounts of shellac being used in this process.

Manufacturing and Testing for the LipidoBrake Tablet

FIG. 37 shows the composition of the atorvastatin overcoat, which achieves the stated goal of over-coating 10 mg of atorvastatin onto 7 Brake tablets, and the desired dose of 9.1 grams of Brake and 10 mg of atorvastatin, the disclosed dose of LipidoBrake based on Brake added on to SoC in Example 2.

Over-coating formulations of atorvastatin calcium in crystalline form (atorvastatin-[R—(R*,R*)]-2-(4-fluorophenyl)-β,δ-dihydroxy-5-(1-methylethyl)-3-phenyl-4-[(phenylamino)-carbonyl]-1H-pyrrole-1-heptanoic acid; calcium salt (2:1) trihydrate) must include stabilizing major excipients such as starch or pre-gelatinized starch (preferably pre-gelatinized starch like starch 1500) and lactose monohydrate. The starch functions as a disintegrant and the lactose is primarily a filler.

Compatible minor excipients such as silicon dioxide, microcrystalline cellulose, Tween as a surfactant (2%), magnesium stearate (preferred lubricant) (2%) may also be included in small amounts. The preferred binder is Povidone (PVP: polyvinyl pyrrolidone), (up to 20%) alternatively low molecular weight HPC (hydroxypropyl cellulose).

A granulate or dry mix will be prepared using atorvastatin calcium in crystalline form and the excipients ratio in the coating formulas listed above. The granulate will be prepared with a mortar and pestle using the aqueous granulation solution. The wet granulate will then be dried in an oven at 60° C. down to limit of detection (LOD)<5% and then milled.

The dissolution profile, stability and other physicochemical properties of this formulation are expected to be little influenced by the granulation, drying and operating temperature parameters used for its production. It is expected to also be stable even with a wide range of starch (preferably pre-gelatinized starch)/lactose ratios in the formula. Preferably such a ratio ranges from about 5%/95% to about 95%/5%.

Preferred coating materials will include any suitable enteric polymer or polymer combination (as for example, that present in Opadry® (Colorcon Inc)).

An immediate-release amount of 1.43 mg atorvastatin will be applied to each 1.663 g core Brake tablet. From the foregoing, it will be appreciated that, although specific embodiments of the invention have been described herein for the purpose of illustration, various modifications may be made without deviating from the spirit and scope of the invention. Accordingly, the present invention is not limited except as by the appended claims.

The atorvastatin coating is directly applied to the Brake shellac coated tablets. The atorvastatin coating is prepared by dissolving Opadry, hydroxypropyl methylcellulose, Povidone and Tween 80 in purified water using a homogenizer. Once these ingredients are dissolved, atorvastatin calcium is dispersed into the solution and homogenized. The homogenized dispersion is then directly applied to the Brake tablets e.g. using a 24" O'Hara Labcoat III pan coater. FIG. 38 shows the spray conditions chosen to overcoat the 10 mg of atorvastatin onto the Brake tablets.

Planned Testing for LipidoBrake Formulation

Assays for atorvastatin will be performed using a high pressure liquid chromatography (HPLC) system. A Waters liquid chromatograph equipped with a ultraviolet (UV) detector operating at a wavelength of 238 nm will be used. The column is a Hypersil BDS (4.6 mm×3 cm) 3-μm column. The mobile phase is composed of a 55:45 mixture of 0.1% phosphoric acid in water-acetonitrile. The injection volume is 20 μL, and the flow rate is 2.5 mL/min. Under these conditions, the atorvastatin retention time is about 1 min.

The standard curve concentration set is 11.1, 22.2 and 44.4 ppm for 10, 20 and 40 mg tablets respectively, made in a water-methanol diluent.

Assay and impurities testing: The tests will be performed on a Waters liquid chromatograph equipped with a UV detector operating at a wavelength of 238 nm. The column is a Purospher RP-18e (4.0 mm×15 cm) 5-μm column. The mobile phase is composed of a 55:45 mixture of 0.1% phosphoric acid in water acetonitrile. The injection volume is 20 µL, and the flow rate is 1.0 mL/min. The atorvastatin retention time is about 10 min.

The standard and sample concentration of the assay is about 200 ppm. The standard for the related compounds is about 2 ppm (0.2% of the sample concentration), made in a water-methanol diluent. Results of related compounds will be expressed as a percentage of the total amount of atorvastatin calcium in the sample. Unknown impurities will be named according to the relative retention time according to the method.

Dissolution testing conditions will be finalized prior to any use of LipidoBrake. Human testing of Brake for ileal brake hormone release in the planned Phase Ib study will validate the final dissolution testing means adopted (after extensive testing and validation). The purpose of this analysis is to collect data on the dissolution performance of LipidoBrake tablets at selected pH levels. The dissolution tests of the Brake cores or atorvastatin coatings will be performed in USP apparatus II fitted with paddles, at 50-100 rpm and 37° C.

The dissolution media will be 0.05 M phosphate buffer adjusted to pH 6.8, 5.5 and potentially others, with various concentrations of surface active agents like polysorbate 80. LipidoBrake tablets will be placed into media of pH 2.0 for 2 hours, then at 7.5 for 4 hours, at a temperature of 37° C.±0.5° C. Samples will be taken every hour for 6 hours. As the overcoating of atorvastatin is designed to perform as immediate release, the expected standard for atorvastatin is dissolution within 2 hrs at pH 2.0.

Clinical Evaluation of LipidoBrake Formulations in Humans

It should be noted to avoid doubt, that animal models are not an effective means of evaluation for the Brake constructs, they must be studied in humans. Animals cannot swallow the large tablets whole (required condition), and even if they could there are different intestinal conditions that would result in either premature release or release of contents too late to target the ileum.

The Phase Ib study will be a single dose study investigating the dietary effect of dextrose released from the LipidoBrake™ tablet on the ileal brake hormones GLP-1 and PYY with target AUC of 250 for GLP-1 and 350 for PYY in humans. The study aims to confirm comparable release effects by Brake™ and LipidoBrake™ prior to the use of the final formulation of LipidoBrake™ in the human study. Only a small number of healthy subjects (Typically 8-16) with an increased BMI will be included in this study.

The objective is to ensure ileal release of the carbohydrates and, as a result, to mimic the hormonal output of a patient with RYGB surgery given a meal challenge. For comparison, the Brake dosage producing the same AUC of GLP-1 as that seen in RYGB patients given a standard meal was investigated as Formulation #2 in FIG. 23.

The net result of inclusion of a low dose of atorvastatin over-coated onto Brake tablets is a product able to cover both the glucose supply side and the lipid supply side of the revised CV risk equation. A previously unexpected clinical benefit of the use of this formulation is the ability to control LDL at very low doses of atorvastatin, thus greatly magnifying the safety of atorvastatin. It should be also noted that while atorvastatin is used in this example, the use of any other HMG-CoA inhibitor may be within the scope of the present invention.

Similar side effect minimizing benefits are conferred onto any statin combined with Brake under the teachings of this invention.

From the foregoing, one skilled in the art will appreciate that, although specific embodiments of the invention have been described herein for the purpose of illustration, various modifications may be made without deviating from the spirit and scope of the invention.

Accordingly, the present invention is not limited except as by the appended claims.

REFERENCES

1. Loomba R, Sanyal A J. The global NAFLD epidemic. Nat Rev Gastroenterol Hepatol. 2013; 10(11):686-90.
2. De Minicis S, Agostinelli L, Rychlicki C, Sorice G P, Saccomanno S, Candelaresi C, et al. HCC development is associated to peripheral insulin resistance in a mouse model of NASH. PLoS One. 2014; 9(5):e97136.
3. Siddique A, Kowdley K V. Insulin resistance and other metabolic risk factors in the pathogenesis of hepatocellular carcinoma. Clin Liver Dis. 2011; 15(2):281-96, vii-x.
4. Marchesini G, Babini M. Nonalcoholic fatty liver disease and the metabolic syndrome. Minerva Cardioangiol. 2006; 54(2):229-39.
5. McCullough A J. Update on nonalcoholic fatty liver disease. J Clin Gastroenterol. 2002; 34(3):255-62.
6. Monte S V, Caruana J A, Ghanim H, Sia C L, Korzeniewski K, Schentag J J, et al. Reduction in endotoxemia, oxidative and inflammatory stress, and insulin resistance after Roux-en-Y gastric bypass surgery in patients with morbid obesity and type 2 diabetes mellitus. Surgery. 2012; 151(4):587-93.
7. Glass L M, Dickson R C, Anderson J C, Suriawinata A A, Putra J, Berk B S, et al. Total Body Weight Loss of >/=10% Is Associated with Improved Hepatic Fibrosis in Patients with Nonalcoholic Steatohepatitis. Dig Dis Sci. 2014.
8. Liu X, Lazenby A J, Clements R H, Jhala N, Abrams G A. Resolution of nonalcoholic steatohepatits after gastric bypass surgery. Obes Surg. 2007; 17(4):486-92.
9. Mattar S G, Velcu L M, Rabinovitz M, Demetris A J, Krasinskas A M, Barinas-Mitchell E, et al. Surgically-induced weight loss significantly improves nonalcoholic fatty liver disease and the metabolic syndrome. Ann Surg. 2005; 242(4):610-7; discussion 8-20.
10. Furuya C K, Jr., de Oliveira C P, de Mello E S, Faintuch J, Raskovski A, Matsuda M, et al. Effects of bariatric surgery on nonalcoholic fatty liver disease: preliminary findings after 2 years. J Gastroenterol Hepatol. 2007; 22(4):510-4.
11. Mathurin P, Hollebecque A, Arnalsteen L, Buob D, Leteurtre E, Caiazzo R, et al. Prospective study of the long-term effects of bariatric surgery on liver injury in patients without advanced disease. Gastroenterology. 2009; 137(2):532-40.
12. Clark J M, Alkhuraishi A R, Solga S F, Alli P, Diehl A M, Magnuson T H. Roux-en-Y gastric bypass improves liver histology in patients with non-alcoholic fatty liver disease. Obes Res. 2005; 13(7):1180-6.
13. Patel N S, Doycheva I, Peterson M R, Hooker J, Kisselva T, Schnabl B, et al. Effect of weight loss on magnetic resonance imaging estimation of liver fat and volume in patients with nonalcoholic steatohepatitis. Clin Gastroenterol Hepatol. 2015; 13(3):561-8 el.

14. Schwimmer J B, Middleton M S, Behling C, Newton K P, Awai H I, Paiz M N, et al. Magnetic resonance imaging and liver histology as biomarkers of hepatic steatosis in children with nonalcoholic fatty liver disease. Hepatology. 2014.
15. Singh D, Das C J, Baruah M P. Imaging of non alcoholic fatty liver disease: A road less travelled. Indian J Endocrinol Metab. 2013; 17(6):990-5.
16. Perazzo H, Poynard T, Dufour J F. The interactions of nonalcoholic fatty liver disease and cardiovascular diseases. Clin Liver Dis. 2014; 18(1):233-48.
17. Bril F, Sninsky J J, Baca A M, Superko H R, Portillo Sanchez P, Biernacki D, et al. Hepatic Steatosis and Insulin Resistance, But Not Steatohepatitis, Promote Atherogenic Dyslipidemia in NAFLD. J Clin Endocrinol Metab. 2016; 101(2):644-52.
18. Long M T, Pedley A, Massaro J M, Hoffmann U, Fox C S. The Association between Non-Invasive Hepatic Fibrosis Markers and Cardiometabolic Risk Factors in the Framingham Heart Study. PLoS One. 2016; 11(6): e0157517.
19. Gross A M, Jaeger P A, Kreisberg J F, Licon K, Jepsen K L, Khosroheidari M, et al. Methylome-wide Analysis of Chronic HIV Infection Reveals Five-Year Increase in Biological Age and Epigenetic Targeting of HLA. Mol Cell. 2016; 62(2):157-68.
20. Horvath S, Garagnani P, Bacalini M G, Pirazzini C, Salvioli S, Gentilini D, et al. Accelerated epigenetic aging in Down syndrome. Aging Cell. 2015; 14(3):491-5.
21. Boks M P, van Mierlo H C, Rutten B P, Radstake T R, De Witte L, Geuze E, et al. Longitudinal changes of telomere length and epigenetic age related to traumatic stress and post-traumatic stress disorder. Psychoneuroendocrinology. 2015; 51:506-12.
22. Marioni R E, Shah S, McRae A F, Chen B H, Colicino E, Harris S E, et al. DNA methylation age of blood predicts all-cause mortality in later life. Genome Biol. 2015; 16:25.
23. Gogebakan O, Kohl A, Osterhoff M A, van Baak M A, Jebb S A, Papadaki A, et al. Effects of weight loss and long-term weight maintenance with diets varying in protein and glycemic index on cardiovascular risk factors: the diet, obesity, and genes (DiOGenes) study: a randomized, controlled trial. Circulation. 2011; 124(25):2829-38.
24. Marcellin P. Hepatitis C: the clinical spectrum of the disease. J Hepatol. 1999; 31 Suppl 1:9-16.
25. Butt A A, Kanwal F. Boceprevir and telaprevir in the management of hepatitis C virus-infected patients. Clin Infect Dis. 2012; 54(1):96-104.
26. Reig M, Boix L, Marino Z, Torres F, Forns X, Bruix J. Liver Cancer Emergence Associated with Antiviral Treatment: An Immune Surveillance Failure? Semin Liver Dis. 2017.
27. Rodriguez de Lope C, Reig M, Matilla A, Ferrer M T, Duenas E, Minguez B, et al. Clinical characteristics of hepatocellular carcinoma in Spain. Comparison with the 2008-2009 period and analysis of the causes of diagnosis out of screening programs. Analysis of 686 cases in 73 centers. Med Clin (Barc). 2017.
28. Reig M, Boix L, Bruix J. The impact of direct antiviral agents on the development and recurrence of hepatocellular carcinoma. Liver Int. 2017; 37 Suppl 1:136-9.
29. Armstrong M J, Houlihan D D, Bentham L, Shaw J C, Cramb R, Olliff S, et al. Presence and severity of non-alcoholic fatty liver disease in a large prospective primary care cohort. J Hepatol. 2012; 56(1):234-40.
30. Dowman J K, Armstrong M J, Tomlinson J W, Newsome P N. Current therapeutic strategies in non-alcoholic fatty liver disease. Diabetes Obes Metab. 2011; 13(8):692-702.
31. Lok A S, Everhart J E, Chung R T, Kim H Y, Everson G T, Hoefs J C, et al. Evolution of hepatic steatosis in patients with advanced hepatitis C: results from the hepatitis C antiviral long-term treatment against cirrhosis (HALT-C) trial. Hepatology. 2009; 49(6):1828-37.
32. Briceno J, Ciria R, Pleguezuelo M, de la Mata M, Muntane J, Naranjo A, et al. Impact of donor graft steatosis on overall outcome and viral recurrence after liver transplantation for hepatitis C virus cirrhosis. Liver Transpl. 2009; 15(1):37-48.
33. Testino G, Sumberaz A, Ancarani A O, Borro P, Ravetti G, Ansaldi F, et al. Influence of body mass index, cholesterol, triglycerides and steatosis on pegylated interferon alfa-2a and ribavirin treatment for recurrent hepatitis C in patients transplanted for HCV and alcoholic cirrhosis. Hepatogastroenterology. 2009; 56(90):501-3.
34. Pekow J R, Bhan A K, Zheng H, Chung R T. Hepatic steatosis is associated with increased frequency of hepatocellular carcinoma in patients with hepatitis C-related cirrhosis. Cancer. 2007; 109(12):2490-6.
35. Pais R, Charlotte F, Fedchuk L, Bedossa P, Lebray P, Poynard T, et al. A systematic review of follow-up biopsies reveals disease progression in patients with non-alcoholic fatty liver. J Hepatol. 2013; 59(3):550-6.
36. Poynard T, Lassailly G, Diaz E, Clement K, Caiazzo R, Tordjman J, et al. Performance of biomarkers FibroTest, ActiTest, SteatoTest, and NashTest in patients with severe obesity: meta analysis of individual patient data. PLoS One. 2012; 7(3):e30325.
37. Monte S V, Schentag J J, Adelman M H, Paladino J A. Characterization of cardiovascular outcomes in a type 2 diabetes glucose supply and insulin demand model. J Diabetes Sci Technol. 2010; 4(2):382-90.
38. Monte S V, Schentag J J, Adelman M H, Paladino J A. Glucose supply and insulin demand dynamics of antidiabetic agents. J Diabetes Sci Technol. 2010; 4(2):365-81.
39. Monte S V, Bright F V, Schentag J J. Patent: Method and System to Provide Personalized Pharmaceutical Compositions and Dosages. U.S. Provisional application 61/254, 373 Filed Oct. 23, 2009. 2009; application Ser. No. 12/911,497 (Published on Apr. 28, 2011 as US2011-0097807A1): Issued as U.S. Pat. No. 8,367,418 B2 on Feb. 5, 2013.
40. Monte S V, Caruana J A, Ghanim H, Sia C L, Korzeniewski K, Schentag J J, et al. Reduction in endotoxemia, oxidative and inflammatory stress, and insulin resistance after Roux-en-Y gastric bypass surgery in patients with morbid obesity and type 2 diabetes mellitus. Surgery. 2011.
41. Ghanim H, Monte S V, Sia C L, Abuaysheh S, Green K, Caruana J A, et al. Reduction in Inflammation and the Expression of Amyloid Precursor Protein and Other Proteins Related to Alzheimer's Disease following Gastric Bypass Surgery. J Clin Endocrinol Metab. 2012; 97(7): E1197-201.
42. Fayad J M, Schentag J J. Compositions, Methods of Treatment and Diagnostics for Treatment of Hepatic Steatosis Alone or in Combination with a Hepatitis C Virus Infection. 2012; WO-2012-118712 and US 2012-026561.
43. Schentag J J, Fayad J M. Patent: Compositions, Methods of Treatment and Diagnostics for Treatment of Hepatic Steatosis alone, or in combination with a Hepatitis C virus infection. Provisional Application U.S. 61/480,788 filed on Apr. 29, 2011; 2011; Application number U.S. Ser. No.

12/932,633 filed on Mar. 2, 2011; Application number PCT/US 12/26561 filed on Feb. 24, 2012 (Published as WO 2012-118712 on Sep. 7, 2012 and PCT/US 2012_026561; published as US2013-0337055 A1 on Dec. 19, 2013): Issued as U.S. Pat. No. 9,370,528 on Jun. 21, 2016.

44. Schentag J, Fayad J M, Monte S V. Method and System to Provide Personalized Pharmaceutical Compositions and Dosages. United States No. 20140037739 A1; Feb. 6, 2014.

45. Sjostrom L, Lindroos A K, Peltonen M, Torgerson J, Bouchard C, Carlsson B, et al. Lifestyle, diabetes, and cardiovascular risk factors 10 years after bariatric surgery. N Engl J Med. 2004; 351(26):2683-93.

46. Sjostrom L, Narbro K, Sjostrom C D, Karason K, Larsson B, Wedel H, et al. Effects of bariatric surgery on mortality in Swedish obese subjects. N Engl J Med. 2007; 357(8):741-52.

47. Fayad J; Singh A S A, Chang K, Fayad C. Stimulation of the ileal break hormones by an orally delivered natural product Aphoeline I to the terminal ileum in health volunteers. American Gastroenterology Association, 2010.

48. National Cholesterol Education Program Expert Panel on Detection E, Treatment of High Blood Cholesterol in A. Third Report of the National Cholesterol Education Program (NCEP) Expert Panel on Detection, Evaluation, and Treatment of High Blood Cholesterol in Adults (Adult Treatment Panel III) final report. Circulation. 2002; 106(25):3143-421.

49. Goff D C, Jr., Lloyd-Jones D M, Bennett G, Coady S, D'Agostino R B, Sr., Gibbons R, et al. 2013 ACC/AHA Guideline on the Assessment of Cardiovascular Risk: A Report of the American College of Cardiology/American Heart Association Task Force on Practice Guidelines. Circulation. 2013.

50. Pencina M J, Navar-Boggan A M, D'Agostino R B, Sr., Williams K, Neely B, Sniderman A D, et al. Application of New Cholesterol Guidelines to a Population-Based Sample. N Engl J Med. 2014.

51. Chen C H, Lin S T, Kuo C L, Nien C K. Clinical significance of elevated alpha-fetoprotein (AFP) in chronic hepatitis C without hepatocellular carcinoma. Hepatogastroenterology. 2008; 55(85):1423-7.

52. Jolly S S, Cairns J A, Yusuf S, Meeks B, Pogue J, Rokoss M J, et al. Randomized Trial of Primary PCI with or without Routine Manual Thrombectomy. N Engl J Med. 2015.

53. Jacobs D M, Stefanovic F, Wilton G, Schentag J J. An integrated Statistical and Neural Net Model of the Warfarin Effect in Managed Care Patients. Clinical Pharmacology: Advances and Applications. 2017; In Press.

54. van Wijk D F, Boekholdt S M, Wareham N J, Ahmadi-Abhari S, Kastelein J J, Stroes E S, et al. C-reactive protein, fatal and nonfatal coronary artery disease, stroke, and peripheral artery disease in the prospective EPIC-Norfolk cohort study. Arterioscler Thromb Vasc Biol. 2013; 33(12):2888-94.

55. Jeong H C, Ahn Y, Park K H, Sim D S, Hong Y J, Kim J H, et al. Effect of statin treatment in patients with acute myocardial infarction and left ventricular systolic dysfunction according to the level of high-sensitivity C-reactive protein. Int Heart J. 2014; 55(2):106-12.

56. Ghany M G, Kim H Y, Stoddard A, Wright E C, Seeff L B, Lok A S. Predicting clinical outcomes using baseline and follow-up laboratory data from the hepatitis C long-term treatment against cirrhosis trial. Hepatology. 2011; 54(5): 1527-37.

57. Thompson A J, Patel K, Chuang W L, Lawitz E J, Rodriguez-Torres M, Rustgi V K, et al. Viral clearance is associated with improved insulin resistance in genotype 1 chronic hepatitis C but not genotype 2/3. Gut. 2012; 61(1):128-34.

58. Lee W Y, Kwon C H, Rhee E J, Park J B, Kim Y K, Woo S Y, et al. The effect of body mass index and fasting glucose on the relationship between blood pressure and incident diabetes mellitus: a 5-year follow-up study. Hypertens Res. 2011; 34(10): 1093-7.

59. Sung K C, Kim S H. Interrelationship between fatty liver and insulin resistance in the development of type 2 diabetes. J Clin Endocrinol Metab. 2011; 96(4): 1093-7.

60. Dixon J B, Bhathal P S, Hughes N R, O'Brien P E. Nonalcoholic fatty liver disease: Improvement in liver histological analysis with weight loss. Hepatology. 2004; 39(6): 1647-54.

61. Hickman I J, Russell A J, Prins J B, Macdonald G A. Should patients with type 2 diabetes and raised liver enzymes be referred for further evaluation of liver disease? Diabetes Res Clin Pract. 2008; 80(1):e10-2.

62. Forlani G, Di Bonito P, Mannucci E, Capaldo B, Genovese S, Orrasch M, et al. Prevalence of elevated liver enzymes in Type 2 diabetes mellitus and its association with the metabolic syndrome. J Endocrinol Invest. 2008; 31(2):146-52.

63. Kirpich I A, Solovieva N V, Leikhter S N, Shidakova N A, Lebedeva O V, Sidorov P I, et al. Probiotics restore bowel flora and improve liver enzymes in human alcohol-induced liver injury: a pilot study. Alcohol. 2008; 42(8): 675-82.

64. Fontana R J, Bonkovsky H L, Naishadham D, Dienstag J L, Sterling R K, Lok A S, et al. Serum fibrosis marker levels decrease after successful antiviral treatment in chronic hepatitis C patients with advanced fibrosis. Clin Gastroenterol Hepatol. 2009; 7(2):219-26.

65. Kwo P Y, Lawitz E J, McCone J, Schiff E R, Vierling J M, Pound D, et al. Efficacy of boceprevir, an NS3 protease inhibitor, in combination with peginterferon alfa-2b and ribavirin in treatment-naive patients with genotype 1 hepatitis C infection (SPRINT-1): an open-label, randomised, multicentre phase 2 trial. Lancet. 2010; 376 (9742):705-16.

66. Sherman K E, Flamm S L, Afdhal N H, Nelson D R, Sulkowski M S, Everson G T, et al. Response-guided telaprevir combination treatment for hepatitis C virus infection. N Engl J Med. 2011; 365(11):1014-24.

67. Bacon B R, Gordon S C, Lawitz E, Marcellin P, Vierling J M, Zeuzem S, et al. Boceprevir for previously treated chronic HCV genotype 1 infection. N Engl J Med. 2011; 364(13): 1207-17.

68. Poordad F, McCone J, Jr., Bacon B R, Bruno S, Manns M P, Sulkowski M S, et al. Boceprevir for untreated chronic HCV genotype 1 infection. N Engl J Med. 2011; 364(13): 1195-206.

69. Poordad F, Theodore D, Sullivan J, Grotzinger K. Medical resource utilisation and healthcare costs in patients with chronic hepatitis C viral infection and thrombocytopenia. J Med Econ. 2011; 14(2):194-206.

70. Poordad F. Big changes are coming in hepatitis C. Curr Gastroenterol Rep. 2011; 13(1):72-7.

71. Jacobson I M, McHutchison J G, Dusheiko G, Di Bisceglie A M, Reddy K R, Bzowej N H, et al. Telaprevir for previously untreated chronic hepatitis C virus infection. N Engl J Med. 2011; 364(25):2405-16.
72. Shah S R, Patel K, Marcellin P, Foster G R, Manns M, Kottilil S, et al. Steatosis is an independent predictor of relapse following rapid virologic response in patients with HCV genotype 3. Clin Gastroenterol Hepatol. 2011; 9(8): 688-93.
73. Tamura Y, Yamagiwa S, Aoki Y, Kurita S, Suda T, Ohkoshi S, et al. Serum alpha-fetoprotein levels during and after interferon therapy and the development of hepatocellular carcinoma in patients with chronic hepatitis C. Dig Dis Sci. 2009; 54(11):2530-7.
74. Goldstein N S, Blue D E, Hankin R, Hunter S, Bayati N, Silverman A L, et al. Serum alpha-fetoprotein levels in patients with chronic hepatitis C. Relationships with serum alanine aminotransferase values, histologic activity index, and hepatocyte MIB-1 scores. Am J Clin Pathol. 1999; 111(6):811-6.
75. Richardson P, Duan Z, Kramer J, Davila J A, Tyson G L, El-Serag H B. Determinants of Serum Alpha-Fetoprotein Levels in Hepatitis C Infected Patients. Clin Gastroenterol Hepatol. 2011.
76. Osaki Y, Ueda Y, Marusawa H, Nakajima J, Kimura T, Kita R, et al. Decrease in alpha-fetoprotein levels predicts reduced incidence of hepatocellular carcinoma in patients with hepatitis C virus infection receiving interferon therapy: a single center study. J Gastroenterol. 2011.
77. Tai W C, Hu T H, Wang J H, Hung C H, Lu S N, Changchien C S, et al. Clinical implications of alpha-fetoprotein in chronic hepatitis C. J Formos Med Assoc. 2009; 108(3):210-8.
78. Chen T M, Huang P T, Tsai M H, Lin L F, Liu C C, Ho K S, et al. Predictors of alpha-fetoprotein elevation in patients with chronic hepatitis C, but not hepatocellular carcinoma, and its normalization after pegylated interferon alfa 2a-ribavirin combination therapy. J Gastroenterol Hepatol. 2007; 22(5):669-75.
79. Di Bisceglie A M, Sterling R K, Chung R T, Everhart J E, Dienstag J L, Bonkovsky H L, et al. Serum alpha-fetoprotein levels in patients with advanced hepatitis C: results from the HALT-C Trial. J Hepatol. 2005; 43(3): 434-41.
80. Holst J J. Glucagonlike peptide 1: a newly discovered gastrointestinal hormone. Gastroenterology. 1994; 107 (6): 1848-55.
81. Ranganath L R, Beety J M, Morgan L M, Wright J W, Howland R, Marks V. Attenuated GLP-1 secretion in obesity: cause or consequence? Gut. 1996; 38(6):916-9.
82. Pironi L, Stanghellini V, Miglioli M, Corinaldesi R, De Giorgio R, Ruggeri E, et al. Fat-induced ileal brake in humans: a dose-dependent phenomenon correlated to the plasma levels of peptide Y Y. Gastroenterology. 1993; 105(3):733-9.
83. Guidone C, Manco M, Valera-Mora E, Iaconelli A, Gniuli D, Mari A, et al. Mechanisms of recovery from type 2 diabetes after malabsorptive bariatric surgery. Diabetes. 2006; 55(7):2025-31.
84. Welsh J B, Kannard B, Nogueira K, Kaufman F R, Shah R. Insights from a large observational database of continuous glucose monitoring adoption, insulin pump usage and glycemic control: the CareLink database. Pediatr Endocrinol Rev. 2010; 7 Suppl 3:413-6.
85. Welsh J A, Sharma A, Abramson J L, Vaccarino V, Gillespie C, Vos M B. Caloric sweetener consumption and dyslipidemia among U S adults. Jama. 2010; 303(15): 1490-7.
86. Baynes K C, Dhillo W S, Bloom S R. Regulation of food intake by gastrointestinal hormones. Curr Opin Gastroenterol. 2006; 22(6):626-31.
87. Burcelin R, Da Costa A, Drucker D, Thorens B. Glucose competence of the hepatoportal vein sensor requires the presence of an activated glucagon-like peptide-1 receptor. Diabetes. 2001; 50(8):1720-8.
88. Drucker D J. Development of glucagon-like peptide-1-based pharmaceuticals as therapeutic agents for the treatment of diabetes. Curr Pharm Des. 2001; 7(14):1399-412.
89. Drucker D J. Glucagon-like peptide 2. J Clin Endocrinol Metab. 2001; 86(4):1759-64.
90. Boushey R P, Yusta B, Drucker D J. Glucagon-like peptide (GLP)-2 reduces chemotherapy-associated mortality and enhances cell survival in cells expressing a transfected GLP-2 receptor. Cancer Res. 2001; 61(2):687-93.
91. Drucker D J. Minireview: the glucagon-like peptides. Endocrinology. 2001; 142(2):521-7.
92. Sumithran P, Prendergast L A, Delbridge E, Purcell K, Shulkes A, Kriketos A, et al. Long-term persistence of hormonal adaptations to weight loss. N Engl J Med. 2011; 365(17):1597-604.
93. Maljaars P W, Peters H P, Mela D J, Masclee A A. Ileal brake: a sensible food target for appetite control. A review. Physiol Behav. 2008; 95(3):271-81.
94. El-Serag H B. Hepatocellular carcinoma. N Engl J Med. 2011; 365(12): 1118-27.
95. Ochner C N, Gibson C, Shanik M, Goel V, Geliebter A. Changes in neurohormonal gut peptides following bariatric surgery. Int J Obes (Lond). 2011; 35(2):153-66.
96. Hvidberg A, Nielsen M T, Hilsted J, Orskov C, Holst J J. Effect of glucagon-like peptide-1 (proglucagon 78-107amide) on hepatic glucose production in healthy man. Metabolism. 1994; 43(1):104-8.
97. Reed M A, Pories W J, Chapman W, Pender J, Bowden R, Barakat H, et al. Roux-en-Y gastric bypass corrects hyperinsulinemia implications for the remission of type 2 diabetes. J Clin Endocrinol Metab. 2011; 96(8):2525-31.
98. Bikman B T, Zheng D, Pories W J, Chapman W, Pender J R, Bowden R C, et al. Mechanism for improved insulin sensitivity after gastric bypass surgery. J Clin Endocrinol Metab. 2008; 93(12):4656-63.
99. Morinigo R, Lacy A M, Casamitjana R, Delgado S, Gomis R, Vidal J. GLP-1 and changes in glucose tolerance following gastric bypass surgery in morbidly obese subjects. Obes Surg. 2006; 16(12):1594-601.
100. Morinigo R, Musri M, Vidal J, Casamitjana R, Delgado S, Lacy A M, et al. Intra-abdominal fat adiponectin receptors expression and cardiovascular metabolic risk factors in obesity and diabetes. Obes Surg. 2006; 16(6): 745-51.
101. Morinigo R, Moize V, Musri M, Lacy A M, Navarro S, Marin J L, et al. Glucagon-like peptide-1, peptide Y Y, hunger, and satiety after gastric bypass surgery in morbidly obese subjects. J Clin Endocrinol Metab. 2006; 91(5):1735-40.
102. Plum L, Ahmed L, Febres G, Bessler M, Inabnet W, Kunreuther E, et al. Comparison of glucostatic parameters after hypocaloric diet or bariatric surgery and equivalent weight loss. Obesity (Silver Spring). 2011; 19(11):2149-57.
103. Olbers T, Bjorkman S, Lindroos A, Maleckas A, Lonn L, Sjostrom L, et al. Body composition, dietary intake, and energy expenditure after laparoscopic Roux-en-Y gastric bypass and laparoscopic vertical banded gastroplasty: a randomized clinical trial. Ann Surg. 2006; 244 (5):715-22.
104. Ramon J M, Gonzalez C G, Dorcaratto D, Goday A, Benaiges A, Gonzalez S, et al. Quality of food intake after bariatric surgery: vertical gastrectomy versus gastric bypass. Cir Esp. 2011.
105. Overs S E, Freeman R A, Zarshenas N, Walton K L, Jorgensen J O. Food Tolerance and Gastrointestinal Quality of Life Following Three Bariatric Procedures: Adjustable Gastric Banding, Roux-en-Y Gastric Bypass, and Sleeve Gastrectomy. Obes Surg. 2011.
106. Shin A C, Berthoud H R. Food reward functions as affected by obesity and bariatric surgery. Int J Obes (Lond). 2011; 35 Suppl 3:S40-4.
107. Leahey™, Bond D S, Raynor H, Roye D, Vithiananthan S, Ryder B A, et al. Effects of bariatric surgery on food cravings: do food cravings and the consumption of craved foods "normalize" after surgery? Surg Obes Relat Dis. 2012; 8(1):84-91.
108. Brunault P, Jacobi D, Leger J, Bourbao-Tournois C, Huten N, Camus V, et al. Observations regarding 'quality of life' and 'comfort with food' after bariatric surgery: comparison between laparoscopic adjustable gastric banding and sleeve gastrectomy. Obes Surg. 2011; 21(8): 1225-31.
109. Shriner R L. Food as a bariatric drug. Curr Pharm Des. 2011; 17(12):1198-208.
110. Schweiger C, Weiss R, Keidar A. Effect of different bariatric operations on food tolerance and quality of eating. Obes Surg. 2010; 20(10):1393-9.
111. Suter M, Calmes J M, Paroz A, Giusti V. A new questionnaire for quick assessment of food tolerance after bariatric surgery. Obes Surg. 2007; 17(1):2-8.
112. Thomas J R, Marcus E. High and low fat food selection with reported frequency intolerance following Roux-en-Y gastric bypass. Obes Surg. 2008; 18(3):282-7.
113. Miras A D, le Roux C W. Bariatric surgery and taste: novel mechanisms of weight loss. Curr Opin Gastroenterol. 2010; 26(2):140-5.
114. Tulipani S, Llorach R, Jauregui O, Lopez-Uriarte P, Garcia-Aloy M, Bullo M, et al. Metabolomics unveils urinary changes in subjects with metabolic syndrome following 12-week nut consumption. J Proteome Res. 2011; 10(11):5047-58.
115. Steen D L, Bhatt D L. Statin potency associated with incident diabetes in a real-world evaluation. Evid Based Med. 2014; 19(2):68.
116. El-Serag H B, Johnson M L, Hachem C, Morgana R O. Statins are associated with a reduced risk of hepatocellular carcinoma in a large cohort of patients with diabetes. Gastroenterology. 2009; 136(5): 1601-8.

What is claimed is:

1. A method for the diagnosis and treatment of non-alcohol fatty liver disease (NAFLD) and/or non-alcoholic steatohepatitis (NASH) in a patient suspected of or having NAFLD and/or NASH, the method comprising obtaining a biological sample from the patient, measuring biomarkers in the biological sample which are indicative of inflammation, steatosis and/or fibrosis of the liver and other potentially affected organs of the patient and incorporating measurements of the biomarkers into a mathematical model, wherein the mathematical model computes the health of the liver and other affected organs to determine whether or not the patient requires therapy for NAFLD and/or NASH; and the patient undergoes therapy for the treatment of NAFLD and/or NASH based upon the results of the mathematical model, wherein the treatment comprises administering an effective amount of a traditional pharmacologically active agent, a composition comprising an ileal brake hormone releasing substance effective to increase the release of ileal brake hormones in said patient or a composition comprising an ileal brake hormone releasing substance effective to increase the release of ileal brake hormones in combination with a pharmacologically active agent.

2. The method according to claim 1 wherein the measurements obtained from the biological sample of the patient indicate insulin resistance in said patient, the current biopsy score of the patient, the risk of progressive changes in the biopsy score, the risk of the progression of steatosis, the risk of progression of fibrosis, the risk of developing hepatocellular carcinoma, the degree of metabolic syndrome associated disease components, the indices of cardiovascular and metabolic risk and wherein said method is used to predict the responsiveness of said patient to said therapy.

3. The method according to claim 1, wherein measurements of the biomarkers are used for:
   A. determining a calculated biopsy score as wCombBiopsy Predict;
   B. determining a wCombLiver signal;
   C. determining an FS index; and
   D. determining a Cardiovascular risk index.

4. The method of claim 3, wherein the wCombLiver Signal is calculated using a weighted function comprised of biomarkers from said patient or subject which includes Alkaline Phosphatase, ALT, AST, Total Bilirubin, Insulin Concentration, hsCRP, platelet count, Total Protein, Prothrombin time, INR, Lymphocyte count, Waist circumference, Direct Bilirubin, lymphocytes, GGT, Weight, BMI, LDH, and HbA1c, Statin dose, Use of Pioglitazone, Use of Fibric acid drugs and Use of Statins.

5. The method of claim 3, wherein said FS index is calculated as:

$$\frac{0.11\left((FBG+TG)+HBA1c\times\frac{HBA1c\times 20}{5}+BMI\times\frac{FBG+TG}{150}+AST\times\frac{TG\times 4}{100}+FB\text{ insulin}\times(BMI-22)\right)}{S/D\text{ ratio}}$$

FBG is Fasting Blood Glucose in mg/dl and normal value is 100 mg/dl
TG is Triglycerides in mg/dl normal value is <150
HBA1c is glycosylated hemoglobin calculated as a ratio to hemoglobin; normal value is <6%
BMI is body mass index as kg/m² where a normal value is 20 and obese begins above 25
AST is Aspartate Transferase (formerly SGOT) in IU/liter and a normal value is 5.50
FB insulin if fasting Blood insulin concentration in nmol/liter, a normal value is 4.0
Where S/D ratio is the $$\text{Glucose Supply }(S)/\text{Insulin Demand }(D) = \frac{1+((CE)+(HGU)+(GNG)+(IR))}{1+(PIE+PGU)}$$

Where S/D ratio (SD) is a ratio of Glucose Supply Index (S) to Insulin Demand Index (D); and wherein (S) is calculated as follows:

1+[aggregate of carbohydrate exposure (CE)+hepatic glucose uptake (HGU)+hepatic gluconeogenesis (GNG) and+insulin resistance (IR)], and (D) is calculated as follows:

1+[aggregate of peripheral glucose uptake (PGU)+ peripheral insulin exposure (PIE)].

6. The method of claim 3, wherein said Cardiovascular risk index is calculated as follows:

$$CV\ \text{Risk Index} = FS\ \text{Index} + \frac{(LDL\ \text{factor} + \text{age}/\text{sex}/\text{cigs factor} + hsCRP\ \text{factor} + RP/200)}{(LL\ \text{Drugs factor} + ASA\ \text{factor})}$$

wherein the FS index is calculated as:

$$\frac{0.11\left((FBG+TG) + HBA1c \times \frac{HBA1c \times 20}{5} + BMI \times \frac{FBG+TG}{150} + AST \times \frac{TG \times 4}{100} + FB\ \text{insulin} \times (BMI - 22)\right)}{S/D\ \text{ratio}}$$

FBG is Fasting Blood Glucose in mg/dl and normal value is 100 mg/dl
TG is Triglycerides in mg/dl normal value is <150
HBA1c is glycosylated hemoglobin calculated as a ratio to hemoglobin; normal value is <6%
BMI is body mass index as kg/m² where a normal value is 20 and obese begins above 25
AST is Aspartate Transferase (formerly SGOT) in IU/liter and a normal value is 5.50
FB insulin if fasting Blood insulin concentration in nmol/liter, a normal value is 4.0
Where S/D ratio is the Glucose Supply(S)/Insulin Demand(D) =

$$\frac{1 + ((CE) + (HGU) + (GNG) + (IR))}{1 + (PIE + PGU)}$$

Where S/D ratio (SD) is a ratio of Glucose Supply Index (S) to Insulin Demand Index (D); and wherein (S) is calculated as follows:

1+[aggregate of carbohydrate exposure (CE)+hepatic glucose uptake (HGU)+hepatic gluconeogenesis (GNG) and +insulin resistance (IR)], and (D) is calculated as follows:

1+[aggregate of peripheral glucose uptake (PGU)+ peripheral insulin exposure (PIE)]

wherein:
HBA1c factor: HBA1c×((HBA1c/5)×20)
BMI factor: BMI×((FBG+TG)/(50×3))
AST factor: AST×((TG/100)×4)
FBInsulin factor: (BMI−22)×FBInsulin
Low density Lipoprotein (LDL factor): 60+LDL/10
Age/gender/cigarette factor: (Packs/day×yrs/8)×age×gender, where gender is 1.0 for male and 0.6 for female,
High sensitivity C-Reactive protein (hsCRP) factor: hsCRP×10
Rate Pressure (RP factor): (HR×SBP)/200 where HR=Heart Rate and SBP=Systolic BP
Lipid Lowering (LL) Drugs factor:

(0.9+Statin Dose, mg in Lipitor equivs/10)+(0.2+ other LL drugs factor/5)

ASA factor: 0.8+(ASA yrs/2) where ASA is low dose Aspirin×years taken.

7. The method of claim 3 comprising determining a higher second wCombLiver signal, wCombBiopsy Predict signal, FS index and CV index relative to the first wCombLiver signal, wCombBiopsy Predict signal, FS index and CV index value, wherein the higher second value in said patient justifies the addition of a composition comprising an ileal brake hormone releasing substance to said patient, said ileal brake hormone releasing substance being released in the ileum of said patient which stimulates the release of ileal brake hormones and produces a GLP-1 Area under the curve or AUC value of approximately or at least an AUC value of 250.

8. The method according to claim 3, wherein the wCombLiver signal, wCombBiopsy Predict signal, FS index and/or CV index is calculated using a programmable spreadsheet or a website application.

9. The method according to claim 3, wherein said patient is clinically diagnosed as being at risk for or having NASH and/or NAFLD and said patient is treated with said pharmacologically active agent and/or said composition comprising an ileal brake hormone releasing substance, wherein said patient responds to said treatment as evidenced by changes in wComb Biopsy Predict signal and calculated FS index or CV index after said patient undergoes treatment for at least six months, or for at least 12 months.

10. The method according to claim 1, wherein said patient has a viral infection and is treated with an anti-viral agent in combination with said pharmacologically active agent and/or said composition comprising an ileal brake hormone releasing substance, said treatment resolving NASH and/or NAFLD, reducing the likelihood of fibrosis and/or cirrhosis and controlling the accelerated aging from chronic viral infection by controlling the onset and progression of aging associated MetS.

11. The method according to claim 1, wherein said traditional pharmaceutically active agent is selected from the group consisting of anti-diabetes drugs, SGLT-2 inhibitors, statin drugs, hormones, GLP-1 drugs, a biguanide (e.g. Metformin), a DPP-IV inhibitor (e.g. Sitagliptin), and mixtures thereof.

12. The method according to claim 11 wherein said traditional pharmaceutically active agent is administered to said patient in combination with a composition comprising an ileal brake hormone releasing substance.

13. The method according to claim 12 wherein said ileal brake hormone releasing substance is selected from the group consisting of starches, sugars, lipids, proteins, aminoacids and mixtures thereof.

14. The method according to claim 13 wherein said ileal brake hormone releasing substance is at least one sugar or at least one sugar in combination with at least one lipid.

15. The method according to claim 14 wherein said sugar is glucose and said lipid is an animal fat or oil, fish oil or a vegetable oil.

16. The method according to claim 11, wherein the metformin is over-coated onto the surface of said ileal brake hormone releasing substance or contained within the coating of the composition comprising said ileal brake hormone releasing substance.

17. The method according to claim 1, wherein said ileal brake hormone releasing substance comprises glucose and one or more lipids in an amount of 5-20% of the total amount of ileal brake hormone releasing substance in said composition.

18. The method according to claim 1, wherein said composition comprises an effective dose of an ileal brake hormone releasing substance, wherein said ileal brake hormone releasing substance on is administered in a dosage from 5 grams to 20 grams of dextrose combined with a dosage of from 0.25 grams to 4 grams of a lipid wherein at least 50% of said ileal brake hormone releasing composition is released in the ileum of said individual.

19. The method according to claim 1, wherein the patient is being treated for NAFLD or NASH with a combination of said ileal brake hormone releasing substance in combination with at least additional one agent selected from the group consisting of obeticholic acid, elafibranor, aramchol, simtuzumab, cenicriviroc, emricasan, IMM124E, BMS-986036, NGM282, GS9674, MSDC-0602, VK2809, MN-001, GS4998, GR-MD-02, NDI-010976, RG-125, DUR-928, CER-209, Solithromycin and PXS-4728A.

20. A method for treating NASH and/or NAFLD which includes biomarker testing, computation of said disease progression, diagnosis of extent and/or severity of disease, risk stratification, and personalized treatment, whereby beneficial outcome from treatment with an ileal brake hormone releasing substance improves the biopsy score thus indicating improvement in the severity of the disease and whereby said treatment lowers the risk for complications of the disease including fibrosis, cirrhosis, and hepatocellular carcinoma.

* * * * *